United States Patent
Labrie et al.

(10) Patent No.: US 9,682,960 B2
(45) Date of Patent: Jun. 20, 2017

(54) NON-STEROIDAL ANTIANDROGENS AND SELECTIVE ANDROGEN RECEPTOR MODULATORS WITH A PYRIDYL MOIETY

(71) Applicants: Fernand Labrie, Quebec (CA); Shankar Mohan Singh, Quebec (CA); Richard Labrecque, St-Nicolas (CA); Liviu Constantin Ciobanu, Quebec (CA)

(72) Inventors: Fernand Labrie, Quebec (CA); Shankar Mohan Singh, Quebec (CA); Richard Labrecque, St-Nicolas (CA); Liviu Constantin Ciobanu, Quebec (CA)

(73) Assignee: ENDORECHERCHE, INC. (CA)

( * ) Notice: Subject to any disclaimer, the term of this patent is extended or adjusted under 35 U.S.C. 154(b) by 0 days.

(21) Appl. No.: 14/567,970

(22) Filed: Dec. 11, 2014

(65) Prior Publication Data
US 2015/0175576 A1 Jun. 25, 2015

Related U.S. Application Data

(60) Provisional application No. 61/918,133, filed on Dec. 19, 2013.

(51) Int. Cl.
| | |
|---|---|
| *C07D 401/04* | (2006.01) |
| *C07D 403/12* | (2006.01) |
| *A61K 31/4439* | (2006.01) |
| *A61K 31/444* | (2006.01) |
| *A61K 31/4709* | (2006.01) |
| *A61K 31/4725* | (2006.01) |
| *A61K 31/496* | (2006.01) |
| *A61K 31/506* | (2006.01) |
| *A61K 31/517* | (2006.01) |
| *A61K 45/06* | (2006.01) |
| *C07D 401/12* | (2006.01) |
| *C07D 401/14* | (2006.01) |
| *A61K 38/09* | (2006.01) |
| *A61K 31/58* | (2006.01) |

(52) U.S. Cl.
CPC .......... *C07D 403/12* (2013.01); *A61K 31/444* (2013.01); *A61K 31/4439* (2013.01); *A61K 31/4709* (2013.01); *A61K 31/4725* (2013.01); *A61K 31/496* (2013.01); *A61K 31/506* (2013.01); *A61K 31/517* (2013.01); *A61K 31/58* (2013.01); *A61K 38/09* (2013.01); *A61K 45/06* (2013.01); *C07D 401/12* (2013.01); *C07D 401/14* (2013.01)

(58) Field of Classification Search
None
See application file for complete search history.

(56) References Cited

U.S. PATENT DOCUMENTS

| | | | |
|---|---|---|---|
| 3,742,951 A | 7/1973 | Zaffaroni | |
| 3,797,494 A | 3/1974 | Zaffaroni | |
| 4,568,343 A | 2/1986 | Leeper et al. | |
| 5,064,654 A | 11/1991 | Berner et al. | |
| 5,071,644 A | 12/1991 | Viegas et al. | |
| 5,071,657 A | 12/1991 | Oloff et al. | |
| 5,411,981 A | 5/1995 | Gaillard-Kelly et al. | |
| 5,556,983 A | 9/1996 | Claussner et al. | |
| 5,750,553 A | 5/1998 | Claussner et al. | |
| 6,071,957 A | 6/2000 | Miller et al. | |
| 6,087,509 A | 7/2000 | Claussner et al. | |

(Continued)

FOREIGN PATENT DOCUMENTS

| | | |
|---|---|---|
| CA | 2 677 295 | 9/2008 |
| CA | 2 773 591 | 3/2011 |
| EP | 0 002 892 A1 | 7/1979 |
| EP | 0 100 172 A1 | 2/1984 |
| EP | 0 279 982 A1 | 8/1988 |
| EP | 0 494 819 A1 | 7/1992 |
| EP | 0 578 516 A1 | 1/1994 |
| EP | 0 580 459 A1 | 1/1994 |
| FR | 2 671 348 A1 | 7/1992 |
| FR | 2 693 461 A1 | 1/1994 |

(Continued)

OTHER PUBLICATIONS

Silverman, R. "The Organic Chemistry of Drug Design and Drug Action," 2004, NY Elsevier, pp. 20-32.*

(Continued)

*Primary Examiner* — Heidi Reese
(74) *Attorney, Agent, or Firm* — Ostrolenk Faber LLP

(57) ABSTRACT

Compounds having the structure or their salts:

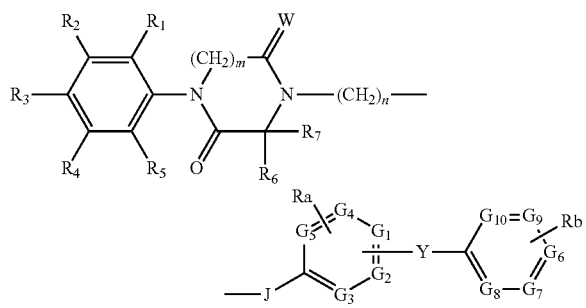

are used to treat or reduce the likelihood of acquiring androgen-dependent diseases, such as prostate cancer, benign prostatic hyperplasia, polycystic ovarian syndrome, acne, hirsutism, seborrhea, androgenic alopecia, male baldness, muscle atrophy and weakness, sarcopenia, male hypogonadism, erectile dysfunction, female sexual dysfunction and osteoporosis. They can be formulated together with pharmaceutically acceptable diluent or carrier or otherwise made into any pharmaceutical dosage form. Combinations with other active pharmaceutical agents are also disclosed.

24 Claims, 8 Drawing Sheets

(56) References Cited

U.S. PATENT DOCUMENTS

| | | | |
|---|---|---|---|
| 6,242,611 B1 | 6/2001 | Claussner et al. | |
| 7,001,911 B2 | 2/2006 | Salvati et al. | |
| 7,138,421 B2 | 11/2006 | Cleve et al. | |
| 7,141,578 B2 | 11/2006 | Salvati et al. | |
| 7,268,232 B2 | 9/2007 | Schlienger et al. | |
| 7,271,188 B2 | 9/2007 | Tachibana et al. | |
| 7,427,682 B2 | 9/2008 | Lanter et al. | |
| 7,709,516 B2 * | 5/2010 | Labrie | C07D 207/40 514/389 |
| 7,759,366 B2 * | 7/2010 | Jaehne | C07D 233/72 514/341 |
| 7,759,520 B2 | 7/2010 | Dalton et al. | |
| 7,803,970 B2 | 9/2010 | Dalton et al. | |
| 2004/0181064 A1 | 9/2004 | Sun et al. | |
| 2009/0270361 A1 | 10/2009 | Ito et al. | |
| 2010/0331418 A1 | 12/2010 | Koh et al. | |
| 2012/0004270 A1 | 1/2012 | Miller | |
| 2012/0041046 A1 | 2/2012 | Varchi et al. | |
| 2012/0184580 A1 | 7/2012 | Chakravarty et al. | |
| 2012/0251551 A1 | 10/2012 | Lücking et al. | |
| 2013/0041007 A1 | 2/2013 | Miller | |
| 2013/0116258 A1 | 5/2013 | Smith et al. | |
| 2013/0197009 A1 | 8/2013 | Ideyama et al. | |
| 2013/0217762 A1 | 8/2013 | Green et al. | |

FOREIGN PATENT DOCUMENTS

| | | |
|---|---|---|
| JP | 2002-88073 A | 3/2002 |
| WO | WO 95/18794 A1 | 7/1995 |
| WO | WO 96/19458 A2 | 6/1996 |
| WO | WO 97/00071 A1 | 1/1997 |
| WO | WO 97/19064 A1 | 5/1997 |
| WO | WO 97/23464 A1 | 7/1997 |
| WO | WO 98/53826 A1 | 12/1998 |
| WO | WO 99/46279 A2 | 9/1999 |
| WO | WO 00/37430 A2 | 6/2000 |
| WO | WO 01/16108 A2 | 3/2001 |
| WO | WO 01/16133 A2 | 3/2001 |
| WO | WO 02/00617 A1 | 1/2002 |
| WO | WO 02/24702 A1 | 3/2002 |
| WO | WO 2004/099188 A1 | 11/2004 |
| WO | WO 2004/111012 | 12/2004 |
| WO | WO 2004/113309 A1 | 12/2004 |
| WO | WO 2005/040136 A1 | 5/2005 |
| WO | WO 2005/049580 A1 | 6/2005 |
| WO | WO 2005/066194 A1 | 7/2005 |
| WO | WO 2005/120483 A2 | 12/2005 |
| WO | WO 2006/124118 A1 | 11/2006 |
| WO | WO 2006/133567 A1 | 12/2006 |
| WO | WO 2007/005887 A2 | 1/2007 |
| WO | WO 2007/127010 A2 | 11/2007 |
| WO | WO 2008/044033 A1 | 4/2008 |
| WO | WO 2008/124000 A2 | 10/2008 |
| WO | WO 2008/124922 A1 | 10/2008 |
| WO | WO 2009/055053 A2 | 4/2009 |
| WO | WO 2009/119880 A1 | 10/2009 |
| WO | WO 2010/143803 A2 | 12/2010 |
| WO | WO 2012/047617 A1 | 4/2012 |
| WO | WO 2012/050868 A1 | 4/2012 |
| WO | WO 2012/143599 A1 | 10/2012 |
| WO | WO 2013/014627 A1 | 1/2013 |
| WO | WO 2013/055577 A1 | 4/2013 |
| WO | WO 2013/057372 A1 | 4/2013 |
| WO | WO 2013/067142 A1 | 5/2013 |
| WO | WO 2013/128421 A1 | 9/2013 |
| WO | WO 2013/152170 A1 | 10/2013 |
| WO | WO 2015/018356 A1 | 2/2015 |

OTHER PUBLICATIONS

International Search Report and Written Opinion of the International Searching Authority dated Apr. 20, 2015 in corresponding International Application No. PCT/CA2014/000894.

Dominique Lesuisse, et al. "Discovery of the first Non-ATP Competitive IGF-1R Kinase Inhibitors: Advantages incomparison With Competitive Inhibitors," Bioorganic & Medicinal Chemistry Letters, vol. 21, (2011), pp. 2224-2228.

Ando, T., Yamawaki, J., Saito, Y., Takai, Y., Yamataka, H.;(1980). Neighboring group participation in solvolysis. X. Dissection of $Ar_1$-5 and $Ar_2$-6 pathways in trifluoroacetolysis of 4-arylbutyl6-methyl-2-naphthalenesulfonates. Bull. Chem. Soc. Jpn., 53(8): 2348-2356.

Aucoin, M.W., Wassersug, R.J.; (2006). The sexuality and social performance of androgen-deprived (castrated) men throughout history: Implications for modern day cancer patients. Soc. Sci. Med., 63: 3162-3173.

Balog, A., Salvati, M.E., Shan, W., Mathur, A., Leith, L.W., Wei, D.D., Attar, R.M., Geng, J., Rizzo, C.A., Wang, C., Krystek, S.R., Tokarski, J.S., Hunt, J.T., Gottardis, M., Weinmann, R.; (2004). The synthesis and evaluation of [2.2.1]-bicycloazahydantoins as androgen receptor antagonists. Bioorg. Med, Chem. Lett., 14: 6107-6111.

Bhasin, S., Pencina, M., Kaur Jasuja, G., Travison, T.G., Coviello, A., Orwoll, E., Wang, P.Y., Nielson, C., Wu, F., Tajar, A., Labrie, F., Vesper, H., Zhang, A., Ulloor, J., Singh, R., D'Agostino, R., Vasan, R.S.; (2011). Reference ranges for testosterone in men generated using liquid chromatography tandem mass spectrometry in a community-based sample of healthy nonobese young men in the Framingham Heart Study and applied to three geographically distinct cohorts. J. Clin. Endocrinol. Metab., 96(8): 2430-2439.

Cantin, L., Faucher, F., Couture, J.-F., Pereira de Jésus-Tran, K., Legrand, P., Ciobanu, L.C., Fréchette, Y., Labrecque, R., Singh, S.M., Labrie, F., Breton, R.; (2007). Structural characterization of the human androgen receptor ligand-binding domain complexed with EM5744, a rationally designed steroidal ligand bearing a bulky chain directed toward helix 12. J. Biol. Chem., 282(42): 30910-30919.

Chengalvala, M., Oh, T., Roy, A.K.; (2003). Selective androgen receptor modulators. Expert Opin. Ther. Patents, 13(1): 59-66.

Cozzoli, A., Capogrosso, R.F., Sblendorio, V.T., Dinardo, M.M., Jagerschmidt, C., Namour, F., Camerino, G.M., De Luca, A.; (2013). GLPG0492, a novel selective androgen receptor modulator. improve muscle performance in the exercised-mdx mouse model of muscular dystrophy . . . Pharmacol. Res., 72: 9-24.

Duke III, C.B., Jones, A., Bohl, C.E., Dalton, J.T., Miller, D.D.; (2011). Unexpected binding orientation of bulky-B-ringanti-androgens and implications for future drug targets. J. Med. Chem., 54: 3973-3976.

Gauthier, S., Martel, C., Labrie, F.; (2012). Steroid derivatives as pure antagonists of the androgen receptor. J. Steroid Biochem. Mol. Biol., 132: 93-104.

Gryder, B.E., Akbashev, M.J., Rood, M.K., Raftery, E.D., Meyers, W.M., Dillard, P., Khan, S., Oyelere, A.K.; (2013). Selectively targeting prostate cancer with antiandrogen equipped histone deacetylase inhibitors. ACS Chem. Biol., 8: 2550-2560.

Guo, C., Linton, A., Kephart, S., Ornelas, M., Pairish, M., Gonzalez, J., Greasley, S., Nagata, A., Burke, B.J., Edwards, M., Hosea, N., Kang, P., Hu, W., Engebretsen, J., Briere, D., Shi, M., Gukasyan, H., Richardson, P., Dack, K., Underwood, T., Johnson, P., Morell, A., Felstead, R., Kuruma, H., Matsimoto, H., Zoubeidi, A., Gleave, M., Los, G., Fanjul, A.N.; (2011). Discovery of aryloxy tetramethylcyclobutanes as novel androgen receptor antagonists. J. Med. Chem., 54: 7693-7704.

Guo, C., Pairish, M., Linton, A., Kephart, S., Ornelas, M., Nagata, A., Burke, B., Dong, L., Engebretsen, J., Fanjul, A.N.; (2012). Design of oxobenzimidazoles and oxindoles as novel androgen receptor antagonists. Bioorg. Med. Chem. Lett., 22: 2572-2578.

Jones, J.O.; (2009). Improving selective androgen receptor modulator discovery and preclinical evaluation. Expert Opin. Drug Discov., 4(9): 981-993.

Kinoyama, I., Taniguchi, N., Yoden, Koutoku, H., Furutani, T., Kudoh, M., Okada, M.; (2004). Synthesis and pharmacological evaluation of novel arylpiperazine derivatives as nonsteroidal androgen receptor antagonists. Chem. Pharm. Bull., 52(11): 1330-1333.

Kinoyama, I., Taniguchi, N., Kawaminami, E., Nozawa, E., Koutoku, H., Furutani, T., Kudoh, M., Okada, M.; (2005).

(56) References Cited

OTHER PUBLICATIONS

N-Arylpiperazine-1-carboxamide derivatives: a novel series of orally active nonsteroidal androgen receptor antagonists. Chem. Pharm. Bull., 53(4): 402-409.
Kinoyama, I., Taniguchi, N., Toyoshima, A., Nozawa, E., Kamikubo, T., Imamura, M., Matsuhisa, A., Samizu, K., Kawanimani, E., Niimi, T., Hamada, N., Koutoku, H., Furutani, T., Kudoh, M., Okada, M., Ohta, M., Tsukamoto, S.-I.; (2006). (+)-(2R,5S)-4-[4-cyano-3-(triflouromethyl)phenyl]-2,5-dimethyl-N-[6-(trifluoromethyl)pyridin-3-yl]piperazine-1-carboxamide (YM580) as an orally potent and peripherally selective nonsteroidal androgen receptor antagonist. J. Med. Chem., 49(2): 716-726.
Labrie, F., Veilleux, R., Fournier, A.; (1988a). Maintenance of androgen responsiveness by glucocorticoids in Shionogi mammary carcinoma cells in culture. J. Natl. Cancer Inst., 80(12): 966-970.
Labrie, F., Veilleux, R., Fournier, A.; (1988b). Glucocorticoids stimulate the growth of mouse mammary carcinoma Shionogi cells in culture. Mol. Cell. Endocrinol., 58: 207-211.
Labrie, F., Veilleux, R., Fournier, A.; (1988c). Low androgen levels induce the development of androgen-hypersensitive cell clones in Shionogi mouse mammary carcinoma cells in culture. J. Natl. Cancer Inst., 80(14): 1138-1147.
Labrie, F.; (2004). Adrenal androgens and intracrinology. Semin, Reprod. Med., 22(4): 299-309.
Labrie, F., Archer, D., Bouchard, C., Fortier, M., Cusan, L., Gomez, J.-L., Girard, G., Baron, M., Ayotte, N., Moreau, M., Dubé, R., Côté, I., Labrie, C., Lavoie, L., Berger, L., Gilbert, L., Martel, C., Balser, J.; (2009). Effect of intravaginal dehydroepiandrosterone (Prasterone) on libido and sexual dysfunction in postmenopausal women. Menopause, 16(5); 923-931.
Labrie, F., Archer, D., Bouchard, C., Fortier, M., Cusan, L., Gomez, J.-L., Girard, G., Baron, M., Ayotte, N., Moreau, M., Dubé, R., Côté, I., Labrie, C., Lavoie, L., Gilbert, L., Martel, C., Balser, J.; (2014). Lack of influence of dyspareunia on the beneficial effect of intravaginal prasterone (dehydroepiandrosterone, DHEA) on sexual dysfunction in postmenopausal women. J. Sex. Med., 11: 1766-1785.
Li, J.J., Sutton, J.C., Nirschl, A., Zou, Y., Wang, H., Sun, C., Pi, Z., Johnson, R., Krystek, S.R., Seethala, R., Golla, R., Sleph, P.G., Beehler, B.C., Grover, G.J., Fura, A., Vyas, V.P., Li, C.Y., Gougoutas, J.Z., Galella, M.A., Zahier, R., Ostrowski, J., Hamann, L.G.; (2007), Discovery of potent and muscle selective androgen receptor modulators through scaffold modifications. J. Med. Chem., 50(13): 3015-3025.
Liu, P.Y., Death, A.K., Handelsman, D.J.; (2003). Androgens and cardiovascular disease. Endocr. Rev., 24: 313-340.
Liu, B., Su, L., Geng, J., Liu, J., Zhao, G.; (2010). Developments in nonsteroidal antiandrogens targeting the androgen receptor. ChemMedChem, 5: 1651-1661.
McGinley, P.L., Koh, J.T.; (2007). Circumventing anti-androgen resistance by molecular design. J. Am. Chem. Soc., 129(13): 3822-3823.
Mohler, M.L., Bohl, C.E., Jones, A, Coss, C.C., Narayanan, R., He, Y., Hwang, D.J., Dalton, J.T., Miller, D.D.; (2009). Nonsteroidal selective androgen receptor modulators (SARMs): dissociating the anabolic and androgenic activities of the androgen receptor for therapeutic benefit. J. Med. Chem., 52(12): 3597-3617.
Mohler, M.L., Coss, C.C., Duke III, C.B., Patil, S.A., Miller, D.D.; Dalton, J.T.; (2012). Androgen receptor antagonists: a patent review (2008-2011). Expert Opin. Ther. Patents, 22(5): 541-565.
Nagata, N., Kawai, K., Nakanishi, I.; (2012). Subtle structural changes in tetrahydroquinolines, a new class of nonsteroidal selective androgen receptor modulators, induce different functions. J. Chem. Inf. Model., 52: 2257-2264.
Negro-Vilar, A.; (1999). Selective androgen receptor modulators (SARMs): a novel approach to androgen therapy for the new millennium, J. Clin. Endocrinol. Metab., 84: 3459-3462.
Nique, F., Hebbe, S., Peixoto, C., Annoot, D., Lefrançois, J.-M., Duval, E., Michoux, L., Triballeau, N., Lemoullec, J.-M., Mollat, P., Thauvin, M., Prangé, T., Minet, D., Clément-Lacroix, P., Robin-Jagerschmidt, C., Fleury, D., Guédin, D., Deprez, P.; (2012a). Discovery of diarylhydantoins as new selective androgen receptor modulators. J. Med. Chem., 55: 8225-8235.

Nique, F., Hebbe, S., Triballeau, N., Peixoto, C., Lefrançois, J.-M., Jary, H., Alvey, L., Manioc M., Housseman, C., Klaassen, H., Van Beeck, K., Guédin, D., Namour, F., Minet, D., Van der Aar, E., Feyen, J., Fletcher, S., Blanqué, R., Robin-Jagerschmidt, C., Deprez, P.; (2012b). Identification of a 4-(hydroxymethyl)diarylhydantoin as a selective androgen receptor modulator. J. Med. Chem., 55, 8236-8247.
Pelletier, G., Ouellet, J., Martel, C., Labrie, F.; (2012). Effects of ovariectomy and dehydroepiandrosterone (DHEA) on vaginal wall thickness and innervation. J. Sex. Med., 9: 2525-2533.
Pelletier, G., Ouellet, J., Martel, C., Labrie, F.; (2013). Androgenic action of dehydroepiandrosterone (DHEA) on nerve density in the ovariectomized rat vagina. J. Sex. Med., 10: 1908-1914.
Poortmans, A., Wyndaele, J.J.; (1998). M. levator ani in the rat: does it really lift the anus? Anat. Rec., May, 251(1): 20-7.
Poutiainen, P.K., Oravilahti, T., Peräkylä, M., Palvimo, J.J., Ihalainen, J.A., Laatikainen, R., Pulkkinen, J.T.; (2012). Design, synthesis, and biological evaluation of nonsteroidal cycloalkane[d]isoxazole-containing androgen receptor modulators. J. Med. Chem., 55: 6316-6327.
Qi, H., Labrie, Y., Grenier, J., Fournier, A., Fillion, C., Labrie, C.; (2001). Androgens induce expression of SPAK, a STE20/SPS1-related kinase, in LNCaP human prostate cancer cells. Mol. Cell. Endocrinol., 182: 181-192.
Salvati, M., Attar, R.M., Balog, A., Dell-John, J., Jure-Kunkel, M., Krystek, S., Obermeier, M., Spires, T.J.R., Vite, G., Gottardis, M.; (2008). BMS-641988: a highly potent and rationally designed inhibitor of the androgen receptor (AR), with efficacy in castration resistant human prostate cancer xenograft models. Eur. J. Cancer Suppl., 6(12): 50.
Simard, J., Dauvois, S., Haagensen, D.E., Lévesque, C., Mérand, Y., Labrie, F.; (1990). Regulation of progesterone-binding breast cyst protein GCDFP-24 secretion by estrogens and androgens in human breast cancer cells: a new marker of steroid action in breast cancer. Endocrinology, 126(6): 3223-3231.
Singh, S.M., Gauthier, S., Labrie, F.; (2000). Androgen receptor antagonists (antiandrogens): structure-activity relationships. Curr. Med. Chem., 7(2): 211-247.
Tucker, H., Crook, J.W., Chesterson, G.J.; (1988). Nonsteroidal antiandrogens. Synthesis and structure-activity relationships of 3-substituted derivatives of 2-hydroxypropionanilides. J. Med. Chem., 31(5): 954-959.
Varchi, G., Guerrini, A., Tesei, A., Brigliadori, G., Bertucci, C., Di Donato, M., Castoria, G.; (2012). Nonsteroidal androgen receptor ligands: versatile syntheses and biological data. ACS Med. Chem. Lett., 3(6): 454-458.
Xiao, H.-Y., Balog, A., Attar, R.M., Faifax, D., Fleming, L.B., Hoist, C.L., Martin, G.S., Rossiter, L.M., Chen, J., Cvjic, M.-E., Dell-John, J., Geng, J., Gottardis, M.M., Han, W.-C., Nation, A., Obermeier, M., Rizzo, C.A., Schweizer, L., Spires Jr., T., Shan, W., Gavai, A., Salvati, M.E., Vite, G.; (2010). Design and synthesis of 4-[3,5-dioxo-11-oxa-4,9-diazatricyclo[5.3.1.0$^{2,6}$]undec-4-yl]-2-trifluoromethyl-benzonitriles as androgen receptor antagonists. Bioorg. Med. Chem. Lett., 20: 4491-4495.
Yang, S.H., Song, C.-H., Van, H.T.M., Park, E., Khadka, D.B., Gong, E.-Y., Lee, K., Cho, W.-J.; (2013). SAR based design of nicotinamides as a novel class of androgen receptor antagonists for prostate cancer. J. Med. Chem., 56, 3414-3418.
Zhang, X., Lanter, J.C., Sui, Z.; (2009). Recent advances in the development of selective androgen receptor modulators. Expert Opin. Ther. Patents, 19(9): 1239-1258.
Zhang, X., Allan, G.F., Tannenbaum, P., Sbriscia, T., Linton, O., Lai, M.-T., Haynes-Johnson, D., Bhattacharjee, S., Lundeen, S.G., Sui, Z.; (2013). Pharmacological characterization of an imidazolopyrazole as novel selective androgen receptor modulator. J. Steroid Biochem. Mol. Biol., 134: 51-58.
Zhang, X., Sui, Z.; (2013). Deciphering the selective androgen receptor modulators paradigm. Expert Opin. Drug Discov., 8(2): 191-218.
Zhou, J., Geng, G., Shi, Q., Sauriol, F., Wu, J.H.; (2009). Design and synthesis of androgen receptor antagonists with bulky side chains for overcoming antiandrogen resistance. J. Med. Chem., 52(17): 5546-5550.

(56) References Cited

OTHER PUBLICATIONS

International Preliminary Report on Patentability with Written Opinion of the International Searching Authority dated Jun. 30, 2016 in corresponding International Application No. PCT/CA2014/000894 (10 total pages).

* cited by examiner

NON-STEROIDAL ANTIANDROGENS AND SELECTIVE ANDROGEN RECEPTOR MODULATORS WITH A PYRIDYL MOIETY

CROSS REFERENCE OF THE RELATED APPLICATION(S)

This present application claims benefit of and priority to U.S. Provisional Application No. 61/918,133 filed on Dec. 19, 2013 by Fernand LABRIE et al. and entitled "NON-STEROIDAL ANTIANDROGENS AND SELECTIVE ANDROGEN RECEPTOR MODULATORS WITH A PYRIDYL MOIETY", the entire contents of which are hereby incorporated by reference.

BACKGROUND OF THE INVENTION

This invention relates to novel inhibitors of androgen activity, for example to non-steroidal compounds having antagonistic activity on androgen receptor. More particularly, the invention relates to certain non-steroidal compounds having specified side-chains (e.g. containing a pyridyl moiety) which interact with the helix 12 of the androgen receptor, and metabolites thereof which block androgen action by acting, among other mechanisms, through the androgen receptor, while not activating such receptor in some or all androgen-sensitive tissues. Some compounds of the invention are Selective Androgen Receptor Modulators (SARMs) which have desirable antagonistic activity in some tissues (e.g. prostate) while exhibiting desirable agonistic activity in other tissues (e.g. muscle, sexual function . . . ).

BRIEF DESCRIPTION OF THE PRIOR ART

During the treatment of certain androgen-dependent diseases, it is important to greatly reduce or, ideally, to eliminate androgen-induced effects. For this purpose, it can be desirable to both block access to the androgen receptors with "antiandrogens", thus preventing androgens from binding and activating those receptors, and also to reduce the concentration of androgens available to activate the receptors. It is possible that, even in the absence of androgens, unoccupied androgen receptors may be biologically active. Hence, antiandrogens which bind and block the receptors may produce better therapeutic results than therapy which only inhibits androgen production.

Antiandrogens may have a beneficial therapeutic effect in slowing or stopping the progress of androgen-dependent diseases, e.g. diseases whose onset or progress is aided by the androgen receptor or androgen receptor modulator activation.

It is desired that an antiandrogen used in therapy to reduce androgen receptor activation has both good affinity for the androgen receptor and a lack of inherent androgenic activity in the tissue(s) of interest. The former refers to the ability of an antiandrogen to bind to the androgen receptor, and thus to block access to the receptor by androgens. The latter refers to the effect the antiandrogen has on the receptor once it binds thereto. Some antiandrogens may possess inherent androgenic activity ("agonistic activity") which undesirably activates the androgen receptors whose activation they are wishing to block. In other words, an antiandrogen with undesirable intrinsic androgenic activity may successfully bind to androgen receptors, desirably blocking access to those receptors by natural androgens, yet may undesirably itself activate the receptor in tissues where an exclusive antiandrogenic action is desired, such a compound being a mixed antagonist/agonist of the androgen receptor.

Known non-steroidal antiandrogens such as flutamide, casodex and anandron lack undesirable androgenic activity, but may have low receptor affinity compared to steroidal antiandrogens (i.e. androgen derivatives having a steroidal nucleus that is modified to provide antiandrogenic activity). Steroidal antiandrogens, however, are believed to more frequently possess undesirable agonistic characteristics, than non-steroidal antiandrogens. Recently, some new non-steroidal antiandrogens possessing long substituents and having a better activity than the above-mentioned non-steroidal antiandrogens were described (Tucker et al., 1988; Balog et al., 2004; Kinoyama et al., 2004; Kinoyama et al., 2005; Kinoyama et al., 2006; McGinley and Koh, 2007; Salvati et al., 2008; Zhou et al., 2009; Xiao et al., 2010; Duke III et al., 2011; Guo et al., 2011; Guo et al., 2012; Yang et al., 2013; Gryder et al., 2013) and disclosed (U.S. Pat. No. 5,411,981, U.S. Pat. No. 6,071,957, U.S. Pat. No. 7,141,578, U.S. Pat. No. 7,001,911, EP 0 100 172, FR 2671348, FR 2693461, EP 002 892, EP 0 494 819, EP 0 578 516, EP 0 580 459, WO 95/18794, WO 96/19458, WO 97/00071, WO 97/19064, WO 97/23464, WO 98/53826, JP 200288073A, WO 00/37430 WO 01/16108, WO 01/16133, WO 02/24702, WO 2004/099188, WO 2004/111012, WO 2004/113309, WO 2005/040136, WO 2006/124118, WO 2007/005887, WO 2007/127010, WO 2008/044033, WO 2008/124000, WO 2009/055053, WO 2009/119880, WO 2010/143803, WO 2012/050868, WO 2012/143599, US 2010/0331418, US 2012/0184580, US 2012/0251551, US 2013/0116258, US 2013/0197009). Moreover, antiandrogens have been reviewed in Mohler et al., 2012, Liu et al., 2010, and Singh et al., 2000.

However, steroidal antiandrogens with very high affinity for the androgen receptor and lacking undesirable agonistic characteristic were disclosed in WO 2005/066194. These compounds possess specified side-chains positioned at the 18-position and which interact with helix 12. Similarly, non-steroidal antiandrogens with very high affinity for the androgen receptor and lacking undesirable agonistic characteristics were disclosed in WO 2006/133567. Moreover, both patent applications have disclosed some compounds as Selective Androgen Receptor Modulators (SARMs).

Steroidal antiandrogens, androgens and Selective Androgen Receptor Modulators (SARMs) with a 4-picolyl side-chain positioned at the 17β-position were disclosed in WO 2008/124922. The biological characteristics of the antiandrogen EM-5854 have been recently reported (Gauthier et al., 2012).

There is thus a need in the Art for non-steroidal antiandrogens having high affinity for the androgen receptor, while substantially lacking undesirable agonistic characteristics and having a good parenteral or oral bioavailability for systemic use.

We have synthesized a new series of non-steroidal antiandrogens possessing a side-chain able to modify the interaction of the steroidal backbone with the Androgen Receptor.

Selective Androgen Receptor Modulators (SARMs) is a new family of compounds having desirable antagonistic activity in some tissues (e.g. prostate) while exhibiting no activity or desirable agonistic activity in other tissues (e.g. bone or muscle). Some were reported in WO 02/00617, WO 2005/120483, U.S. Pat. No. 7,803,970, U.S. Pat. No. 7,427, 682, U.S. Pat. No. 7,268,232, U.S. Pat. No. 7,759,520. Some of these SARMs are in clinical trials for building muscle and promoting bone (Ostarine developed by GTx in the United States), hypogonadism, benign prostatic hyperplasia, osteoporosis and female sexual dysfunction (LGD 2226 2941 developed by Ligand in the United States) or age-related decline (BMS 564929 developed by Bristol-Myers Squibb in the United States). Moreover, Selective Androgen Receptor Modulators have been reviewed in Zhang and Sui, 2013, Zhang et al., 2009, Mohler et al., 2009, Jones 2009, and Chengalvala, et al., 2003 (see references herein). Some other SARMs were very recently described (Nique et al., 2012a; Nique et al., 2012b; Nagata et al., 2012; Poutiainen et al., 2012; Varchi et al., 2012; Zhang et al., 2013; Cozzoli et al., 2013) and disclosed (WO 2012/047617, WO 2012/143599, WO 2013/014627, WO 2013/055577, WO 2013/057372, WO 2013/128421, WO 2013/152170, US 2012/0004270, US 2012/0041046, US 2013/0041007, US 2013/0217762).

SARMs are also potential drugs for the prevention and treatment of osteopenia, bone fractures, alveolar bone loss, bone reconstruction, osteotomy, wasting diseases (cancer), loss of lean mass, obesity, muscle damage, hot flashes, periodontal disease, periodontitis, mandibular bone loss, Sjogren syndrome, eye dryness, dry skin, breast cancer, muscle wasting, sarcopenia, cancer cachexia, frailty, male hormonal contraception, erectile dysfunction, decreased libido, acne, hirsutism, seborrhea, androgenic alopecia, polycystic ovary disease, precocious puberty, testicular feminization, hot flashes, metabolic syndrome, gynecomastia, endometriosis and possibly prostate cancer when the selective androgen receptor modulator (SARM) is ideally free of androgenic activity in the prostate.

During the course of our antiandrogen development program, we have synthesized a series of non-steroidal compounds possessing the biological properties of selective androgen receptor modulators. Particularly, we have focused our research on compounds having biological characteristics suitable for the treatment of benign prostatic hyperplasia and the prevention of prostate cancer. For that purpose, SARMs must have potent antiandrogenic activity in androgen-sensitive cells with no or negligible agonistic activity in these cells. The compounds must also have a good anabolic activity in the muscle to avoid atrophy of the skeletal muscles which naturally occurs with aging and the use of the current available antiandrogens.

SUMMARY OF THE INVENTION

It is an object of the present invention to provide antiandrogens, having good affinity for the androgen receptor, while substantially lacking androgenic activity. These antiandrogens may be useful in the treatment and prevention of androgen-dependent diseases as described in more detail infra.

It is an object of the present invention to provide a compound having the following characteristics:

a) binds to the androgen receptor;

b) interferes directly or indirectly with helix 12 of the androgen receptor by means of a chain sufficiently narrow and long to pass through the channel joining the androgen binding site to helix 12;

c) and blocks normal helix 12-positioning observed when the androgen receptor is bound by an agonist.

It is an object of the present invention to provide a compound of the formula:

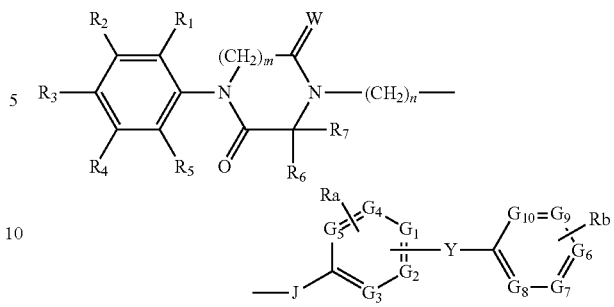

wherein n is an integer from 0 to 6;
wherein m is an integer from 0 to 1;
wherein J and Y are independently a direct bond or selected from the group consisting of —O—, —CO—, —CH$_2$—, —S—, —SO—, —SO$_2$—, —NH—, —CHR$_1$—, —C(R$_1$)$_2$— and —NR$_1$—;
wherein Ra and Rb are independently selected from the group consisting of hydrogen, halogen, —OCH$_3$, C$_1$-C$_3$ alkyl, C$_2$-C$_3$ alkenyl, nitrile, trifluoromethyl, amide, amine, and alkylsulfone;
wherein R$_1$ is selected from the group consisting of hydrogen, halogen and C$_1$-C$_3$ alkyl;
wherein R$_2$ is selected from the group consisting of hydrogen, halogen, —OCH$_3$, —SCH$_3$, alkylsulfoxide, alkylsulfone, nitrile, —NO$_2$, C$_1$-C$_3$ alkyl, and trifluoromethyl;
wherein R$_3$ is selected from the group consisting of halogen, nitrile, —COCH$_3$, —SO$_2$CH$_3$, and —NO$_2$;
wherein R$_4$ and R$_5$ are independently selected from the group consisting of hydrogen, C$_1$-C$_6$ alkyl, halogen, —OCH$_3$, —SCH$_3$, alkylsulfoxide, alkylsulfone, nitrile, —NO$_2$, and trifluoromethyl or R$_4$ and R$_5$ together form a cycle optionally having a heteroatom selected from the group consisting of nitrogen, oxygen, and sulfur;
wherein R$_6$ and R$_7$ are independently selected from the group consisting of hydrogen and C$_1$-C$_6$ alkyl or R$_6$ and R$_7$ together form a cycle optionally having a heteroatom selected from the group consisting of nitrogen, oxygen, and sulfur;
wherein W is selected from the group consisting of oxygen and sulfur;
wherein G$_1$, G$_2$, G$_3$, G$_4$, and G$_5$ are independently selected from the group consisting of carbon, methine, nitrogen and nitrogen-oxide with a maximum of two nitrogen or nitrogen-oxide in the ring;
wherein G$_6$, G$_7$, G$_8$, G$_9$, and G$_{10}$ are independently selected from the group consisting of carbon, methine, nitrogen and nitrogen-oxide with a minimum of one nitrogen or nitrogen-oxide in the ring; and
wherein Y is linked to G$_1$, G$_2$ or G$_4$; or a pharmaceutically acceptable salt thereof.

In one embodiment, a compound has the following formula:

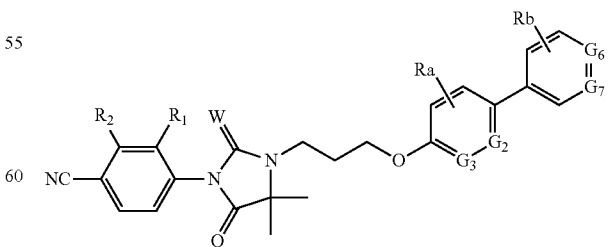

wherein Ra and Rb are independently selected from the group consisting of hydrogen, halogen, —OCH$_3$, C$_1$-C$_3$ alkyl, C$_2$-C$_3$ alkenyl, nitrile, trifluoromethyl, amide, amine, and alkylsulfone;

wherein $R_1$ is selected from the group consisting of hydrogen, fluoro, and methyl;
wherein $R_2$ is selected from the group consisting of hydrogen, halogen, —$OCH_3$, —$SCH_3$, alkylsulfoxide, alkylsulfone, nitrile, —$NO_2$, $C_1$-$C_3$ alkyl, and trifluoromethyl;
wherein W is selected from the group consisting of oxygen and sulfur;
wherein $G_2$ and $G_3$ are independently selected from the group consisting of carbon, methine, nitrogen and nitrogen-oxide with a maximum of one nitrogen or nitrogen-oxide in the ring; and
wherein $G_6$ and $G_7$ are independently selected from the group consisting of carbon, methine, nitrogen and nitrogen-oxide with a minimum of one nitrogen or nitrogen-oxide in the ring; or a pharmaceutically acceptable salt thereof.

In another embodiment, a compound has the following formula:

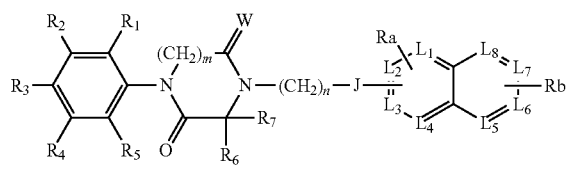

wherein n is an integer from 0 to 6;
wherein m is an integer from 0 to 1;
wherein J is independently a direct bond or selected from the group consisting of —O—, —CO—, —$CH_2$—, —S—, —SO—, —$SO_2$—, —NH—, —$CHR_1$—, —$C(R_1)_2$— and —$NR_1$—;
wherein Ra and Rb are independently selected from the group consisting of hydrogen, halogen, —$OCH_3$, $C_1$-$C_3$ alkyl, $C_2$-$C_3$ alkenyl, nitrile, trifluoromethyl, amide, amine, and alkylsulfone;
wherein $R_1$ is selected from the group consisting of hydrogen, halogen and $C_1$-$C_3$ alkyl;
wherein $R_2$ is selected from the group consisting of hydrogen, halogen, —$OCH_3$, —$SCH_3$, alkylsulfoxide, alkylsulfone, nitrile, —$NO_2$, $C_1$-$C_3$ alkyl, and trifluoromethyl;
wherein $R_3$ is selected from the group consisting of halogen, nitrile, —$COCH_3$, —$SO_2CH_3$, and —$NO_2$;
wherein $R_4$ and $R_5$ are independently selected from the group consisting of hydrogen, $C_1$-$C_6$ alkyl, halogen, —$OCH_3$, —$SCH_3$, alkylsulfoxide, alkylsulfone, nitrile, —$NO_2$, and trifluoromethyl or $R_4$ and $R_5$ together form a cycle optionally having a heteroatom selected from the group consisting of nitrogen, oxygen, and sulfur;
wherein $R_6$ and $R_7$ are independently selected from the group consisting of hydrogen and $C_1$-$C_6$ alkyl or $R_6$ and $R_7$ together form a cycle optionally having a heteroatom selected from the group consisting of nitrogen, oxygen, and sulfur;
wherein W is selected from the group consisting of oxygen and sulfur;
wherein $L_1$, $L_2$, $L_3$, and $L_4$ are independently selected from the group consisting of carbon, methine, nitrogen and nitrogen-oxide with a maximum of two nitrogen or nitrogen-oxide in the ring; and
wherein $L_5$, $L_6$, $L_7$, and $L_8$ are independently selected from the group consisting of carbon, methine, nitrogen and nitrogen-oxide with a minimum of one nitrogen or nitrogen-oxide in the ring;
or a pharmaceutically acceptable salt thereof.

In another embodiment, a compound has the following formula:

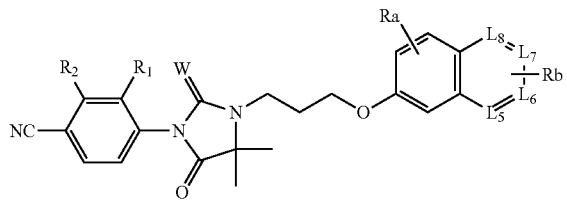

wherein Ra and Rb are independently selected from the group consisting of hydrogen, halogen, —$OCH_3$, $C_1$-$C_3$ alkyl, $C_2$-$C_3$ alkenyl, nitrile, trifluoromethyl, amide, amine, and alkylsulfone;
wherein $R_1$ is selected from the group consisting of hydrogen, fluoro, and methyl;
wherein $R_2$ is selected from the group consisting of hydrogen, halogen, —$OCH_3$, —$SCH_3$, alkylsulfoxide, alkylsulfone, nitrile, —$NO_2$, $C_1$-$C_3$ alkyl, and trifluoromethyl;
wherein W is selected from the group consisting of oxygen and sulfur; and
wherein $L_5$, $L_6$, $L_7$, and $L_8$ are independently selected from the group consisting of carbon, methine, nitrogen and nitrogen-oxide with a minimum of one nitrogen or nitrogen-oxide in the ring; or a pharmaceutically acceptable salt thereof.

In another embodiment, a compound has the following formula:

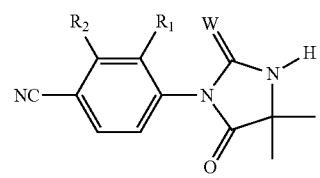

wherein $R_1$ is selected from the group consisting of fluoro and methyl;
wherein $R_2$ is selected from the group consisting of hydrogen, halogen, —$OCH_3$, —$SCH_3$, alkylsulfoxide, alkylsulfone, nitrile, —$NO_2$, $C_1$-$C_3$ alkyl, and trifluoromethyl; and
wherein W is selected from the group consisting of oxygen and sulphur.

In another embodiment, the invention provides a pharmaceutical composition comprising a pharmaceutically acceptable diluent or carrier and a therapeutically effective amount of at least one compound which:

a) binds to the androgen receptor;
b) interferes directly or indirectly with helix 12 of the androgen receptor by means of a chain sufficiently narrow and long to pass through the channel joining the androgen binding site to helix 12;
c) and blocks normal helix 12-positioning observed when the androgen receptor is bound by an agonist.

In another embodiment, the invention provides a pharmaceutical composition comprising a pharmaceutically acceptable diluent or carrier and a therapeutically effective amount of at least one compound of the following formula:

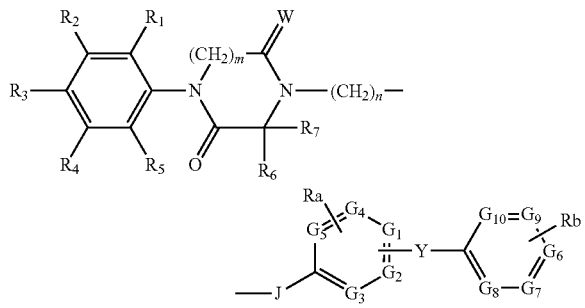

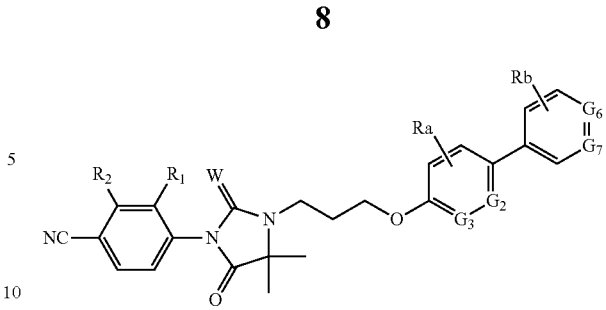

wherein n is an integer from 0 to 6;

wherein m is an integer from 0 to 1;

wherein J and Y are independently a direct bond or selected from the group consisting of —O—, —CO—, —CH$_2$—, —S—, —SO—, —SO$_2$—, —NH—, —CHR$_1$—, —C(R$_1$)$_2$— and —NR$_1$—;

wherein Ra and Rb are independently selected from the group consisting of hydrogen, halogen, —OCH$_3$, C$_1$-C$_3$ alkyl, C$_2$-C$_3$ alkenyl, nitrile, trifluoromethyl, amide, amine, and alkylsulfone;

wherein R$_1$ is selected from the group consisting of hydrogen, halogen and C$_1$-C$_3$ alkyl;

wherein R$_2$ is selected from the group consisting of hydrogen, halogen, —OCH$_3$, —SCH$_3$, alkylsulfoxide, alkylsulfone, nitrile, —NO$_2$, C$_1$-C$_3$ alkyl, and trifluoromethyl;

wherein R$_3$ is selected from the group consisting of halogen, nitrile, —COCH$_3$, —SO$_2$CH$_3$, and —NO$_2$;

wherein R$_4$ and R$_5$ are independently selected from the group consisting of hydrogen, C$_1$-C$_6$ alkyl, halogen, —OCH$_3$, —SCH$_3$, alkylsulfoxide, alkylsulfone, nitrile, —NO$_2$, and trifluoromethyl or R$_4$ and R$_5$ together form a cycle optionally having a heteroatom selected from the group consisting of nitrogen, oxygen, and sulfur;

wherein R$_6$ and R$_7$ are independently selected from the group consisting of hydrogen and C$_1$-C$_6$ alkyl or R$_6$ and R$_7$ together form a cycle optionally having a heteroatom selected from the group consisting of nitrogen, oxygen, and sulfur;

wherein W is selected from the group consisting of oxygen and sulfur;

wherein G$_1$, G$_2$, G$_3$, G$_4$, and G$_5$ are independently selected from the group consisting of carbon, methine, nitrogen and nitrogen-oxide with a maximum of two nitrogen or nitrogen-oxide in the ring;

wherein G$_6$, G$_7$, G$_8$, G$_9$, and G$_{10}$ are independently selected from the group consisting of carbon, methine, nitrogen and nitrogen-oxide with a minimum of one nitrogen or nitrogen-oxide in the ring; and wherein Y is linked to G$_1$, G$_2$ or G$_4$; or a pharmaceutically acceptable salt thereof.

In another embodiment, the invention provides a pharmaceutical composition comprising a pharmaceutically acceptable diluent or carrier and a therapeutically effective amount of at least one compound of the following formula:

wherein Ra and Rb are independently selected from the group consisting of hydrogen, halogen, —OCH$_3$, C$_1$-C$_3$ alkyl, C$_2$-C$_3$ alkenyl, nitrile, trifluoromethyl, amide, amine, and alkylsulfone;

wherein R$_1$ is selected from the group consisting of hydrogen, fluoro, and methyl;

wherein R$_2$ is selected from the group consisting of hydrogen, halogen, —OCH$_3$, —SCH$_3$, alkylsulfoxide, alkylsulfone, nitrile, —NO$_2$, C$_1$-C$_3$ alkyl, and trifluoromethyl;

wherein W is selected from the group consisting of oxygen and sulfur;

wherein G$_2$ and G$_3$ are independently selected from the group consisting of carbon, methine, nitrogen and nitrogen-oxide with a maximum of one nitrogen or nitrogen-oxide in the ring; and wherein G$_6$ and G$_7$ are independently selected from the group consisting of carbon, methine, nitrogen and nitrogen-oxide with a minimum of one nitrogen or nitrogen-oxide in the ring; or a pharmaceutically acceptable salt thereof.

In another embodiment, the invention provides a pharmaceutical composition comprising a pharmaceutically acceptable diluent or carrier and a therapeutically effective amount of at least one compound of the following formula:

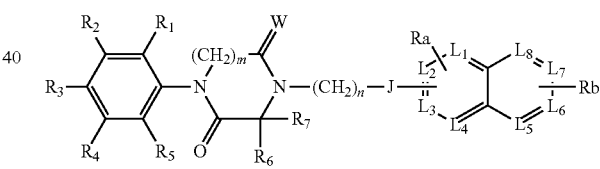

wherein n is an integer from 0 to 6;

wherein m is an integer from 0 to 1;

wherein J is independently a direct bond or selected from the group consisting of —O—, —CO—, —CH$_2$—, —S—, —SO—, —SO$_2$—, —NH—, —CHR$_1$—, —C(R$_1$)$_2$— and —NR$_1$—;

wherein Ra and Rb are independently selected from the group consisting of hydrogen, halogen, —OCH$_3$, C$_1$-C$_3$ alkyl, C$_2$-C$_3$ alkenyl, nitrile, trifluoromethyl, amide, amine, and alkylsulfone;

wherein R$_1$ is selected from the group consisting of hydrogen, halogen and C$_1$-C$_3$ alkyl;

wherein R$_2$ is selected from the group consisting of hydrogen, halogen, —OCH$_3$, —SCH$_3$, alkylsulfoxide, alkylsulfone, nitrile, —NO$_2$, C$_1$-C$_3$ alkyl, and trifluoromethyl;

wherein R$_3$ is selected from the group consisting of halogen, nitrile, —COCH$_3$, —SO$_2$CH$_3$, and —NO$_2$;

wherein R$_4$ and R$_5$ are independently selected from the group consisting of hydrogen, C$_1$-C$_6$ alkyl, halogen, —OCH$_3$, —SCH$_3$, alkylsulfoxide, alkylsulfone, —NO$_2$, and trifluoromethyl or R$_4$ and R$_5$ together form a cycle optionally having a heteroatom selected from the group consisting of nitrogen, oxygen, and sulfur;
wherein $R_6$ and $R_7$ are independently selected from the group consisting of hydrogen and $C_1$-$C_6$ alkyl or $R_6$ and $R_7$ together form a cycle optionally having a heteroatom selected from the group consisting of nitrogen, oxygen, and sulfur;
wherein W is selected from the group consisting of oxygen and sulfur;
wherein $L_1$, $L_2$, $L_3$, and $L_4$ are independently selected from the group consisting of carbon, methine, nitrogen and nitrogen-oxide with a maximum of two nitrogen or nitrogen-oxide in the ring; and
wherein $L_5$, $L_6$, $L_7$, and $L_8$ are independently selected from the group consisting of carbon, methine, nitrogen and nitrogen-oxide with a minimum of one nitrogen or nitrogen-oxide in the ring;
or a pharmaceutically acceptable salt thereof.

In another embodiment, the invention provides a pharmaceutical composition comprising a pharmaceutically acceptable diluent or carrier and a therapeutically effective amount of at least one compound of the following formula:

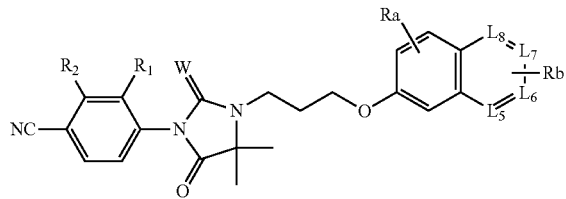

wherein Ra and Rb are independently selected from the group consisting of hydrogen, halogen, —OCH$_3$, $C_1$-$C_3$ alkyl, $C_2$-$C_3$ alkenyl, nitrile, trifluoromethyl, amide, amine, and alkylsulfone;
wherein $R_1$ is selected from the group consisting of hydrogen, fluoro, and methyl;
wherein $R_2$ is selected from the group consisting of hydrogen, halogen, —OCH$_3$, —SCH$_3$, alkylsulfoxide, alkylsulfone, nitrile, —NO$_2$, $C_1$-$C_3$ alkyl, and trifluoromethyl;
wherein W is selected from the group consisting of oxygen and sulfur; and
wherein $L_5$, $L_6$, $L_7$, and $L_8$ are independently selected from the group consisting of carbon, methine, nitrogen and nitrogen-oxide with a minimum of one nitrogen or nitrogen-oxide in the ring; or a pharmaceutically acceptable salt thereof.

In another embodiment, the invention provides a pharmaceutical composition comprising a pharmaceutically acceptable diluent or carrier and a therapeutically effective amount of at least one compound of the following formula:

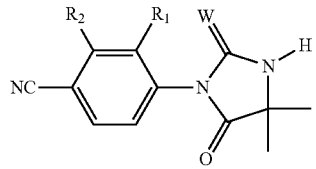

wherein $R_1$ is selected from the group consisting of fluoro and methyl;
wherein $R_2$ is selected from the group consisting of hydrogen, halogen, —OCH$_3$, —SCH$_3$, alkylsulfoxide, alkylsulfone, nitrile, —NO$_2$, $C_1$-$C_3$ alkyl, and trifluoromethyl; and wherein W is selected from the group consisting of oxygen and sulphur.

In another embodiment, the invention provides topical or systemic pharmaceutical compositions containing the compounds of the invention together with pharmaceutically acceptable diluents or carriers.

In another aspect, compounds of the invention, or pharmaceutical compositions containing them, are used in the treatment or prevention of androgen-exacerbated skin diseases such as acne, hirsutism, seborrhea, androgenic alopecia, male baldness and the like.

In another embodiment, compounds of the invention, or pharmaceutical compositions containing them, are used in the treatment or prevention of androgen-exacerbated systemic diseases such as prostate cancer, benign prostatic hyperplasia, precocious puberty, polycystic ovarian syndrome, hyperandrogenic syndromes, and the like.

In another embodiment, treatment and prevention regimens for androgen-exacerbated diseases include use of the compounds disclosed herein, as part of a combination therapy which further utilizes other active compounds selected from the group consisting of 5alpha-reductase inhibitor, type 5 and/or type 15 17beta-hydroxysteroid dehydrogenase inhibitors, 17alpha-hydroxylase/17,20-lyase inhibitor, and other inhibitors of androgen biosynthesis.

In another embodiment, treatment and prevention regimens for androgen-exacerbated diseases include use of the compounds disclosed herein and orchiectomy or administration of LHRH agonist or antagonist.

In another aspect, compounds of the present invention having tissue-specific antiandrogenic activity and tissue-specific androgenic activity can be used to treat or reduce the risk of developing diseases related to loss of androgenic stimulation.

It is another object to provide selective androgen receptor modulators, or pharmaceutical compositions containing them, for treatment (or reduction of the likelihood of acquiring) diseases related to loss of androgen stimulation such as muscle atrophy and weakness, skin atrophy, bone loss, osteoporosis, anemia, atherosclerosis, cardiovascular disease, loss of energy, loss of well-being, loss of libido, male hypogonadism, sarcopenia, sexual impotence, erectile dysfunction, female sexual dysfunction, type 2 diabetes, and abdominal fat accumulation.

It is another object to provide treatment or reduction of the risk of developing diseases related to loss of androgen stimulation such as muscle atrophy and weakness, skin atrophy, bone loss, osteoporosis, anemia, atherosclerosis, cardiovascular disease, loss of energy, loss of well-being, loss of libido, male hypogonadism, sarcopenia, sexual impotence, erectile dysfunction, female sexual dysfunction, type 2 diabetes, and abdominal fat accumulation.

In another aspect, compounds of the invention are used in the manufacture of a medicament for treatment of diseases discussed herein.

It is another object to provide pharmaceutical compounds with good systemic bioavailability.

Figure 3:
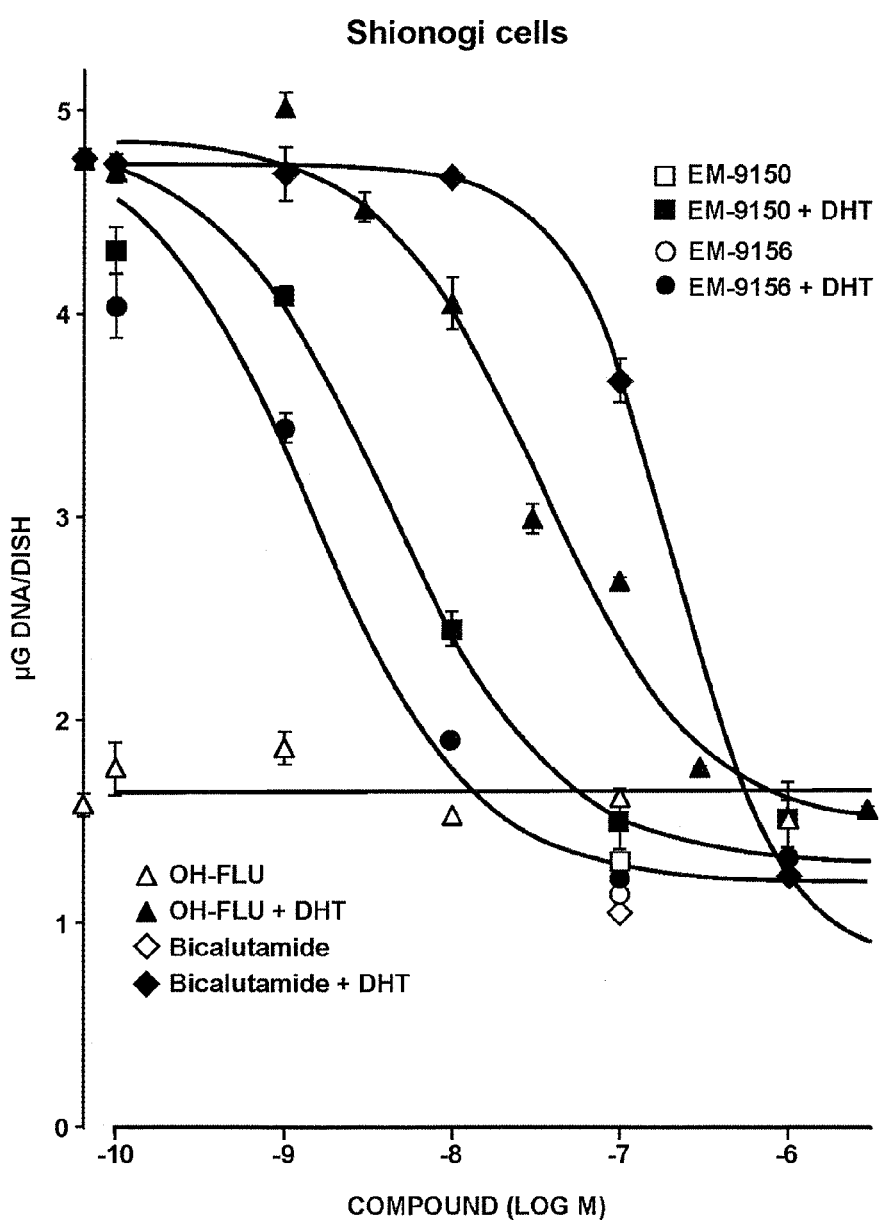

FIG. 3 shows the effect of increasing concentrations of hydroxyflutamide (OH-FLU), bicalutamide, EM-9150 and EM-9156 on basal and dihydrotestosterone (DHT; 0.3 nM)-stimulated cell proliferation in the androgen-sensitive mouse mammary Shionogi cells in culture. Twenty-four hours after plating at an initial density of 2×10$^4$ cells/2-cm$^2$ well, cells were exposed for 10 days to the indicated concentrations of compounds. Media were changed at 2- or 3-day intervals. Data are expressed as the means±SEM of triplicate dishes. When the SEM overlaps with the symbol, only the symbol is shown.

Figure 4:
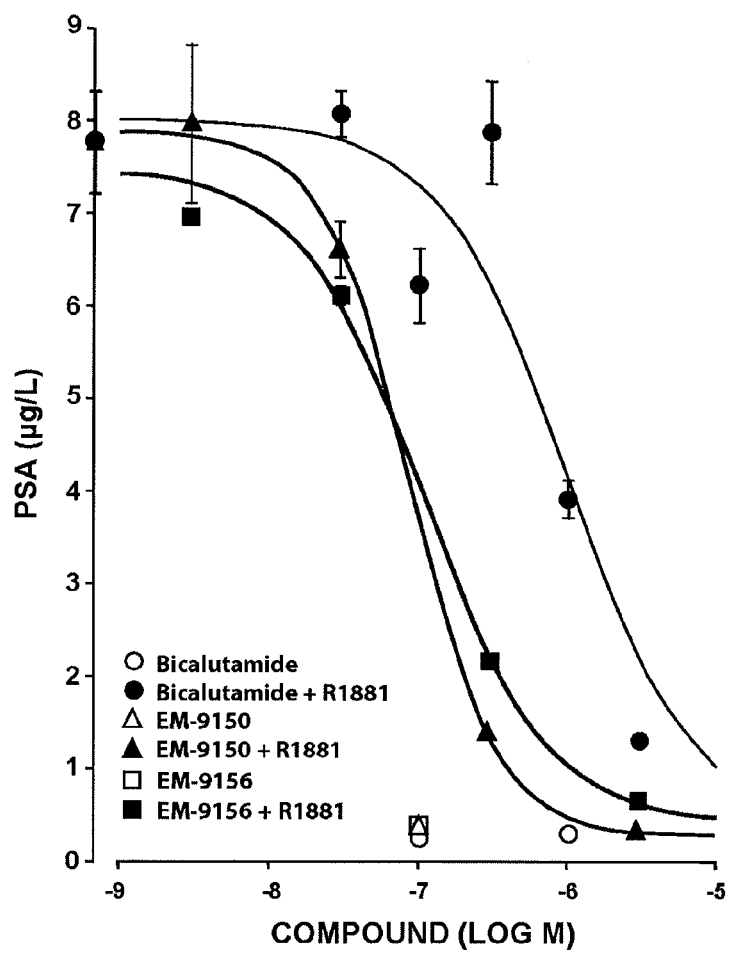

FIG. 4 shows the effect of increasing concentrations of bicalutamide, EM-9150 and EM-9156 on basal and R1881 (1.0 nM)-stimulated prostate specific antigen (PSA) levels measured in culture medium following a 72 h-incubation period with human prostate cancer LNCaP cells. Data are expressed as the means±SEM of duplicate dishes. When the SEM overlaps with the symbol, only the symbol is shown.

Figure 5:
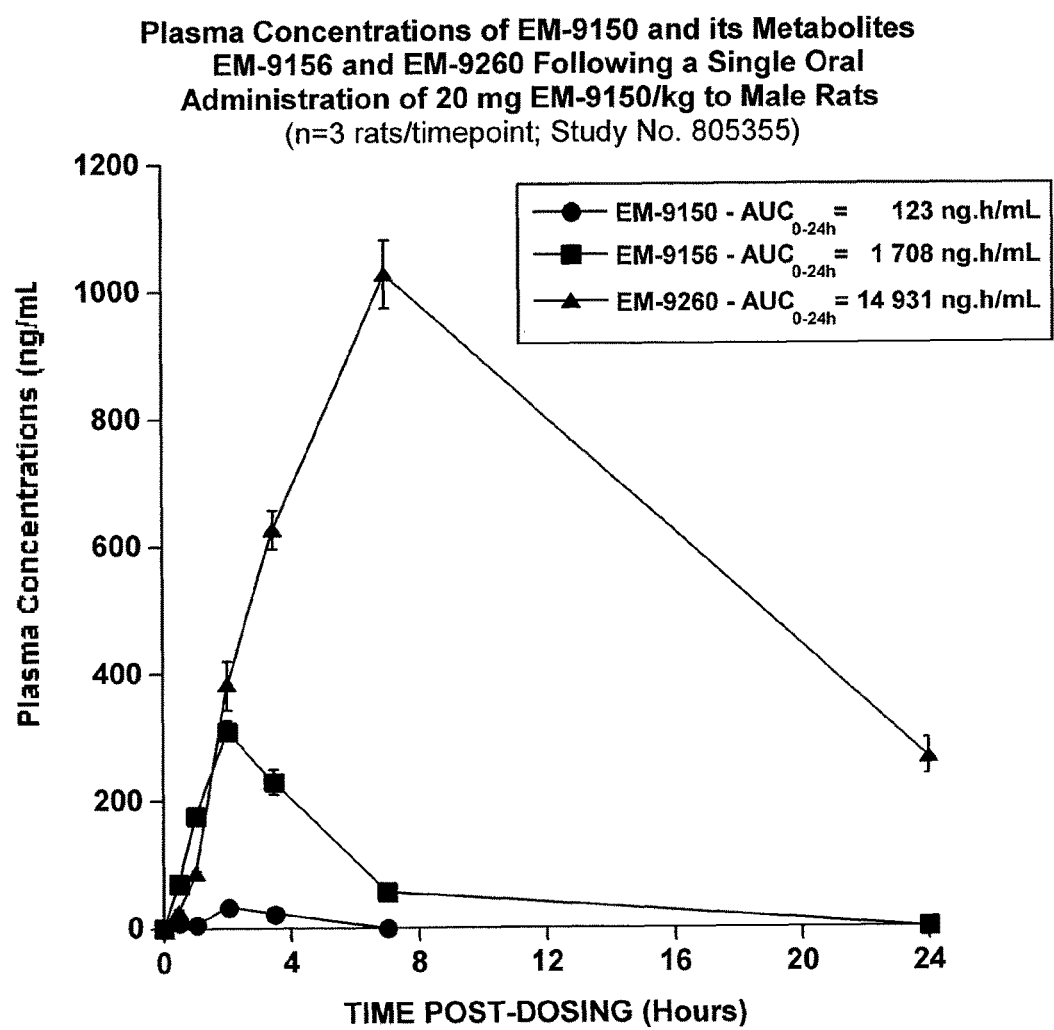

FIG. 5 shows the plasma levels of EM-9150 and its two metabolites (EM-9156 and EM-9260) following single oral administration of 20 mg EM-9150/kg to 8-week-old male rats. Plasma concentrations measured by LC-MS/MS are expressed as the mean±SEM of 3 animals per group and were used to calculate the Areas Under the Curve (AUC$_{0-24h}$).

Figure 6:
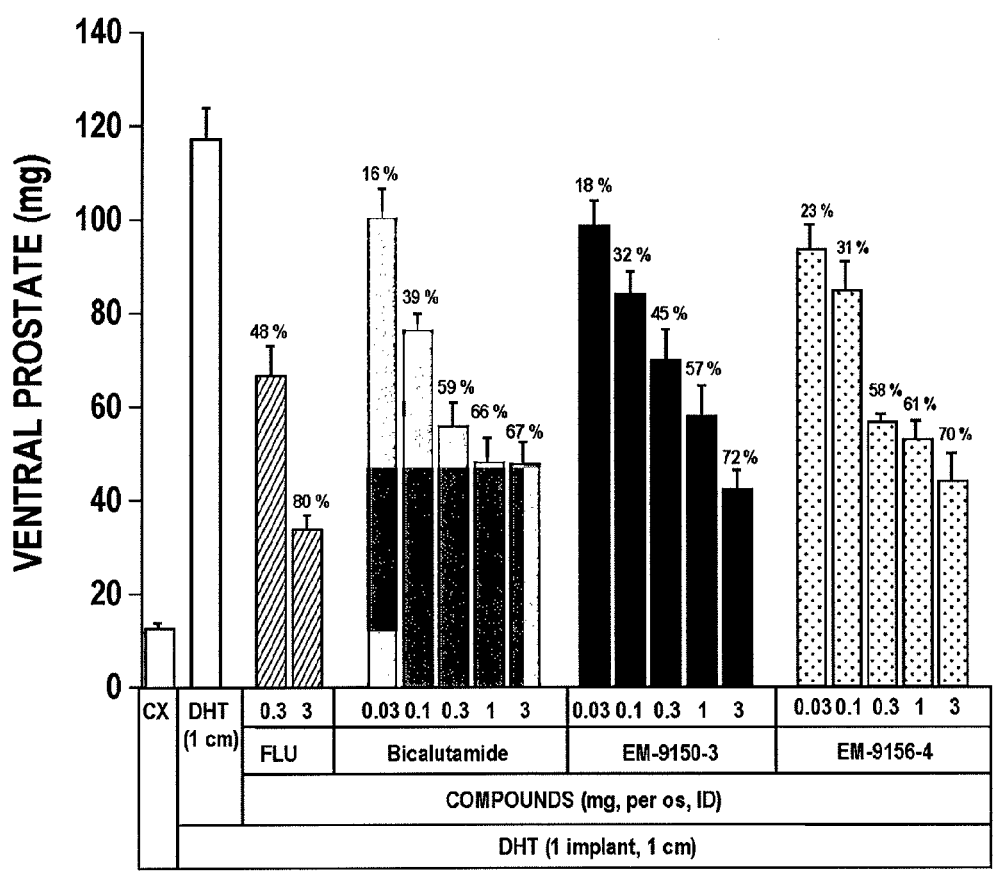

FIG. 6 shows the effect of 7-day daily treatment with increasing doses (0.03 to 3 mg/rat: ca 0.3 to 30 mg/kg) of flutamide (FLU), bicalutamide, EM-9150 and EM-9156 on ventral prostate weight in castrated (CX) immature male rats bearing a DHT implant. Data are expressed as the mean±SEM of 5 animals per group. Inhibition values of the DHT-stimulated prostate weight are indicated in percentage. Compounds were administered as suspensions in 0.4% aqueous methylcellulose.

Figure 7:
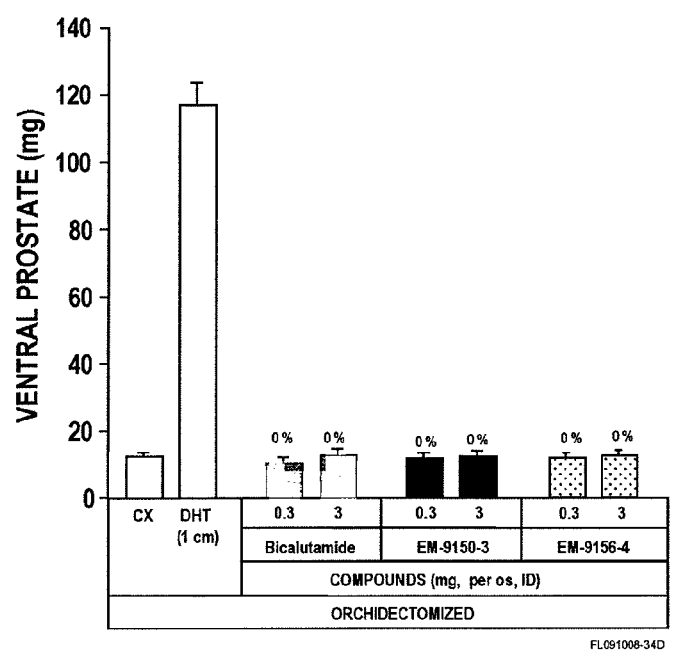

FIG. 7 shows the effect of 7-day daily treatment with 0.3 and 3 mg/rat (ca 3 and 30 mg/kg) of bicalutamide, EM-9150 and EM-9156 on ventral prostate weight in castrated (CX) immature male rats in order to verify the absence of androgenic activity. Data are expressed as the mean±SEM (n=5). Compounds were administered as suspensions in 0.4% aqueous methylcellulose.

Figure 8:
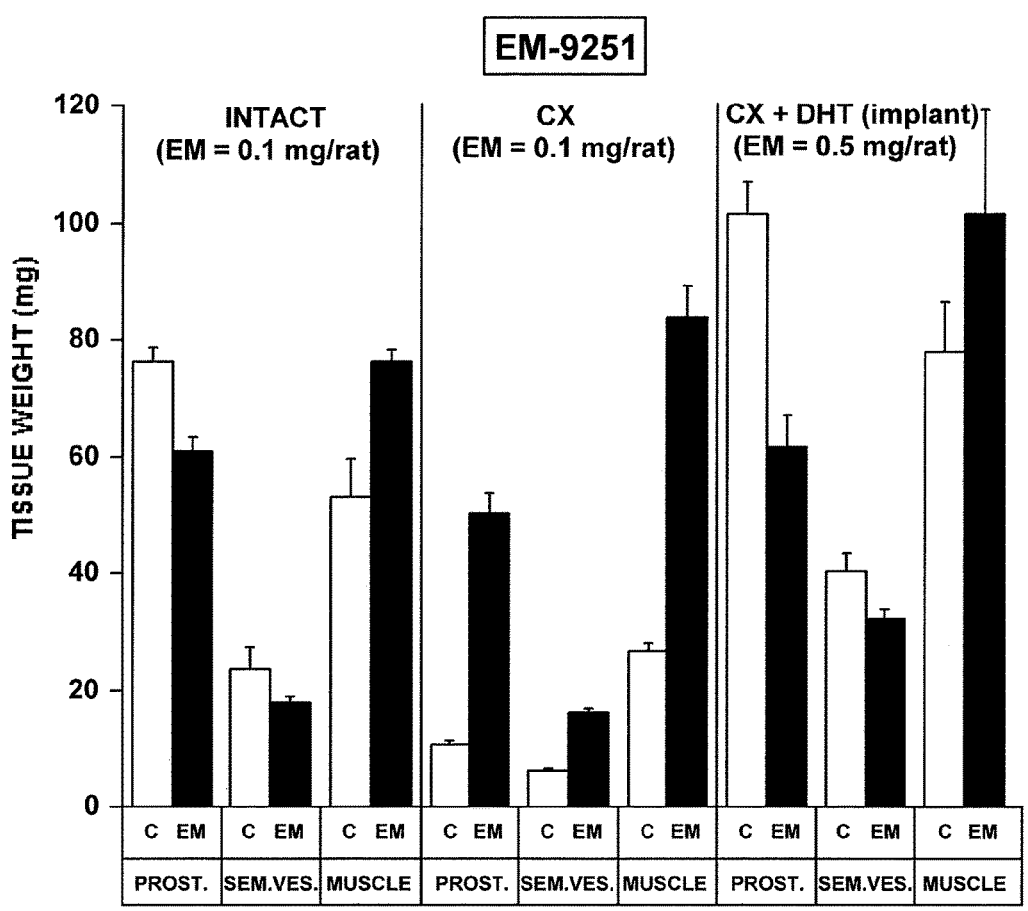

FIG. 8 shows the effect of 7-day daily treatment with 0.1 mg/rat or 0.5 mg/rat of EM-9251 on the weight of ventral prostate, seminal vesicles and bulbocavernosus muscles in intact, castrated, and castrated with bearing a DHT implant, immature male rats. Data are expressed as the mean±SEM of 3 animals per group.

DETAILED DESCRIPTION OF THE PREFERRED EMBODIMENTS

Our compounds are specially designed to impede repositioning of the mobile carboxyl-terminal helix 12 of the androgen receptor, thus blocking the ligand-dependent transactivation function (AF-2) located in the ligand-binding domain (ARLBD). This concept developed in order to obtain a new class of antiandrogens has been described with the structural characterization of the human androgen receptor ligand-binding domain (hARLBD) complexed with the agonist EM-5744, a 5α-dihydrotestosterone derivative bearing a chain at 18-position (—CH$_2$OCH$_2$-3,5-F$_2$-Ph) (Cantin et al., 2007); the antagonistic steroidal derivatives bearing a chain at the 18-position (WO 2005/066194); and the antagonistic non-steroidal derivatives (WO 2006/133567) which mimic the steroidal derivatives of WO 2005/066194.

Our invention is an improvement of the compounds of WO 2006/133567 wherein the terminal secondary and tertiary amines, sulfoxides and other functions have been replaced by a pyridyl moiety.

Set forth in the table below is a comparison of biological activity of the preferred compounds in the World Patent Application Publication WO 2006/133567 with the preferred compounds of the present application (i.e. EM-9150). Table 1 shows in vitro data which include the binding to human and rat androgen receptors and antiandrogenic activity in mouse mammary carcinoma Shionogi cells and human prostatic carcinoma LNCaP cells. Table 1 also shows in vivo data which include antagonistic activity on the ventral prostate in the immature rat. Detailed explanations on how the data were collected and reported follow the table.

TABLE 1

| | In vitro | | | | In vivo | |
|---|---|---|---|---|---|---|
| | Human Androgen Receptor Binding | Rat Androgen Receptor Binding | Shionogi Cells Antiandrogenic activity | LNCaP Cells Antiandrogenic activity (PSA) | Immature rat CX + DHT Ventral prostate Antagonistic activity | |
| Name | RBA (%) R1881 = 100 | RBA (%) R1881 = 100 | IC$_{50}$ (nM) | % inhibition at 10$^{-7}$M | 0.1 mg/rat/po % inhibition | 0.5 mg/rat/po % inhibition |
| 1 | 2 | 3 | 4 | 5 | 6 | 7 |
| EM-7365 | 24 | ND | 6.0 | ND | ND | 22 |
| EM-7105 | 41 ± 30 (n = 5) | 3.9 | 9.4 ± 3.2 (n = 4) | 26 | 20 ± 7 | 51 |
| EM-7333 | ~0.3 | ND | 139 | ND | ND | 33 (s.c.) |
| EM-7148 | 11 ± 1 (n = 2) | ND | 9.2 ± 3.0 (n = 2) | 33 | ND | 58 (s.c.) |
| EM-8360 | 18 | ND | 7.1 | 46 | ND | 56 ± 1 |
| EM-9150 | 74 ± 19 (n = 6) | 6.5 | 13 ± 3 (n = 5) | ~57 | 30 ± 7 (n = 3) | 55 ± 5 |
| EM-9052 | 2010 ± 640 (n = 2) | ND | 61$^a$ | 26 | 21 ± 5 | 59 ± 0 |
| EM-9156 | 17 ± 4 (n = 8) | 5.3 | 14 ± 3 (n = 7) | ~50 | 27 ± 3 (n = 5) | ND |

$^a$31% of stimulation at 10$^{-7}$M on basal Shionogi cells.
ND = not determined
s.c. = subcutaneous EM-7365
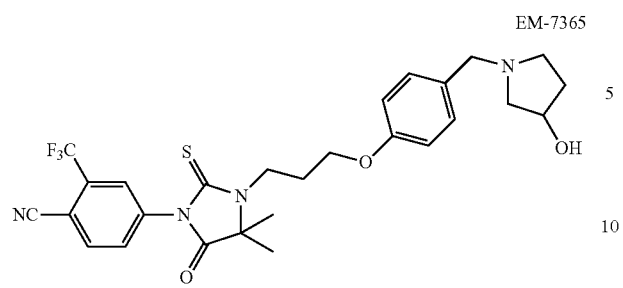

EM-9150
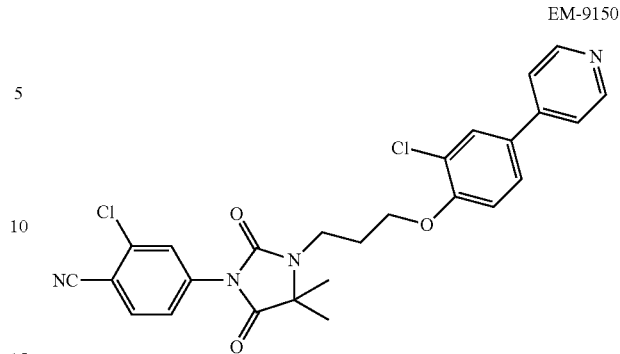

EM-7105
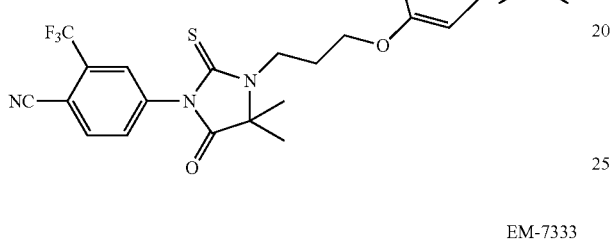

EM-9052
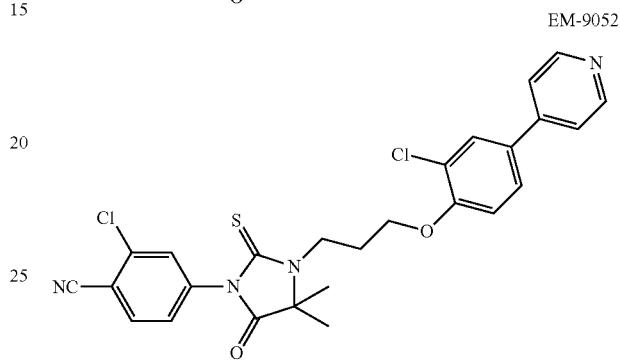

EM-7333
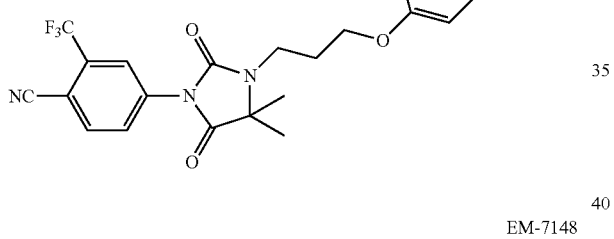

EM-9156
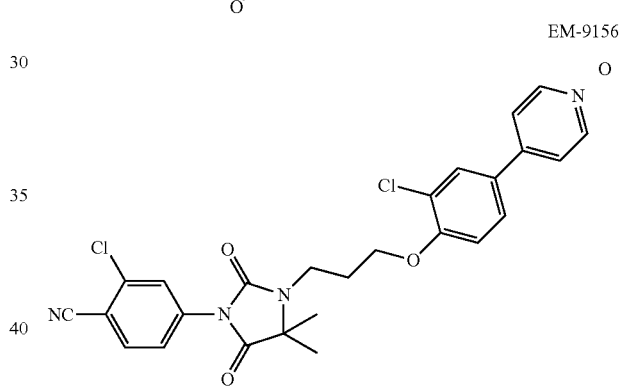

EM-7148
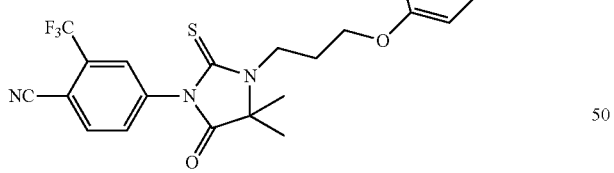

EM-8360

Legend of the Table 1:
In Column 1, the laboratory name of the antiandrogens is reported.

Column 2 represents the Relative Binding Affinity (RBA) of the antiandrogens expressed as percentage (%) on Human Androgen Receptor in transfected cells relative to R1881 as calculated by the formula:

% RBA=100×IC$_{50}$R1881/IC$_{50}$ (compound)

Higher values are preferable.

Column 3 represents the Relative Binding Affinity (RBA) of the antiandrogens expressed as percentage (%) on Rat Androgen Receptor in prostate cytosol relative to R1881 as calculated by the formula:

% RBA=100×IC$_{50}$R1881/IC$_{50}$ (compound)

Higher values are preferable.

Column 4 represents the dose (expressed in nM) that inhibits by 50% (IC$_{50}$) the DHT-stimulated Shionogi mouse mammary carcinoma cell number. Lower values are preferable.

Column 5 represents the % of inhibition of PSA level at $10^{-7}$M of compounds in R1881-stimulated human prostatic carcinoma LNCaP cells. Higher values are preferable.

Column 6 represents the % of oral antiandrogenic efficacy in rat prostate at dose of 0.1 mg/animal, expressed in percentage of inhibition.
The percentage of inhibition (% inhib) is calculated by the following formula:

% Inhibition=100−[$W$(compound)−$W$(control $CX$)/$W$(control DHT)−$W$(control $CX$)]×100.

$W$ is the weight of the prostate.
Higher values are preferable.
Column 7 represents the % of oral antiandrogenic efficacy in rat prostate at dose of 0.5 mg/animal, expressed in percentage of inhibition.
The percentage of inhibition (% inhib) is calculated by the following formula:

% Inhibition=100−[$W$(compound)−$W$(control $CX$)/$W$(control DHT)−$W$(control $CX$)]×100.

$W$ is the weight of the prostate.
Higher values are preferable.

The preferred compounds in the World Patent Application Publication WO/2006/133567 are EM-7365, EM-7105, EM-7148 and EM-8360 and one of the preferred compounds of the present application (EM-9150) as presented. We have included in Table 1, EM-9156, a known active metabolite of EM-9150. We can mention that compounds EM-7365, EM-7105, EM-7148 and EM-8360 are thiohydantoin derivatives (moiety D from WO/2006/133567) while EM-9150 is a hydantoin derivative. It is well known from our data that some important differences between thiohydantoin and hydantoin derivatives were observed particularly in in vitro assays. In order to obtain the best possible comparison of the two groups of compounds from the two applications, we have also included in Table 1 some corresponding hydantoin or thiohydantoin derivatives. Consequently, we have inserted in Table 1, EM-7133 which is the corresponding hydantoin of the thiohydantoin EM-7105. With the same approach, we have inserted in Table 1, EM-9052 which is the corresponding thiohydantoin of the hydantoin EM-9150. In the case of the other compounds in this table, we do not have the corresponding compounds available. The main observations on the comparison of the biological activities between EM-7365, EM-7105, EM-7148 and EM-8360 with EM-9150 are a) EM-9150 has an equivalent in vivo activity compared to EM-7105, EM-7148 and EM-8360 (but EM-7365 is less active) based on the percentage of inhibition of the rat prostate weight in column 7, at the 0.5 mg dose (i.e. 22% for EM-7365 compared to 51%, 58%, 56% and 55%, respectively for EM-7105, EM-7148, EM-8360 and EM-9150); b) EM-9150 has a better affinity for the human androgen receptor than EM-7365, EM-7105, EM-7148 and EM-8360 (column 2, RBA: 74 versus 24, 41, 11 and 18, respectively); c) EM-9150 has a better affinity for the rat androgen receptor than EM-7105 (column 3, RBA: 6.5 versus 3.9); d) EM-9150 has a comparable antiproliferative activity on DHT-stimulated Shionogi mouse mammary carcinoma cells than EM-7365, EM-7105, EM-7148 and EM-8360 but probably not significantly different (column 4, $IC_{50}$ in nM: 13 versus 6.0, 9.4, 9.2 and 7.1 respectively); and e) EM-9150 is more potent on the PSA level at $10^{-7}$M in R1881-stimulated human prostatic carcinoma LNCaP cells than EM-7105, EM-7148 and EM-8360 (column 5, percentages of inhibition: 57 versus 26, 33 and 46, respectively). Most importantly, EM-9150 has one the best affinities for the human androgen receptor in the present application (EM-9150, RBA-74) and in World Patent Application Publication WO/2006/133567 (EM-7334 and EM-7612, RBA=0.5) for a hydantoin derivative. The most important difference between comparable thiohydantoins and hydantoins (i.e. EM-9052 versus EM-9150 and EM-7105 versus EM-7333) is the affinity for the human androgen receptor (RBA(hAR)). In fact, EM-9052 binds to the human androgen receptor 27 times more than EM-9150 (RBA: 2010 versus 74) and EM-7105 binds around 140 times more than EM-7333 (RBA: 41 versus ~0.3). Although all the affinities for the human androgen receptor of the hydantoins from the corresponding thiohydantoins (WO 2006/133567) are not known, we estimate that we should not find values over 5-10, then much smaller than the one of EM-9150 (RBA-74). We have also observed that thiohydantoins could be transformed in vivo in to hydantoins, thus suggesting that overall in vitro activity profile of compounds EM-7365, EM-7105, EM-7148 and 8360 could be less active than expected when in vivo administered. EM-9156, an active metabolite of EM-9150, has a biological activity similar to that of EM-9150. In conclusion, EM-9150 has a higher RBA for the human androgen receptor than the thiohydantoin derivatives described in Table 1 from WO 2006/133567 (EM-7365, EM-7105, EM-7148 and EM-8360). In fact, the RBA(hAR) of EM-9150 is 1.8 to 6.7 times higher than the discussed thiohydantoin derivatives. EM-9150 inhibits 2 times and more PSA levels in human LNCaP cells compared to the thiohydantoins. The mentioned observations, especially the higher binding affinity to the human androgen receptor, strongly anticipate a better in vivo human activity of EM-9150 compared to the best thiohydantoins derivatives of WO 2006/133567 publication even if the in vivo rat antagonistic activity looks similar.

The same comparison as described above could be done between our best Selective Androgen Receptor Modulators (see Table 4) with the best Selective Androgen Receptor Modulators described in WO 2006/133567 (see Table 3) and demonstrates the superiority of the present compounds over those from WO 2006/133567.

Our invention includes quinoline and isoquinoline derivatives in replacement of the phenylpyridine moiety. The quinoline and isoquinoline moieties are fused rings of the phenylpyridine moiety. In the same manner, the quinoxaline moiety is fused ring of phenylpyrazine; quinazoline is fused ring of phenylpyrimidine, and cinnoline and phthalazine are fused rings of phenylpyridazine. The preferred right portion of

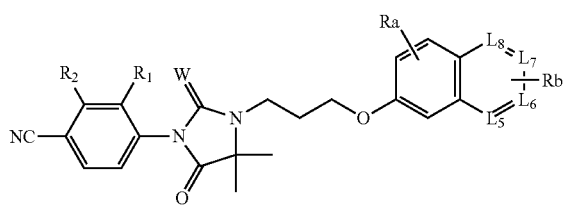

consists of

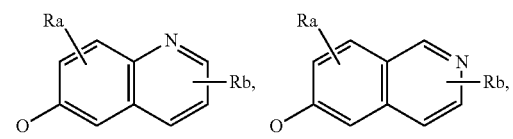

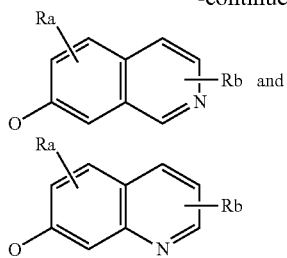

or the corresponding nitrogen-oxide
when one of $L_5$, $L_6$, $L_7$ and $L_8$ groups is a nitrogen or nitrogen-oxide; or

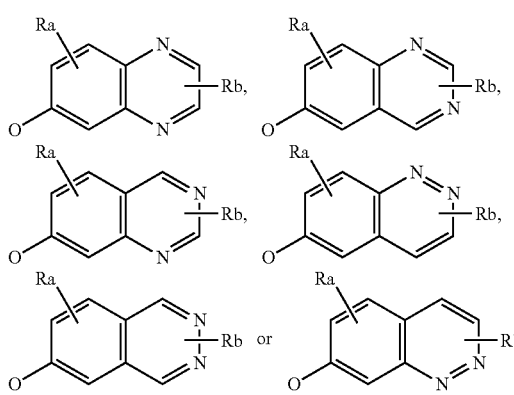

or the corresponding nitrogen-oxide
when two of $L_5$, $L_6$, $L_7$ and $L_8$ groups are a nitrogen or nitrogen-oxide.

It is preferred that m is 0; wherein n is 3; wherein J is an oxygen; wherein $G_1$, $G_8$ and $G_{10}$ are carbon or methine; wherein Y is a direct bond; wherein J and Y are in para-position from each other; and wherein $G_6$ or $G_7$ or $G_9$ is a nitrogen or nitrogen-oxide.

It is preferred that $R_1$ is hydrogen or methyl.

It is preferred that $R_2$ is fluorine, chlorine or trifluoromethyl.

It is preferred that $R_3$ is nitrile.

It is preferred that $R_4$ and $R_5$ are hydrogen.

It is preferred that $R_6$ and $R_7$ are methyl.

It is preferred that m is 0.

It is preferred that W is oxygen or sulfur.

It is preferred that n is 3.

It is preferred that J is oxygen.

It is preferred that $G_1$, $G_2$, $G_3$, $G_4$, $G_5$, $G_8$ and $G_{10}$ are independently carbon or methine.

It is preferred that $G_6$, $G_7$ and $G_9$ are independently nitrogen, nitrogen-oxide, carbon or methine.

It is preferred that Ra and Rb are independently hydrogen, fluorine, chlorine, trifluoromethyl, methyl or nitrile.

It is preferred that Y is a direct bond and is in para-position to J.

In preferred embodiments, two or preferably more of the preferences herein are used in combination.

Antiandrogens having a molecular structure selected from the group consisting of, and pharmaceutical composition comprising these ones, are particularly preferred:

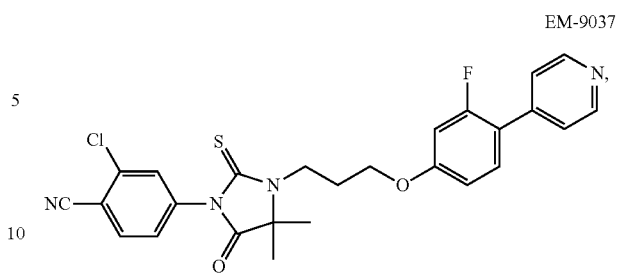

EM-9037

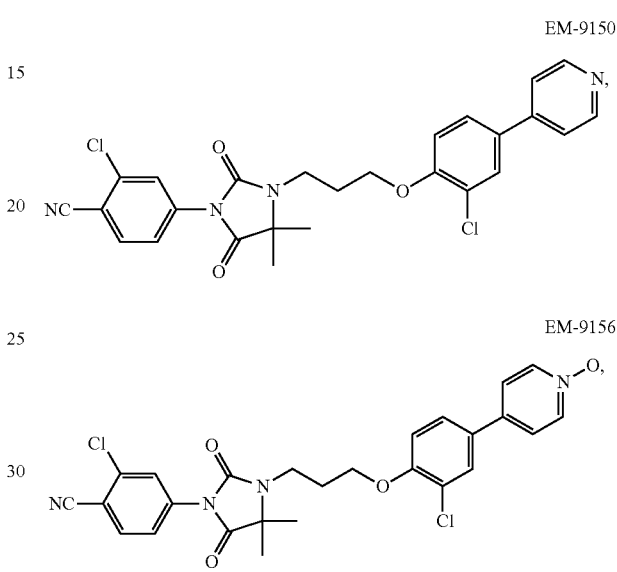

EM-9150

EM-9156

EM-9198

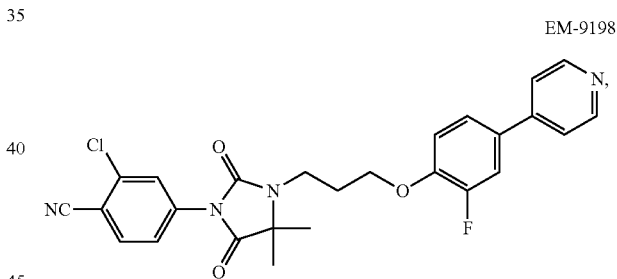

EM-9204

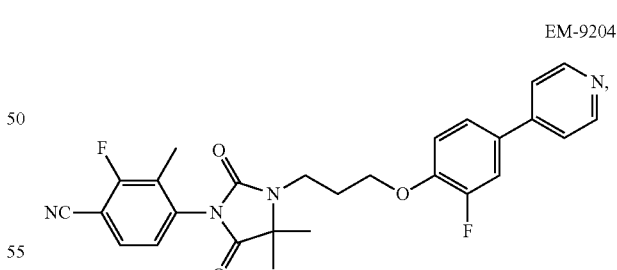

EM-9205

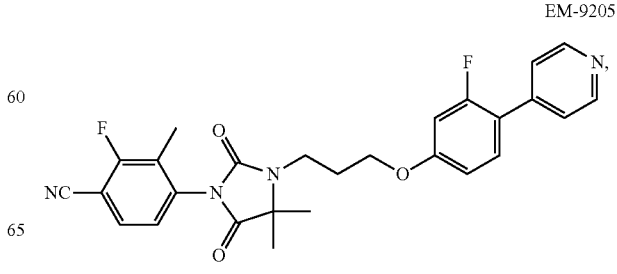

EM-9287

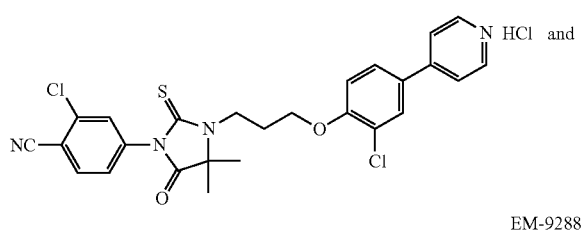

EM-9288

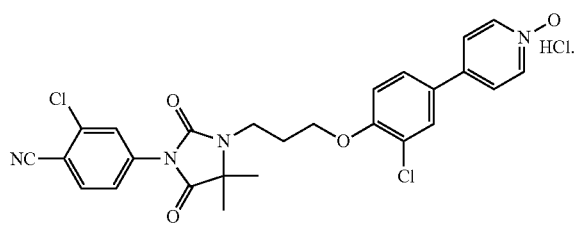

Figure 1:
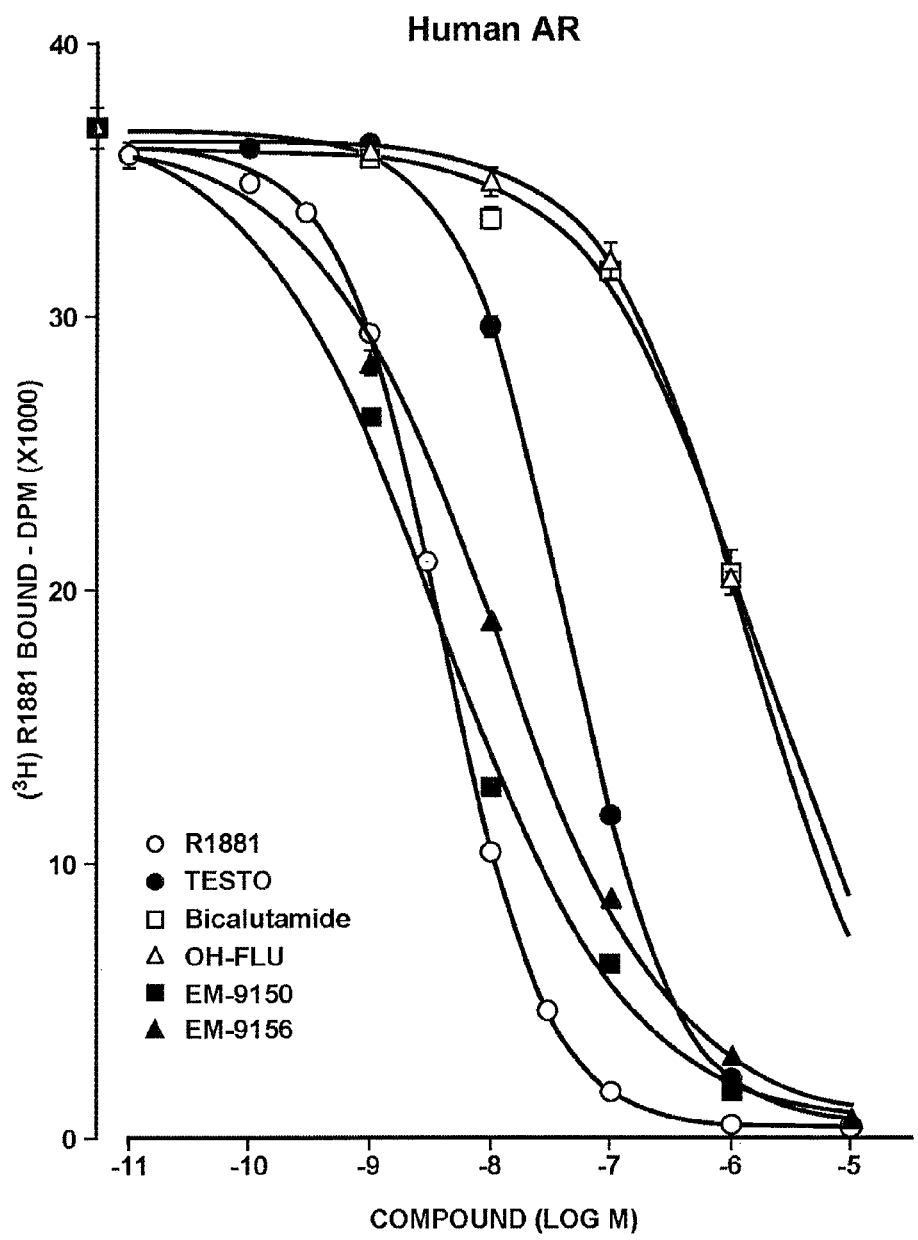
FIG. 1 shows the effect of increasing concentrations of methyltrienolone (R1881), testosterone (TESTO), bicalutamide, hydroxyflutamide (OH-FLU), EM-9150 and EM-9156 on [$^3$H]R1881 binding to the human androgen receptor. The incubation was performed with 4 nM [$^3$H]R1881 for 16 h at 0-4° C. in the presence or absence of the indicated concentrations of unlabeled compounds.
Figure 2:
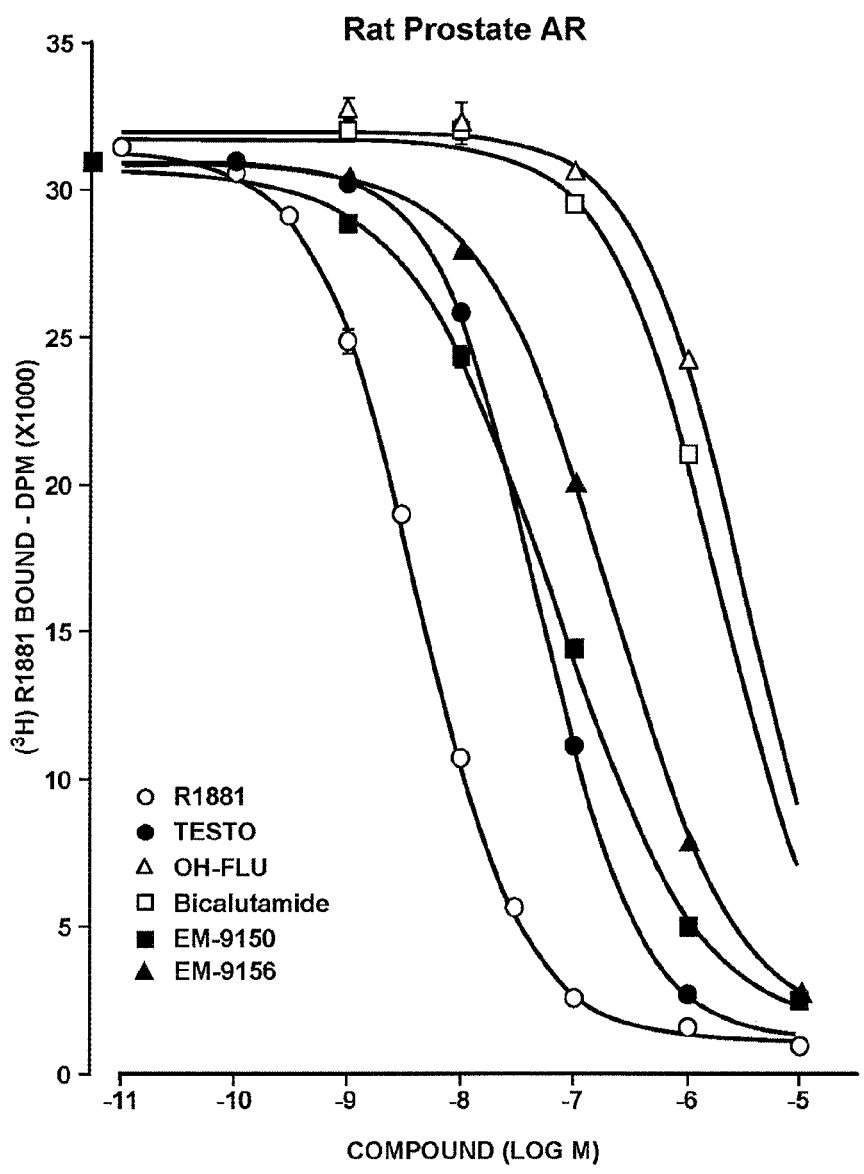
FIG. 2 shows the effect of increasing concentrations of methyltrienolone (R1881), testosterone (TESTO), hydroxyflutamide (OH-FLU), bicalutamide, EM-9150 and EM-9156 on [$^3$H]R1881 binding to the rat prostate androgen receptor. The incubation was performed with 4 nM [$^3$H]R1881 for 16 h at 0-4° C. in the presence or absence of the indicated concentrations of unlabeled compounds.

In addition to the preferred compounds section (Table 3), the biological properties of EM-9150 and its metabolite EM-9156 are illustrated in FIGS. 1-7. In summary, preclinical studies have shown that EM-9150 is 247 and 352 times and EM-9156 is 57 and 81 times more potent than bicalutamide (Casodex, CAS) and OH-flutamide (OH-FLU), the active metabolite of flutamide (FLU), respectively, to displace the metabolically stable androgen methyltrienolone (R1881) from the human AR (FIG. 1 as example). In the rat AR assay, EM-9150 is 32 and 65 times and EM-9156 is 27 and 53 times more potent than bicalutamide and OH-flutamide, respectively (FIG. 2). In mouse androgen-sensitive Shionogi carcinoma cells, EM-9150 is 5.2- and 14.6-fold and EM-9156 is 4.5- and 12-7-fold more potent than OH-flutamide and bicalutamide, respectively, in reversing DHT-stimulated cell proliferation, in addition to the absence of stimulation at $10^{-7}$M of basal levels of cell proliferation (FIG. 3 as example). In the human prostatic carcinoma cell line LNCaP, EM-9150 and EM-9156 are 11.0 and 9.2 times more potent than bicalutamide in blocking R1881-stimulated PSA secretion, in addition to the absence of stimulation at $10^{-7}$M of basal levels, respectively (FIG. 4). The mean plasma levels of EM-9150, and of its metabolites EM-9156 and EM-9260 led to $AUC_{0-24hr}$ values of 123, 1708 and 14931 ng·hr/mL, respectively following single oral administration of 20 mg EM-9150/kg to male rats (FIG. 5). After daily oral dosing for 7 days, EM-9150 and EM-9156 show no agonistic activity on ventral prostate weight in the immature castrated rat (FIG. 7) while the antagonistic activity in immature castrated rats supplemented with DHT is comparable to bicalutamide and flutamide (FIG. 6 as example).

Under some circumstances (e.g. at certain concentrations), the compounds of the invention, and pharmaceutical compositions containing them, can be androgenic and may be utilized in accordance with the invention in the prevention and treatment of diseases where androgens are beneficial such as muscle atrophy and weakness, abdominal fat accumulation, skin atrophy, anemia, bone loss, osteoporosis, atherosclerosis, cardiovascular diseases, type 2 diabetes, loss of energy, loss of well-being, loss of libido, male hypogonadism, sarcopenia, sexual impotence, erectile dysfunction or female sexual dysfunction. The previously mentioned diseases where an androgen is useful is supported in Negro-Vilar, 1999 (muscle atrophy and weakness, osteoporosis, anemia, cardiovascular diseases, male hypogonadism, loss of libido and abdominal fat accumulation), Liu et al., 2003 (cardiovascular diseases, abdominal fat accumulation, atherosclerosis, type 2 diabetes, loss of libido and erectile dysfunction), Labrie 2004, (muscle atrophy and weakness, bone loss, osteoporosis, abdominal fat accumulation, skin atrophy, loss of energy, loss of well-being, loss of libido and type 2 diabetes), Labrie et al., 2014 (muscle atrophy and weakness and female sexual dysfunction), Labrie et al., 2009 (muscle atrophy and weakness, abdominal fat accumulation, bone loss, type 2 diabetes, loss of libido and female sexual dysfunction), Pelletier et al., 2012 and 2013 (female sexual dysfunction), Bhasin et al., 2011 (osteoporosis, cardiovascular diseases, type 2 diabetes, sarcopenia and erectile dysfunction), and Aucoin et al., 2006 (loss of libido, sexual impotence, erectile dysfunction).

Selective Androgen Receptor Modulators having a molecular structure selected from the group consisting of, and pharmaceutical composition comprising these ones, are particularly preferred:

EM-8796

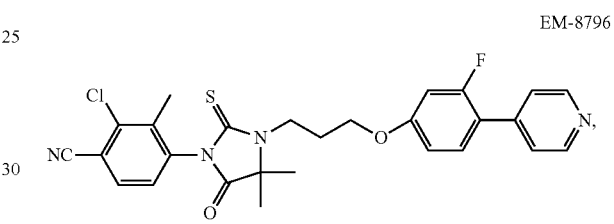

EM-8797

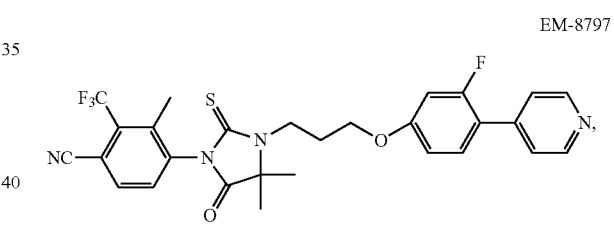

EM-8887

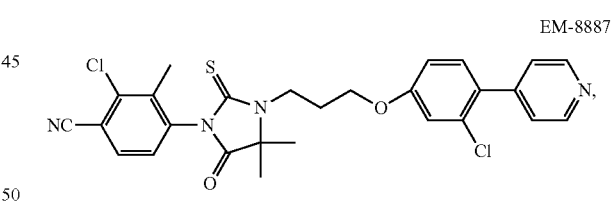

EM-9251

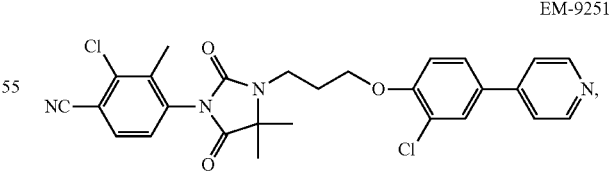

EM-9252

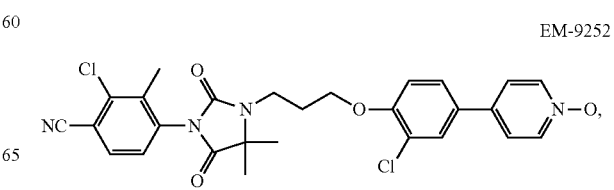

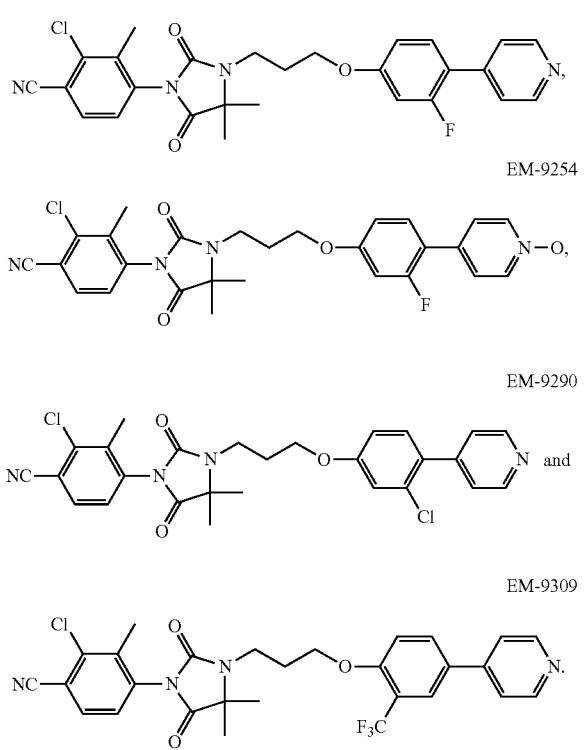

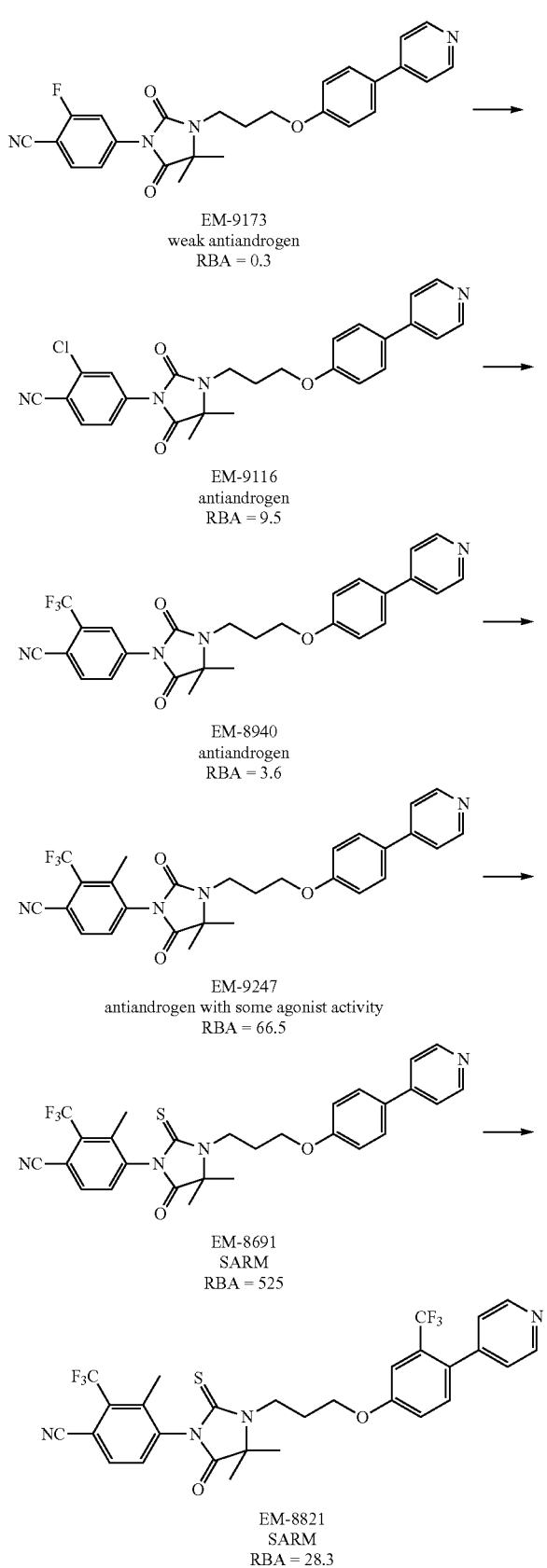

In addition to the preferred compounds section (Table 4), one of the biological properties of EM-9251 is illustrated in FIG. 8. In vivo preclinical studies have shown that EM-9251, after oral dosing for 7 days in the immature castrated rat, a mixed agonistic-antagonistic activity on the prostate and seminal vesicles and an agonistic activity on the bulbocavernosus muscles were observed. However, in the immature intact rat, an antagonistic activity on the prostate and seminal vesicles and an agonistic activity on the bulbocavernosus muscles were observed.

In the course of our antiandrogen development program, specifically on hydantoin and thiohydantoin derivatives with a phenylpyridyl chain, we have found compounds which exhibit SARM properties (described in this document). Starting with a pure antiandrogen, we observed that a small increase in the size of the molecule from left to right can give a SARM. Preferred substituents on these compounds are $R_1$, $R_2$, W, Ra and Rb (as described above). For example, when we exchange $R_2$ by a larger group in the weak antiandrogen EM-9173, we observe that EM-9116 and EM-8940 become better antiandrogens with higher affinity for the androgen receptor (F to Cl: EM-9116; Cl to $CF_3$: EM-8940). Moreover, when we introduce a methyl group at $R_1$ position, EM-9247 becomes an antiandrogen with some agonistic activity. Then, when we exchange the oxygen by a sulfur at W position (EM-8691), we obtain a potent SARM with high affinity for the androgen receptor. Finally, the introduction of a trifluoromethyl group at Ra position (EM-8821) gives a weaker SARM with decreased affinity. Contrary to our analogous work on steroidal antiandrogens (WO 2008/124922), we do not observe androgens when increasing the size of the substituents. Thus, it is not obvious to make good predictions of the biological activity of this compounds family although some trends are observable.

The metabolism of some of compounds described in Tables 3-5 has been studied (see Scheme 1). For example, when EM-9150 is orally administered in the rat, EM-9156 was measured in the circulation. This transformation comes from the oxidation of pyridyl moiety to the pyridyl N-oxide moiety. The reverse process, namely the reduction of EM-9156 to EM-9150, is observed but is not favoured in comparison to the oxidation of EM-9150 to EM-9156. Moreover, EM-9150 and EM-9156 are N-dealkylated to give EM-9260, the corresponding 4,4-dimethyl-2,5-dioxo-1-imidazolidinyl (hydantoin) derivative. FIG. 5 shows the plasma concentrations of EM-9150, EM-9156 and EM-9260 in 3 rats receiving 20 mg/kg of EM-9150 orally for 24 hours. These results show under these conditions, $AUC_{0-24h}$ values of 123, 1708 and 14931 ng·h/mL for EM-9150, EM-9156 and EM-9260, respectively. Consequently, the in vivo results of EM-9150 should be interpreted as the sum of the action of three components, namely EM-9150 and its two metabolites EM-9156 and EM-9260.

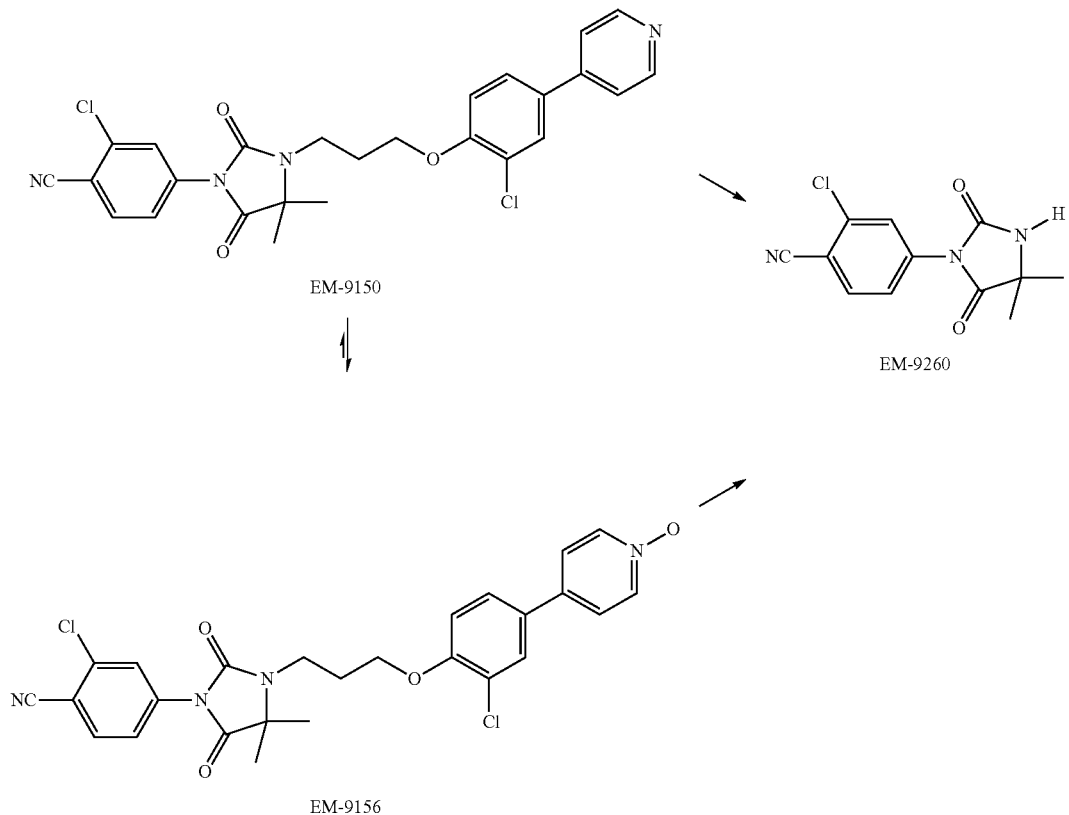

Scheme 1

Table 2 summarizes the biological characteristics of the three compounds EM-9150, EM-9156 and EM-9260 in addition with another group of three compounds, namely EM-9251, EM-9252 and EM-9289 with the same metabolic pathway. According to Table 2, the first group of compounds (EM-9150, EM-9156 and EM-9260) are antiandrogens in the models studied (in vitro antiandrogenic activity on Shionogi cells (column 2), in vivo antiandrogenic activity on rat prostate, seminal vesicles and bulbocavernosus muscles (columns 4-6), and no in vivo androgenic activity on rat prostate, seminal vesicles and bulbocavernosus muscles (columns 7-9)). On the other hand, the second group of compounds (EM-9251, EM-9252 and EM-9289) are selective androgen receptor modulators (SARMs) in the models studied (mixed in vitro activity on Shionogi cells (column 2), mixed in vivo activity on rat prostate and seminal vesicles (columns 4, 5, 7 and 8), and in vivo androgenic activity on bulbocavernosus muscles (columns 6 and 9).

TABLE 2

| | IN VITRO | | IN VIVO Immature rat | | | | | |
|---|---|---|---|---|---|---|---|---|
| | Shionogi Anti-Androgenic Activity | Human Androgen Receptor Binding (%) RBA | CX + DHT Antagonistic activity 0.5 mg/rat/po % Inhibition | | | CX Agonistic activity 0.1 mg/rat/po % Stimulation | | |
| Structure and Name | $IC_{50}$ (nM) | R1881 = 100 | Prostate | SV | Bulbo | Prostate | SV | Bulbo |
| 1 | 2 | 3 | 4 | 5 | 6 | 7 | 8 | 9 |
| Testosterone | | 11.1 ± 0.3 (n = 269) | ND | ND | ND | 99 (s.c.) | 11.5 (s.c.) | 171 (s.c.) |
| EM-9150 | 13 ± 3 (n = 5) | 74 ± 19 (n = 6) | 55 | 92 | 67 | 0 | 0 | 1 |
| EM-9156 | 15 ± 3 (n = 7) | 17 ± 4 (n = 8) | 55 (0.3 mg/rat) | 89 (0.3 mg/rat) | 57 (0.3 mg/rat) | 1 | 0 | 5 |
| EM-9260 | ~100 | ~0.1 | 71 | 96 | 84 | 0 | 2 | 4 |
| EM-9251 | 67.7[a] | 253 | 45 | 26 | −46 | 41 ± 2 (n = 2) | 27 ± 1 (n = 2) | 119 ± 24 (n = 2) |
| EM-9252 | >100[a] | 96.3 | 40 | 35 | −101 | 46 ± 5 (n = 2) | 29 ± 5 (n = 2) | 105 ± 9 (n = 2) |

TABLE 2-continued

| | IN VITRO | | IN VIVO Immature rat | | | | | |
|---|---|---|---|---|---|---|---|---|
| | Shionogi Anti-Androgenic Activity | Human Androgen Receptor Binding (%) RBA | CX + DHT Antagonistic activity 0.5 mg/rat/po % Inhibition | | | CX Agonistic activity 0.1 mg/rat/po % Stimulation | | |
| Structure and Name 1 | $IC_{50}$ (nM) 2 | R1881 = 100 3 | Prostate 4 | SV 5 | Bulbo 6 | Prostate 7 | SV 8 | Bulbo 9 |
| 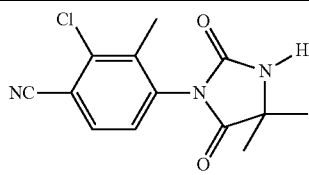 EM-9289 | ~1000[a] | 1.0 | 47 | 50 | −66 | 50 ± 6 (n = 2) | 38 ± 5 (n = 2) | 138 ± 15 (n = 2) |

[a]These compounds have a stimulation at $10^{-7}$M on basal Shionogi cells.
ND = not determined
s.c. = subcutaneous Legend of the Table 2:
In Column 1, the molecular structure and the laboratory name of the antiandrogens or SARMs is reported.
Column 2 represents the dose (expressed in nM) that inhibits by 50% ($IC_{50}$) the DHT-stimulated Shionogi mouse mammary carcinoma cell number. Lower values are preferable.
Column 3 represents the Relative Binding Affinity (RBA) of the antiandrogens or SARMs expressed as percentage (%) on Human Androgen Receptor in transfected cells relative to R1881 as calculated by the formula:

$$\% \ RBA = 100 \times IC_{50} R1881/IC_{50} \ (\text{compound})$$

Higher values are preferable.
Column 4 represents the % of antiandrogenic efficacy in rat prostate, expressed in percentage of inhibition.
The percentage of inhibition is calculated by the following formula:

$$\% \ \text{Inhibition} = 100 - [W(\text{compound}) - W(\text{control } CX)/W(\text{DHT}) - W(\text{control } CX)] \times 100.$$

W is the weight of the prostate.
Higher values are preferable.
Column 5 represents the % of antiandrogenic efficacy in rat seminal vesicles, expressed in percentage of inhibition.
The percentage of inhibition is calculated by the following formula:

$$\% \ \text{Inhibition} = 100 - [W(\text{compound}) - W(\text{control } CX)/W(\text{DHT}) - W(\text{control } CX)] \times 100.$$

W is the weight of the seminal vesicles.
Higher values are preferable.
Column 6 represents the % of antiandrogenic efficacy in rat bulbocavernosus muscles, expressed in percentage of inhibition.
The percentage of inhibition is calculated by the following formula:

$$\% \ \text{Inhibition} = 100 - [W(\text{compound}) - W(\text{control } CX)/W(\text{DHT}) - W(\text{control } CX)] \times 100.$$

W is the weight of the bulbocavernosus muscles.
Column 7 represents the % of androgenic efficacy in rat prostate, expressed in percentage of stimulation.

The percentage of stimulation is calculated by the following formula:

$$\% \ \text{Stimulation} = [W(\text{compound}) - W(\text{control } CX)/W(\text{DHT}) - W(\text{control } CX)] \times 100.$$

W is the weight of the prostate.
Lower values are preferable.
Column 8 represents the % of androgenic efficacy in rat seminal vesicles, expressed in percentage of stimulation.
The percentage of stimulation is calculated by the following formula:

$$\% \ \text{Stimulation} = [W(\text{compound}) - W(\text{control } CX)/W(\text{DHT}) - W(\text{control } CX)] \times 100.$$

W is the weight of the seminal vesicles.
Lower values are preferable.
Column 9 represents the % of androgenic efficacy in rat bulbocavernosus muscles, expressed in percentage of stimulation.
The percentage of stimulation is calculated by the following formula:

$$\% \ \text{Stimulation} = [W(\text{compound}) - W(\text{control } CX)/W(\text{DHT}) - W(\text{control } CX)] \times 100.$$

W is the weight of the bulbocavernosus muscles.
Antiandrogens or SARMs of the invention are preferably formulated together with pharmaceutically acceptable diluents, excipients or carriers (including capsules) into pharmaceutical compositions at conventional antiandrogen concentrations for antiandrogens used in the prior art. Taking into account the higher potency of the compounds of this invention, the attending clinician may elect to modify the concentration and/or dosage in order to adjust the dose to the particular response of each patient. Preferably, the attending clinician will, especially at the beginning of treatment, monitor an individual patient's overall response and serum levels of antiandrogen or SARM (in comparison to the preferred serum concentrations discussed below), and monitor the patient's overall response to treatment, adjusting dosages as necessary where a given patients' metabolism or reaction to treatment is atypical. As discussed in more detail below, carriers, excipients or diluents include solids and liquids. When a composition is prepared other than for immediate use, an art-recognized preservative is typically included (e.g. benzyl alcohol). The novel pharmaceutical compositions of the invention may be used in the treatment of androgen-related diseases, or to reduce the likelihood of acquiring such diseases. When administered systemically (e.g., for treatment of prostate cancer, benign prostatic hyperplasia, precocious puberty, polycystic ovarian syndrome, diseases related to loss of androgen stimulation (male hypogonadism, female sexual dysfunction, erectile dysfunction and sarcopenia) and other diseases not primarily affecting the skin) conventional diluents or carriers which are known in the art to be pharmaceutically acceptable for systemic use are used, e.g., saline, water, aqueous ethanol, oil, etc. The carrier is often a mixture of ingredients.

When formulated for systemic use, the antiandrogens or SARMs may be prepared for administration in conventional ways such as orally or by injection. The antiandrogen can be administered, for example, by the oral route. The compounds of the present invention may be formulated with conventional pharmaceutical excipients, (e.g. spray dried lactose and magnesium stearate) into tablets or capsules for oral administration. Of course, taste-improving substances can be added in the case of oral administration forms. When capsules for oral ingestion are desired, any pharmaceutical capsules known in the art may be filled with the active ingredients of the invention, with or without additional diluents and other additives discussed herein.

The active substance can be worked into tablets or dragee cores by being mixed with solid, pulverulent carrier substances, such as sodium citrate, calcium carbonate or dicalcium phosphate, and binders such as polyvinyl pyrrolidone, gelatin or cellulose derivatives, possibly by adding also lubricants such as magnesium stearate, sodium lauryl sulfate, "Carbowax" or polyethylene glycol.

As further forms, one can use plug capsules, e.g. of hard gelatin, as well as closed soft-gelatin capsules comprising a softener or plasticizer, e.g. glycerine. The plug capsules contain the active substance preferably in the form of granulate, e.g. in mixture with fillers, such as lactose, saccharose, mannitol, starches, such as potato starch or amylopectin, cellulose derivatives or highly dispersed silicic acids. In soft-gelatin capsules, the active substance is preferably dissolved or suspended in suitable liquids, such as vegetable oils or liquid polyethylene glycols.

A dry delivery system, as described in U.S. Pat. Nos. 3,742,951, 3,797,494 or 4,568,343 may be used.

Alternatively, the active ingredient may be placed into a transdermal patch having structures known in the art, for example, structures such as those set forth in E.P. Patent No. 0279982.

Solvents or devices as described in U.S. Pat. Nos. 5,064,654, 5,071,644 or 5,071,657 can also be used to facilitate transdermal penetration when systemic effects are desired. When used to treat systemic diseases, the site of application on the skin should be changed in order to avoid excess local concentration of antiandrogens.

In some embodiments, the antiandrogens of the invention are utilized for the treatment of androgen-related diseases of the skin such as acne, seborrhea, hirsutism, androgenic alopecia and male baldness. When used for any of these purposes, the antiandrogens are preferably administered topically together with a conventional topical carrier or diluent. When used topically, it is preferred that the diluent or carrier does not promote transdermal penetration of the active ingredients into the blood stream or other tissues where they might cause unwanted systemic effects.

When the compound is administered in a cutaneous or topical carrier or diluent, the carrier or diluent may be chosen from any known in the cosmetic and medical arts, e.g. any gel, cream, lotion, ointment, liquid or non liquid carrier, emulsifier, solvent, liquid diluent or other similar vehicle which does not exert deleterious effect on the skin or other living animal tissue. The carrier or diluent is usually a mixture of several ingredients, including, but not limited to liquid alcohols, liquid glycols, liquid polyalkylene glycols, water, liquid amides, liquid esters, liquid lanolin, lanolin derivatives and similar materials. Alcohols include mono and polyhydric alcohols, including ethanol, glycerol, sorbitol, isopropanol, diethylene glycol, propylene glycol, ethylene glycol, hexylene glycol, mannitol and methoxyethanol. Typical carriers may also include ethers, e.g. diethyl and dipropyl ether, methoxypolyoxyethylenes, carbowaxes, polyethyleneglycerols, polyoxyethylenes and sorbitols. Usually, the topical carrier includes both water and alcohol in order to maximize the hydrophylic and lipophylic solubility, e.g. a mixture of ethanol or isopropanol with water.

A topical carrier may also include various other ingredients commonly used in ointments and lotions and well known in the cosmetic and medical arts. For example, fragrances, antioxidants, perfumes, gelling agents, thickening agents such as carboxymethylcellulose, surfactants, stabilizers, emollients, coloring agents and other similar agents may be present.

The concentration of active ingredient in the ointment, cream, gel or lotion is typically from about 0.1 to 20 percent preferably between 0.5 and 5 percent and most preferably 2 percent (by weight relative to the total weight of the lotion, cream, gel or ointment). Within the preferred ranges, higher concentrations allow a suitable dosage to be achieved while applying the lotion, ointment, gel or cream in a lesser amount or with less frequency.

Several non-limiting examples infra describe the preparation of a typical lotion and gel, respectively. In addition to vehicles, one skilled in the art may choose other vehicles in order to adapt to specific dermatologic needs.

When antiandrogens or SARMs are administered systemically, they are preferably administered orally or parenterally. Naturally, topical administration is preferred when the desired site of action is the skin.

Concentration of the active antiandrogen or SARM varies in a known manner depending upon the method of administering the pharmaceutical composition. A composition suitable for oral administration may preferably include at least one antiandrogen wherein the total concentration of all such antiandrogens in said pharmaceutical composition is from about 1% to 95% of the composition (by weight), and preferably from about 5% to about 20%. Where a combination of antiandrogens is used, the total dosage of the sum of all antiandrogens should be equal to the dosage range recited above. Blood level of the antiandrogen is a preferred criteria of adequate dosage which takes into account individual variation in absorption and metabolism.

When prepared for parental injection, the antiandrogen or SARM is preferably added at a concentration between about 0.1 mg/ml and about 200 mg/ml (preferably about 2.5 mg/ml to about 100 mg/me.

When systemic activity is desired, it is necessary only that the antiandrogen or SARM be administered in a manner and at a dosage sufficient to allow blood serum concentration to obtain desired levels. Serum antiandrogen concentration should typically be maintained between 0.1 and 1000 micrograms per liter, preferably between 50 and 1000 micrograms per liter and most preferably between 50 and 500 micrograms per liter. Adequate serum levels may also be assessed by a patient's response to therapy.

For typical patients, the appropriate dosage of the antiandrogen or SARM to achieve desired serum concentration is between 10 and 1500 milligrams of active ingredient per day per 50 kg of body weight when administered orally. When administered by injection, about 2 to 1000 mg per day per 50 kg of body weight is recommended, preferably from 5 to 100.

For topical use lotion, ointment, gel or cream should be thoroughly rubbed into the skin so that no excess is plainly visible, and the skin is preferably not washed in that region for at least 30 minutes. The amount applied should provide at least 0.02 milligrams of antiandrogen or SARM per square centimeter (preferably from 0.1 to 1 mg/cm$^2$) per application. It is desirable to apply the topical composition to the effected region from 1 to 6 times daily, e.g. 3 times daily at approximately regular intervals.

In some embodiments of the invention, the antiandrogen of the invention is used in combination with another active ingredient as part of a combination therapy. For example, the novel antiandrogen may be utilized together with a separate 5α-reductase inhibitor, a type 5 or type 15 17β-hydroxysteroid dehydrogenase inhibitor (Prostate Short-Chain Dehydrogenase Reductase 1 inhibitor), or a 17α-hydroxylase/17,20-lyase (CYP17) inhibitor which may be incorporated into the same pharmaceutical composition as is the antiandrogen, or which may be separately administered. Combination therapy could thus include treatment with one or more compounds which inhibit the production of dihydrotestosterone or its precursors. In some preferred embodiments of the invention, the topical pharmaceutical composition further includes an inhibitor of steroid 5α-reductase activity. One such inhibitor ("Propecia or Proscar") is commercially available form Merck Sharp and Dohme. Another inhibitor <<Dutasteride>> which inhibits both 5α-reductase co-enzymes is also commercially available from GlaxoSmithKline. Inhibitors of type 5 17β-hydroxysteroid dehydrogenase (more particularly compound EM-1404) are disclosed in the international publication WO 99/46279. EM-1791, one of inhibitors type 15 17β-hydroxysteroid dehydrogenase is described in WO 2005/066194. Inhibitors of 17α-hydroxylase/17,20-lyase (CYP17) are selected from the group comprising ketoconazole, abiraterone acetate, galeterone (VN/124-1, TOK-001) and orteronel (TAK-700).

When 5alpha-reductase inhibitors are used in combination therapies, in accordance with the invention described herein, oral dosage is preferably between 0.1 mg and 100 mg per day per 50 kg body weight, more preferably between 0.5 mg/day and 10 mg/day, for example 5.0 mg per day of finasteride or 0.5 mg per day of dutasteride.

When type 5 17beta-hydroxysteroid dehydrogenase inhibitors are used in combination therapies, in accordance with the invention described herein, oral dosage is preferably between 5 mg and 500 mg per day per 50 kg body weight, more preferably between 10 mg/day and 400 mg/day, for example 300 mg per day of EM-1404.

When type 5 or type 15 17β-hydroxysteroid dehydrogenase inhibitors are used in combination therapies, in accordance with the invention described herein, oral dosage is preferably between 10 mg and 1000 mg per day per 50 kg body weight, more preferably between 25 mg/day and 1000 mg/day, for example 200 mg per day of EM-1404 or EM-2881.

When 17α-hydroxylase/17,20-lyase (CYP17) inhibitors are used in combination therapies, in accordance with the invention described herein, oral dosage is preferably between 10 mg and 5000 mg per day per 50 kg body weight, more preferably between 100 mg/day and 3000 mg/day, for example 1000 mg per day of abiraterone acetate.

In some embodiments of the invention, the antiandrogen of the invention is used in combination with orchiectomy or with a LHRH agonist or antagonist as part of a combination therapy. Preferred LHRH agonists are leuprolide acetate available under the trademark "Lupron" from Abbott Laboratories Ltd., "Viadur" from Bayer AG, "Eligard" from Sanofi-Aventis, and "Prostap SR" and "Prostap 3" from Takeda UK, Goserelin acetate available under the trademark "Zoladex" and "Zoladex LA" from AstraZeneca, Nafarelin available under the trademark "Synarel" from Searle (now part of Pfizer), Buserelin acetate available under the trademark "Suprefact" or "Suprefact Depot" from Sanofi-Aventis and "CinnaFact" from CinnaGen, Histrelin acetate available under the trademark "Vantas" and "Supprelin LA" from Endo Pharmaceuticals, Triptorelin acetate or pamoate available under the trademark "Decapeptyl" from Ipsen, "Diphereline" and "Gonapeptyl" from Ferring Pharmaceuticals, and "Trelstar" from Watson. Preferred LHRH antagonists are Abarelix available under the trademark "Plenaxis" from Speciality European Pharma, Teverelix developed by Ardana, Cetrorelix acetate available under the trademark "Cetrotide" from Merck Serono, Ganirelix acetate available under the trademark "Antagon" from Organon International, Iturelix under the trademark "Antide" from Serono, Acyline developed by Merrion Pharmaceuticals, Degarelix under the trademark "Firmagon" from Ferring Pharmaceuticals, and Ornirelix developed by Oakwood Laboratories. Other LHRH antagonists are Azaline B (Salk Institute), Ozarelix (Spectrum Pharmaceuticals), LXT-101 (Department of Pharmaceutical Chemistry, Beijing Institute of Pharmacology and Toxicology), Elagolix (Neurocrine Biosciences), and TAK-013 and TAK-385 (Takeda). Any FDA-approved LHRH (or GnRH) agonist or antagonist can be used.

The most preferred route of administration of the LHRH agonist or antagonist is subcutaneous or intramuscular depot injection. The LHRH agonist or antagonist may be administered at from about 10 to 1500 μg per day and about 250 (preferably 50 μg to 500 μg per day) for the LHRH agonist and to about 100 to 2000 μg per day for the LHRH antagonist being preferred following the recommendation of the distributor.

A patient in need of treatment or reducing the risk of onset of a given disease is one who has either been diagnosed with such disease or one who is susceptible to acquiring such disease. The invention is especially useful for individuals who, due to heredity, environmental factors or other recognized risk factor, are at higher risk than the general population of acquiring the conditions to which the present invention relates.

Except where otherwise stated, the preferred dosage of the active compounds of the invention is identical for both therapeutic and prophylactic purposes. The dosage for each active component discussed herein is the same regardless of the disease being treated (or prevented).

Where two are more different active agents are discussed as part of a combination therapy herein (e.g. an enzyme inhibitor and an antiandrogen), a plurality of different compounds are administered rather than a single compound having multiple activities.

Except where otherwise indicated, the term "compound" and any associated molecular structure may include any possible stereoisomers thereof, in the form of a racemic mixture or in optically active form.

Except where otherwise noted or where apparent from context, dosages herein refer to weight of active compounds unaffected by pharmaceutical excipients, diluents, carriers or other ingredients, although such additional ingredients are desirably included, as shown in the examples herein. Any dosage form (capsule, tablet, injection or the like) commonly used in the pharmaceutical industry is appropriate for use herein, and the terms "excipient", "diluent" or "carrier" include such non-active ingredients as are typically included, together with active ingredients in such dosage forms in the industry.

All of the active ingredients used in any of the combination therapies discussed herein may be formulated in pharmaceutical compositions which also include one or more of the other active ingredients. Alternatively, they may each be administered separately but sufficiently simultaneous in time so that a patient eventually has elevated blood levels or otherwise enjoys the benefits of each of the active ingredients (or strategies) simultaneously. In some preferred embodiments of the invention, for example, one or more active ingredients are to be formulated in a single pharmaceutical composition. In other embodiments of the invention, a kit is provided which includes at least two separate containers wherein the contents of at least one other container with respect to active ingredients contained therein. Two or more different containers are used in the combination therapies of the invention. Combination therapies discussed herein also include use of one active ingredient of the combination in the manufacture of a medicament for the treatment (or prevention) of the disease in question where the treatment or prevention further includes another active ingredient or strategy of the combination. For example, in prostate cancer therapy an LHRH agonist or antagonist or an inhibitor of type 3 17β-hydroxysteroid dehydrogenase can be used.

Preferred Compounds

Set forth in the tables below are lists of preferred compounds and their properties and efficacy. The Tables 3, 4 and 5 show in vitro data which include the binding to human androgen receptor and antiandrogenic activity on mouse mammary carcinoma Shionogi cells. Tables 3, 4 and 5 also show in vivo data which include antagonistic activity on three tissues of immature rat (ventral prostate, seminal vesicles and bulbocavernosus muscles). In addition, Tables 4 and 5 report the agonistic activity on the same tissues. Detailed explanations on how the data were collected and reported follow the tables.

TABLE 3

| | | IN VITRO | | IN VIVO | | |
| | | Shionogi Anti-androgenic Activity $IC_{50}$ | Human Androgen Receptor Binding (%) RBA R1881 = | Immature rat CX + DHT Antagonistic activity 0.5 mg/rat/po % Inhibition | | |
| Name 1 | Structure 2 | (nM) 3 | 100 4 | Prostate 5 | SV 6 | Bulbo 7 |
| OH-FLU | [structure] | 67 ± 2 (n = 312) | 0.21 ± 0.09 (n = 3) | ND | ND | ND |
| FLU | [structure] | ND | ND | 47.9 ± 0.6 (n = 131) | 82.8 ± 0.7 (n = 131) | 67.3 ± 1.6 (n = 46) |
| CAS | [structure] | 190 ± 36 (n = 3) | 0.3 | 53 ± 2 (n = 26) | 89 ± 1 (n = 26) | 74 ± 2 (n = 23) |

TABLE 3-continued

| Name | Structure | IN VITRO Shionogi Anti-androgenic Activity IC$_{50}$ (nM) | Human Androgen Receptor Binding (%) RBA R1881 = 100 | IN VIVO Immature rat CX + DHT Antagonistic activity 0.5 mg/rat/po % Inhibition | | |
|---|---|---|---|---|---|---|
| 1 | 2 | 3 | 4 | Prostate 5 | SV 6 | Bulbo 7 |
| EM-8840 | | 24 ± 6 (n = #) | 1090 ± 500 (n = 2) | 62 | 80 | 42 |
| EM-8841 | | 73 ± 5 (n = 2) | 1200 ± 330 (n = 2) | 57 | 85 | 65 |
| EM-8851 | | 77 ± 20 (n = 3) | 3310 ± 1780 (n = 2) | 62 | 86 | 91 |
| EM-8871 | | 66 | 558 ± 102 (n = 2) | 41 | 70 | 66 |
| EM-8872 | | 36 | 723 ± 59 (n = 2) | 56 | 79 | 62 |

TABLE 3-continued

|  |  | IN VITRO | | IN VIVO Immature rat CX + DHT Antagonistic activity 0.5 mg/rat/po % Inhibition | | |
|---|---|---|---|---|---|---|
| Name 1 | Structure 2 | Shionogi Anti-androgenic Activity IC$_{50}$ (nM) 3 | Human Androgen Receptor Binding (%) RBA R1881 = 100 4 | Prostate 5 | SV 6 | Bulbo 7 |
| EM-8888 |  | 111 | 1880 ± 1040 (n = 2) | 57 | 81 | 57 |
| EM-8890 |  | 13.2 | 59 ± 25 (n = 2) | 50 | 86 | 25 |
| EM-8900 |  | 3.8 | 130 ± 60 (n = 2) | 54 | 79 | 29 |
| EM-8908 |  | 50 | 944 ± 265 (n = 2) | 55 | 73 | 48 |
| EM-8923 |  | 48 | 136 | 50 | 83 | 61 |

TABLE 3-continued

| Name | Structure | IN VITRO Shionogi Anti-androgenic Activity IC$_{50}$ (nM) | Human Androgen Receptor Binding (%) RBA R1881 = 100 | IN VIVO Immature rat CX + DHT Antagonistic activity 0.5 mg/rat/po % Inhibition | | |
|---|---|---|---|---|---|---|
| | | | | Prostate | SV | Bulbo |
| 1 | 2 | 3 | 4 | 5 | 6 | 7 |
| EM-8929 | | 17 ± 10 (n = 2) | 100 ± 12 (n = 2) | 59 | 88 | 43 |
| EM-9000 | | 20 ± 10 (n = 2) | 1.5 ± 0.3 (n = 2) | 53 | 85 | 90 |
| EM-9011 | | 6.6 ± 0.8 (n = 2) | 43 ± 9 (n = 2) | 63 | 85 | 66 |
| EM-9025 | | 2.7 | 39 | 51 | 76 | 61 |
| EM-9037 | | 8.7 | 1040 ± 350 (n = 2) | 71 | 89 | 61 |

TABLE 3-continued

| Name 1 | Structure 2 | IN VITRO | | IN VIVO Immature rat CX + DHT Antagonistic activity 0.5 mg/rat/po % Inhibition | | |
|---|---|---|---|---|---|---|
| | | Shionogi Anti-androgenic Activity IC$_{50}$ (nM) 3 | Human Androgen Receptor Binding (%) RBA R1881 = 100 4 | Prostate 5 | SV 6 | Bulbo 7 |
| EM-9039 | | 4.3 | 762 ± 396 (n = 2) | 62 | 89 | 59 |
| EM-9043 | | 3.4 | 175 | 43 ± 8 (n = 2) 0.1 mg/rat | 61 ± 3 (n = 2) 0.1 mg/rat | 52 ± 8 (n = 2) 0.1 mg/rat |
| EM-9049 | | 6.8 | 269 | 51 | 78 | 53 |
| EM-9050 | | 12 ± 2 (n = 2) | 317 ± 122 (n = 2) | 54 | 92 | 64 |
| EM-9052 | | 61 | 2010 ± 640 (n = 2) | 59 | 84 | 70 |

TABLE 3-continued

| Name 1 | Structure 2 | Shionogi Anti-androgenic Activity IC$_{50}$ (nM) 3 | Human Androgen Receptor Binding (%) RBA R1881 = 100 4 | IN VIVO Immature rat CX + DHT Antagonistic activity 0.5 mg/rat/po % Inhibition | | |
|---|---|---|---|---|---|---|
| | | | | Prostate 5 | SV 6 | Bulbo 7 |
| EM-9055 | | 10.6 | 7.3 | 51 | 91 | 73 |
| EM-9066 | | 11 ± 4 (n = 2) | 10.3 ± 1.3 (n = 2) | 50 ± 1 (n = 2) | 90 ± 1 (n = 2) | 64 ± 15 (n = 2) |
| EM-9067 | | 12.0 | 2.4 | 54 | 89 | 80 |
| EM-9070 | | 14.9 | 191 | 52 | 83 | 55 |
| EM-9089 | | 49 | 2.0 | 56 | 89 | 77 |

TABLE 3-continued

| Name | Structure | IN VITRO Shionogi Anti-androgenic Activity IC$_{50}$ (nM) | Human Androgen Receptor Binding (%) RBA R1881 = 100 | IN VIVO Immature rat CX + DHT Antagonistic activity 0.5 mg/rat/po % Inhibition | | |
|---|---|---|---|---|---|---|
| | | | | Prostate | SV | Bulbo |
| 1 | 2 | 3 | 4 | 5 | 6 | 7 |
| EM-9092 | | 11.2 | 72 | 57 | 90 | 55 |
| EM-9111 | | 19.0 | 1.0 ± 0.0 (n = 2) | 53 | 87 | 63 |
| EM-9114 | | 19.2 ± 0.3 (n = 2) | 7.9 ± 4.1 (n = 3) | 65 | 88 | 98 |
| EM-9115 | | 18 ± 4 (n = 5) | 12.5 ± 2.3 (n = 6) | 63 ± 2 (n = 2) | 89 ± 2 (n = 2) | 93 ± 2 (n = 2) |
| EM-9116 | | 17 ± 5 (n = 5) | 9.2 ± 1.9 (n = 5) | 57 ± 2 (n = 2) | 88 ± 2 (n = 2) | 87 ± 2 (n = 2) |

TABLE 3-continued

| Name | Structure | Shionogi Anti-androgenic Activity IC$_{50}$ (nM) | Human Androgen Receptor Binding (%) RBA R1881 = 100 | IN VIVO Immature rat CX + DHT Antagonistic activity 0.5 mg/rat/po % Inhibition ||| 
|---|---|---|---|---|---|---|
| | | | | Prostate | SV | Bulbo |
| 1 | 2 | 3 | 4 | 5 | 6 | 7 |
| EM-9117 | | 31 ± 10 (n = 5) | 2.5 ± 0.5 (n = 5) | 61 ± 9 (n = 2) | 90 ± 2 (n = 2) | 91 ± 11 (n = 2) |
| EM-9118 | | 15 ± 3 (n = 6) | 2.2 ± 0.4 (n = 6) | 58 ± 3 (n = 2) | 90 ± 1 (n = 2) | 83 ± 7 (n = 2) |
| EM-9119 | | 12.1 ± 0.5 (n = 2) | 122 | 58 | 81 | 74 |
| EM-9120 | | 9.2 ± 0.8 (n = 2) | 106 | 48 (0.2 mg/rat) | 82 (0.2 mg/rat) | 76 (0.2 mg/rat) |
| EM-9126 | | 173 | <0.1 | 47 | 79 | 90 |

TABLE 3-continued

| Name 1 | Structure 2 | Shionogi Anti-androgenic Activity IC$_{50}$ (nM) 3 | Human Androgen Receptor Binding (%) RBA R1881 = 100 4 | IN VIVO Immature rat CX + DHT Antagonistic activity 0.5 mg/rat/po % Inhibition | | |
|---|---|---|---|---|---|---|
| | | | | Prostate 5 | SV 6 | Bulbo 7 |
| EM-9150 | | 13 ± 3 (n = 5) | 74 ± 19 (n = 6) | 55 | 92 | 67 |
| EM-9156 | | 15 ± 3 (n = 7) | 17 ± 4 (n = 8) | 55 (0.3 mg/rat) | 89 (0.3 mg/rat) | 57 (0.3 mg/rat) |
| EM-9176 | | >100 | ~0.1 | 34 (0.1 mg/rat) | 51 (0.1 mg/rat) | 17 (0.1 mg/rat) |
| EM-9180 | | 24 | 1.7 | 53 | 85 | 71 |
| EM-9198 | | 5.3 | 22 | 52 | 90 | 71 |

TABLE 3-continued

| Name 1 | Structure 2 | Shionogi Anti-androgenic Activity IC$_{50}$ (nM) 3 | Human Androgen Receptor Binding (%) RBA R1881 = 100 4 | IN VIVO Immature rat CX + DHT Antagonistic activity 0.5 mg/rat/po % Inhibition Prostate 5 | SV 6 | Bulbo 7 |
|---|---|---|---|---|---|---|
| EM-9199 | | 27 | 2.3 | 52 | 86 | 79 |
| EM-9200 | | 66 | 2.5 | 56 | 95 | 78 |
| EM-9201 | | 9.7 | 70.8 | 10 | 48 | 29 |
| EM-9204 | | 7.0 | 22 | 62 | 91 | 66 |
| EM-9205 | | 14.8 | 17.9 | 65 | 87 | 73 |

TABLE 3-continued

| Name 1 | Structure 2 | IN VITRO | | IN VIVO Immature rat CX + DHT Antagonistic activity 0.5 mg/rat/po % Inhibition | | |
|---|---|---|---|---|---|---|
| | | Shionogi Anti- androgenic Activity $IC_{50}$ (nM) 3 | Human Androgen Receptor Binding (%) RBA R1881 = 100 4 | Prostate 5 | SV 6 | Bulbo 7 |
| EM-9208 | | 55 | 2.2 | 52 | 88 | 76 |
| EM-9221 | | 10.6 | 2.7 | 50 | 83 | 82 |
| EM-9225 | | 25 | 0.8 | 32 0.1 mg/rat | 68 (0.1 mg/rat) | 30 (0.1 mg/rat) |
| EM-9226 | | 23 | 2.4 | 54 | 87 | 73 |
| EM-9227 | | 16.4 | 4.9 | 61 | 93 | 84 |

TABLE 3-continued

|  |  | IN VITRO | | IN VIVO | | |
|---|---|---|---|---|---|---|
|  |  | Shionogi Anti-androgenic Activity IC$_{50}$ | Human Androgen Receptor Binding (%) RBA R1881 = | Immature rat CX + DHT Antagonistic activity 0.5 mg/rat/po % Inhibition | | |
| Name 1 | Structure 2 | (nM) 3 | 100 4 | Prostate 5 | SV 6 | Bulbo 7 |
| EM-9228 | | 53 | 0.4 | 57 | 94 | 81 |
| EM-9261 | | 27 | 2.5 | 57 | 88 | 85 |
| EM-9267 | | 16.0 | 5.5 | 55 | 87 | 76 |
| EM-9287 | | 12 ± 3 (n = 3) | 125 ± 9 (n = 3) | 37 (0.3 mg/rat) | 101 (0.3 mg/rat) | 71 (0.3 mg/rat) |
| EM-9288 | | 9.2 ± 2.0 (n = 3) | 24 ± 8 (n = 2) | 50 (0.3 mg/rat) | 101 (0.3 mg/rat) | 80 (0.3 mg/rat) |

TABLE 3-continued

| Name | Structure | Shionogi Anti-androgenic Activity IC$_{50}$ (nM) | Human Androgen Receptor Binding (%) RBA R1881 = 100 | IN VIVO Immature rat CX + DHT Antagonistic activity 0.5 mg/rat/po % Inhibition | | |
|---|---|---|---|---|---|---|
| | | | | Prostate | SV | Bulbo |
| 1 | 2 | 3 | 4 | 5 | 6 | 7 |
| EM-9340 | | 126 | 0.2 | 58 | 90 | 89 |
| EM-9342 | | 66 | 0.4 | 60 | 96 | 98 |
| EM-9343 | | 21 | 6.1 | 33 (0.1 mg/rat) | 64 (0.1 mg/rat) | 38 (0.1 mg/rat) |
| EM-9344 | | 51 | 0.8 | 35 ± 5 (n = 2, 0.1 mg/rat) | 65 ± 6 (n = 2, 0.1 mg/rat) | 56 ± 3 (n = 2, 0.1 mg/rat) |
| EM-9345 | | ~80 | 0.5 | 31 (0.1 mg/rat) | 56 (0.1 mg/rat) | 47 (0.1 mg/rat) |

ND = not determined

Legend of the Table 3:
In Column 1, the laboratory name of the antiandrogens is reported.
Column 2, the molecular structure of the antiandrogens is reported.
Column 3 represents the dose (expressed in nM) that inhibits by 50% ($IC_{50}$) the DHT-stimulated Shionogi mouse mammary carcinoma cell number. Lower values are preferable.
Column 4 represents the Relative Binding Affinity (RBA) of the antiandrogens expressed as percentage (%) on Human Androgen Receptor in transfected cells relative to R1881 as calculated by the formula:

$$\% \text{ RBA} = 100 \times IC_{50} R1881/IC_{50} \text{ (compound)}$$

Higher values are preferable.

Column 5 represents the % of antiandrogenic efficacy in rat prostate, expressed in percentage of inhibition.
The percentage of inhibition (% inhib) is calculated by the following formula:

$$\% \text{ Inhibition} = 100 - [W(\text{compound}) - W(\text{control } CX)/W(\text{DHT}) - W(\text{control } CX)] \times 100.$$

W is the weight of the prostate.
Higher values are preferable.

Column 6 represents the % of antiandrogenic efficacy in rat seminal vesicles, expressed in percentage of inhibition.
The percentage of inhibition (% inhib) is calculated by the following formula:

$$\% \text{ Inhibition} = 100 - [W(\text{compound}) - W(\text{control } CX)/W(\text{DHT}) - W(\text{control } CX)] \times 100.$$

W is the weight of the seminal vesicles.
Higher values are preferable.

Column 7 represents the % of antiandrogenic efficacy in rat bulbocavernosus muscles, expressed in percentage of inhibition.
The percentage of inhibition (% inhib) is calculated by the following formula:

$$\% \text{ Inhibition} = 100 - [W(\text{compound}) - W(\text{control } CX)/W(\text{DHT}) - W(\text{control } CX)] \times 100.$$

W is the weight of the bulbocavernosus muscles.
Higher values are preferable.

TABLE 4

| Structure and Name | IN VITRO | | IN VIVO Immature rat | | | | | | |
|---|---|---|---|---|---|---|---|---|---|
| | Shionogi Anti-androgenic Activity[a] IC$_{50}$ | Human Androgen Receptor Binding (%) RBA | CX + DHT Antagonistic activity 0.5 mg/rat/po % Inhibition | | | CX Agonistic activity 0.1 mg/rat/po % Stimulation | | | |
| 1 | (nM) 2 | R1881 = 100 3 | Prostate 4 | SV 5 | Bulbo 6 | Prostate 7 | SV 8 | Bulbo 9 | |
| Testosterone | | 11.1 ± 0.3 (n = 269) | ND | ND | ND | 99 (s.c.) | 115 (s.c.) | 171 (s.c.) | |
| EM-8656 | >100 | 477 ± 16 (n = 2) | 17 | 0 | 0 | 38 | 24 | 73 | |
| EM-8664 | >100 | 664 | 36 | −25 | −150 | 62 | 66 | 177 | |
| EM-8685 | >100 | 144 | 15 | −18 | −110 | 41 | 20 | 136 | |

TABLE 4-continued
| Structure and Name 1 | IN VITRO | | IN VIVO | | | | | | |
|---|---|---|---|---|---|---|---|---|---|
| | Shionogi Anti-androgenic Activity[a] IC$_{50}$ (nM) 2 | Human Androgen Receptor Binding (%) R1881 = 100 RBA (n = 3) 3 | Immature rat | | | | | | |
| | | | CX + DHT Antagonistic activity 0.5 mg/rat/po % Inhibition | | | CX Agonistic activity 0.1 mg/rat/po % Stimulation | | |
| | | | Prostate 4 | SV 5 | Bulbo 6 | Prostate 7 | SV 8 | Bulbo 9 |
| 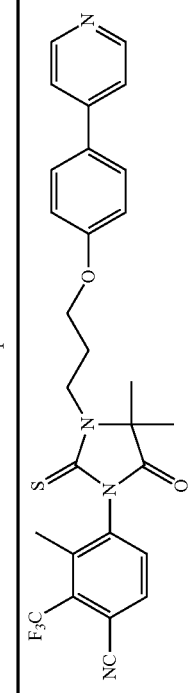 EM-8691 | >100 | 525 ± 362 | 21 | 14 | −115 | 39 | 24 | 163 |
| 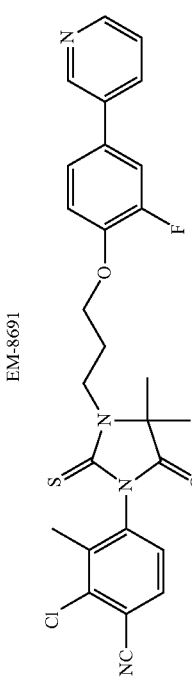 EM-8714 | 97 | 355 | ND | ND | ND | 45 | 18 | 78 |
| 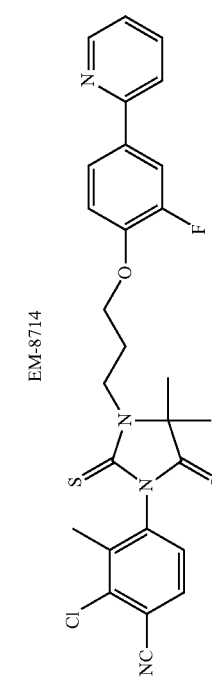 EM-8715 | 57.3 | 155 | ND | ND | ND | 35 | 11 | 58 |

TABLE 4-continued
| Structure and Name | Shionogi Anti-androgenic Activity[a] IC$_{50}$ (nM) | Human Androgen Receptor Binding (%) R1881 = 100 RBA | CX + DHT Antagonistic activity 0.5 mg/rat/po % Inhibition | | CX Agonistic activity 0.1 mg/rat/po % Stimulation | | |
|---|---|---|---|---|---|---|---|
| | | | Prostate | SV | Bulbo | Prostate | SV | Bulbo |
| 1 | 2 | 3 | 4 | 5 | 6 | 7 | 8 | 9 |
| 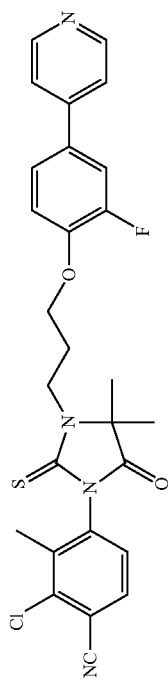 EM-8723 | 120 | 408 | 35 | −10 | −57 | 60 | 56 | 129 |
| 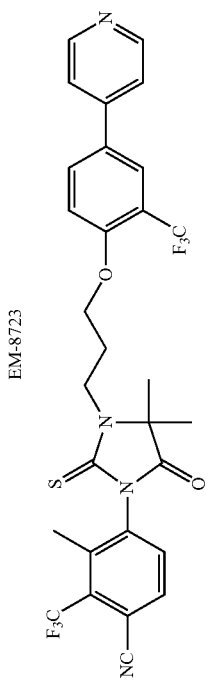 EM-8772 | 137 | 2.6 | 52 | 19 | −79 | 29 | 15 | 104 |
| 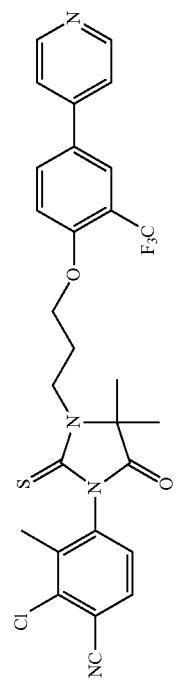 EM-8773 | 125 | 28.1 | 61 | 16 | −91 | 30 | 30 | 123 |

TABLE 4-continued

| | IN VITRO | | IN VIVO Immature rat | | | | | |
|---|---|---|---|---|---|---|---|---|
| | Shionogi Anti-androgenic Activity[a] IC$_{50}$ | Human Androgen Receptor Binding (%) R1881 = 100 RBA | CX + DHT Antagonistic activity 0.5 mg/rat/po % Inhibition | | | CX Agonistic activity 0.1 mg/rat/po % Stimulation | | |
| Structure and Name 1 | (nM) 2 | 3 | Prostate 4 | SV 5 | Bulbo 6 | Prostate 7 | SV 8 | Bulbo 9 |
| EM-8793 | 48.2 | 412 | 35 | −1 | −46 | 29 | 42 | 139 |
| EM-8796 | 188 | 698 | 23 | −119 | −132 | 58 | 127 | 168 |
| EM-8797 | 108 | 400 | 28 | −90 | −94 | 50 | 58 | 143 |

TABLE 4-continued

|  | IN VITRO | | IN VIVO Immature rat | | | | | | |
|---|---|---|---|---|---|---|---|---|---|
|  | Shionogi Anti-androgenic Activity[a] IC$_{50}$ | Human Androgen Receptor Binding (%) RBA | CX + DHT Antagonistic activity 0.5 mg/rat/po % Inhibition | | | CX Agonistic activity 0.1 mg/rat/po % Stimulation | | | |
| Structure and Name 1 | (nM) 2 | R1881 = 100 3 | Prostate 4 | SV 5 | Bulbo 6 | Prostate 7 | SV 8 | Bulbo 9 |
| EM-8798 | 130 | 219 | 16 | 0 | 0 | 49 | 25 | 114 |
| EM-8799 | 116 | 877 | 0 | 0 | 0 | 58 | 55 | 126 |
| EM-8815 | 80 | 159 | 8 (0.2 mg/rat) | −24 (0.2 mg/rat) | −126 (0.2 mg/rat) | 59 | 75 | 163 |

TABLE 4-continued

| Structure and Name 1 | IN VITRO | | IN VIVO Immature rat | | | | | |
|---|---|---|---|---|---|---|---|---|
| | Shionogi Anti-androgenic Activity[a] IC$_{50}$ (nM) 2 | Human Androgen Receptor Binding (%) R1881 = 100 RBA 3 | CX + DHT Antagonistic activity 0.5 mg/rat/po % Inhibition | | | CX Agonistic activity 0.1 mg/rat/po % Stimulation | | |
| | | | Prostate 4 | SV 5 | Bulbo 6 | Prostate 7 | SV 8 | Bulbo 9 |
| EM-8820 | 21.8 | 263 | 26 | 1 | −146 | 33 | 58 | 154 |
| EM-8821 | 11.5 | 28.3 | 34 | −5 | −134 | 22 | 22 | 74 |
| EM-8827 | 118 ± 14 (n = 2) | 113 | 3 (0.1 mg/rat) | 1 (0.1 mg/rat) | −108 (0.1 mg/rat) | 41 | 38 | 133 |

TABLE 4-continued

| | IN VITRO | | IN VIVO Immature rat | | | | | |
|---|---|---|---|---|---|---|---|---|
| | Shionogi Anti-androgenic Activity[a] IC$_{50}$ | Human Androgen Receptor Binding (%) RBA | CX + DHT Antagonistic activity 0.5 mg/rat/po % Inhibition | | | CX Agonistic activity 0.1 mg/rat/po % Stimulation | | |
| Structure and Name 1 | (nM) 2 | R1881 = 100 3 | Prostate 4 | SV 5 | Bulbo 6 | Prostate 7 | SV 8 | Bulbo 9 |
| EM-8828 | 96.5 | 112 | 31 | −26 | −137 | 40 | 31 | 161 |
| EM-8887 | 133 | 1890 ± 1040 (n = 2) | 32 | −64 | −134 | 55 | 107 | 214 |
| EM-8889 | 17.1 | 439 | 20 | 0 | 0 | 35 | 32 | 130 |

TABLE 4-continued

| Structure and Name 1 | IN VITRO | | IN VIVO Immature rat | | | | | |
|---|---|---|---|---|---|---|---|---|
| | Shionogi Anti-androgenic Activity[a] IC$_{50}$ (nM) 2 | Human Androgen Receptor Binding (%) R1881 = 100 RBA 3 | CX + DHT Antagonistic activity 0.5 mg/rat/po % Inhibition | | | CX Agonistic activity 0.1 mg/rat/po % Stimulation | | |
| | | | Prostate 4 | SV 5 | Bulbo 6 | Prostate 7 | SV 8 | Bulbo 9 |
| EM-8913 | >100 | 114 | 29 | −59 | −138 | 54 | 65 | 160 |
| EM-8922 | 79 | 414 | 20 | 0 | 0 | 52 | 54 | 134 |
| EM-8933 | 110 | 134 | 28 | 2 | 0 | 46 | 43 | 136 |

TABLE 4-continued

| Structure and Name | Shionogi Anti-androgenic Activity[a] IC$_{50}$ (nM) | Human Androgen Receptor Binding (%) R1881 = 100 RBA | CX + DHT Antagonistic activity 0.5 mg/rat/po % Inhibition | | | CX Agonistic activity 0.1 mg/rat/po % Stimulation | | |
|---|---|---|---|---|---|---|---|---|
| | | | Prostate | SV | Bulbo | Prostate | SV | Bulbo |
| 1 | 2 | 3 | 4 | 5 | 6 | 7 | 8 | 9 |
| EM-8974 | 112 | 41.9 | 34 | 11 | −96 | 61 | 24 | 139 |
| EM-8977 | 100 | 89.8 | −11 | −15 | −121 | 72 | 65 | 194 |
| EM-8993 | 59.5 | 4.8 | 24 | −43 | −74 | 50 | 61 | 123 |

TABLE 4-continued

| Structure and Name 1 | IN VITRO | | IN VIVO Immature rat | | | | | | |
|---|---|---|---|---|---|---|---|---|---|
| | Shionogi Anti-androgenic Activity[a] IC$_{50}$ (nM) 2 | Human Androgen Receptor Binding (%) R1881 = 100 RBA 3 | CX + DHT Antagonistic activity 0.5 mg/rat/po % Inhibition | | | CX Agonistic activity 0.1 mg/rat/po % Stimulation | | | |
| | | | Prostate 4 | SV 5 | Bulbo 6 | Prostate 7 | SV 8 | Bulbo 9 | |
| EM-8996 | 100 | 48.9 | 27 | −56 | −78 | 49 | 53 | 131 | |
| EM-9036 | >100 | 131 | 27 (0.1 mg/rat) | −50 (0.1 mg/rat) | −184 (0.1 mg/rat) | 24 (0.02 mg/rat) | 24 (0.02 mg/rat) | 142 (0.02 mg/rat) | |
| EM-9251 | 67.7 | 253 | 45 | 26 | −46 | 41 ± 2 (n = 2) | 27 ± 1 (n = 2) | 119 ± 24 (n = 2) | |

TABLE 4-continued

| Structure and Name 1 | IN VITRO | | IN VIVO Immature rat | | | | | |
|---|---|---|---|---|---|---|---|---|
| | Shionogi Anti-androgenic Activity[a] IC$_{50}$ (nM) 2 | Human Androgen Receptor Binding (%) R1881 = 100 RBA 3 | CX + DHT Antagonistic activity 0.5 mg/rat/po % Inhibition | | | CX Agonistic activity 0.1 mg/rat/po % Stimulation | | |
| | | | Prostate 4 | SV 5 | Bulbo 6 | Prostate 7 | SV 8 | Bulbo 9 |
| EM-9252 | >100 | 96.3 | 40 | 35 | −101 | 46 ± 5 (n = 2) | 29 ± 5 (n = 2) | 105 ± 9 (n = 2) |
| EM-9253 | 29.9 | 125 | 30 | 44 | −44 | 34 ± 1 (n = 2) | 18 ± 2 (n = 2) | 114 ± 18 (n = 2) |
| EM-9254 | 54.8 | 38.8 | 45 | 53 | −47 | 47 ± 6 (n = 3) | 23 ± 1 (n = 3) | 101 ± 5 (n = 3) |

TABLE 4-continued

| Structure and Name 1 | IN VITRO | | IN VIVO Immature rat | | | | | |
|---|---|---|---|---|---|---|---|---|
| | Shionogi Anti-androgenic Activity[a] IC$_{50}$ (nM) 2 | Human Androgen Receptor Binding (%) R1881 = 100 RBA 3 | CX + DHT Antagonistic activity 0.5 mg/rat/po % Inhibition | | | CX Agonistic activity 0.1 mg/rat/po % Stimulation | | |
| | | | Prostate 4 | SV 5 | Bulbo 6 | Prostate 7 | SV 8 | Bulbo 9 |
| EM-9290 | 64.8 | 197 | 41 | 47 | −75 | 39 ± 6 (n = 2) | 16 ± 2 (n = 2) | 88 ± 12 (n = 2) |
| EM-9291 | 75.5 | 64.2 | 42 | 56 | −45 | 47 ± 7 (n = 2) | 21 ± 7 (n = 2) | 91 ± 2 (n = 2) |
| EM-9297 | 72.8 | 101 | 31 ± 11 (n = 2, 0.1 mg/rat) | 37 ± 7 (n = 2, 0.1 mg/rat) | −57 ± 2 (n = 2, 0.1 mg/rat) | 31 | 26 | 120 |

TABLE 4-continued

| Structure and Name 1 | IN VITRO | | IN VIVO Immature rat | | | | | | |
|---|---|---|---|---|---|---|---|---|---|
| | Shionogi Anti-androgenic Activity[a] IC$_{50}$ (nM) 2 | Human Androgen Receptor Binding (%) R1881 = 100 RBA 3 | CX + DHT Antagonistic activity 0.5 mg/rat/po % Inhibition | | | CX Agonistic activity 0.1 mg/rat/po % Stimulation | | | |
| | | | Prostate 4 | SV 5 | Bulbo 6 | Prostate 7 | SV 8 | Bulbo 9 | |
| EM-9300 | 62.2 | 77.8 | 13 (0.1 mg/rat) | 21 (0.1 mg/rat) | −11 (0.1 mg/rat) | 40 ± 3 (n = 2) | 25 ± 2 (n = 2) | 127 ± 8 (n = 2) | |
| EM-9301 | 55.7 | 34.6 | 28 ± 4 (n = 2, 0.1 mg/rat) | 32 ± 4 (n = 2, 0.1 mg/rat) | −19 ± 13 (n = 2, 0.1 mg/rat) | 42 ± 1 (n = 2) | 29 ± 2 (n = 2) | 104 ± 17 (n = 2) | |
| EM-9305 | 32.3 | 26.2 | 27 ± 3 (n = 5, 0.1 mg/rat) | 31 ± 5 (n = 5, 0.1 mg/rat) | −45 ± 5 (n = 5, 0.1 mg/rat) | 34 ± 5 (n = 2) | 28 ± 3 (n = 2) | 110 ± 5 (n = 2) | |

TABLE 4-continued

| Structure and Name 1 | IN VITRO | | IN VIVO Immature rat | | | | | | |
|---|---|---|---|---|---|---|---|---|---|
| | Shionogi Anti-androgenic Activity[a] IC$_{50}$ (nM) 2 | Human Androgen Receptor Binding (%) R1881 = 100 RBA 3 | CX + DHT Antagonistic activity 0.5 mg/rat/po % Inhibition | | | CX Agonistic activity 0.1 mg/rat/po % Stimulation | | | |
| | | | Prostate 4 | SV 5 | Bulbo 6 | Prostate 7 | SV 8 | Bulbo 9 | |
| EM-9309 | 66.9 | 157 | 19 ± 12 (n = 2, 0.1 mg/rat) | 19 ± 8 (n = 2, 0.1 mg/rat) | −53 ± 8 (n = 2, 0.1 mg/rat) | 36 ± 1 (n = 2) | 24 ± 2 (n = 2) | 107 ± 9 (n = 2) | |
| EM-9310 | 60.0 | 92.8 | 25 ± 8 (n = 2, 0.1 mg/rat) | 37 ± 3 (n = 2, 0.1 mg/rat) | −39 ± 25 (n = 2, 0.1 mg/rat) | 44 ± 7 (n = 2) | 18 ± 2 (n = 2) | 109 ± 9 (n = 2) | |
| EM-9311 | >100 | 89.0 | 26 ± 13 (n = 2, 0.1 mg/rat) | 40 ± 1 (n = 2, 0.1 mg/rat) | −41 ± 12 (n = 2, 0.1 mg/rat) | 39 ± 1 (n = 2) | 24 ± 3 (n = 2) | 119 ± 8 (n = 2) | |

TABLE 4-continued

| Structure and Name 1 | IN VITRO | | IN VIVO Immature rat | | | | | |
|---|---|---|---|---|---|---|---|---|
| | Shionogi Anti-androgenic Activity[a] IC$_{50}$ (nM) 2 | Human Androgen Receptor Binding (%) R1881 = 100 RBA 3 | CX + DHT Antagonistic activity 0.5 mg/rat/po % Inhibition | | | CX Agonistic activity 0.1 mg/rat/po % Stimulation | | |
| | | | Prostate 4 | SV 5 | Bulbo 6 | Prostate 7 | SV 8 | Bulbo 9 |
| EM-9313 | >100 | 34.1 | 21 ± 8 (n = 2, 0.1 mg/rat) | 47 ± 20 (n = 2, 0.1 mg/rat) | −31 ± 17 (n = 2, 0.1 mg/rat) | 36 ± 2 (n = 2) | 14 ± 9 (n = 2) | 88 ± 2 (n = 2) |
| EM-9318 | 100 | 46.1 | 30 ± 5 (n = 2, 0.1 mg/rat) | 51 ± 13 (n = 2, 0.1 mg/rat) | −44 ± 2 (n = 2, 0.1 mg/rat) | 42 ± 3 (n = 2) | 14 ± 9 (n = 2) | 92 ± 27 (n = 2) |
| EM-9319 | 97.8 | 9.6 | 26 ± 3 (n = 2, 0.1 mg/rat) | 39 ± 19 (n = 2, 0.1 mg/rat) | −59 ± 4 (n = 2, 0.1 mg/rat) | 39 ± 2 (n = 2) | 17 ± 10 (n = 2) | 110 ± 10 (n = 2) |

TABLE 4-continued

| Structure and Name 1 | IN VITRO | | IN VIVO | | | | | | |
|---|---|---|---|---|---|---|---|---|---|
| | Shionogi Anti-androgenic Activity[a] IC$_{50}$ (nM) 2 | Human Androgen Receptor Binding (%) R1881 = 100 RBA 3 | Immature rat | | | | | | |
| | | | CX + DHT Antagonistic activity 0.5 mg/rat/po % Inhibition | | | CX Agonistic activity 0.1 mg/rat/po % Stimulation | | | |
| | | | Prostate 4 | SV 5 | Bulbo 6 | Prostate 7 | SV 8 | Bulbo 9 | |
| EM-9333 | 73.0 | 64.1 | 29 ± 9 (n = 3, 0.1 mg/rat) | 32 ± 3 (n = 3, 0.1 mg/rat) | −17 ± 2 (n = 3, 0.1 mg/rat) | 38 ± 2 (n = 2) | 19 ± 5 (n = 2) | 93 ± 23 (n = 2) | |
| EM-9334 | 28.9 | 17.8 | 33 (0.1 mg/rat) | 33 (0.1 mg/rat) | −21 (0.1 mg/rat) | 30 | 17 | 86 | |
| EM-9336 | ND | 32.3 | 15 (0.1 mg/rat) | 29 (0.1 mg/rat) | 13 (0.1 mg/rat) | 27 | 8 | 59 | |

TABLE 4-continued

| Structure and Name | IN VITRO | | IN VIVO Immature rat | | | | | |
|---|---|---|---|---|---|---|---|---|
| | Shionogi Anti-androgenic Activity[a] IC$_{50}$ (nM) | Human Androgen Receptor Binding (%) R1881 = 100 RBA | CX + DHT Antagonistic activity 0.5 mg/rat/po % Inhibition | | | CX Agonistic activity 0.1 mg/rat/po % Stimulation | | |
| | | | Prostate | SV | Bulbo | Prostate | SV | Bulbo |
| | 2 | 3 | 4 | 5 | 6 | 7 | 8 | 9 |
| 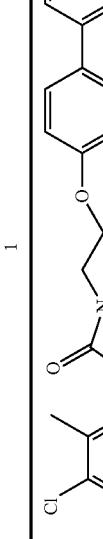 EM-9337 | ND | 28.3 | 35 (0.1 mg/rat) | 36 (0.1 mg/rat) | 3 (0.1 mg/rat) | 33 | 17 | 95 |
| 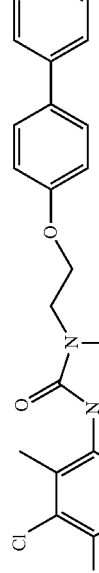 EM-9339 | ND | 4.0 | 30 (0.1 mg/rat) | 30 (0.1 mg/rat) | −11 (0.1 mg/rat) | 27 | 12 | 68 |

[a]Almost compounds have a stimulation at $10^{-7}$ M on basal Shionogi cells.
ND = not determined
s.c. = subcutaneous Legend of the Table 4:
In Column 1, the molecular structure and the laboratory name of the SARMs is reported.
Column 2 represents the dose (expressed in nM) that inhibits by 50% ($IC_{50}$) the DHT-stimulated Shionogi mouse mammary carcinoma cell number. Lower values are preferable.
Column 3 represents the Relative Binding Affinity (RBA) of the SARMs expressed as percentage (%) on Human Androgen Receptor in transfected cells relative to R1881 as calculated by the formula:

% RBA=100×$IC_{50}$R1881/$IC_{50}$ (compound)

Higher values are preferable.
Column 4 represents the % of antiandrogenic efficacy in rat prostate, expressed in percentage of inhibition.
The percentage of inhibition is calculated by the following formula:

% Inhibition=100−[W(compound)−W(control CX)/W (DHT)−W(control CX)]×100.

W is the weight of the prostate.
Higher values are preferable.
Column 5 represents the % of antiandrogenic efficacy in rat seminal vesicles, expressed in percentage of inhibition.
The percentage of inhibition is calculated by the following formula:

% Inhibition=100−[W(compound)−W(control CX)/W (DHT)−W(control CX)]×100.

W is the weight of the seminal vesicles.
Higher values are preferable.
Column 6 represents the % of antiandrogenic efficacy in rat bulbocavernosus muscles, expressed in percentage of inhibition.

The percentage of inhibition is calculated by the following formula:

% Inhibition=100−[W(compound)−W(control CX)/W (DHT)−W(control CX)]×100.

W is the weight of the bulbocavernosus muscles.
Lower values are preferable.
Column 7 represents the % of androgenic efficacy in rat prostate, expressed in percentage of stimulation.
The percentage of stimulation is calculated by the following formula:

Stimulation=[W(compound)−W(control CX)/W (DHT)−W(control CX)]×100.

W is the weight of the prostate.
Lower values are preferable.
Column 8 represents the % of androgenic efficacy in rat seminal vesicles, expressed in percentage of stimulation.
The percentage of stimulation is calculated by the following formula:

% Stimulation=[W(compound)−W(control CX)/W (DHT)−W(control CX)]×100.

W is the weight of the seminal vesicles.
Lower values are preferable.
Column 9 represents the % of androgenic efficacy in rat bulbocavernosus muscles, expressed in percentage of stimulation.
The percentage of stimulation is calculated by the following formula:

% Stimulation=[W(compound)−W(control CX)/W (DHT)−W(control CX)]×100.

W is the weight of the bulbocavernosus muscles.
Higher values are preferable.

TABLE 5

| | | IN VITRO | | IN VIVO | | | | |
| | | | | Immature rat | | | | |
| | | Human | | | | | | |
| | Shionogi | Androgen | | | | | | |
| | Anti- | Receptor | CX + DHT | | | CX | | |
| | Andro- | Binding | Antagonistic | | | Agonistic | | |
| | genic | (%) | activity | | | activity | | |
| | Activity | RBA | 0.5 mg/rat/po | | | 0.1 mg/rat/po | | |
| | $IC_{50}$ | R1881 = | % Inhibition | | | % Stimulation | | |
| Structure and Name | (nM) | 100 | Prostate | SV | Bulbo | Prostate | SV | Bulbo |
| 1 | 2 | 3 | 4 | 5 | 6 | 7 | 8 | 9 |
| Testosterone | | 11.1 ± 0.3 (n = 269) | ND | ND | ND | 99 (s.c.) | 115 (s.c.) | 171 (s.c.) |
| 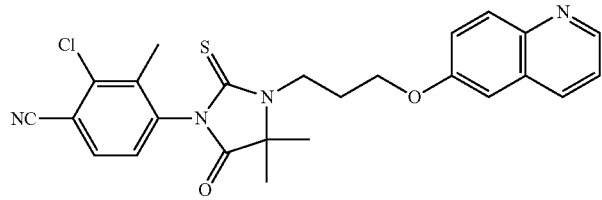<br>EM-8728 | 53.4[a] | 125.4 | 11 | 0 | 0 | 48 | 25 | 98 |

TABLE 5-continued

| | IN VITRO | | IN VIVO Immature rat | | | | | |
|---|---|---|---|---|---|---|---|---|
| | Shionogi Anti-Androgenic Activity IC$_{50}$ | Human Androgen Receptor Binding (%) RBA R1881 = | CX + DHT Antagonistic activity 0.5 mg/rat/po % Inhibition | | | CX Agonistic activity 0.1 mg/rat/po % Stimulation | | |
| Structure and Name 1 | (nM) 2 | 100 3 | Prostate 4 | SV 5 | Bulbo 6 | Prostate 7 | SV 8 | Bulbo 9 |
| EM-8730 | 105.3$^a$ | 140.5 | 0 | 0 | 0 | 59 | 73 | 178 |
| EM-8786 | 191 ± 87 (n = 2) | 8.9 ± 0.2 (n = 2) | 51 | 35 | −265 | 35 ± 10 (n = 2) | 10 ± 10 (n = 2) | 124 ± 32 (n = 2) |
| EM-8869 | ~1000$^a$ | 56 | 1 | 3 | 0 | 31 | 18 | 101 |
| EM-8889 | 31.1 | 38.1 | 32 | 51 | 20 | 1 | 0 | 3 |
| EM-8990 | 9.7 | 53.6 | 37 | 62 | 56 | 0 | 1 | 3 |
| EM-8991 | 38.5 | 28.5 | 41 | 74 | 58 | 2 | 2 | 1 |

TABLE 5-continued

| Structure and Name | IN VITRO | | IN VIVO Immature rat | | | | | |
|---|---|---|---|---|---|---|---|---|
| | Shionogi Anti-Androgenic Activity IC$_{50}$ (nM) | Human Androgen Receptor Binding (%) RBA R1881 = 100 | CX + DHT Antagonistic activity 0.5 mg/rat/po % Inhibition | | | CX Agonistic activity 0.1 mg/rat/po % Stimulation | | |
| 1 | 2 | 3 | Prostate 4 | SV 5 | Bulbo 6 | Prostate 7 | SV 8 | Bulbo 9 |
| EM-9010 | 10 | 29.5 | 37 | 44 | 50 | 0 | 0 | 5 |
| EM-9021 | 5.0$^a$ | 166.8 | 42 | 74 | 58 | 1 | 0 | 9 |
| EM-9028 | 2.6 | 25.3 | 42 | 64 | 10 | 2 | 2 | 1 |
| EM-9090 | 33.1 | 2.5 | 6 | 31 | 28 | 1 | 0 | 11 |
| EM-9093 | 23.1 | 0.6 | 20 (0.2 mg/rat) | 47 (0.2 mg/rat) | 21 (0.2 mg/rat) | 0 | 0 | 9 |

TABLE 5-continued

| | | IN VITRO | | IN VIVO Immature rat | | | | | |
|---|---|---|---|---|---|---|---|---|---|
| | | Shionogi | Human Androgen | CX + DHT Antagonistic activity 0.5 mg/rat/po % Inhibition | | | CX Agonistic activity 0.1 mg/rat/po % Stimulation | | |
| | | Anti-Androgenic Activity $IC_{50}$ | Receptor Binding (%) RBA R1881 = | | | | | | |
| Structure and Name | | (nM) | 100 | Prostate | SV | Bulbo | Prostate | SV | Bulbo |
| 1 | | 2 | 3 | 4 | 5 | 6 | 7 | 8 | 9 |
| EM-9302 | | 109.8 | 1.3 | 9 (0.1 mg/rat) | 10 (0.1 mg/rat) | −16 (0.1 mg/rat) | 29 | 8 | 57 |

[a] These compounds have a stimulation at $10^{-7}$M on basal Shionogi cells.
ND = not determined
s.c. = subcutaneous Legend of the Table 5:
In Column 1, the molecular structure and the laboratory name of the antiandrogens or SARMs is reported.
Column 2 represents the dose (expressed in nM) that inhibits by 50% ($IC_{50}$) the DHT-stimulated Shionogi mouse mammary carcinoma cell number. Lower values are preferable.
Column 3 represents the Relative Binding Affinity (RBA) of the antiandrogens or SARMs expressed as percentage (%) on Human Androgen Receptor in transfected cells relative to R1881 as calculated by the formula:

% RBA=100×$IC_{50}$R1881/$IC_{50}$ (compound)

Higher values are preferable.
Column 4 represents the % of antiandrogenic efficacy in rat prostate, expressed in percentage of inhibition.
The percentage of inhibition is calculated by the following formula:

% Inhibition=100−[W(compound)−W(control CX)/W (DHT)−W(control CX)]×100.

W is the weight of the prostate.
Higher values are preferable.
Column 5 represents the % of antiandrogenic efficacy in rat seminal vesicles, expressed in percentage of inhibition.
The percentage of inhibition is calculated by the following formula:

% Inhibition=100−[W(compound)−W(control CX)/W (DHT)−W(control CX)]×100.

W is the weight of the seminal vesicles.
Higher values are preferable.
Column 6 represents the % of antiandrogenic efficacy in rat bulbocavernosus muscles, expressed in percentage of inhibition.
The percentage of inhibition is calculated by the following formula:

% Inhibition=100−[W(compound)−W(control CX)/W (DHT)−W(control CX)]×100.

W is the weight of the bulbocavernosus muscles.
Column 7 represents the % of androgenic efficacy in rat prostate, expressed in percentage of stimulation.
The percentage of stimulation is calculated by the following formula:

% Stimulation=[W(compound)−W(control CX)/W (DHT)−W(control CX)]×100.

W is the weight of the prostate.
Lower values are preferable.
Column 8 represents the % of androgenic efficacy in rat seminal vesicles, expressed in percentage of stimulation.
The percentage of stimulation is calculated by the following formula:

% Stimulation=[W(compound)−W(control CX)/W (DHT)−W(control CX)]×100.

W is the weight of the seminal vesicles.
Lower values are preferable.
Column 9 represents the % of androgenic efficacy in rat bulbocavernosus muscles, expressed in percentage of stimulation.
The percentage of stimulation is calculated by the following formula:

% Stimulation=[W(compound)−W(control CX)/W (DHT)−W(control CX)]×100.

W is the weight of the bulbocavernosus muscles.

Efficacy of the Preferred Inhibitors

1) Materials and Methods
A—Androgen Receptor (AR) Assay
AR Transfection
Preparation of Human Embryonic Kidney (HEK-293) Cells Transfected with the Human Androgen Receptor (hAR):
Cells are cultured in 6-well Falcon flasks to approximately 3×$10^5$ cells/well in Dulbecco's modified Eagle's medium (DMEM) supplemented with 10% calf fetal serum at 37° C. under a 95% air, 5% $CO_2$ humidified atmosphere. Five µg of pCMVneo-hAR plasmid are transfected using the lipofectin transfection kit (Life Technologies, Ontario, Canada). After 6 h of incubation at 37° C., the transfection medium is removed and 2 ml of DMEM are added. Cells are further cultured for 48 h and then transferred into 10 cm petri dishes and cultured in DMEM containing 700 µg/ml of G-418 in order to inhibit the growth of non-transfected cells. Medium containing G-418 is changed every two days until resistant colonies are observed. Positive clones are selected by PCR. HEK 293 cells transfected with hAR are frozen until being used for the binding assay.

HEK-293 hAR Cell Cytosol Preparation:

On the morning of the binding assay, a pellet of HEK-293 hAR cells is thawed and suspended in buffer A (25 mM Tris-HCl, 1.5 mM EDTA disodium salt, 10 mM α-monothioglycerol, 10% glycerol, and 10 mM sodium molybdate, pH 7.4; 625 000 cells/0.1 ml). The cell suspension is sonicated for three periods of 30 sec (with intervals for cooling) and then centrifuged at 105 000×g for 90 min.

Rat Prostate Cytosol Preparation:

On the morning of the binding assay, ventral prostates collected from 24 h-gonadectomized rats were homogenized in buffer A (1 g of tissue in 5 mL) and the homogenate was centrifuged as described above.

Androgen Receptor Assay

Androgen binding is measured using the hydroxylapatite (HAP) assay. In brief, the radioactive steroid [$^3$H]R1881 solubilized in ethanol is diluted with buffer B (10 mM Tris-HCl, 1.5 mM EDTA disodium salt, 10 mM α-monothioglycerol, pH 7.4). Aliquots of the cell or prostate cytosol preparation (0.1 ml) are then incubated with 5 nM [$^3$H] R1881 (0.1 ml, ~100 000 cpm) in the presence or absence of the indicated concentrations of unlabeled compounds (0.1 ml, prepared in buffer B containing 30% ethanol) for 16-18 h at 0-4° C. Triamcinolone acetonide (TAC; 100 nM) is added to mask progesterone receptors. Unbound steroids are separated by incubation for 40 min at 0-4° C. with 0.3 ml HAP prepared in buffer P (50 mM Tris-HCl, 10 mM KH$_2$PO$_4$, pH 7.4). After incubation with HAP and 10 min of centrifugation at 1000×g, the pellet is washed 3 times with 1 ml of buffer P. Thereafter, the radioactivity is extracted from the pellet by incubation at room temperature for 60 min with 1 ml of ethanol. After centrifugation, the supernatant is decanted into a scintillation vial and the pellet is extracted again with ethanol. After the addition of scintillation liquid, the radioactivity is measured in a liquid scintillation counter.

Calculations

Dose-response curves as well as IC$_{50}$ values of the tested compounds (concentration of the compound causing a 50% displacing of [$^3$H](R1881) were calculated using a weighted iterative nonlinear least-square regression.

Relative binding affinity (RBA) was calculated by the following formula:

$$RBA (\%) [IC_{50}(R1881)/IC_{50} (compound)] \times 100$$

B—In Vitro Assay of Androgenic/Antiandrogenic Activity

The in vitro androgenic/antiandrogenic activity was measured using Shionogi mouse mammary carcinoma cells (clone 107) (Labrie et al., 1988a; Labrie et al., 1988b; Labrie et al., 1988c).

Materials

Minimal essential culture medium (MEM) and non-essential amino acids were purchased from Gibco BRL (NY, USA) while charcoal-stripped fetal calf serum (FBS) was purchased from Wisent Inc. (Montreal, Canada). Dihydrotestosterone (DHT) was obtained from Steraloids (Wilton, N.H.) while the compounds to be tested were synthesized in our laboratory.

Maintenance of Stock Cell Cultures

Shionogi cells were routinely grown in MEM supplemented with 100 nM DHT, 5% (v/v) charcoal-stripped FBS, 100 IU penicillin/ml, 50 µg streptomycin sulfate/ml, and 1% (v/v) non-essential amino acids, as previously described (Labrie et al., 1988a; Labrie et al., 1988b; Labrie et al., 1988c). Cells were incubated at 37° C. in a humidified atmosphere of 5% CO2 and 95% air. Cells were subcultured at near-confluence by gentle digestion in a solution of 0.1% trypsin (Wisent Inc.) in Hepes buffer containing 3 mM ethylenediaminetetraacetic acid (EDTA) (pH 7.2). Cells were then pelleted by centrifugation, resuspended in culture medium, and replated.

Measurement of Cell Proliferation

Cells were plated in 24-well plates at a density of 18 000 cells/well and allowed to adhere to the surface of the plates for 24 h. Thereafter, medium was replaced with fresh medium containing 2% (v/v) charcoal-stripped FBS and the indicated concentrations of compounds diluted from stock solutions at a ×1000 concentration in 99% redistilled ethanol in the presence or absence of DHT (0.3 nM). Control cells received only the ethanolic vehicle (0.1% EtOH, v/v). Such a concentration of ethanol does not affect cell growth. The indicated increasing concentrations of agents were added to triplicate dishes, and cells were grown for 10 days with changes of medium every 2-3 days. Cell number was determined by measurement of DNA content as previously described (Simard et al., 1990).

Calculations

Dose-response curves as well as IC$_{50}$ values of the tested compounds are calculated using a weighted iterative non-linear least-squares regression. All results are expressed as means±SEM, except when SEM overlaps with the symbol used in which instances only the symbol is illustrated. IC$_{50}$ is the concentration of the compound giving a 50% inhibition of DHT action on cell growth. The percentage of stimulation on basal level at a specific concentration of a compound (i.e. $10^{-7}$ M) is calculated by [(DNA content with a compound−DNA content without a compound)/DNA content without a compound]×100.

Measurement of Prostate Specific Antigen (PSA) in LNCaP Cells

LNCaP cells were cultured as previously described (Qi et al. 2001). In brief, the LNCaP cells were cultured for 6 days in 1.0 ml RPMI 1640 supplemented with hormone-depleted 0.25% FCS before each experiment. At the start of the experiment, half of the medium (0.5 ml) was replaced with 0.5 ml of identical medium containing the appropriate concentrations of tested compounds, in the presence or absence of 1.0 nM of R1881. After 72 h of incubation of LNCaP cells with compounds, 0.5 ml of culture medium was removed for PSA determination. PSA levels were measured using the PSA [$^{125}$I] IRMA KIT (REF: RK-10CT) from Izotop (Institute of Isotopes Ltd, Budapest, Hungary).

C—Determination of Oral Absorption of Compounds

Experiment 1

Animals

Intact 6 week-old male rats (Crl:CD(SD)) weighing 150-205 g were obtained from Charles-River Canada Inc. (St-Constant, Quebec, Canada) and housed up to 3 per cage in plastic bins in a temperature (19° C. to 25° C.)- and light (12 h light/day)-controlled environment. They were acclimatized to laboratory conditions for 2 weeks prior to the pharmacokinetic (PK) study. The rats were fed rodent chow (PMI Nutrition International Certified Rodent Chow No. 5CR4 (14% protein)) and tap water ad libitum. Animals were weighing 165-200 g at the time of dosing.

Dosing and Blood Collection

EM-9150 was administered orally by gavage (in the afternoon) at a dose of 20 mg/kg (5 ml/kg) to 9 intact male rats. EM-9150 was administered as a suspension in 0.4% aqueous methylcellulose (MeC). Blood samples (~0.4 mL/timepoint/rat) were collected by jugular venipuncture at 0.5, 1, 2, 3.5, 7 and 24 h post-dosing from 3 animals/timepoint. Blood samples were put into tubes containing EDTA($K_3$) as anticoagulant and centrifuged at 4° C. for 10 min at 2700 rpm. The resulting plasma was separated and transferred to 2 polypropylene tubes, frozen immediately over dry ice and kept in a freezer set to maintain −80° C. until analysis.

Plasma Analysis

Plasma concentrations of EM-9150 and its metabolites EM-9156 and EM-9260 were determined using a GLP-validated liquid chromatography with mass spectrometric detection assay (LC-MS/MS). Plasma concentrations for each compound versus time were put in graph (FIG. 5) and were used to calculate the area under the plasma concentration curve from 0 to 24 hr post-dose [$AUC_{(0-24h)}$]. $AUC_{(0-24hr)}$ values were calculated using a linear trapezoidal method.

Experiment 2

Animals

Castrated male Sprague-Dawley rats (Crl:CD(SD)Br) weighing 275-375 g were used for pharmacokinetic studies. Animals were fasted (access to water only) from around 16 h00 the afternoon prior to the dosing day.

Dosing and Blood Collection

EM-9150 was administered orally by gavage (in the morning) at a dose of 0.5 mg/animal (1.0 ml/animal; 3 animals/compound). EM-9150 was dissolved in dimethylsulfoxide (DMSO, 10% final concentration) and administered as a solution/suspension in 0.9% NaCl-1% gelatin). Blood samples (~0.5 mL/timepoint) were collected by jugular venipuncture on animals under isoflurane anesthesia at 1, 2, 3, 4, 7 and 24 h post-dosing. Blood samples were put into tubes containing EDTA($K_3$) as anticoagulant and centrifuged at 4° C. for 10 min at 1700-2400 g. The resulting plasma was frozen on dry ice and kept at −80° C. pending analysis. After the blood collection 7 h post-dosing, the ventral prostate and the bulbocavernosus muscles were collected from one rat per group for determination of the intraprostatic and intramuscular concentration of EM-9150 and its metabolite EM-9156. Prostates and bulbocavernosus muscles were frozen in liquid nitrogen and kept at −80° C. until being used. A buffer and an ethanol-acetone solution were added to the tissue and homogenized with a Polytron. The supernatant was collected, evaporated to dryness and reconstituted in buffer.

Plasma Analyses

Plasma concentrations of EM-9150 and its metabolite EM-9156 were determined using liquid chromatography with mass spectrometric detection assay (LC-MS/MS). The plasma concentration of each compound versus time was used to calculate the area under the plasma concentration curve from 0 to 24 hr post-dose [$AUC_{(0-24h)}$]. $AUC_{(0-24hr)}$ values were calculated using a linear trapezoidal method. Intraprostatic and intramuscular concentrations of the compounds were also determined by LC-MS/MS.

D—Systemic Antiandrogenic/Androgenic Activity in Orchidectomized Immature Male Rats Animals Immature male rats (Crl:CD(SD)Br) 22 to 24-day old weighting 60-80 g at start of treatment were obtained from Charles-River, Inc. (St-Constant, Quebec, Canada) and housed up to 5 per cage in plastic bins in a temperature (23±1° C.)- and light (12 h light/day, lights on at 7 h15)-controlled environment. The rats were fed rodent chow and tap water ad libitum. Compounds were tested in castrated rats supplemented (antagonistic activity) or not (agonistic activity) with an androgen. The day following their arrival, the designed animals were orchidectomized (CX) under Isoflurane anesthesia (Study Day 1) via the scrotal route and were then randomly assigned to groups of 3 to 5 animals. At the time of orchidectomy, one silastic implant of dihydrotestosterone (DHT; 1 cm length of pure DHT in silastic tubing having inner and outer diameter of 0.078 and 0.125 inches, respectively), was inserted subcutaneously in the dorsal area of animals assigned to the evaluation of antiandrogenic activity. In the case of intact animal experiments, the orchidectomy and the silastic implant installation are omitted.

Treatments

Tested compounds were administered orally once daily for 7 days from Study Day 2 to Study Day 8 at doses generally ranging from 0.1 and 0.5 mg/animal. Compounds were either solubilized in dimethylsulfoxide (DMSO, 10% final concentration) and were administered as a solution/suspension in 0.9% NaCl-1% gelatin or were administered as suspensions in 0.4% aqueous methylcellulose. Animals of the control groups received the corresponding vehicle alone during the 7-day period. Some animals were treated with the antiandrogen Flutamide or Casodex as reference. The animals under isoflurane anesthesia were killed by cervical dislocation on day 9 of the study, approximately 24 h after the last dosing. The ventral prostate, seminal vesicles and bulbocavernosus muscles were rapidly dissected and weighed.

Calculations

For antagonistic activity, the percentage of inhibition is calculated using the following formula:

% inhibition=100−[[W(compound)−W(control CX)/W (control DHT)−W(control CX)]×100].

For agonistic activity, the percentage of stimulation versus DHT is calculated by the following formula:

% stimulation=[W(compound)−W(control CX)/W (control DHT)−W(control CX)]×100.

For calculations with intact animals, control DHT is replaced by control intact and the % stimulation is subtracted by 100%.

W is the weight of the prostate, seminal vesicles or bulbocavernosus muscles.

Discussion

A series of non-steroidal compounds, with an arylhydantoin or arylthiohydantoin backbone possessing a side-chain containing a phenylpyridine or quinoline or isoquinoline able to modify the interaction of the non-steroidal backbone with the Androgen Receptor, were synthesized. As seen in Tables 1 to 5 and FIGS. 1 and 2, these compounds show affinities for the Human Androgen Receptor (and Rat Androgen receptor) with a Relative Binding Affinity (RBA) ranging from the modest value of about 0.1% to a high value of 3310% (for EM-8851) compared to a value of 100% for R1881, a well-known synthetic and metabolism-resistant synthetic androgen having an affinity for the human androgen receptor similar to DHT (dihydrotestosterone), the most potent natural androgen. The reported RBAs of these new compounds are higher than the antiandrogen references, namely hydroxyflutamide and bicalutamide (0.21% and 0.3%). For example, the RBA values of some of our preferred antiandrogens, namely EM-9150 (74±19%), EM-9198 (22%), EM-9204 (22%) and EM-9205 (17.9%) are 352, 105, 105 and 85 times higher than the RBA value of hydroxyflutamide, respectively. Moreover, the RBA values of some of our preferred SARMs, namely EM-9251 (253%), EM-9253 (125%), EM-9290 (197%) and EM-9309 (157%) are 1200, 595, 938 and 748 times higher than the RBA value of hydroxyflutamide, respectively. The effect of the variation of some substituents on the affinity to the androgen receptor has been previously discussed above.

Antiandrogens of the Invention

All antiandrogens of the invention show a potent and pure antiandrogenic activity in Shionogi mouse mammary carcinoma cells as well as in vivo on prostate and seminal vesicle weight in the rat. These compounds reverse the 0.3 nM DHT-induced cell proliferation with $IC_{50}$ values ranging from 2.6 nM (EM-9028) to 126 nM while the $IC_{50}$ of hydroxyflutamide and bicalutamide are 67±2 nM and 190±36 nM, respectively (Tables 1, 2, 3 and 5, and FIG. 3). Thus, the $IC_{50}$ values of some of the preferred antiandrogens, namely EM-9150 (13±3 nM), EM-9198 (5.3 nM), EM-9204 (7.0 nM) and EM-9205 (14.8 nM) are 5.2, 6.4, 4.8 and 2.3 times higher than the $IC_{50}$ value of hydroxyflutamide when compared in the same experiment.

The most active antiandrogens of the invention on the DHT-induced proliferation of Shionogi cells, namely EM-8900, EM-9025, EM-9028, EM-9039 and EM-9043 ($IC_{50}$=2.6 to 4.3 nM) are approximately 7 to 22 times more potent than hydroxyflutamide. Most importantly, none of these compounds has any activity on the basal level of Shionogi cell proliferation, thus indicating their pure antiandrogenic activity.

The antiandrogens of the invention show a potent inhibition of the prostate specific antigen (PSA) levels measured in culture medium following a 72 h-incubation period with human prostate cancer LNCaP cells (Table 1 and FIG. 4). For example, EM-9150 is 10 times more potent than bicalutamide in blocking R1881-stimulated PSA secretion, in addition to no stimulation at $10^{-7}$M on basal level (FIG. 4). The same results are observed with EM-9156 and other compounds.

These compounds show a fair to excellent oral bioavailability (FIG. 5). The metabolism of these compounds has been discussed above. For example, of major interest are the findings 7 h after oral dosing with 0.5 mg of EM-9150/rat of plasma, intraprostatic and intramuscular concentrations of EM-9150 measured at 0.9 ng/ml, 2.9 ng/g and 1.2 ng/g, respectively and EM-9156, one of its active metabolites, measured at 22.3 ng/ml, 19.3 ng/g and 12.7 ng/g, respectively. This experiment confirms that both compounds reach target tissues. The concentration of EM-9150 in the rat prostate is approximately 3 times higher than in plasma in comparison to EM-9156 wherein both concentrations are similar but higher than EM-9150. This observation is very important due to the fact that the major metabolite EM-9260 which represents approximately 90% of the plasma exposure of EM-9150, does not bind well to the androgen receptor (RBA-0.1%) contrary to EM-9150 and EM-9156 where very good affinities were observed (RBA=74±19% and 17±4%, respectively) (Table 2, FIG. 5). Moreover, these three antiandrogenic compounds are active in vitro and in vivo.

The major interest of these compounds is that they show a potent and pure antiandrogenic activity in vivo in male rats. As seen in Tables 1, 2, 3 and 5 and FIG. 6 in orchidectomized immature male rats bearing DHT implants, daily oral administration of 0.5 mg/rat of these compounds reversed by 32-71% and 44-96% the stimulatory effect of DHT on ventral prostate and seminal vesicle weight, respectively, while the same dose of flutamide (0.5 mg/rat) is required to achieve comparable inhibitions (48% and 83% inhibitions on prostate and seminal vesicle weight, respectively). At the dose of 0.5 mg/rat, the inhibitions achieved by some of the preferred antiandrogens, namely EM-9150, EM-9198, EM-9204 and EM-9205 are 55%, 52% 62% and 65% on ventral prostate, and 92%, 90%, 91% and 87% on seminal vesicle-DHT stimulated weight, respectively (Table 3). FIG. 6 shows the effect of 7-day daily treatment with increasing doses of flutamide (FLU), bicalutamide and EM-9150 on ventral prostate weight in castrated (CX) immature male rats bearing a DHT implant. These compounds have similar activities but bicalutamide seems reaching a plateau at higher doses where it is not the case with EM-9150. The antiandrogens described in the invention also inhibit the weight of bulbocavernosus muscles in rat model with DHT implants.

Interestingly, the daily oral administration of these compounds to orchidectomized immature rats has no stimulatory effect on ventral prostate and seminal vesicle weight including bulbocavernosus muscle weight, thus showing that these compounds exert a pure antiandrogenic activity without any intrinsic androgenic activity (Tables 3 and 5, and FIG. 7).

The present data show that the non-steroidal antiandrogens described in the invention are more potent on androgen-sensitive parameters than currently available antiandrogens, thus indicating that these compounds should be developed as systemic antiandrogens for the treatment of androgen-dependant diseases especially prostate cancer.

Since EM-9150 and EM-9156 are 10 times more potent than bicalutamide in blocking the stimulatory effect of the androgen R1881 on PSA secretion in human LNCaP cells and similar in vivo activity in rat, in addition to the absence of agonistic effect, the present data suggest that assuming similar metabolism in men and rat, EM-9150 and EM-9156 could be 10 times more potent than bicalutamide for the treatment of men with prostate cancer.

SARMs of the Invention

As shown in Tables 2, 4 and 5, SARMs of the invention have usually a mixed androgenic/antiandrogenic activity on the proliferation of Shionogi cells. The $IC_{50}$ values of some of the preferred SARMs, namely EM-9251 (67.7 nM), EM-9253 (29.9 nM), EM-9290 (64.8 nM) and EM-9309 (66.9 nM) are similar to the $IC_{50}$ value of hydroxyflutamide (67±2 nM) but with a stimulation at $10^{-7}$ M on basal levels except EM-9253 (38%, 25% and 13%, respectively).

In animal models, the prostate is a well-recognized parameter of androgenic activity, while the androgen-sensitive bulbocavernosus muscles, which are located beside the levator ani muscle (Poortmans and Wyndaele; 1998), are a valuable tool to evaluate anabolic activity. As shown in Tables 2, 4 and 5, and in FIG. 8, SARMs of the invention have shown mixed androgenic/antiandrogenic activity in the immature rat models. In fact, these compounds have a slight to moderate stimulatory effect on the prostate and seminal vesicles in CX rats while a strong androgenic effect is observed in the muscle. On the other hand, these compounds reverse the DHT-induced stimulation of the prostate but none of these compounds exerts an antiandrogenic activity in the muscle (seminal vesicles show variable results in this model (inhibition, stimulation or no effect)). Moreover, in intact rat model, we observed in some cases (i.e. EM-9251) a clear inhibition of the prostate and seminal vesicles but always a stimulation of the muscle. Thus, EM-9251 inhibits intact rat prostate and seminal vesicles of 25±4% and 35±7%, respectively, while stimulates the bulbocavernosus muscles of 77±6% (FIG. 8).

At the dose of 0.1 mg/rat, the highest stimulations achieved by the SARMs of the invention, namely EM-8664, EM-8730, EM-8796, EM-8887 and EM-8977 are 177%, 178% 168%, 214% and 194% on bulbocavernosus muscles, respectively (Tables 4 and 5). At the same dose, the stimulations achieved by some of our preferred SARMs, namely EM-9251, EM-9253, EM-9290 and EM-9309 are 119±24, 114±18, 88±2 and 107±9, respectively (Table 4). In Table 4, we found that thiohydantoin derivatives have higher stimulation of the bulbocavernosus muscles than the hydantoin derivatives. On the other hand, the thiohydantoin derivatives have a stimulation (or inactive) of the seminal vesicles in reversing the DHT-induced stimulation of the rat seminal vesicles in comparison to hydantoin derivatives where inhibitions are observed (Table 4, column 5). Subclasses of SARMs are anticipated.

At column 6 of Tables 2, 4 and 5, the negative values of the percentage of inhibition of bulbocavernosus muscles are a further proof of the stimulation of bulbocavernosus muscles of SARM compounds observed in column 9.

One of the major interest of these SARMs is that they show some potent antiandrogenic activity in vivo in male rats but with some agonistic activity. As seen in Tables 2, 4 and 5 in orchidectomized immature male rats bearing DHT implants, daily oral administration of 0.5 mg/rat of these compounds reversed by 0-61% the stimulatory effect of DHT on ventral prostate weight, while the same dose of flutamide (0.5 mg/rat) is required to achieve comparable inhibitions in the best cases (48% inhibition on prostate). At the dose of 0.5 mg/rat, the inhibitions achieved by some of the preferred SARMs, namely EM-9251, EM-9253 and EM-9290 are 45%, 30% and 41% on ventral prostate-DHT stimulated weight (Tables 2 and 4).

With the above-indicated activities, SARMs of the invention are useful in the treatment and prevention of the benign prostatic hyperplasia and in the prevention of the prostate cancer. This could be useful also while avoiding stimulation of the prostate and seminal vesicles to treat sarcopenia and other diseases/medical problems in need of androgenic activity: male hypogonadism, loss of libido, erectile dysfunction and female sexual dysfunction as indicated by the increase in vaginal nerve density in Pelletier et al. 2012 and 2013.

EXAMPLES OF SYNTHESIS OF PREFERRED INHIBITORS

Proton NMR spectra were recorded on a Bruker Avance 400 MHz instrument. The following abbreviations have been used: s, singlet; d, doublet; dd, doublet of doublet; t, triplet; q, quadruplet; p, pentet; b, broad; and m, multiplet. The chemical shifts (d) were referenced to chloroform (7.26 ppm for $^1$H), acetone (2.05 ppm for $^1$H) or methanol (3.33 ppm for $^1$H) and were expressed in ppm. Thin-layer chromatography (TLC) was performed on 0.25 mm Kieselgel 60F254 plates (E. Merck, Darmstadt, FRG). For flash chromatography, Merck-Kieselgel 60 (230-400 mesh A.S.T.M.) was used. Unless otherwise noted, starting material and reactant were obtained commercially and were used as such or purified by standard means. All purified and dried solvents and reactants were stored under argon. Anhydrous reactions were performed under an inert atmosphere, the set-up assembled and cooled under argon. Organic solutions were usually dried over sodium sulfate, evaporated on a rotatory evaporator and under reduced pressure. Starting materials and reagents were mainly available from Aldrich Chemical Company, Inc. (Milwaukee, Wis.).

Example 1

Synthesis of EM-9150 and Derivatives

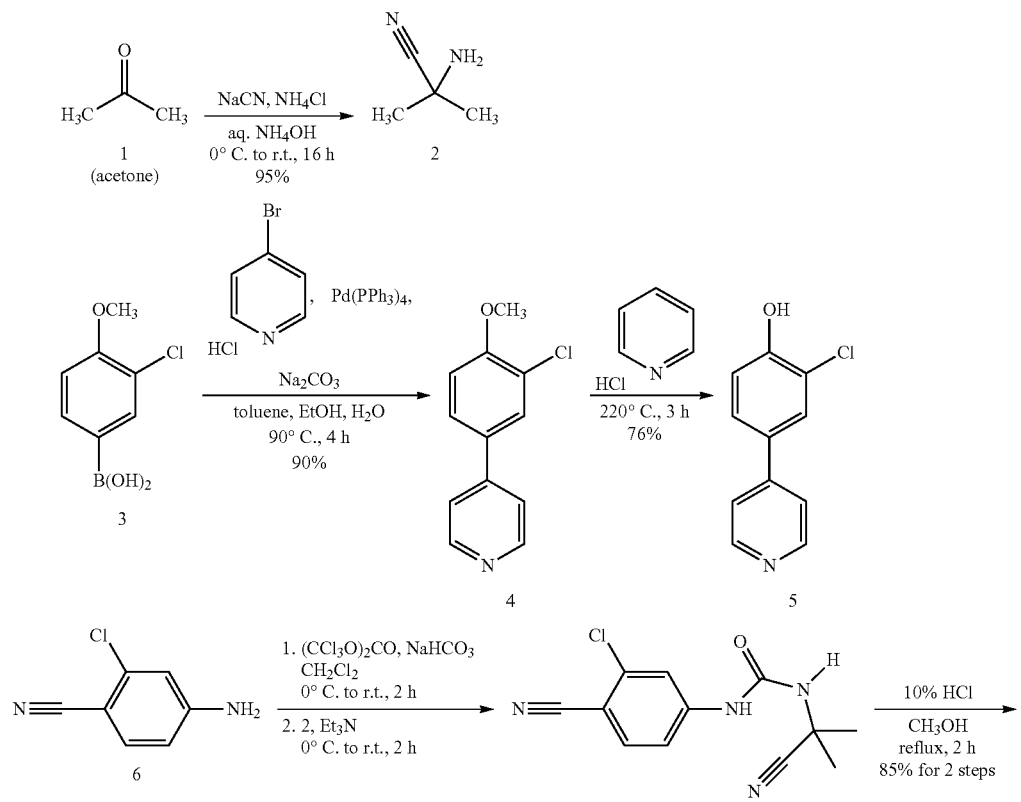

Scheme 2

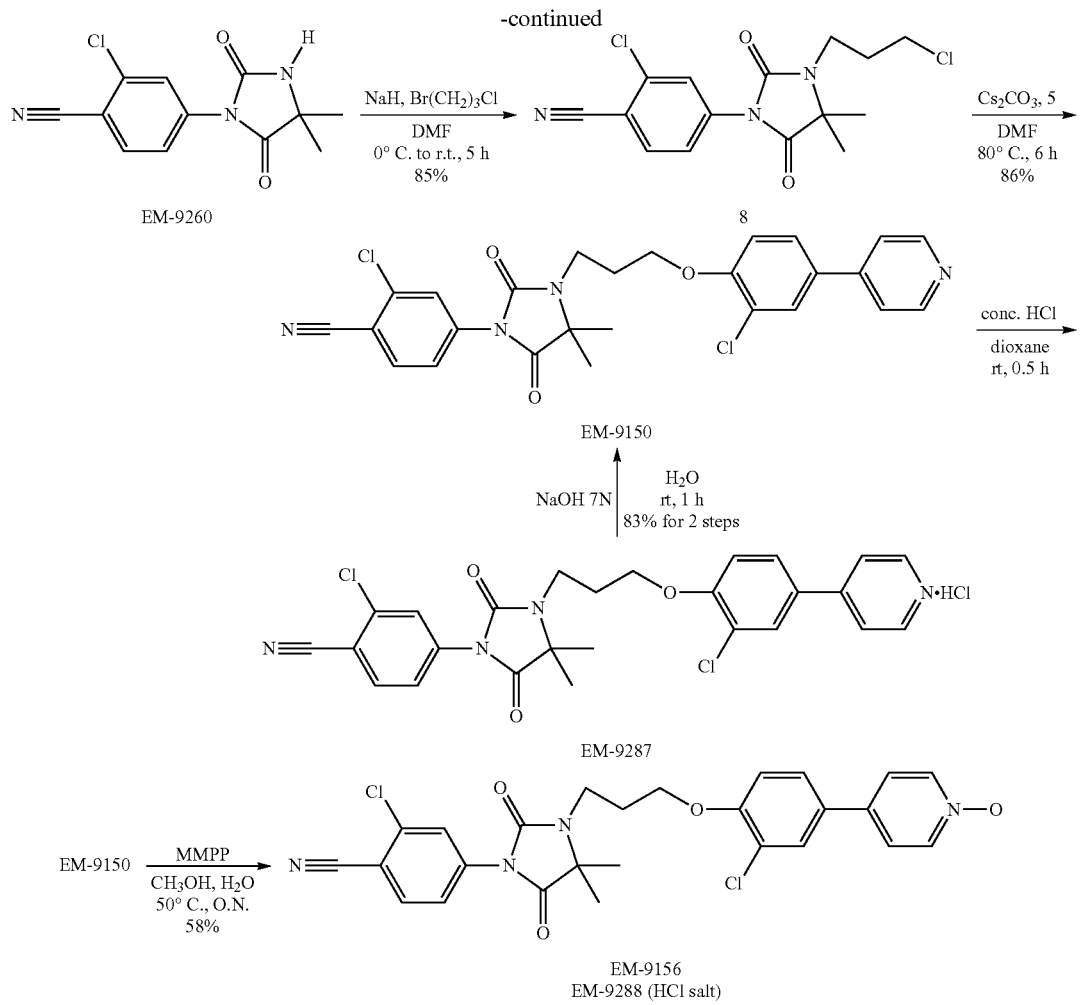

Preparation of Compound 2

A solution of sodium cyanide (30.7 g, 0.62 mol) and ammonium chloride (39.5 g, 0.74 mol) in 28% aqueous ammonium hydroxide solution (240 mL, 1.7 mol) was stirred with a mechanical stirrer, cooled to 0° C., slowly treated with acetone (1) (36.8 mL, 0.50 mol) and stirred overnight after removing the ice-water bath. The reaction mixture was extracted with dichloromethane (3×300 mL). The combined organic layer was dried over sodium sulfate, filtered and evaporated in vacuo to give compound 2 as clear liquid (40 g, 95%). $^1$H NMR (400 MHz, CDCl$_3$) δ: 1.48 (s, 6H, 2 Me), 1.64 (bs, 2H, NH$_2$).

Preparation of Compound 4

A mixture of 4-bromopyridine hydrochloride (52.8 g, 0.27 mol) and 3-chloro-4-methoxyphenylboronic acid (3) (60.8 g, 0.33 mol) in toluene-ethanol-water (2:2:1, 675 mL) was flushed with argon for 15 min, slowly treated with sodium carbonate (115 g, 1.08 mol), flushed with argon for an additional 10 min period, treated with tetrakis(triphenylphosphine)palladium(0) (7.87 g, 6.81 mmol), and heated at 90° C. for 4 h. The reaction mixture was cooled to room temperature, evaporated (toluene and ethanol), diluted with water (1.1 L), acidified with concentrated HCl to pH 1, and filtered on a Buchner funnel. The filtrate was neutralized with sodium hydroxide pellets followed by sodium carbonate to pH 7. The suspension was filtered on a Buchner funnel, and the obtained solid 4 was dried overnight and used in the next step without further purification (53.9 g, 90%).

Preparation of Compound 5

A mixture of compound 4 (53.9 g, 0.25 mol) and pyridine hydrochloride (280 g, 2.4 mol) was heated to 220° C. for 3 h, cooled to room temperature, poured in water (1.2 L), neutralized with sodium carbonate to pH 7, and filtered on a Buchner funnel. The obtained solid 5 was dried overnight without further purification (38.3 g, 76%). $^1$H NMR (400 MHz, acetone-d$_6$) δ: 7.15 (d, 1H, Ar), 7.65 (m, 3H, Ar and Pyr), 7.8 (s, 1H, Ar), 8.6 (d, 2H, Pyr), 9.2 (bs, 1H, OH).

Preparation of EM-9260

Under an argon atmosphere, a solution of triphosgene (8.31 g, 28 mmol) in dichloromethane (700 mL) was cooled to 0° C., treated with sodium bicarbonate (33.6 g, 400 mmol) and 4-amino-2-chlorobenzonitrile (6) (12.2 g, 80 mmol) by portions and stirred with a mechanical stirrer for 15 min. and 2 h after removing the ice-water bath. The reaction mixture which contains the crude isocyanate derivative was cooled to 0° C., slowly treated with triethylamine (25.7 mL, 184 mmol) and 2-amino-2-methylpropionitrile (2) (7.4 mL, 80 mmol) and stirred for 2 h after removing the ice-water bath. The reaction mixture was filtered on a Buchner funnel and the filtrate was evaporated in vacuo. The crude urea intermediate 7 was dissolved in methanol (200 mL). The solution was stirred with a mechanical stirrer, treated with an aqueous 10% hydrochloric acid solution until pH 1 was obtained, and refluxed for 2 h. The reaction mixture was successively cooled to room temperature and with an ice-water bath, and treated with cold water (250 mL). The suspension was filtered then the filtrate was extracted with dichloromethane (2×300 mL). The combined organic layer was evaporated in vacuo. The residue was dissolved in methanol (100 mL), and the obtained solution was treated with cold water (125 mL) and filtered. The combined solids were dried overnight and diluted in dichloromethane (850 mL). The suspension were stirred with a mechanical stirrer for 2 h and filtered, and the filtrate was evaporated in vacuo to give the desired EM-9260 (18.0 g, 85%). $^1$H NMR (400 MHz, acetone-$d_6$) δ: 1.53 (s, 6H, 2 Me), 7.74 (bs, 1H, NH), 7.81 (dd, J=1.9 and 8.5 Hz, 1H, Ar), 7.95 (d, J=1.9 Hz, 1H, Ar), 8.00 (d, J=8.5 Hz, 1H, Ar).

Preparation of Compound 8

Under an argon atmosphere, a suspension of sodium hydride (2.27 g, 0.095 mol, rinsed with hexanes) in anhydrous N,N-dimethylformamide (45 mL) was cooled at 0° C. and slowly treated with 3-bromo-1-chloropropane (4.9 mL, 0.049 mol) and with a solution of EM-9260 (10.0 g, 0.038 mol) in anhydrous N,N-dimethylformamide (30 mL). The reaction mixture was stirred for 5 h and gradually warmed to room temperature during this period. Then, the reaction mixture was poured in cooled-ice water (300 mL) and filtered on a Buchner funnel. The obtained solid 8 was dried overnight and used in the next step without further purification (11.0 g, 85%). $^1$H NMR (400 MHz, acetone-$d_6$) δ: 1.6 (s, 6H, 2 Me), 2.2 (m, 2H, CH$_2$), 3.5 (t, 2H, CH$_2$Cl), 3.7 (t, 2H, CH$_2$N), 7.8 (d, 1H, Ar), 7.9 (s, 1H, Ar), 8.0 (d, 1H, Ar).

Preparation of EM-9150

A mixture of compound 8 (55.0 g, 0.16 mol) and compound 5 (36.4 g, 0.18 mol) in anhydrous N,N-dimethylformamide (325 mL) was treated with cesium carbonate (68.5 g, 0.21 mol) and heated at 80° C. for 6 h. The reaction mixture was cooled at room temperature, diluted with acetone (1 L), poured in cooled-ice water (2 L), and filtered on a Buchner funnel. The obtained lightly orange solid EM-9150 was dried overnight without further purification (70.6 g, 86%). $^1$H NMR (400 MHz, acetone-$d_6$) δ: 1.60 (s, 6H, 2 Me), 2.32 (p, J=6.6 Hz, 2H, CH$_2$), 3.71 (t, J=7.0 Hz 2H, CH$_2$N), 4.35 (t, J=5.9 Hz 2H, CH$_2$O), 7.27 (d, J=8.6 Hz, 1H, Ar), 7.65 (d, J=6.1 Hz, 2H, Pyr), 7.76 (dd, J=2.3 and 8.6 Hz, 1H, Ar), 7.79 (dd, J=1.9 and 8.5 Hz, 1H, Ar), 7.85 (d, J=2.3 Hz, 1H, Ar), 7.88 (d, J=1.9 Hz, 1H, Ar), 7.97 (d, J=8.5 Hz, 1H, Ar), 8.62 (d, J=6.2 Hz, 2H, Pyr).

Purification of EM-9150

A solution of EM-9150 (100.7 g, 0.198 mol) in 1,4-dioxane (1.5 L) which was slightly heated for complete dissolution was slowly treated with concentrated hydrochloric acid (14.75 M) (14.8 mL, 0.218 mol). The reaction mixture was stirred for 0.5 h and filtered. The obtained EM-9287 as a lightly beige solid was dried. $^1$H NMR (400 MHz, methanol-$d_4$) δ: 1.60 (s, 6H, 2 Me), 2.33 (p, J=5.7 Hz, 2H, CH$_2$), 3.72 (t, J=6.6 Hz 2H, CH$_2$N), 4.41 (t, J=5.5 Hz 2H, CH$_2$O), 7.35 (d, J=8.8 Hz, 1H, Ar), 7.70 (dd, J=1.9 and 8.5 Hz, 1H, Ar), 7.74 (d, J=1.8 Hz, 1H, Ar), 7.87 (d, J=8.6 Hz, 1H, Ar), 8.01 (dd, J=2.4 and 8.7 Hz, 1H, Ar), 8.11 (d, J=2.4 Hz, 1H, Ar), 8.36 (d, J=7.0 Hz, 2H, Pyr), 8.81 (d, J=6.9 Hz, 2H, Pyr). The crude EM-9287 was suspended in water (1.5 L) and treated with an aqueous solution of sodium hydroxide 7N (31 mL, 0.22 mol). The reaction mixture was stirred for 1 h and filtered. The obtained EM-9150 as a lightly yellow solid was dried to give 83.7 g (83%) and further purified by flash chromatography (silica gel, 4 separations of around 20 g, 30-80% acetone in dichloromethane) to give 83.0 g of pure EM-9150 (chemical purity of 99.3% by HPLC).

Preparation of EM-9156 and EM-9288

To a suspension of EM-9150 (550 mg, 1.08 mmol) in methanol-water/5:2 (20 mL) was added magnesium monoperoxyphthalate (MMPP) (1.33 g, 2.7 mmol). The solution was heated at 50° C. overnight. After completion of the reaction (TLC), the mixture was diluted with aqueous saturated sodium bicarbonate and extracted with dichloromethane (3×). The combined organic layer was dried over sodium sulfate, filtered, and concentrated under reduced pressure. The crude compound was purified by flash chromatography (silica gel, 20% acetone-dichloromethane) to give 332 mg (58%) of EM-9156. $^1$H NMR (400 MHz, acetone-$d_6$) δ: 1.59 (s, 6H, 2 Me), 2.31 (p, J=6.4 Hz, 2H, CH$_2$), 3.70 (t, J=7.0 Hz 2H, CH$_2$N), 4.34 (t, J=5.8 Hz 2H, CH$_2$O), 7.25 (d, J=8.7 Hz, 1H, Ar), 7.71 (m, 3H, Ar and Pyr), 7.78 (dd, J=1.9 and 8.5 Hz, 1H, Ar), 7.82 (d, J=2.3 Hz, 1H, Ar), 7.88 (d, J=1.9 Hz, 1H, Ar), 7.97 (d, J=8.5 Hz, 1H, Ar), 8.17 (d, J=7.4 Hz, 2H, Pyr). EM-9288, the hydrochloride salt of EM-9156, was prepared by using the procedure described for EM-9287. $^1$H NMR (400 MHz, methanol-$d_4$) δ: 1.60 (s, 6H, 2 Me), 2.32 (p, J=5.6 Hz, 2H, CH$_2$), 3.72 (t, J=6.7 Hz 2H, CH$_2$N), 4.38 (t, J=5.4 Hz 2H, CH$_2$O), 7.31 (d, J=8.7 Hz, 1H, Ar), 7.70 (dd, J=1.9 and 8.5 Hz, 1H, Ar), 7.75 (d, J=1.8 Hz, 1H, Ar), 7.88 (m, 2H, Ar), 7.99 (d, J=1.5 Hz, 1H, Ar), 8.16 (bs, 2H, Pyr), 8.71 (bs, 2H, Pyr).

Example 2

Synthesis of EM-9251 and Derivatives

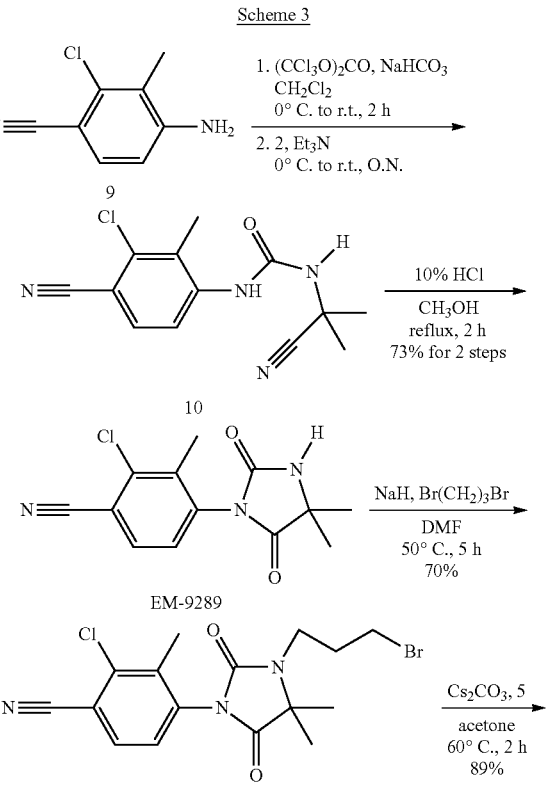

Scheme 3

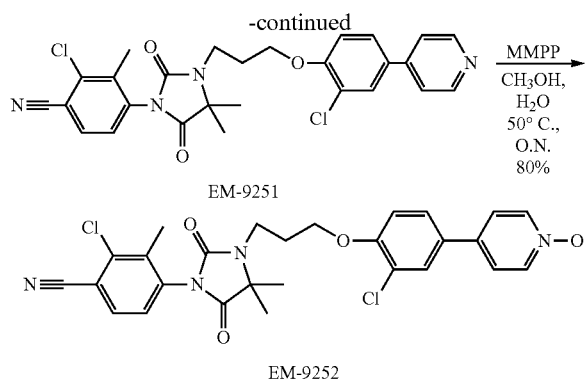

EM-9251

EM-9252

Preparation of EM-9289

Under an argon atmosphere, a solution of triphosgene (2.08 g, 7.01 mmol) in dichloromethane (200 mL) was cooled to 0° C., treated with sodium bicarbonate (8.5 g, 100 mmol) and 3-chloro-4-cyano-2-methylaniline (9) (obtained from the procedure described in Li, J. J. et al., J. Med. Chem., 2007, 50(13), 3015-3025, supporting information, pages S2 and S3) (3.33 g, 20 mmol) by portions and stirred for 15 min. and 2 h after removing the ice-water bath. The reaction mixture which contains the crude isocyanate derivative was cooled to 0° C., slowly treated with triethylamine (6.2 mL, 44 mmol) and 2-amino-2-methylpropionitrile (2) (1.9 mL, 21 mmol) and stirred overnight after removing the ice-water bath. The reaction mixture was filtered on a Buchner funnel and the filtrate was evaporated in vacuo. The crude urea intermediate 10 was dissolved in methanol (100 mL). The solution was stirred, treated with an aqueous 10% hydrochloric acid solution until pH 1 was obtained, and refluxed for 4 h. The reaction mixture was successively cooled to room temperature and with an ice-water bath, and treated with cold water (200 mL). The suspension was filtered then the filtrate was extracted with dichloromethane (3×150 mL). The combined organic layer was evaporated in vacuo. The solids were combined to give the desired EM-9289 (4.04 g, 73%). $^1$H NMR (400 MHz, acetone-$d_6$) δ: 1.55 (s, 3H, Me), 1.56 (s, 3H, Me), 2.29 (s, 3H, Me of aromatic group), 7.52 (d, J=8.3 Hz, 1H, Ar), 7.70 (bs, 1H, NH), 7.88 (dd, J=0.4 and 8.3 Hz, 1H, Ar).

Preparation of Compound 11

Under an argon atmosphere, a suspension of sodium hydride (60% dispersed in mineral oil, 75 mg, 1.9 mmol) and EM-9289 (420 mg, 1.5 mmol) in anhydrous N,N-dimethylformamide (9 mL) was stirred for 30 min. and slowly treated with 1,3-dibromopropane (0.75 mL, 7.4 mmol). The reaction mixture was heated at 50° C. for 5 h. Then, the reaction mixture was cooled at room temperature, diluted with water (50 mL) and extracted with ether (4×25 mL). The combined organic layer was dried over sodium sulfate, filtered, and concentrated under reduced pressure. The crude compound was purified by flash chromatography (silica gel, 0-100% acetone-hexanes) to give 400 mg (70%) of compound 11.

Preparation of EM-9251

A mixture of compound 11 (100 mg, 0.25 mmol) and compound 5 (70 mg, 0.34 mmol) in acetone (3 mL) was treated with cesium carbonate (148 mg, 0.46 mmol) and heated at 60° C. for 2 h. The reaction mixture was cooled at room temperature and filtered on Celite™. The filtrate was evaporated under reduced pressure and the residue (solubilized in dichloromethane) was filtered on silica gel. The crude compound was purified by flash chromatography (silica gel, 20% acetone-dichloromethane) to give 116 mg (89%) of EM-9251. $^1$H NMR (400 MHz, acetone-$d_6$) δ: 1.61 (s, 3H, Me), 1.62 (s, 3H, Me), 2.29 (s, 3H, Me of aromatic group), 2.32 (p, J=6.4 Hz, 2H, $CH_2$), 3.69 (dt, J=1.9 and 7.2 Hz, 2H, $CH_2N$), 4.32 (dt, J=1.2 and 6.0 Hz, 2H, $CH_2O$), 7.27 (d, J=8.6 Hz, 1H, Ar), 7.50 (d, J=8.3 Hz, 1H, Ar), 7.65 (d, J=6.1 Hz, 2H, Pyr), 7.76 (dd, J=2.3 and 8.6 Hz, 1H, Ar), 7.85 (dd, J=0.4 and 8.3 Hz, 1H, Ar), 7.87 (d, J=2.3 Hz, 1H, Ar), 8.62 (d, J=6.1 Hz, 2H, Pyr).

Preparation of EM-9252

EM-9252 was prepared starting from EM-9251 by using the procedure described for EM-9156 except that the extractions were done with ethyl acetate instead of dichloromethane. The crude compound was purified by flash chromatography (silica gel, 5% methanol-dichloromethane) to give 48 mg (80%) of EM-9252. $^1$H NMR (400 MHz, acetone-$d_6$) δ: 1.60 (s, 3H, Me), 1.62 (s, 3H, Me), 2.29 (s, 3H, Me of aromatic group), 2.31 (p, J=7.3 Hz, 2H, $CH_2$), 3.69 (dt, J=1.8 and 7.0 Hz, 2H, $CH_2N$), 4.32 (dt, J=1.3 and 5.9 Hz, 2H, $CH_2O$), 7.25 (d, J=8.7 Hz, 1H, Ar), 7.50 (d, J=8.3 Hz, 1H, Ar), 7.71 (d, J=7.4 Hz, 2H, Pyr), 7.72 (dd, J=2.5 and 8.6 Hz, 1H, Ar), 7.85 (d, J=2.4 Hz, 1H, Ar), 7.86 (dd, J=0.4 and 7.5 Hz, 1H, Ar), 8.16 (d, J=7.4 Hz, 2H, Pyr).

Example 3

Synthesis of EM-9052

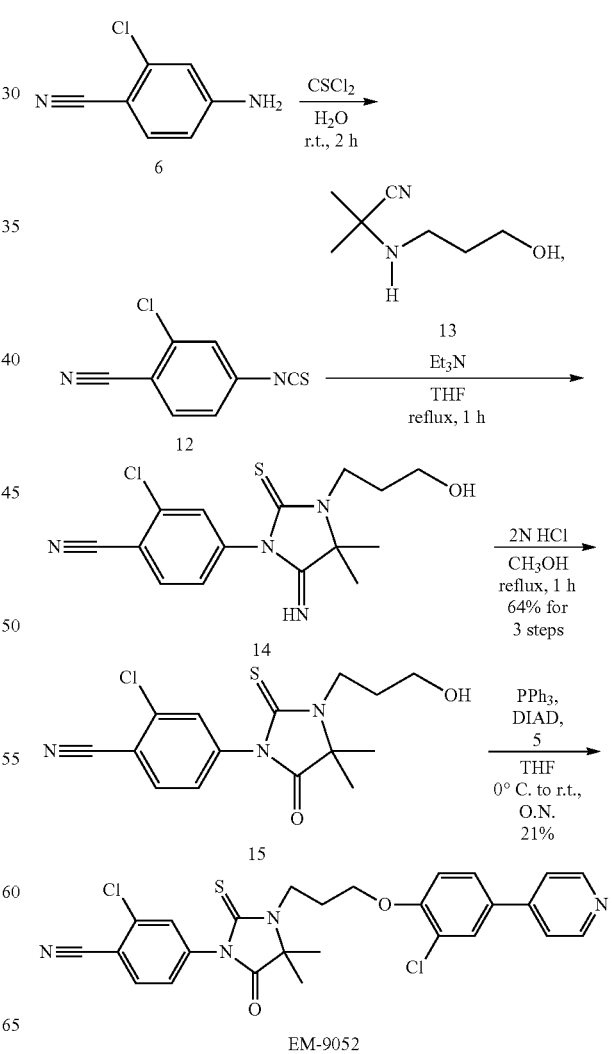

Scheme 4

EM-9052

117

Preparation of Compound 12

A suspension of 3-chloro-4-cyanoaniline (6) (1.12 g, 7.3 mmol) in water (15 mL) was slowly treated with thiophosgene (0.84 mL, 11 mmol) and stirred for 2 h. The reaction mixture was diluted with water and extracted with dichloromethane (3×). The combined organic layer was dried over sodium sulfate, filtered, and concentrated under reduced pressure. The crude isothiocyanate 12 was used in the next step without further purification.

Preparation of Compound 14

A solution of isothiocyanate 12 (1.43 g, 7.3 mmol), 2-(3-hydroxy-propylamino)-2-methyl-propionitrile (13) (obtained from the procedure described in WO 2006/133567, page 58) and triethylamine (0.1 mL, 0.7 mmol) in anhydrous tetrahydrofuran (35 mL) was refluxed for 1 h. The reaction mixture was cooled to room temperature and concentrated under reduced pressure. The crude alcohol 14 was used in the next step without further purification.

Preparation of Compound 15

A solution of alcohol 14 (2.47 g, 7.3 mmol) in a mixture of methanol and aqueous 2N hydrochloric acid solution in a 1:1 ratio (36 mL) was refluxed for 1 h. Then, the reaction mixture was cooled at room temperature, diluted with water and extracted with dichloromethane (3×). The combined organic layer was dried over sodium sulfate, filtered, and concentrated under reduced pressure. The crude compound was purified by chromatography (Biotage system, silica gel, 20-30% acetone-hexanes) to give 1.58 g (64% for 3 steps) of compound 15.

Preparation of EM-9052

Under an argon atmosphere, a solution of alcohol 15 (102 mg, 0.30 mmol), phenol 5 (60 mg, 0.29 mmol) and triphenylphosphine (81 mg, 0.31 mmol) in anhydrous tetrahydrofuran (3 mL) was cooled to 0° C. and slowly treated with diisopropyl azodicarboxylate (DIAD) (0.06 mL, 0.3 mmol). The reaction mixture was stirred overnight after removing the ice-water bath. The reaction mixture was concentrated under reduced pressure. The crude compound (solubilized in acetone) was filtered on silica gel. The crude compound was purified by flash chromatography (silica gel, 40% acetone-hexanes) to give 32 mg (21%) of EM-9052. $^1$H NMR (400 MHz, acetone-$d_6$) δ: 1.67 (s, 6H, 2 Me), 2.46 (m, 2H, CH$_2$), 4.08 (m, 2H, CH$_2$N), 4.36 (t, J=6.0 Hz, 2H, CH$_2$O), 7.29 (d, J=8.6 Hz, 1H, Ar), 7.66 (m, 3H, Ar and Pyr), 7.77 (dd, J=2.3 and 8.6 Hz, 1H, Ar), 7.84 (d, J=1.9 Hz, 1H, Ar), 7.88 (d, J=2.3 Hz, 1H, Ar), 8.04 (d, J=8.3 Hz, 1H, Ar), 8.59 (d, J=6.1 Hz, 2H, Pyr).

Example 4

Synthesis of EM-8799

Scheme 5

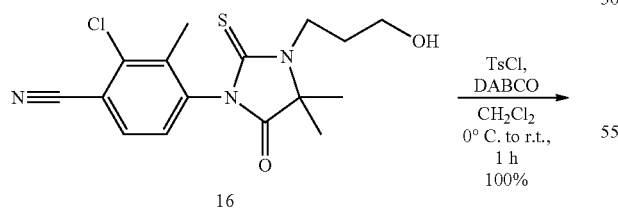

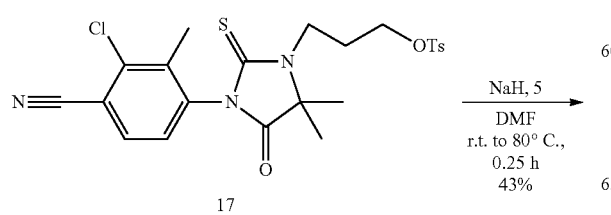

118

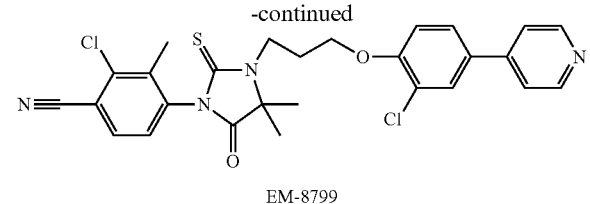

EM-8799

Preparation of Compound 17

Under an argon atmosphere, a solution of compound 16 (obtained by the same procedure than compound 15 (except that methanol was evaporated before work-up without dilution with water) in 24% yield starting with 3-chloro-4-cyano-2-methylaniline (9) (obtained from the procedure described in Li, J. J. et al. J. Med. Chem. 2007, 50(13), 3015-3025, supporting information, pages S2 and S3)) (89 mg, 0.25 mmol) in dichloromethane (1 mL) was cooled to 0° C., treated with 1,4-diazabicyclo[2.2.2]octane (DABCO) (62 mg, 0.55 mmol) and p-toluenesulfonyl chloride (75 mg, 0.39 mmol) and stirred 1 h after removing the ice-water bath. The reaction mixture was diluted with aqueous saturated ammonium chloride and extracted with dichloromethane (2×). The combined organic layer was dried over sodium sulfate, filtered, and concentrated under reduced pressure. The crude tosylate 17 was used in the next step without further purification.

Preparation of EM-8799

Under an argon atmosphere, a solution of phenol 5 (78 mg, 0.38 mmol) in N,N-dimethylformamide (1 mL) was treated with sodium hydride (60% dispersed in mineral oil, 19 mg, 0.48 mmol), stirred for 30 min., treated with a solution of tosylate 17 (128 mg, 0.25 mmol) in N,N-dimethylformamide (2 mL) and heated at 80° C. for 15 min. The reaction mixture was cooled at room temperature, diluted with ether and washed with water (2×). The organic layer was dried over sodium sulfate, filtered, and concentrated under reduced pressure. The crude compound (solubilized in dichloromethane) was filtered on silica gel. The crude compound was also purified by two flash chromatographies (silica gel, 30% acetone-hexanes and 20-50% ether-dichloromethane) to give 58 mg (43%) of EM-8799. $^1$H NMR (400 MHz, acetone-$d_6$) δ: 1.69 (s, 3H, Me), 1.69 (s, 3H, Me), 2.27 (s, 3H, Me of aromatic group), 2.47 (p, J=7.1 Hz, 2H, CH$_2$), 4.07 (m, 2H, CH$_2$N), 4.35 (t, J=6.0 Hz, 2H, CH$_2$O), 7.29 (d, J=8.6 Hz, 1H, Ar), 7.55 (d, J=8.2 Hz, 1H, Ar), 7.66 (d, J=6.2 Hz, 2H, Pyr), 7.77 (dd, J=2.3 and 8.6 Hz, 1H, Ar), 7.88 (d, J=2.1 Hz, 1H, Ar), 7.90 (d, J=7.6 Hz, 1H, Ar), 8.62 (d, J=6.0 Hz, 2H, Pyr).

Example 5

Synthesis of EM-8798

Scheme 6

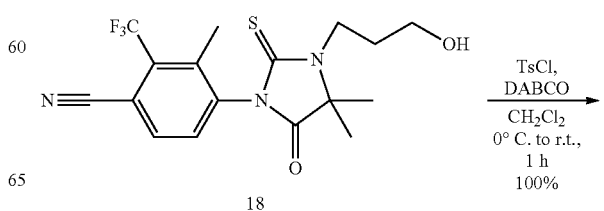

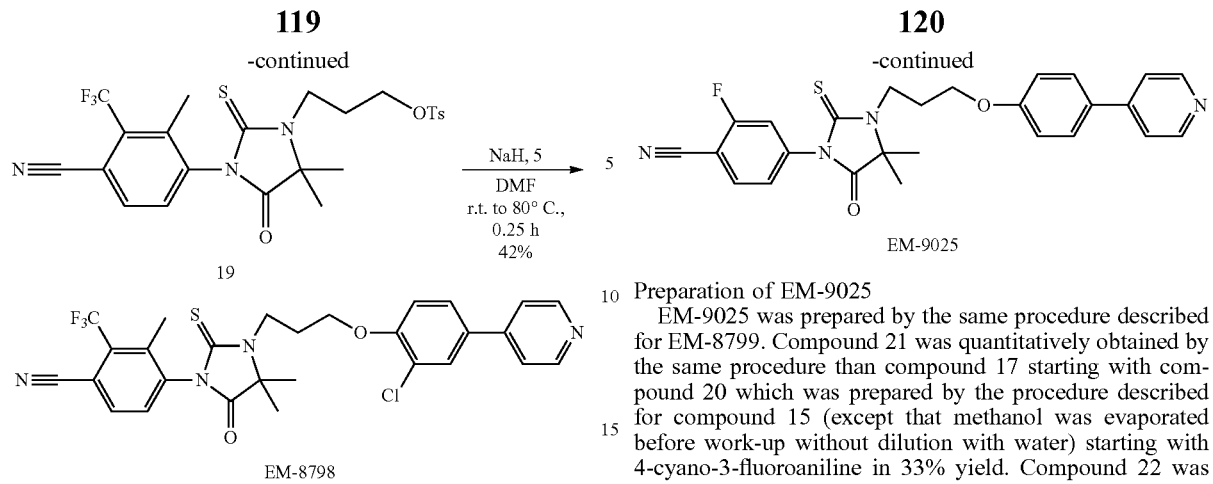

EM-8798

Preparation of EM-8798

EM-8798 was prepared by the same procedure described for EM-8799. Compound 19 was quantitatively obtained by the same procedure than compound 17 starting with compound 18 which was prepared by the procedure described for compound 15 (except that an aqueous saturated sodium bicarbonate was used instead of water in the dilution of the reaction mixture) starting with 4-cyano-2-methyl-3-trifluoromethylaniline (obtained from the procedure described in US 2004/0181064, pages 41-42) in 52% yield. The crude EM-8798 was purified by flash chromatography (silica gel, 30% acetone-hexanes) to give 55 mg of the desired compound in 42% yield. $^1$H NMR (400 MHz, acetone-d$_6$) δ: 1.71 (s, 6H, Me), 2.35 (d, J=2.1 Hz, 3H, Me of aromatic group), 2.48 (p, J=7.1 Hz, 2H, CH$_2$), 4.09 (m, 2H, CH$_2$N), 4.35 (t, J=6.0 Hz, 2H, CH$_2$O), 7.29 (d, J=8.6 Hz, 1H, Ar), 7.66 (d, J=6.2 Hz, 2H, Pyr), 7.77 (dd, J=2.3 and 8.6 Hz, 1H, Ar), 7.87 (d, J=7.9 Hz, 1H, Ar), 7.89 (d, J=2.2 Hz, 1H, Ar), 8.06 (d, J=8.2 Hz, 1H, Ar), 8.62 (d, J=6.1 Hz, 2H, Pyr).

Example 6

Synthesis of EM-9025

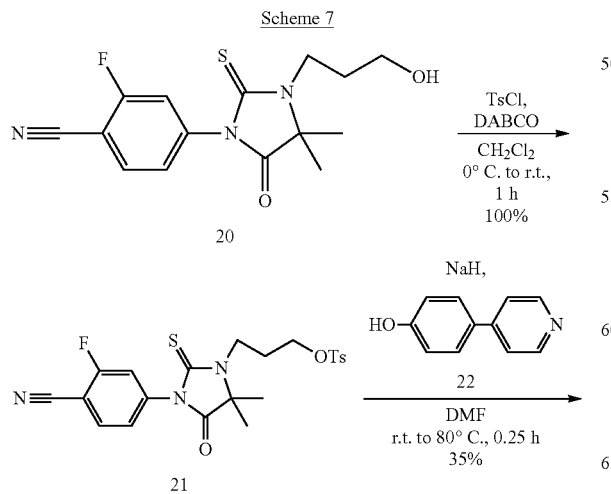

Preparation of EM-9025

EM-9025 was prepared by the same procedure described for EM-8799. Compound 21 was quantitatively obtained by the same procedure than compound 17 starting with compound 20 which was prepared by the procedure described for compound 15 (except that methanol was evaporated before work-up without dilution with water) starting with 4-cyano-3-fluoroaniline in 33% yield. Compound 22 was obtained by a similar procedure described in WO 2009/079412 (page 97) using 1-bromo-4-(methoxymethoxy)benzene and 4-pyridineboronic acid in 57% for 3 steps. The crude EM-9025 (dichloromethane was used instead of ether for the extraction, and filtration on silica gel was omitted) was purified by flash chromatography (silica gel, 40% acetone-hexanes) to give 46 mg of the desired compound in 35% yield. $^1$H NMR (400 MHz, acetone-d$_6$) δ: 1.65 (s, 6H, 2 Me), 2.41 (m, 2H, CH$_2$), 4.03 (m, 2H, CH$_2$N), 4.24 (t, J=6.2 Hz, 2H, CH$_2$O), 7.12 (d, J=8.8 Hz, 2H, Ar), 7.55 (dd, J=1.4 and 8.3 Hz, 1H, Ar), 7.61 (d, J=1.8 Hz, 1H, Ar), 7.62 (d, J=6.1 Hz, 2H, Pyr), 7.77 (d, J=8.8 Hz, 2H, Ar), 8.00 (dd, J=7.4 and 8.2 Hz, 1H, Ar), 8.59 (d, J=6.2 Hz, 2H, Pyr).

Example 7

Synthesis of EM-9126

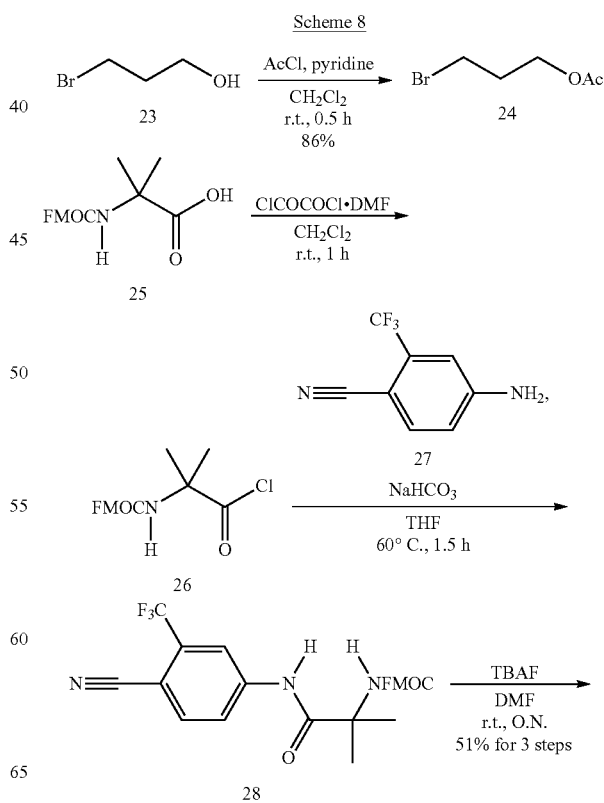

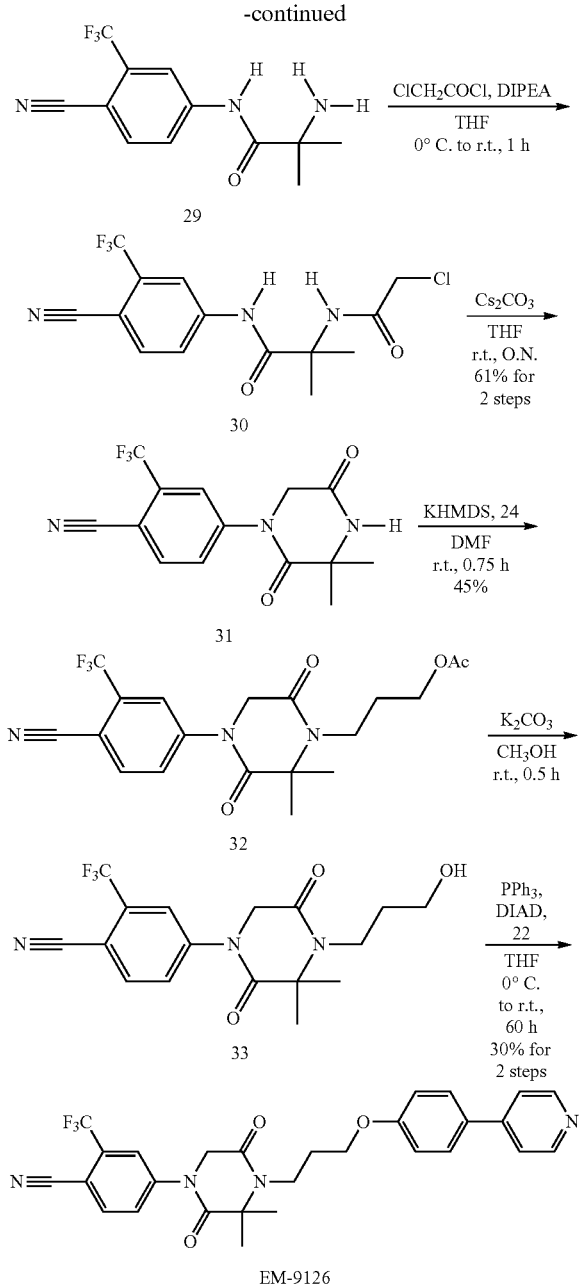

Preparation of Compound 24

A solution of 3-bromopropanol (23) (2.0 g, 14 mmol) in dichloromethane (50 mL) was treated with acetyl chloride (1.2 mL, 17 mmol), stirred for 20 min., treated with pyridine (1.4 mL, 17 mmol) and stirred for 30 min. The reaction mixture was diluted with ether, washed water and an aqueous saturated sodium bicarbonate, dried over sodium sulfate, filtered, and concentrated under reduced pressure. The crude acetate 24 (2.25 g, 86%) was used in the appropriate step without further purification.

Preparation of Compound 26

A solution of 2-(Fmoc-amino)isobutyric acid (25) (6.48 g, 20.0 mmol) in dichloromethane (180 mL) was treated with oxalyl chloride (2.6 mL, 30 mmol) and few drops of N,N-dimethylformamide and stirred for 1 h. The reaction mixture was concentrated under reduced pressure. The crude acyl chloride 26 was used in the next step without further purification.

Preparation of Compound 28

A solution of acyl chloride 26 (6.84 g, 20.0 mmol) in anhydrous tetrahydrofuran (90 mL) was treated with 4-cyano-3-trifluoromethylaniline (27) (3.36 g, 18.1 mmol) and sodium bicarbonate (1.90 g, 22.6 mmol) and heated at 60° C. for 1.5 h. The reaction mixture was cooled at room temperature, diluted with ether and washed with an aqueous saturated sodium bicarbonate (2×) and water. The organic layer was dried over sodium sulfate, filtered, and concentrated under reduced pressure. The crude amide 28 was used in the next step without further purification.

Preparation of Compound 29

A solution of amide 28 (8.9 g, 18 mmol) in N,N-dimethylformamide (60 mL) was treated with a 1.0 M tetrabutylammonium fluoride solution in tetrahydrofuran (27 mL, 27 mmol) and stirred overnight. The reaction mixture was diluted with ether and washed with an aqueous saturated sodium bicarbonate (2×) and water. The organic layer was dried over sodium sulfate, filtered, and concentrated under reduced pressure. The crude compound was purified by chromatography (Biotage system, silica gel, 50-100% ethyl acetate-hexanes) to give 2.5 g (51% for 3 steps) of amine 29.

Preparation of Compound 30

A solution of amine 29 (2.5 g, 9.2 mmol) in anhydrous tetrahydrofuran (45 mL) was cooled at 0° C., treated with diisopropylamine (2.4 mL, 14 mmol) and chloroacetyl chloride (0.81 mL, 10 mmol), and stirred for 1 h after removing the ice-water bath. The reaction mixture was diluted with water and extracted with dichloromethane (3×). The combined organic layer was dried over sodium sulfate, filtered, and concentrated under reduced pressure. The crude diamide 30 (3.58 g) was used in the next step without further purification.

Preparation of Compound 31

A solution of diamide 30 (3.21 g, 9.2 mmol) in anhydrous tetrahydrofuran (185 mL) was slowly treated with cesium carbonate (7.55 g, 23 mmol) and stirred overnight. The reaction mixture was filtered on Celite™. The filtrate was evaporated under reduced pressure. The crude compound was purified by flash chromatography (silica gel, 15-20% acetone-dichloromethane) to give 1.76 g (61% for 2 steps) of cyclic diamide 31. $^1$H NMR (400 MHz, acetone-$d_6$) δ: 1.58 (s, 6H, Me), 4.59 (s, 2H, CH$_2$), 7.60 (bs, 1H, NH), 7.97 (dd, J=2.0 and 8.4 Hz, 1H, Ar), 8.14 (d, J=2.4 Hz, 1H, Ar), 8.15 (d, J=8.0 Hz, 1H, Ar).

Preparation of Compound 32

Under an argon atmosphere, a solution of cyclic diamide 31 (106 mg, 0.34 mmol) in anhydrous N,N-dimethylformamide (1.6 mL) was treated with a 0.5 M potassium bis(trimethylsilyl)amide solution in toluene (0.81 mL, 0.40 mmol), stirred for 5 min., treated with a solution of 3-bromopropyl acetate (24) (88 mg, 0.49 mmol) in anhydrous N,N-dimethylformamide (0.5 mL) and stirred for 45 min. Then, the reaction mixture was diluted with ether, washed with water (2×), dried over sodium sulfate, filtered, and concentrated under reduced pressure. The crude compound was purified by flash chromatography (silica gel, 20% acetone-hexanes) to give 63 mg (45%) of acetate 32 (the O-alkylation product (22 mg, 16%) and the starting material 31 (24 mg, 22%) were also obtained).

Preparation of Compound 33

A solution of acetate 32 (63 mg, 0.15 mmol) in methanol (2 mL) was treated with potassium carbonate (75 mg, 0.54 mmol) and stirred for 0.5 h. The reaction mixture was diluted with ether, washed with water (2×), dried over sodium sulfate, filtered, and concentrated under reduced pressure. The crude alcohol 33 was used in the next step without further purification. $^1$H NMR (400 MHz, acetone-$d_6$) δ: 1.66 (s, 6H, 2 Me), 1.81 (p, J=7.1 Hz, 2H, $CH_2$), 3.56 (q, J=5.9 Hz, 2H, $CH_2O$), 3.63 (t, J=7.3 Hz, 2H, $CH_2N$), 3.82 (t, J=5.8 Hz, 1H, OH), 4.65 (s, 2H, $NCH_2CO$), 7.97 (dd, J=1.9 and 8.5 Hz, 1H, Ar), 8.15 (d, J=1.8 Hz, 1H, Ar), 8.15 (d, J=8.3 Hz, 1H, Ar).

Preparation of EM-9126

Under an argon atmosphere, a solution of alcohol 33 (44 mg, 0.12 mmol), phenol 22 (20 mg, 0.12 mmol) and triphenylphosphine (35 mg, 0.13 mmol) in anhydrous tetrahydrofuran (1.5 mL) was cooled to 0° C. and slowly treated with diisopropyl azodicarboxylate (DIAD) (0.025 mL, 0.13 mmol). The reaction mixture was stirred for 60 h after removing the ice-water bath. The reaction mixture was concentrated under reduced pressure. The crude compound (solubilized in acetone) was filtered on silica gel. The crude compound was purified by flash chromatography (silica gel, 50% acetone-hexanes) to give 18.5 mg (30% for 2 steps) of EM-9126. $^1$H NMR (400 MHz, acetone-$d_6$) δ: 1.69 (s, 6H, 2 Me), 2.17 (m, 2H, $CH_2$), 3.72 (m, 2H, $CH_2N$), 4.18 (t, J=6.2 Hz, 2H, $CH_2O$), 4.64 (s, 2H, $NCH_2CO$), 7.10 (d, J=8.8 Hz, 2H, Ar), 7.62 (d, J=6.2 Hz, 2H, Pyr), 7.76 (d, J=8.8 Hz, 2H, Ar), 7.97 (dd, J=1.9 and 8.6 Hz, 1H, Ar), 8.15 (2s, 2H, Ar), 8.59 (d, J=6.1 Hz, 2H, Pyr).

Example 8

Synthesis of EM-9199

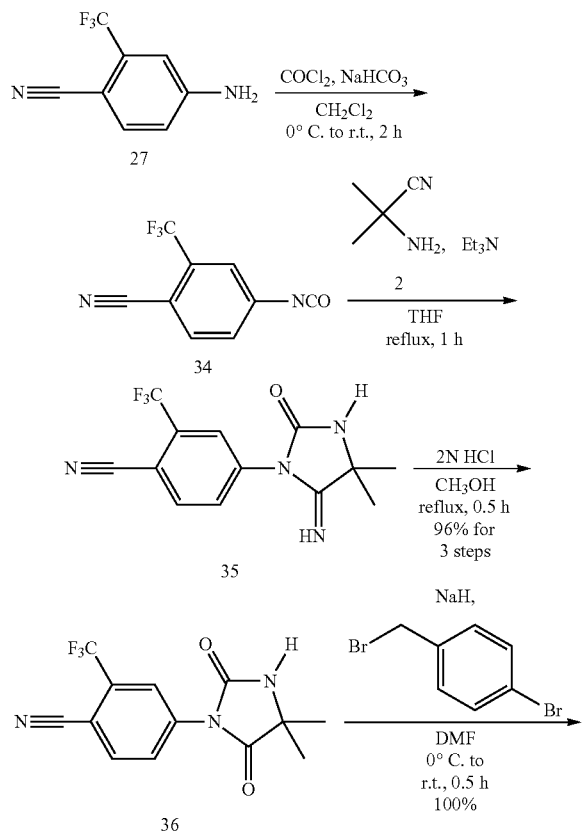

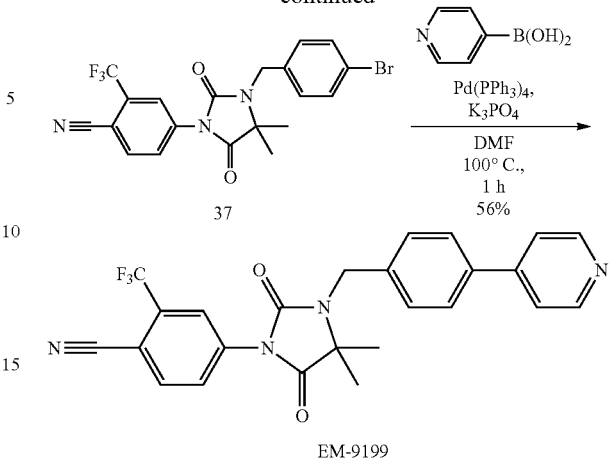

Preparation of Compound 34

A suspension of 4-cyano-3-trifluomethylaniline (27) (2.01 g, 10.8 mmol) and sodium bicarbonate (2.25 g, 26.8 mmol) in dichloromethane (50 mL) was cooled at 0° C., slowly treated with a 20% phosgene solution in toluene (11 mL, 20.9 mmol) and stirred for 2 h after removing the ice-water bath. The reaction mixture was filtered and concentrated under reduced pressure. The crude isocyanate 34 was used in the next step without further purification.

Preparation of Compound 35

A solution of isocyanate 35 (2.29 g, 10.8 mmol), 2-amino-2-methylpropionitrile (2) (1.1 g, 13 mmol) and triethylamine (0.15 mL, 1.1 mmol) in anhydrous tetrahydrofuran (40 mL) was refluxed for 1 h. The reaction mixture was cooled to room temperature and concentrated under reduced pressure. The crude compound 35 was used in the next step without further purification.

Preparation of Compound 36

A solution of compound 35 (3.19 g, 10.8 mmol) in a mixture of methanol and aqueous 2N hydrochloric acid solution in a 1:1 ratio (36 mL) was refluxed for 0.5 h. Then, the reaction mixture was cooled at room temperature, diluted with water and extracted with dichloromethane (3×). The combined organic layer was dried over sodium sulfate, filtered, and concentrated under reduced pressure to give 3.07 g (96% for 3 steps) of compound 36. The crude compound 36 was used in the next step without further purification.

Preparation of Compound 37

Under an argon atmosphere, a solution of compound 36 (501 mg, 1.69 mmol) and 4-bromobenzyl bromide (630 mg, 2.5 mmol) in anhydrous N,N-dimethylformamide (8 mL) was cooled at 0° C., treated with sodium hydride (60% dispersed in mineral oil, 100 mg, 2.5 mmol) and stirred 0.5 h after removing the ice-water bath. Then, the reaction mixture was diluted with ether, washed with water (2×), dried over sodium sulfate, filtered, and concentrated under reduced pressure. The crude compound was purified by chromatography (Biotage system, silica gel, 0-30% acetone-hexanes) to give 786 mg (100%) of bromide 37.

Preparation of Compound EM-9199

Under an argon atmosphere, a suspension of bromide 37 (100 mg, 0.21 mmol), 4-pyridineboronic acid (41 mg, 0.33 mmol) and tripotassium phosphate (136 mg, 0.64 mmol) in anhydrous N,N-dimethylformamide (2 mL) was bubbled with argon for 10 min., treated with tetrakis(triphenylphosphine)palladium(0) (25 mg, 0.022 mmol) and heated at 100° C. for 1 h. Then, the reaction mixture was cooled to room temperature, diluted with ether, washed with water (2×), dried over sodium sulfate, filtered, and concentrated under reduced pressure. The crude compound was purified by two flash chromatographies (silica gel, 30% acetone-hexanes and 2% methanol-dichloromethane) to give 55 mg (56%) of EM-9199. $^1$H NMR (400 MHz, acetone-$d_6$) δ: 1.52 (s, 6H, 2 Me), 4.80 (s, 2H, CH$_2$), 7.67 (m, 4H, Ar and Pyr), 7.79 (d, J=8.4 Hz, 2H, Ar), 8.23 (m, 2H, Ar), 8.34 (s, 1H, Ar), 8.64 (d, J=6.1 Hz, 2H, Pyr).

Example 9

Synthesis of EM-9340

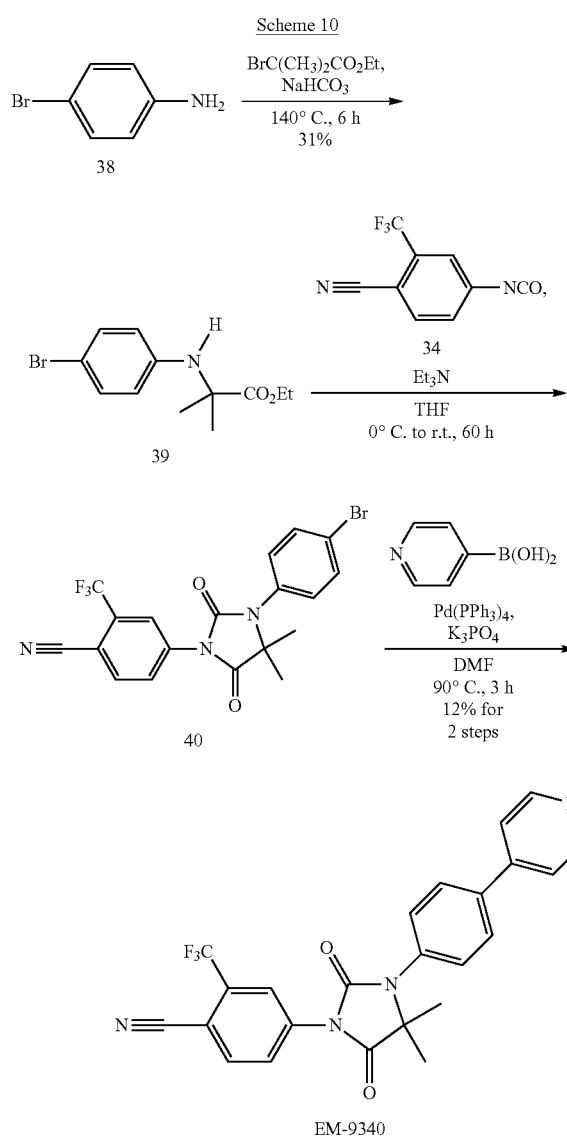

Preparation of Compound 39

A mixture of 4-bromoaniline (38) (2.05 g, 11.9 mmol), ethyl α-bromoisobutyrate (3.0 mL, 20 mmol) and sodium bicarbonate (1.5 g, 18 mmol) was heated at 140° C. for 6 h. The reaction mixture was cooled to room temperature, treated with silica gel and flash chromatographied (10% ether-hexanes) to give 1.06 g (31%) of the ester 39 as an oil.

Preparation of Compound 40

Under an argon atmosphere, a solution of ester 39 (1.17 g, 4.09 mmol) in anhydrous tetrahydrofuran (14 mL) was cooled at 0° C., treated with 4-cyano-3-trifluoromethylphenyl isocyanate (34) (0.87 mg, 4.1 mmol) and triethylamine (0.57 mL, 4.1 mmol), stirred overnight after removing the ice-water bath, treated with the same amount of isocyanate (34) and triethylamine, and stirred 1 h. Then, the reaction mixture was diluted with ether, washed with water (2×), dried over sodium sulfate, filtered, and concentrated under reduced pressure. The crude compound was purified by flash chromatography (silica gel, 10% acetone-hexanes) to give 750 mg of a mixture of bromide 40 with ethyl (4-cyano-3-trifluoromethylphenyl) carbamate in a 1:2.2 ratio.

Preparation of Compound EM-9340

Under an argon atmosphere, a suspension of impure bromide 40 (150 mg, 0.15 mmol), 4-pyridineboronic acid (80 mg, 0.65 mmol) and tripotassium phosphate (212 mg, 1.00 mmol) in anhydrous N,N-dimethylformamide (3 mL) was bubbled with argon for 10 min., treated with tetrakis(triphenylphosphine)palladium(0) (44 mg, 0.038 mmol) and heated at 90° C. for 3 h (incomplete reaction). Then, the reaction mixture was cooled to room temperature, diluted with ether, washed with water (2×), dried over sodium sulfate, filtered, and concentrated under reduced pressure. The crude compound was purified by two flash chromatographies (silica gel, 20% acetone-hexanes and 10% acetone-dichloromethane) to give 45 mg (12% for two steps) of EM-9340. $^1$H NMR (400 MHz, acetone-$d_6$) δ: 1.66 (s, 6H, 2 Me), 7.66 (d, J=8.6 Hz, 2H, Ar), 7.73 (d, J=6.1 Hz, 2H, Pyr), 7.95 (d, J=8.7 Hz, 2H, Ar), 8.21 (dd, J=1.6 and 8.5 Hz, 1H, Ar), 8.26 (d, J=8.5 Hz, 1H, Ar), 8.32 (d, J=1.3 Hz, 1H, Ar), 8.69 (d, J=6.1 Hz, 2H, Pyr).

Example 10

Synthesis of EM-9336

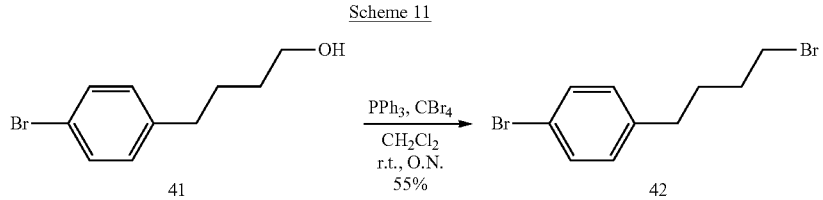

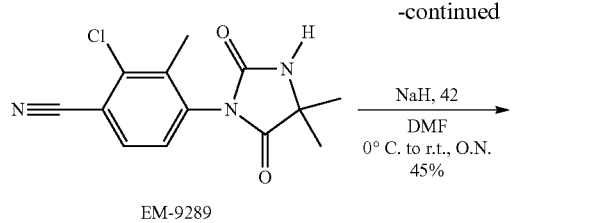

EM-9289

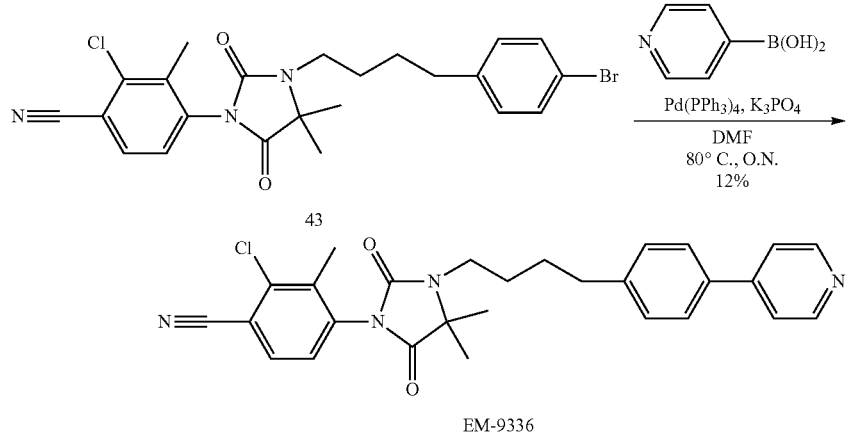

EM-9336

Preparation of Compound 42

Under an argon atmosphere, a suspension of 4-(4-bromophenyl)-1-butanol (41) (obtained from the method described in Ando T. et al., Bull. Chem. Soc. Jpn., 1980, 53(8), 2348-2356) (3.44 g, 15 mmol), triphenylphosphine (4.6 g, 17 mmol) and tetrabromomethane (7.5 g, 23 mmol) in dichloromethane (200 mL) was stirred overnight. The reaction mixture was quenched with water and extracted with dichloromethane (3×). The combined organic layer was dried over sodium sulfate and concentrated under reduced pressure. The crude compound was purified by chromatography (Biotage system, silica gel, 0-10% acetone-hexanes) to give 2.43 g (55%) of bromide 42.

Preparation of Compound 43

Under an argon atmosphere, a suspension of sodium hydride (60% dispersed in mineral oil, 120 mg, 3.0 mmol) and EM-9289 (560 mg, 2.0 mmol) in anhydrous N,N-dimethylformamide (10 mL) was stirred for 30 min., cooled at 0° C., slowly treated with a solution of bromide 42 (900 mg, 3.1 mmol) in anhydrous N,N-dimethylformamide (2 mL), and stirred overnight after removing the ice-water bath. Then, the reaction mixture was diluted with water and extracted with dichloromethane (2×) and ethyl acetate (2×). The combined organic layer was dried over sodium sulfate, filtered, and concentrated under reduced pressure. The crude compound was purified by chromatography (Biotage system, silica gel, 0-20% acetone-hexanes) to give 435 mg (45%) of bromide 43. $^1$H NMR (400 MHz, acetone-$d_6$) δ: 1.54 (s, 3H, Me), 1.56 (s, 3H, Me), 1.73 (m, 4H, CH$_2$), 2.28 (s, 3H, Me of aromatic group), 2.68 (t, J=7.2 Hz, 2H, benzylic CH$_2$), 3.45 (t, J=7.3 Hz, 2H, CH$_2$N), 7.21 (d, J=8.4 Hz, 2H, Ar), 7.45 (d, J=8.4 Hz, 2H, Ar), 7.51 (d, J=8.3 Hz, 1H, Ar), 7.87 (d, J=8.3 Hz, 1H, Ar).

Preparation of Compound EM-9336

Under an argon atmosphere, a suspension of bromide 43 (214 mg, 0.438 mmol), 4-pyridineboronic acid (65 mg, 0.53 mmol) and tripotassium phosphate (280 mg, 1.3 mmol) in anhydrous N,N-dimethylformamide (12 mL) was bubbled with argon for 15 min., treated with tetrakis(triphenylphosphine)palladium(0) (76 mg, 0.066 mmol) and heated at 80° C. overnight. Then, the reaction mixture was cooled to room temperature, diluted with water, and extracted with dichloromethane (3×) and ethyl acetate. The combined organic layer was dried over sodium sulfate, filtered, and concentrated under reduced pressure. The crude compound was purified by flash chromatography (silica gel, 0-20% acetone-toluene) to give 25 mg (12%) of EM-9336. $^1$H NMR (400 MHz, acetone-$d_6$) δ: 1.55 (s, 3H, Me), 1.57 (s, 3H, Me), 1.78 (m, 4H, CH$_2$), 2.28 (s, 3H, Me of aromatic group), 2.77 (t, J=7.1 Hz, 2H, benzylic CH$_2$), 3.48 (t, J=7.1 Hz, 2H, CH$_2$N), 7.41 (d, J=8.3 Hz, 2H, Ar), 7.52 (d, J=8.3 Hz, 1H, Ar), 7.65 (d, J=6.1 Hz, 2H, Pyr), 7.72 (d, J=8.3 Hz, 2H, Ar), 7.87 (d, J=8.3 Hz, 1H, Ar), 8.62 (d, J=6.1 Hz, 2H, Pyr).

The following compounds from Table 3 are obtained from the procedures described in Examples 1-10. The $^1$H NMR description for each compound is presented (except compounds which are already found in Examples 1-10):

EM-8840

$^1$H NMR (400 MHz, acetone-$d_6$) δ: 1.68 (s, 6H, 2 Me), 2.41 (m, 2H, CH$_2$), 4.05 (m, 2H, CH$_2$N), 4.23 (t, J=6.2 Hz, 2H, CH$_2$O), 7.12 (d, J=8.8 Hz, 2H, Ar), 7.44 (bs, 1H, Pyr), 7.67 (d, J=8.8 Hz, 2H, Ar), 7.99 (d, J=7.9 Hz, 1H, Pyr), 8.03 (dd, J=1.8 and 8.3 Hz, 1H, Ar), 8.17 (d, J=1.7 Hz, 1H, Ar), 8.25 (d, J=8.3 Hz, 1H, Ar), 8.6 (bs, 1H, Pyr), 8.9 (bs, 1H, Pyr).

EM-8841

$^1$H NMR (400 MHz, acetone-$d_6$) δ: 1.68 (s, 6H, 2 Me), 2.42 (m, 2H, CH$_2$), 4.05 (m, 2H, CH$_2$N), 4.24 (t, J=6.2 Hz, 2H, CH$_2$O), 7.12 (d, J=8.8 Hz, 2H, Ar), 7.62 (d, J=5.9 Hz, 2H, Pyr), 7.77 (d, J=8.8 Hz, 2H, Ar), 8.03 (dd, J=1.6 and 8.3 Hz, 1H, Ar), 8.17 (d, J=1.8 Hz, 1H, Ar), 8.25 (d, J=8.3 Hz, 1H, Ar), 8.60 (bs, 2H, Pyr).

EM-8851

$^1$H NMR (400 MHz, acetone-$d_6$) δ: 1.66 (s, 6H, 2 Me), 2.42 (m, 2H, CH$_2$), 4.05 (m, 2H, CH$_2$N), 4.27 (t, J=6.2 Hz, 2H, CH$_2$O), 6.93 (dd, J=2.4 and 13.1 Hz, 1H, Ar), 6.98 (dd, J=2.5 and 8.5 Hz, 1H, Ar), 7.55 (bs, 2H, Pyr), 7.60 (t, J=8.9

Hz, 1H, Ar), 8.03 (dd, J=1.7 and 8.2 Hz, 1H, Ar), 8.17 (d, J=1.8 Hz, 1H, Ar), 8.25 (d, J=8.3 Hz, 1H, Ar), 8.7 (bs, 2H, Pyr).

EM-8871

$^1$H NMR (400 MHz, acetone-$d_6$) δ: 1.67 (s, 6H, 2 Me), 2.42 (m, 2H, CH$_2$), 4.05 (m, 2H, CH$_2$N), 4.27 (t, J=6.2 Hz, 2H, CH$_2$O), 7.09 (ddd, J=1.1, 2.3 and 8.2 Hz, 1H, Ar), 7.37 (m, 2H, Ar), 7.46 (t, J=8.2 Hz, 1H, Ar), 7.66 (d, J=6.2 Hz, 2H, Pyr), 8.02 (dd, J=1.8 and 8.2 Hz, 1H, Ar), 8.16 (d, J=1.5 Hz, 1H, Ar), 8.25 (d, J=8.3 Hz, 1H, Ar), 8.64 (d, J=6.1 Hz, 2H, Pyr).

EM-8872

$^1$H NMR (400 MHz, acetone-$d_6$) δ: 1.68 (s, 6H, 2 Me), 2.45 (m, 2H, CH$_2$), 4.07 (m, 2H, CH$_2$N), 4.35 (t, J=6.1 Hz, 2H, CH$_2$O), 7.31 (t, J=8.7 Hz, 1H, Ar), 7.64 (m, 4H, Ar and Pyr), 8.02 (dd, J=1.7 and 8.2 Hz, 1H, Ar), 8.15 (d, J=1.6 Hz, 1H, Ar), 8.25 (d, J=8.2 Hz, 1H, Ar), 8.62 (d, J=6.2 Hz, 2H, Pyr).

EM-8888

$^1$H NMR (400 MHz, acetone-$d_6$) δ: 1.68 (s, 6H, 2 Me), 2.42 (m, 2H, CH$_2$), 4.05 (m, 2H, CH$_2$N), 4.27 (t, J=6.1 Hz, 2H, CH$_2$O), 7.09 (dd, J=2.6 and 8.6 Hz, 1H, Ar), 7.18 (d, J=2.5 Hz, 1H, Ar), 7.42 (d, J=8.7 Hz, 1H, Ar), 7.43 (d, J=6.0 Hz, 2H, Pyr), 8.03 (dd, J=1.5 and 8.2 Hz, 1H, Ar), 8.17 (d, J=1.5 Hz, 1H, Ar), 8.26 (d, J=8.2 Hz, 1H, Ar), 8.64 (d, J=6.1 Hz, 2H, Pyr).

EM-8890

$^1$H NMR (400 MHz, acetone-$d_6$) δ: 1.68 (s, 6H, 2 Me), 2.45 (m, 2H, CH$_2$), 4.07 (m, 2H, CH$_2$N), 4.34 (t, J=6.1 Hz, 2H, CH$_2$O), 7.34 (m, 5H, Ar and Pyr), 8.03 (dd, J=1.7 and 8.1 Hz, 1H, Ar), 8.17 (d, J=1.5 Hz, 1H, Ar), 8.26 (d, J=8.2 Hz, 1H, Ar), 8.63 (d, J=6.0 Hz, 2H, Pyr).

EM-8900

$^1$H NMR (400 MHz, acetone-$d_6$) δ: 1.67 (s, 6H, 2 Me), 2.47 (m, 2H, CH$_2$), 4.04 (m, 2H, CH$_2$N), 4.40 (t, J=5.9 Hz, 2H, CH$_2$O), 7.43 (d, J=8.6 Hz, 1H, Ar), 7.71 (d, J=6.1 Hz, 2H, Pyr), 8.05 (m, 3H, Ar), 8.17 (d, J=1.7 Hz, 1H, Ar), 8.26 (d, J=8.2 Hz, 1H, Ar), 8.64 (d, J=6.1 Hz, 2H, Pyr).

EM-8908

$^1$H NMR (400 MHz, acetone-$d_6$) δ: 1.68 (s, 6H, 2 Me), 2.51 (s, 3H, Me), 2.40 (m, 2H, CH$_2$), 4.04 (m, 2H, CH$_2$N), 4.22 (t, J=6.2 Hz, 2H, CH$_2$O), 7.09 (d, J=8.8 Hz, 2H, Ar), 7.28 (d, J=7.9 Hz, 1H, Pyr), 7.63 (d, J=8.8 Hz, 2H, Ar), 7.86 (dd, J=2.5 and 8.0 Hz, 1H, Pyr), 8.03 (dd, J=2.0 and 8.0 Hz, 1H, Ar), 8.17 (d, J=1.7 Hz, 1H, Ar), 8.26 (d, J=8.2 Hz, 1H, Ar), 8.70 (d, J=2.3 Hz, 1H, Pyr).

EM-8923

$^1$H NMR (400 MHz, acetone-$d_6$) δ: 1.68 (s, 6H, 2 Me), 2.41 (m, 2H, CH$_2$), 4.05 (m, 2H, CH$_2$N), 4.23 (t, J=6.2 Hz, 2H, CH$_2$O), 7.11 (d, J=8.6 Hz, 2H, Ar), 7.14 (dd, J=2.9 and 8.3 Hz, 1H, Pyr), 7.65 (d, J=8.8 Hz, 2H, Ar), 8.03 (dd, J=1.7 and 8.2 Hz, 1H, Ar), 8.16 (d, J=2.5 Hz, 1H, Ar), 8.19 (dd, J=2.6 and 8.4 Hz, 1H, Pyr), 8.26 (d, J=8.3 Hz, 1H, Ar), 8.45 (d, J=2.4 Hz, 1H, Pyr).

EM-8929

$^1$H NMR (400 MHz, acetone-$d_6$) δ: 1.67 (s, 6H, 2 Me), 2.41 (m, 2H, CH$_2$), 4.04 (m, 2H, CH$_2$N), 4.23 (t, J=6.2 Hz, 2H, CH$_2$O), 7.11 (d, J=8.8 Hz, 2H, Ar), 7.68 (d, J=7.3 Hz, 2H, Pyr), 7.74 (d, J=8.8 Hz, 2H, Ar), 8.02 (dd, J=1.8 and 8.3 Hz, 1H, Ar), 8.15 (s, 1H, Ar), 8.16 (d, J=7.3 Hz, 2H, Pyr), 8.26 (d, J=8.3 Hz, 1H, Ar).

EM-9000

$^1$H NMR (400 MHz, acetone-$d_6$) δ: 1.60 (s, 6H, 2 Me), 2.27 (p, J=6.8 Hz, 2H, CH$_2$), 3.67 (t, J=7.2 Hz, 2H, CH$_2$N), 4.22 (t, J=6.1 Hz, 2H, CH$_2$O), 7.08 (d, J=8.8 Hz, 2H, Ar), 7.66 (d, J=7.3 Hz, 2H, Pyr), 7.71 (d, J=8.8 Hz, 2H, Ar), 8.14 (dd, J=2.0 and 8.3 Hz, 1H, Ar), 8.15 (d, J=7.2 Hz, 2H, Pyr), 8.19 (d, J=8.5 Hz, 1H, Ar), 8.26 (d, J=1.6 Hz, 1H, Ar).

EM-9011

$^1$H NMR (400 MHz, acetone-$d_6$) δ: 1.66 (s, 6H, 2 Me), 2.41 (m, 2H, CH$_2$), 4.04 (m, 2H, CH$_2$N), 4.27 (t, J=6.2 Hz, 2H, CH$_2$O), 6.93 (dd, J=2.4 and 13.1 Hz, 1H, Ar), 6.98 (dd, J=2.4 and 8.7 Hz, 1H, Ar), 7.54 (dt, J=1.6 and 4.5 Hz, 2H, Pyr), 7.55-763 (m, 3H, Ar), 8.00 (t, J=7.8 Hz, 1H, Ar), 8.63 (d, J=6.1 Hz, 2H, Pyr).

EM-9037

$^1$H NMR (400 MHz, acetone-$d_6$) δ: 1.66 (s, 6H, 2 Me), 2.42 (m, 2H, CH$_2$), 4.04 (m, 2H, CH$_2$N), 4.27 (t, J=6.1 Hz, 2H, CH$_2$O), 6.93 (dd, J=2.4 and 13.0 Hz, 1H, Ar), 6.98 (dd, J=2.8 and 8.4 Hz, 1H, Ar), 7.54 (dt, J=1.6 and 4.5 Hz, 2H, Pyr), 7.60 (t, J=8.9 Hz, 1H, Ar), 7.67 (dd, J=1.9 and 8.3 Hz, 1H, Ar), 7.85 (d, J=1.9 Hz, 1H, Ar), 8.05 (d, J=8.4 Hz, 1H, Ar), 8.63 (d, J=6.2 Hz, 2H, Pyr).

EM-9039

$^1$H NMR (400 MHz, acetone-$d_6$) δ: 1.66 (s, 6H, 2 Me), 2.41 (m, 2H, CH$_2$), 4.04 (m, 2H, CH$_2$N), 4.24 (t, J=6.2 Hz, 2H, CH$_2$O), 7.12 (d, J=8.9 Hz, 2H, Ar), 7.62 (d, J=6.2 Hz, 2H, Pyr), 7.67 (dd, J=1.9 and 8.3 Hz, 1H, Ar), 7.77 (d, J=8.8 Hz, 2H, Ar), 7.85 (d, J=1.9 Hz, 1H, Ar), 8.04 (d, J=8.4 Hz, 1H, Ar), 8.59 (d, J=6.2 Hz, 2H, Pyr).

EM-9043

$^1$H NMR (400 MHz, methanol-$d_4$) δ: 1.64 (s, 6H, 2 Me), 2.43 (m, 2H, CH$_2$), 4.03 (m, 2H, CH$_2$N), 4.28 (t, J=5.9 Hz, 2H, CH$_2$O), 7.21 (m, 2H, Ar), 7.94 (m, 3H, Ar), 8.08 (d, J=1.5 Hz, 1H, Ar), 8.14 (d, J=8.3 Hz, 1H, Ar), 8.22 (m, 2H, Pyr), 8.77 (m, 2H, Pyr).

EM-9049

$^1$H NMR (400 MHz, acetone-$d_6$) δ: 1.66 (s, 6H, 2 Me), 2.41 (m, 2H, CH$_2$), 4.04 (m, 2H, CH$_2$N), 4.23 (t, J=6.2 Hz, 2H, CH$_2$O), 7.11 (d, J=8.8 Hz, 2H, Ar), 7.42 (ddd, 0.7, 4.8 and 7.9 Hz, 1H, Pyr), 7.67 (m, 3H, Ar), 7.85 (d, J=1.8 Hz, 1H, Ar), 7.99 (dt, J=0.7 and 7.9 Hz, 1H, Pyr), 8.04 (d, J=8.3 Hz, 1H, Ar), 8.52 (dd, J=1.5 and 4.7 Hz, 1H, Pyr), 8.84 (d, J=1.8 Hz, 1H, Pyr).

EM-9050

$^1$H NMR (400 MHz, acetone-$d_6$) δ: 1.67 (s, 6H, 2 Me), 2.40 (m, 2H, CH$_2$), 4.03 (m, 2H, CH$_2$N), 4.50 (t, J=6.2 Hz, 2H, CH$_2$O), 6.97 (dd, J=0.4 and 8.6 Hz, 1H, Pyr), 7.67 (d, J=6.2 Hz, 2H, Pyr), 8.03 (dd, J=1.7 and 8.3 Hz, 1H, Ar), 8.13 (dd, J=2.6 and 8.6 Hz, 1H, Pyr), 8.17 (d, J=1.7 Hz, 1H, Ar), 8.25 (d, J=8.3 Hz, 1H, Ar), 8.61 (dd, J=0.3 and 2.5 Hz, 1H, Pyr), 8.64 (d, J=5.9 Hz, 2H, Pyr).

EM-9055

$^1$H NMR (400 MHz, acetone-$d_6$) δ: 1.61 (s, 6H, 2 Me), 2.31 (p, J=6.5 Hz, 2H, CH$_2$), 3.70 (t, J=7.1 Hz, 2H, CH$_2$N), 4.33 (t, J=6.0 Hz, 2H, CH$_2$O), 7.28 (t, J=8.8 Hz, 1H, Ar), 7.63 (m, 4H, Ar and Pyr), 8.13 (dd, J=1.8 and 8.5 Hz, 1H, Ar), 8.18 (d, J=8.4 Hz, 1H, Ar), 8.24 (d, J=1.5 Hz, 1H, Ar), 8.62 (d, J=5.4 Hz, 2H, Pyr).

EM-9066

$^1$H NMR (400 MHz, acetone-$d_6$) δ: 1.60 (s, 6H, 2 Me), 2.29 (p, J=7.1 Hz, 2H, CH$_2$), 3.68 (t, J=7.2 Hz, 2H, CH$_2$N), 4.26 (t, J=6.1 Hz, 2H, CH$_2$O), 6.91 (dd, J=2.4 and 13.1 Hz, 1H, Ar), 6.96 (dd, J=2.6 and 8.6 Hz, 1H, Ar), 7.53 (dt, J=1.6 and 4.5 Hz, 2H, Pyr), 7.58 (t, J=8.9 Hz, 1H, Ar), 8.15 (dd, J=1.7 and 8.4 Hz, 1H, Ar), 8.20 (d, J=8.5 Hz, 1H, Ar), 8.26 (d, J=1.8 Hz, 1H, Ar), 8.63 (d, J=6.1 Hz, 2H, Pyr).

EM-9067

$^1$H NMR (400 MHz, acetone-$d_6$) δ: 1.60 (s, 6H, 2 Me), 2.28 (p, J=7.0 Hz, 2H, CH$_2$), 3.67 (t, J=7.2 Hz, 2H, CH$_2$N), 4.25 (t, J=6.1 Hz, 2H, CH$_2$O), 6.90 (dd, J=2.4 and 13.3 Hz, 1H, Ar), 6.95 (dd, J=2.6 and 8.6 Hz, 1H, Ar), 7.59 (m, 3H, Ar and Pyr), 8.15 (dd, J=1.7 and 8.5 Hz, 1H, Ar), 8.19 (m, 3H, Ar and Pyr), 8.26 (dd, J=0.4 and 1.3 Hz, 1H, Ar).

EM-9070
$^1$H NMR (400 MHz, acetone-$d_6$) δ: 1.66 (s, 6H, 2 Me), 1.93 (m, 2H, $CH_2$), 2.09 (m, 2H, $CH_2$), 3.93 (m, 2H, $CH_2N$), 4.16 (t, J=6.2 Hz, 2H, $CH_2O$), 7.09 (d, J=8.8 Hz, 2H, Ar), 7.41 (ddd, J=0.8, 4.8 and 8.0 Hz, 1H, Pyr), 7.65 (d, J=8.8 Hz, 2H, Ar), 7.98 (ddd, J=1.7, 2.4 and 7.9 Hz, 1H, Pyr), 8.03 (dd, J=1.6 and 8.3 Hz, 1H, Ar), 8.18 (d, J=1.9 Hz, 1H, Ar), 8.25 (d, J=8.3 Hz, 1H, Ar), 8.52 (dd, J=1.6 and 4.7 Hz, 1H, Pyr), 8.83 (dd, J=0.7 and 2.3 Hz, 1H, Pyr).

EM-9089
$^1$H NMR (400 MHz, acetone-$d_6$) δ: 1.61 (s, 6H, 2 Me), 2.31 (p, J=6.6 Hz, 2H, $CH_2$), 3.70 (t, J=7.2 Hz, 2H, $CH_2N$), 4.32 (t, J=6.1 Hz, 2H, $CH_2O$), 7.31-739 (m, 5H, Ar and Pyr), 8.15 (dd, J=1.8 and 8.5 Hz, 1H, Ar), 8.21 (d, J=8.5 Hz, 1H, Ar), 8.27 (d, J=1.7 Hz, 1H, Ar), 8.63 (bs, 2H, Pyr).

EM-9092
$^1$H NMR (400 MHz, acetone-$d_6$) δ: 1.68 (s, 6H, 2 Me), 2.45 (m, 2H, $CH_2$), 4.07 (m, 2H, $CH_2N$), 4.35 (t, J=6.2 Hz, 2H, $CH_2O$), 7.54 (dd, J=3.0 and 8.8 Hz, 1H, Pyr), 7.99 (d, J=6.2 Hz, 2H, Pyr), 8.03 (dd, J=1.8 and 8.3 Hz, 1H, Ar), 8.06 (d, J=8.8 Hz, 1H, Pyr), 8.16 (d, J=1.7 Hz, 1H, Ar), 8.25 (d, J=8.3 Hz, 1H, Ar), 8.47 (d, J=2.8 Hz, 1H, Pyr), 8.65 (d, J=6.2 Hz, 2H, Pyr).

EM-9111
$^1$H NMR (400 MHz, acetone-$d_6$) δ: 1.60 (s, 6H, 2 Me), 2.31 (p, J=7.1 Hz, 2H, $CH_2$), 3.70 (t, J=7.2 Hz, 2H, $CH_2N$), 4.33 (t, J=6.1 Hz, 2H, $CH_2O$), 7.52 (dd, J=3.0 and 8.8 Hz, 1H, Pyr), 7.98 (d, J=6.2 Hz, 2H, Pyr), 8.04 (d, J=8.9 Hz, 1H, Pyr), 8.15 (dd, J=1.8 and 8.3 Hz, 1H, Ar), 8.19 (d, J=8.3 Hz, 1H, Ar), 8.26 (d, J=1.8 Hz, 1H, Ar), 8.45 (d, J=2.7 Hz, 1H, Pyr), 8.64 (d, J=6.2 Hz, 2H, Pyr).

EM-9114
$^1$H NMR (400 MHz, acetone-$d_6$) δ: 1.60 (s, 6H, 2 Me), 2.26 (p, J=7.3 Hz, 2H, $CH_2$), 3.66 (t, J=7.3 Hz, 2H, $CH_2N$), 4.50 (t, J=6.3 Hz, 2H, $CH_2O$), 6.96 (dd, J=0.6 and 8.6 Hz, 1H, Pyr), 7.66 (d, J=6.1 Hz, 2H, Pyr), 8.12 (dd, J=2.6 and 8.6 Hz, 1H, Pyr), 8.16 (dd, J=1.8 and 8.5 Hz, 1H, Ar), 8.20 (d, J=8.4 Hz, 1H, Ar), 8.28 (dd, J=0.4 and 1.3 Hz, 1H, Ar), 8.60 (dd, J=0.5 and 2.6 Hz, 1H, Pyr), 8.64 (d, J=5.3 Hz, 2H, Pyr).

EM-9115
$^1$H NMR (400 MHz, acetone-$d_6$) δ: 1.69 (s, 6H, 2 Me), 2.28 (p, J=7.0 Hz, 2H, $CH_2$), 3.67 (t, J=7.1 Hz, 2H, $CH_2N$), 4.26 (t, J=6.1 Hz, 2H, $CH_2O$), 6.91 (dd, J=2.4 and 13.1 Hz, 1H, Ar), 6.97 (dd, J=2.6 and 8.7 Hz, 1H, Ar), 7.53 (dt, J=1.5 and 4.5 Hz, 2H, Pyr), 7.59 (t, J=8.9 Hz, 1H, Ar), 7.81 (dd, J=1.9 and 8.5 Hz, 1H, Ar), 7.93 (d, J=1.9 Hz, 1H, Ar), 7.99 (d, J=8.5 Hz, 1H, Ar), 8.63 (d, J=5.3 Hz, 2H, Pyr).

EM-9116
$^1$H NMR (400 MHz, acetone-$d_6$) δ: 1.58 (s, 6H, 2 Me), 2.27 (p, J=7.0 Hz, 2H, $CH_2$), 3.66 (t, J=7.2 Hz, 2H, $CH_2N$), 4.23 (t, J=6.1 Hz, 2H, $CH_2O$), 7.10 (d, J=8.8 Hz, 2H, Ar), 7.62 (d, J=6.1 Hz, 2H, Pyr), 7.76 (d, J=8.9 Hz, 2H, Ar), 7.80 (dd, J=1.9 and 8.5 Hz, 1H, Ar), 7.93 (d, J=1.9 Hz, 1H, Ar), 7.98 (d, J=8.5 Hz, 1H, Ar), 8.59 (d, J=6.1 Hz, 2H, Pyr).

EM-9117
$^1$H NMR (400 MHz, acetone-$d_6$) δ: 1.58 (s, 6H, 2 Me), 2.27 (p, J=6.9 Hz, 2H, $CH_2$), 3.66 (t, J=7.1 Hz, 2H, $CH_2N$), 4.25 (t, J=6.1 Hz, 2H, $CH_2O$), 6.91 (dd, J=2.4 and 13.3 Hz, 1H, Ar), 6.95 (dd, J=2.5 and 8.5 Hz, 1H, Ar), 7.59 (m, 3H, Ar and Pyr), 7.80 (dd, J=1.9 and 8.5 Hz, 1H, Ar), 7.93 (d, J=1.8 Hz, 1H, Ar), 7.99 (d, J=8.5 Hz, 1H, Ar), 8.19 (d, J=7.3 Hz, 2H, Pyr).

EM-9118
$^1$H NMR (400 MHz, acetone-$d_6$) δ: 1.58 (s, 6H, 2 Me), 2.26 (p, J=7.0 Hz, 2H, $CH_2$), 3.66 (t, J=7.2 Hz 2H, $CH_2N$), 4.22 (t, J=6.1 Hz 2H, $CH_2O$), 7.08 (d, J=8.9 Hz, 2H, Ar), 7.66 (d, J=7.3 Hz, 2H, Pyr), 7.72 (d, J=8.9 Hz, 2H, Ar), 7.80 (dd, J=1.9 and 8.5 Hz, 1H, Ar), 7.92 (d, J=1.9 Hz, 1H, Ar), 7.98 (d, J=8.5 Hz, 1H, Ar), 8.14 (d, J=7.3 Hz, 2H, Pyr).

EM-9119
$^1$H NMR (400 MHz, acetone-$d_6$) δ: 1.66 (s, 6H, 2 Me), 2.41 (m, 2H, $CH_2$), 4.03 (m, 2H, $CH_2N$), 4.26 (t, J=6.2 Hz, 2H, $CH_2O$), 6.92 (dd, J=2.3 and 13.3 Hz, 1H, Ar), 6.98 (dd, J=2.7 and 8.6 Hz, 1H, Ar), 7.60 (m, 3H, Ar and Pyr), 7.67 (dd, J=1.9 and 8.3 Hz, 1H, Ar), 7.85 (d, J=1.8 Hz, 1H, Ar), 8.05 (d, J=8.3 Hz, 1H, Ar), 8.19 (d, J=7.3 Hz, 2H, Pyr).

EM-9120
$^1$H NMR (400 MHz, acetone-$d_6$) δ: 1.66 (s, 6H, 2 Me), 2.41 (m, 2H, $CH_2$), 4.03 (m, 2H, $CH_2N$), 4.23 (t, J=6.2 Hz, 2H, $CH_2O$), 7.10 (d, J=8.9 Hz, 2H, Ar), 7.67 (m, 3H, Ar and Pyr), 7.74 (d, J=8.8 Hz, 2H, Ar), 7.85 (d, J=1.9 Hz, 1H, Ar), 8.04 (d, J=8.3 Hz, 1H, Ar), 8.15 (d, J=7.3 Hz, 2H, Pyr).

EM-9176
$^1$H NMR (400 MHz, acetone-$d_6$) δ: 1.57 (s, 6H, 2 Me), 2.26 (p, J=6.6 Hz, 2H, $CH_2$), 3.66 (t, J=7.2 Hz, 2H, $CH_2N$), 4.22 (t, J=6.1 Hz, 2H, $CH_2O$), 7.08 (d, J=8.9 Hz, 2H, Ar), 7.66 (d, J=7.3 Hz, 2H, Pyr), 7.71 (m, 4H, Ar), 7.94 (t, J=8.0 Hz, 1H, Ar), 8.15 (d, J=7.3 Hz, 2H, Pyr).

EM-9180
$^1$H NMR (400 MHz, acetone-$d_6$) δ: 1.64 (s, 6H, 2 Me), 3.87 (t, J=5.7 Hz, 2H, $CH_2N$), 4.36 (t, J=5.7 Hz, 2H, $CH_2O$), 7.10 (d, J=8.9 Hz, 2H, Ar), 7.65 (d, J=7.3 Hz, 2H, Pyr), 7.72 (d, J=8.9 Hz, 2H, Ar), 8.15 (d, J=7.4 Hz, 2H, Pyr), 8.17 (dd, J=1.7 and 8.3 Hz, 1H, Ar), 8.20 (d, J=8.5 Hz, 1H, Ar), 8.29 (d, J=1.3 Hz, 1H, Ar).

EM-9198
$^1$H NMR (400 MHz, acetone-$d_6$) δ: 1.59 (s, 6H, 2 Me), 2.30 (p, J=6.7 Hz, 2H, $CH_2$), 3.69 (t, J=7.0 Hz, 2H, $CH_2N$), 4.33 (t, J=6.0 Hz, 2H, $CH_2O$), 7.29 (t, J=8.8 Hz, 1H, Ar), 7.63 (m, 4H, Ar and Pyr), 7.79 (dd, J=1.9 and 8.5 Hz, 1H, Ar), 7.90 (d, J=1.9 Hz, 1H, Ar), 7.97 (d, J=8.5 Hz, 1H, Ar), 8.62 (d, J=6.1 Hz, 2H, Pyr).

EM-9200
$^1$H NMR (400 MHz, acetone-$d_6$) δ: 1.52 (s, 6H, 2 Me), 4.80 (s, 2H, $CH_2$), 7.45 (ddd, J=0.7, 4.7 and 7.9 Hz, 1H, Pyr), 7.65 (d, J=8.3 Hz, 2H, Ar), 7.71 (d, J=8.4 Hz, 2H, Ar), 8.03 (ddd, J=1.7, 2.3 and 7.9 Hz, 1H, Ar), 8.23 (m, 2H, Ar), 8.34 (s, 1H, Ar), 8.57 (dd, J=1.5 and 4.7 Hz, 1H, Pyr), 8.88 (d, J=1.7 Hz, 1H, Pyr).

EM-9201
$^1$H NMR (400 MHz, acetone-$d_6$) δ: 1.93 (m, 4H, $CH_2$ of cyclopentyl group), 2.13 (m, 2H, $CH_2$ of cyclopentyl group), 2.19 (m, 2H, $CH_2$ of cyclopentyl group), 2.31 (p, J=7.1 Hz, 2H, $CH_2$), 3.63 (t, J=7.2 Hz, 2H, $CH_2N$), 4.26 (t, J=6.0 Hz, 2H, $CH_2O$), 6.91 (dd, J=2.4 and 13.1 Hz, 1H, Ar), 6.96 (dd, J=2.5 and 8.6 Hz, 1H, Ar), 7.53 (dt, J=1.5 and 4.5 Hz, 2H, Pyr), 7.59 (t, J=8.9 Hz, 1H, Ar), 7.81 (dd, J=1.9 and 8.5 Hz, 1H, Ar), 7.94 (d, J=1.9 Hz, 1H, Ar), 7.98 (d, J=8.5 Hz, 1H, Ar), 8.63 (d, J=5.7 Hz, 2H, Pyr).

EM-9204
$^1$H NMR (400 MHz, acetone-$d_6$) δ: 1.60 (s, 3H, Me), 1.62 (s, 3H, Me), 2.17 (d, J=2.3 Hz, 3H, Me of aromatic group), 2.30 (p, J=6.7 Hz, 2H, $CH_2$), 3.67 (2t, J=7.1 Hz, 2H, $CH_2N$), 4.32 (t, J=6.1 Hz, 2H, $CH_2O$), 7.29 (t, J=8.6 Hz, 1H, Ar), 7.36 (dd, J=0.7 and 8.3 Hz, 1H, Ar), 7.59-7.67 (m, 4H, Ar and Pyr), 7.78 (t, J=7.7 Hz, 1H, Ar), 8.61 (d, J=6.1 Hz, 2H, Pyr).

EM-9205
$^1$H NMR (400 MHz, acetone-$d_6$) δ: 1.59 (s, 3H, Me), 1.62 (s, 3H, Me), 2.17 (d, J=2.2 Hz, 3H, Me of aromatic group), 2.28 (p, J=7.0 Hz, 2H, $CH_2$), 3.66 (t, J=7.2 Hz, 2H, $CH_2N$), 4.25 (t, J=6.1 Hz, 2H, $CH_2O$), 6.91 (dd, J=2.4 and 13.1 Hz, 1H, Ar), 6.96 (dd, J=2.5 and 8.6 Hz, 1H, Ar), 7.38 (dd, J=0.7 and 8.3 Hz, 1H, Ar), 7.53 (dt, J=1.6 and 4.5 Hz, 2H, Pyr), 7.59 (t, J=8.9 Hz, 1H, Ar), 7.79 (dd, J=7.5 and 7.9 Hz, 1H, Ar), 8.63 (d, J=6.1 Hz, 2H, Pyr).

EM-9208
$^1$H NMR (400 MHz, acetone-$d_6$) δ: 1.59 (s, 3H, Me), 1.62 (s, 3H, Me), 2.17 (d, J=2.2 Hz, 3H, Me of aromatic group), 2.27 (p, J=7.0 Hz, 2H, CH$_2$), 3.65 (t, J=7.2 Hz, 2H, CH$_2$N), 4.24 (t, J=6.1 Hz, 2H, CH$_2$O), 6.91 (dd, J=2.4 and 13.3 Hz, 1H, Ar), 6.95 (dd, J=2.5 and 8.5 Hz, 1H, Ar), 7.37 (d, J=8.4 Hz, 1H, Ar), 7.58 (d, J=7.2 Hz, 2H, Pyr), 7.60 (t, J=9.2 Hz, 1H, Ar), 7.79 (dd, J=7.3 and 7.8 Hz, 1H, Ar), 8.18 (d, J=7.3 Hz, 2H, Pyr).

EM-9221
$^1$H NMR (400 MHz, acetone-$d_6$) δ: 1.58 (s, 6H, 2 Me), 2.25 (p, J=7.2 Hz, 2H, CH$_2$), 2.32 (s, 3H, Me of aromatic group), 3.65 (t, J=7.2 Hz 2H, CH$_2$N), 4.19 (t, J=6.1 Hz 2H, CH$_2$O), 6.89 (dd, J=2.5 and 8.4 Hz, 1H, Ar), 6.92 (d, J=2.4 Hz, 1H, Ar), 7.23 (d, J=8.4 Hz, 1H, Ar), 7.35 (d, J=7.2 Hz, 2H, Pyr), 7.81 (dd, J=1.9 and 8.5 Hz, 1H, Ar), 7.93 (d, J=1.8 Hz, 1H, Ar), 7.99 (d, J=8.5 Hz, 1H, Ar), 8.16 (d, J=7.2 Hz, 2H, Pyr).

EM-9225
$^1$H NMR (400 MHz, acetone-$d_6$) δ: 1.58 (s, 6H, 2 Me), 2.25 (p, J=7.2 Hz, 2H, CH$_2$), 3.64 (t, J=7.3 Hz, 2H, CH$_2$N), 4.49 (t, J=6.2 Hz, 2H, CH$_2$O), 6.93 (dd, J=0.6 and 8.7 Hz, 1H, Pyr), 7.71 (d, J=7.4 Hz, 2H, Pyr), 7.82 (dd, J=1.9 and 8.5 Hz, 1H, Ar), 7.95 (d, J=1.9 Hz, 1H, Ar), 7.99 (d, J=8.5 Hz, 1H, Ar), 8.09 (dd, J=2.6 and 8.7 Hz, 1H, Pyr), 8.19 (d, J=7.3 Hz, 2H, Pyr), 8.58 (d, J=2.1 Hz, 1H, Pyr).

EM-9226
$^1$H NMR (400 MHz, acetone-$d_6$) δ: 1.59 (s, 6H, 2 Me), 2.29 (p, J=6.7 Hz, 2H, CH$_2$), 3.68 (t, J=7.0 Hz, 2H, CH$_2$N), 4.32 (t, J=6.0 Hz, 2H, CH$_2$O), 7.26 (t, J=8.7 Hz, 1H, Ar), 7.56 (ddd, J=1.1, 2.2 and 8.5 Hz, 1H, Ar), 7.59 (dd, J=2.3 and 12.4 Hz, 1H, Ar), 7.69 (d, J=7.4 Hz, 2H, Pyr), 7.78 (dd, J=1.9 and 8.5 Hz, 1H, Ar), 7.89 (d, J=1.9 Hz, 1H, Ar), 7.97 (d, J=8.5 Hz, 1H, Ar), 8.16 (d, J=7.4 Hz, 2H, Pyr).

EM-9227
$^1$H NMR (400 MHz, acetone-$d_6$) δ: 1.55 (s, 6H, 2 Me), 4.82 (s, 2H, CH$_2$), 7.47 (d, J=11.6 Hz, 1H, Ar), 7.49 (dd, J=1.6 and 9.4 Hz, 1H, Ar), 7.57 (dt, J=1.6 and 4.5 Hz, 2H, Pyr), 7.63 (t, J=8.0 Hz, 1H, Ar), 8.22 (m, 2H, Ar), 8.33 (s, 1H, Ar), 8.67 (d, J=6.1 Hz, 2H, Pyr).

EM-9228
$^1$H NMR (400 MHz, acetone-$d_6$) δ: 1.55 (s, 6H, 2 Me), 4.81 (s, 2H, CH$_2$), 7.45 (d, J=10.7 Hz, 1H, Ar), 7.48 (d, J=6.8 Hz, 1H, Ar), 7.64 (m, 3H, Ar and Pyr), 8.22 (m, 4H, Ar and Pyr), 8.33 (s, 1H, Ar).

EM-9261
$^1$H NMR (400 MHz, acetone-$d_6$) δ: 1.62 (s, 6H, 2 Me), 2.26 (p, J=6.0 Hz, 2H, CH$_2$), 3.70 (t, J=6.8 Hz 2H, CH$_2$N), 3.81 (s, 3H, OMe), 4.27 (t, J=5.7 Hz 2H, CH$_2$O), 7.09 (d, J=8.3 Hz, 1H, Ar), 7.33 (d, J=2.0 Hz, 1H, Ar), 7.36 (dd, J=2.1 and 8.2 Hz, 1H, Ar), 7.63 (d, J=6.2 Hz, 2H, Pyr), 7.72 (dd, J=1.9 and 8.5 Hz, 1H, Ar), 7.77 (d, J=1.7 Hz, 1H, Ar), 7.93 (d, J=8.6 Hz, 1H, Ar), 8.58 (d, J=6.1 Hz, 2H, Pyr).

EM-9267
$^1$H NMR (400 MHz, acetone-$d_6$) δ: 1.59 (s, 6H, 2 Me), 2.28 (p, J=7.1 Hz, 2H, CH$_2$), 3.67 (t, J=7.2 Hz 2H, CH$_2$N), 4.24 (t, J=6.1 Hz 2H, CH$_2$O), 7.12 (d, J=8.9 Hz, 2H, Ar), 7.55 (dd, J=5.0 and 7.0 Hz, 1H, Pyr), 7.67 (dd, J=1.5 and 8.9 Hz, 2H, Ar), 7.80 (dd, J=2.0 and 8.5 Hz, 1H, Ar), 7.93 (d, J=1.8 Hz, 1H, Ar), 7.98 (d, J=8.6 Hz, 1H, Ar), 8.44 (dd, J=0.9 and 5.0 Hz, 1H, Pyr), 8.52 (d, J=2.9 Hz, 1H, Pyr).

EM-9342
$^1$H NMR (400 MHz, acetone-$d_6$) δ: 1.65 (s, 3H, Me), 1.71 (s, 3H, Me), 2.48 (t, J=2.1 Hz, 3H, Me of aromatic group), 7.50 (ddd, J=0.8, 4.8 and 7.9 Hz, 1H, Pyr), 7.65 (d, J=8.6 Hz, 2H, Ar), 7.87 (d, J=8.6 Hz, 2H, Ar), 7.97 (d, J=8.3 Hz, 1H, Ar), 8.10 (m, 2H, Ar and Pyr), 8.62 (dd, J=1.5 and 4.8 Hz, 1H, Pyr), 8.94 (d, J=1.7 Hz, 1H, Pyr).

EM-9343
$^1$H NMR (400 MHz, acetone-$d_6$) δ: 1.51 (s, 3H, Me), 1.53 (s, 3H, Me), 2.35 (s, 3H, Me of aromatic group), 4.78 (s, 2H, CH$_2$), 7.61 (d, J=8.3 Hz, 1H, Ar), 7.65 (d, J=8.6 Hz, 2H, Ar), 7.67 (d, J=6.3 Hz, 2H, Pyr), 7.81 (d, J=8.3 Hz, 2H, Ar), 7.91 (dd, J=0.4 and 8.3 Hz, 1H, Ar), 8.64 (d, J=5.9 Hz, 2H, Pyr).

EM-9344
$^1$H NMR (400 MHz, acetone-$d_6$) δ: 1.65 (s, 3H, Me), 1.72 (s, 3H, Me), 2.48 (t, J=2.1 Hz, 3H, Me of aromatic group), 7.67 (d, J=8.6 Hz, 2H, Ar), 7.72 (d, J=6.1 Hz, 2H, Pyr), 7.95 (d, J=8.7 Hz, 2H, Ar), 7.97 (d, J=9.4 Hz, 1H, Ar), 8.09 (d, J=8.2 Hz, 1H, Ar), 8.68 (d, J=6.1 Hz, 2H, Pyr).

EM-9345
$^1$H NMR (400 MHz, acetone-$d_6$) δ: 1.51 (s, 3H, Me), 1.52 (s, 3H, Me), 2.34 (s, 3H, Me of aromatic group), 4.76 (s, 2H, CH$_2$), 7.60 (d, J=8.4 Hz, 1H, Ar), 7.63 (d, J=8.4 Hz, 2H, Ar), 7.74 (d, J=7.3 Hz, 2H, Pyr), 7.78 (d, J=8.4 Hz, 2H, Ar), 7.90 (dd, J=0.3 and 8.3 Hz, 1H, Ar), 8.19 (d, J=7.3 Hz, 2H, Pyr).

The following compounds from Table 4 are obtained from the procedures described in Examples 1-10. The $^1$H NMR description for each compound is presented (except compounds which are already found in Examples 1-10):

EM-8656
$^1$H NMR (400 MHz, acetone-$d_6$) δ: 1.68 (s, 3H, Me), 1.68 (s, 3H, Me), 2.27 (s, 3H, Me of aromatic group), 2.42 (p, J=7.3 Hz, 2H, CH$_2$), 4.04 (m, 2H, CH$_2$N), 4.23 (t, J=6.2 Hz, 2H, CH$_2$O), 7.12 (d, J=8.8 Hz, 2H, Ar), 7.42 (ddd, 0.7, 4.8 and 7.9 Hz, 1H, Pyr), 7.55 (d, J=8.3 Hz, 1H, Ar), 7.67 (d, J=8.8 Hz, 2H, Ar), 7.90 (d, J=8.3 Hz, 1H, Ar), 7.99 (m, 1H, Pyr), 8.52 (dd, J=1.5 and 4.7 Hz, 1H, Pyr), 8.84 (d, J=1.9 Hz, 1H, Pyr).

EM-8664
$^1$H NMR (400 MHz, acetone-$d_6$) δ: 1.67 (s, 3H, Me), 1.68 (s, 3H, Me), 2.27 (s, 3H, Me of aromatic group), 2.42 (p, J=7.3 Hz, 2H, CH$_2$), 4.04 (m, 2H, CH$_2$N), 4.24 (t, J=6.2 Hz, 2H, CH$_2$O), 7.12 (d, J=8.9 Hz, 2H, Ar), 7.55 (d, J=8.2 Hz, 1H, Ar), 7.62 (d, J=6.2 Hz, 2H, Pyr), 7.77 (d, J=8.8 Hz, 2H, Ar), 7.90 (dd, J=0.4 and 8.3 Hz, 1H, Ar), 8.59 (d, J=6.1 Hz, 2H, Pyr).

EM-8685
$^1$H NMR (400 MHz, acetone-$d_6$) δ: 1.68 (s, 3H, Me), 1.69 (s, 3H, Me), 2.27 (s, 3H, Me of aromatic group), 2.42 (p, J=7.3 Hz, 2H, CH$_2$), 4.05 (m, 2H, CH$_2$N), 4.24 (t, J=6.2 Hz, 2H, CH$_2$O), 7.16 (d, J=8.8 Hz, 2H, Ar), 7.55 (d, J=8.2 Hz, 1H, Ar), 7.75 (d, J=8.8 Hz, 2H, Ar), 7.90 (d, J=8.2 Hz, 1H, Ar), 9.03 (s, 2H, Pyr), 9.09 (s, 1H, Pyr).

EM-8691
$^1$H NMR (400 MHz, acetone-$d_6$) δ: 1.69 (s, 3H, Me), 1.70 (s, 3H, Me), 2.35 (d, J=2.0 Hz, 3H, Me of aromatic group), 2.42 (p, J=7.2 Hz, 2H, CH$_2$), 4.04 (m, 2H, CH$_2$N), 4.24 (t, J=6.2 Hz, 2H, CH$_2$O), 7.12 (d, J=8.8 Hz, 2H, Ar), 7.62 (d, J=6.2 Hz, 2H, Pyr), 7.77 (d, J=8.8 Hz, 2H, Ar), 7.88 (d, J=8.2 Hz, 1H, Ar), 8.06 (d, J=8.2 Hz, 1H, Ar), 8.59 (d, J=6.2 Hz, 2H, Pyr).

EM-8714
$^1$H NMR (400 MHz, acetone-$d_6$) δ: 1.68 (s, 3H, Me), 1.69 (s, 3H, Me), 2.26 (s, 3H, Me of aromatic group), 2.45 (p, J=7.2 Hz, 2H, CH$_2$), 4.06 (m, 2H, CH$_2$N), 4.33 (t, J=6.1 Hz, 2H, CH$_2$O), 7.30 (t, J=8.6 Hz, 1H, Ar), 7.44 (ddd, 0.7, 4.8 and 8.0 Hz, 1H, Pyr), 7.51 (ddd, 1.1, 2.2 and 9.6 Hz, 1H, Ar), 7.54 (d, J=8.3 Hz, 1H, Ar), 7.57 (dd, J=2.2 and 12.6 Hz, 1H, Ar), 7.90 (d, J=8.2 Hz, 1H, Ar), 8.02 (m, 1H, Pyr), 8.55 (dd, J=1.5 and 4.7 Hz, 1H, Pyr), 8.87 (dd, J=0.6 and 2.3 Hz, 1H, Pyr).

EM-8715

$^1$H NMR (400 MHz, acetone-$d_6$) δ: 1.68 (s, 3H, Me), 1.69 (s, 3H, Me), 2.26 (s, 3H, Me of aromatic group), 2.45 (p, J=7.3 Hz, 2H, CH$_2$), 4.06 (m, 2H, CH$_2$N), 4.33 (t, J=6.1 Hz, 2H, CH$_2$O), 7.26 (t, J=8.7 Hz, 1H, Ar), 7.30 (ddd, 1.1, 4.8 and 7.4 Hz, 1H, Pyr), 7.54 (d, J=8.2 Hz, 1H, Ar), 7.90 (m, 4H, Ar and Pyr), 7.97 (dd, J=2.1 and 13.0 Hz, 1H, Ar), 8.64 (ddd, J=0.9, 1.7 and 4.7 Hz, 1H, Pyr).

EM-8723

$^1$H NMR (400 MHz, acetone-$d_6$) δ: 1.68 (s, 3H, Me), 1.69 (s, 3H, Me), 2.26 (s, 3H, Me of aromatic group), 2.45 (p, J=7.2 Hz, 2H, CH$_2$), 4.06 (m, 2H, CH$_2$N), 4.34 (t, J=6.1 Hz, 2H, CH$_2$O), 7.31 (t, J=8.6 Hz, 1H, Ar), 7.54 (d, J=8.3 Hz, 1H, Ar), 7.60-7.68 (m, 4H, Ar and Pyr), 7.89 (d, J=8.3 Hz, 1H, Ar), 8.61 (d, J=6.1 Hz, 2H, Pyr).

EM-8772

$^1$H NMR (400 MHz, acetone-$d_6$) δ: 1.69 (s, 3H, Me), 1.70 (s, 3H, Me), 2.35 (d, J=2.1 Hz, 3H, Me of aromatic group), 2.48 (p, J=7.4 Hz, 2H, CH$_2$), 4.04 (m, 2H, CH$_2$N), 4.40 (t, J=5.9 Hz, 2H, CH$_2$O), 7.43 (d, J=8.7 Hz, 1H, Ar), 7.71 (d, J=6.2 Hz, 2H, Pyr), 7.89 (d, J=8.2 Hz, 1H, Ar), 8.05 (m, 3H, Ar), 8.64 (d, J=6.2 Hz, 2H, Pyr).

EM-8773

$^1$H NMR (400 MHz, acetone-$d_6$) δ: 1.67 (s, 3H, Me), 1.67 (s, 3H, Me), 2.27 (s, 3H, Me of aromatic group), 2.47 (p, J=7.3 Hz, 2H, CH$_2$), 4.02 (m, 2H, CH$_2$N), 4.40 (t, J=5.9 Hz, 2H, CH$_2$O), 7.43 (d, J=8.6 Hz, 1H, Ar), 7.56 (d, J=8.2 Hz, 1H, Ar), 7.70 (d, J=6.1 Hz, 2H, Pyr), 7.90 (d, J=8.3 Hz, 1H, Ar), 8.05 (s, 1H, Ar), 8.08 (dd, J=2.1 and 8.7 Hz, 1H, Ar), 8.64 (d, J=6.1 Hz, 2H, Pyr).

EM-8793

$^1$H NMR (400 MHz, acetone-$d_6$) δ: 1.70 (s, 3H, Me), 1.70 (s, 3H, Me), 2.34 (q, J=2.1 Hz, 3H, Me of aromatic group), 2.45 (p, J=7.1 Hz, 2H, CH$_2$), 4.06 (m, 2H, CH$_2$N), 4.34 (t, J=6.1 Hz, 2H, CH$_2$O), 7.31 (t, J=8.6 Hz, 1H, Ar), 7.60-7.68 (m, 4H, Ar and Pyr), 7.86 (d, J=8.2 Hz, 1H, Ar), 8.05 (d, J=8.2 Hz, 1H, Ar), 8.62 (bs, 2H, Pyr).

EM-8796

$^1$H NMR (400 MHz, acetone-$d_6$) δ: 1.68 (s, 3H, Me), 1.68 (s, 3H, Me), 2.27 (s, 3H, Me of aromatic group), 2.43 (p, J=7.3 Hz, 2H, CH$_2$), 4.04 (m, 2H, CH$_2$N), 4.27 (t, J=6.2 Hz, 2H, CH$_2$O), 6.93 (dd, J=2.4 and 13.1 Hz, 1H, Ar), 6.98 (dd, J=2.5 and 8.5 Hz, 1H, Ar), 7.54 (d, J=6.1 Hz, 2H, Pyr), 7.55 (d, J=8.2 Hz, 1H, Ar), 7.60 (t, J=8.9 Hz, 1H, Ar), 7.90 (dd, J=0.4 and 8.3 Hz, 1H, Ar), 8.63 (d, J=6.1 Hz, 2H, Pyr).

EM-8797

$^1$H NMR (400 MHz, acetone-$d_6$) δ: 1.69 (s, 3H, Me), 1.70 (s, 3H, Me), 2.35 (d, J=2.1 Hz, 3H, Me of aromatic group), 2.43 (p, J=7.2 Hz, 2H, CH$_2$), 4.05 (m, 2H, CH$_2$N), 4.27 (t, J=6.1 Hz, 2H, CH$_2$O), 6.93 (dd, J=2.4 and 13.1 Hz, 1H, Ar), 6.98 (dd, J=2.4 and 8.6 Hz, 1H, Ar), 7.54 (dt, J=1.6 and 4.5 Hz, 2H, Pyr), 7.60 (t, J=8.9 Hz, 1H, Ar), 7.88 (d, J=8.3 Hz, 1H, Ar), 8.06 (d, J=8.2 Hz, 1H, Ar), 8.63 (d, J=6.2 Hz, 2H, Pyr).

EM-8815

$^1$H NMR (400 MHz, acetone-$d_6$) δ: 1.66 (s, 3H, Me), 1.67 (s, 3H, Me), 2.27 (s, 3H, Me of aromatic group), 2.40 (p, J=7.3 Hz, 2H, CH$_2$), 4.03 (m, 2H, CH$_2$N), 4.52 (t, J=6.3 Hz, 2H, CH$_2$O), 6.97 (dd, J=0.6 and 8.7 Hz, 1H, Pyr), 7.55 (d, J=8.3 Hz, 1H, Ar), 7.67 (d, J=6.1 Hz, 2H, Pyr), 7.90 (dd, J=0.3 and 8.3 Hz, 1H, Ar), 8.13 (dd, J=2.6 and 8.7 Hz, 1H, Pyr), 8.61 (dd, J=0.4 and 2.5 Hz, 1H, Pyr), 8.64 (d, J=5.8 Hz, 2H, Pyr).

EM-8820

$^1$H NMR (400 MHz, acetone-$d_6$) δ: 1.68 (s, 3H, Me), 1.69 (s, 3H, Me), 2.27 (s, 3H, Me of aromatic group), 2.45 (p, J=7.3 Hz, 2H, CH$_2$), 4.07 (m, 2H, CH$_2$N), 4.33 (t, J=6.1 Hz, 2H, CH$_2$O), 7.32-7.40 (m, 5H, Ar and Pyr), 7.55 (d, J=8.3 Hz, 1H, Ar), 7.90 (d, J=8.3 Hz, 1H, Ar), 8.64 (bs, 2H, Pyr).

EM-8821

$^1$H NMR (400 MHz, acetone-$d_6$) δ: 1.70 (s, 3H, Me), 1.71 (s, 3H, Me), 2.27 (d, J=2.1 Hz, 3H, Me of aromatic group), 2.46 (p, J=7.2 Hz, 2H, CH$_2$), 4.08 (m, 2H, CH$_2$N), 4.34 (t, J=6.1 Hz, 2H, CH$_2$O), 7.32-7.41 (m, 5H, Ar and Pyr), 7.88 (d, J=8.2 Hz, 1H, Ar), 8.06 (d, J=8.2 Hz, 1H, Ar), 8.65 (bs, 2H, Pyr).

EM-8827

$^1$H NMR (400 MHz, acetone-$d_6$) δ: 1.67 (s, 3H, Me), 1.67 (s, 3H, Me), 2.25 (s, 3H, Me of aromatic group), 2.44 (p, J=7.3 Hz, 2H, CH$_2$), 4.05 (m, 2H, CH$_2$N), 4.33 (t, J=6.3 Hz, 2H, CH$_2$O), 7.54 (d, J=8.3 Hz, 1H, Ar), 7.54 (d, J=8.8 Hz, 1H, Pyr), 7.89 (dd, J=0.3 and 8.3 Hz, 1H, Ar), 8.02 (bs, 2H, Pyr), 8.05 (d, J=8.8 Hz, 1H, Pyr), 8.45 (d, J=2.8 Hz, 1H, Pyr), 8.68 (bs, 2H, Pyr).

EM-8828

$^1$H NMR (400 MHz, acetone-$d_6$) δ: 1.66 (s, 3H, Me), 1.67 (s, 3H, Me), 2.26 (s, 3H, Me of aromatic group), 2.40 (p, J=7.4 Hz, 2H, CH$_2$), 4.03 (m, 2H, CH$_2$N), 4.23 (t, J=6.1 Hz, 2H, CH$_2$O), 7.10 (d, J=8.9 Hz, 1H, Pyr), 7.49 (d, J=8.6 Hz, 1H, Pyr), 7.54 (d, J=8.4 Hz, 1H, Ar), 7.57 (dd, J=3.1 and 8.9 Hz, 1H, Pyr), 7.64 (dd, J=2.9 and 8.7 Hz, 1H, Pyr), 7.87 (d, J=3.0 Hz, 1H, Pyr), 7.90 (d, J=8.3 Hz, 1H, Ar), 8.24 (d, J=2.9 Hz, 1H, Pyr).

EM-8887

$^1$H NMR (400 MHz, acetone-$d_6$) δ: 1.68 (s, 3H, Me), 1.69 (s, 3H, Me), 2.27 (s, 3H, Me of aromatic group), 2.43 (p, J=7.3 Hz, 2H, CH$_2$), 4.05 (m, 2H, CH$_2$N), 4.27 (t, J=6.1 Hz, 2H, CH$_2$O), 7.09 (dd, J=2.5 and 8.6 Hz, 1H, Ar), 7.18 (d, J=2.5 Hz, 1H, Ar), 7.42 (d, J=8.5 Hz, 1H, Ar), 7.43 (d, J=6.0 Hz, 2H, Pyr), 7.55 (d, J=8.3 Hz, 1H, Ar), 7.90 (d, J=8.0 Hz, 1H, Ar), 8.64 (d, J=6.0 Hz, 2H, Pyr).

EM-8889

$^1$H NMR (400 MHz, acetone-$d_6$) δ: 1.70 (s, 3H, Me), 1.70 (s, 3H, Me), 2.35 (q, J=2.1 Hz, 3H, Me of aromatic group), 2.43 (p, J=7.3 Hz, 2H, CH$_2$), 4.06 (m, 2H, CH$_2$N), 4.27 (t, J=6.1 Hz, 2H, CH$_2$O), 7.09 (dd, J=2.5 and 8.6 Hz, 1H, Ar), 7.18 (d, J=2.5 Hz, 1H, Ar), 7.42 (d, J=8.6 Hz, 1H, Ar), 7.43 (d, J=6.0 Hz, 2H, Pyr), 7.88 (d, J=8.3 Hz, 1H, Ar), 8.07 (d, J=8.2 Hz, 1H, Ar), 8.64 (d, J=6.1 Hz, 2H, Pyr).

EM-8913

$^1$H NMR (400 MHz, methanol-$d_4$) δ: 1.64 (s, 6H, Me), 2.26 (s, 3H, Me of aromatic group), 2.41 (p, J=6.5 Hz, 2H, CH$_2$), 4.01 (m, 2H, CH$_2$N), 4.22 (t, J=6.0 Hz, 2H, CH$_2$O), 7.14 (d, J=8.9 Hz, 2H, Ar), 7.44 (d, J=8.2 Hz, 1H, Ar), 7.78 (d, J=8.9 Hz, 2H, Ar), 7.81 (d, J=8.5 Hz, 1H, Ar), 7.85 (d, J=7.3 Hz, 2H, Pyr), 8.59 (d, J=7.3 Hz, 2H, Pyr).

EM-8922

$^1$H NMR (400 MHz, acetone-$d_6$) δ: 1.67 (s, 3H, Me), 1.68 (s, 3H, Me), 2.27 (s, 3H, Me of aromatic group), 2.42 (p, J=7.3 Hz, 2H, CH$_2$), 4.04 (m, 2H, CH$_2$N), 4.23 (t, J=6.2 Hz, 2H, CH$_2$O), 7.11 (d, J=8.8 Hz, 2H, Ar), 7.14 (dd, J=2.8 and 8.7 Hz, 1H, Pyr), 7.55 (d, J=8.3 Hz, 1H, Ar), 7.65 (d, J=8.8 Hz, 2H, Ar), 7.90 (d, J=8.2 Hz, 1H, Ar), 8.19 (dt, J=2.1 and 8.7 Hz, 1H, Pyr), 8.45 (s, 1H, Pyr).

EM-8933

$^1$H NMR (400 MHz, acetone-$d_6$) δ: 1.68 (s, 3H, Me), 1.69 (s, 3H, Me), 2.27 (s, 3H, Me of aromatic group), 2.45 (p, J=7.4 Hz, 2H, CH$_2$), 4.06 (m, 2H, CH$_2$N), 4.35 (t, J=6.1 Hz, 2H, CH$_2$O), 7.45 (dd, J=2.7 and 8.7 Hz, 1H, Ar), 7.53 (d, J=2.9 Hz, 1H, Ar), 7.55 (d, J=8.7 Hz, 1H, Ar), 7.57 (d, J=6.1

Hz, 2H, Pyr), 7.66 (d, J=8.7 Hz, 1H, Ar), 7.90 (d, J=8.3 Hz, 1H, Ar), 8.71 (d, J=5.7 Hz, 2H, Pyr).

EM-8974
$^1$H NMR (400 MHz, acetone-$d_6$) δ: 1.69 (s, 3H, Me), 1.70 (s, 3H, Me), 2.35 (q, J=2.1 Hz, 3H, Me of aromatic group), 2.42 (p, J=7.2 Hz, 2H, CH$_2$), 4.06 (m, 2H, CH$_2$N), 4.26 (t, J=6.2 Hz, 2H, CH$_2$O), 7.14 (d, J=8.9 Hz, 2H, Ar), 7.55 (dd, J=5.0 and 7.0 Hz, 1H, Pyr), 7.68 (dd, J=1.5 and 8.8 Hz, 2H, Ar), 7.89 (d, J=8.5 Hz, 1H, Ar), 8.08 (d, J=8.6 Hz, 1H, Ar), 8.45 (dd, J=0.9 and 4.9 Hz, 1H, Pyr), 8.53 (d, J=2.9 Hz, 1H, Pyr).

EM-8977
$^1$H NMR (400 MHz, acetone-$d_6$) δ: 1.68 (s, 3H, Me), 1.69 (s, 3H, Me), 2.27 (s, 3H, Me of aromatic group), 2.43 (p, J=7.2 Hz, 2H, CH$_2$), 4.05 (m, 2H, CH$_2$N), 4.25 (t, J=6.0 Hz, 2H, CH$_2$O), 7.13 (d, J=8.8 Hz, 2H, Ar), 7.42 (d, J=4.9 Hz, 1H, Pyr), 7.53 (d, J=8.6 Hz, 2H, Ar), 7.55 (d, J=8.1 Hz, 1H, Ar), 7.90 (d, J=8.4 Hz, 1H, Ar), 8.53 (d, J=4.9 Hz, 1H, Pyr), 8.65 (s, 1H, Pyr).

EM-8993
$^1$H NMR (400 MHz, acetone-$d_6$) δ: 1.67 (s, 3H, Me), 1.68 (s, 3H, Me), 2.27 (s, 3H, Me of aromatic group), 2.40 (p, J=7.3 Hz, 2H, CH$_2$), 3.10 (s, 6H, NMe$_2$), 4.03 (m, 2H, CH$_2$N), 4.19 (t, J=6.2 Hz, 2H, CH$_2$O), 6.68 (d, J=8.8 Hz, 1H, Pyr), 7.03 (d, J=8.8 Hz, 2H, Ar), 7.52 (d, J=8.8 Hz, 1H, Ar), 7.55 (d, J=8.3 Hz, 1H, Ar), 7.74 (dd, J=2.6 and 8.8 Hz, 1H, Pyr), 7.90 (d, J=8.3 Hz, 1H, Ar), 8.37 (d, J=2.0 Hz, 1H, Pyr).

EM-8996
$^1$H NMR (400 MHz, acetone-$d_6$) δ: 1.67 (s, 3H, Me), 1.68 (s, 3H, Me), 2.27 (s, 3H, Me of aromatic group), 2.41 (p, J=7.3 Hz, 2H, CH$_2$), 3.11 (s, 6H, NMe$_2$), 4.03 (m, 2H, CH$_2$N), 4.22 (t, J=6.2 Hz, 2H, CH$_2$O), 6.69 (d, J=8.5 Hz, 1H, Pyr), 6.85 (dd, J=2.4 and 12.8 Hz, 1H, Ar), 6.89 (dd, J=2.5 and 8.4 Hz, 1H, Ar), 7.41 (t, J=8.9 Hz, 1H, Ar), 7.55 (d, J=8.3 Hz, 1H, Ar), 7.66 (d, J=8.9 Hz, 1H, Pyr), 7.90 (d, J=8.1 Hz, 1H, Ar), 8.27 (s, 1H, Pyr).

EM-9036
$^1$H NMR (400 MHz, acetone-$d_6$) δ: 1.68 (s, 3H, Me), 1.68 (s, 3H, Me), 2.27 (s, 3H, Me of aromatic group), 2.42 (p, J=7.3 Hz, 2H, CH$_2$), 4.04 (m, 2H, CH$_2$N), 4.27 (t, J=6.1 Hz, 2H, CH$_2$O), 7.09 (dd, J=2.6 and 8.6 Hz, 1H, Ar), 7.18 (d, J=2.5 Hz, 1H, Ar), 7.42 (d, J=9.3 Hz, 1H, Ar), 7.48 (d, J=7.3 Hz, 2H, Pyr), 7.55 (d, J=8.2 Hz, 1H, Ar), 7.90 (d, J=8.1 Hz, 1H, Ar), 8.20 (d, J=7.2 Hz, 2H, Pyr).

EM-9253
$^1$H NMR (400 MHz, acetone-$d_6$) δ: 1.60 (s, 3H, Me), 1.62 (s, 3H, Me), 2.28 (p, J=6.9 Hz, 2H, CH$_2$), 2.29 (s, 3H, Me of aromatic group), 3.66 (t, J=7.2 Hz, 2H, CH$_2$N), 4.25 (t, J=6.1 Hz, 2H, CH$_2$O), 6.91 (dd, J=2.4 and 13.1 Hz, 1H, Ar), 6.96 (dd, J=2.3 and 8.5 Hz, 1H, Ar), 7.51 (d, J=8.7 Hz, 1H, Ar), 7.53 (d, J=4.6 Hz, 2H, Pyr), 7.59 (t, J=8.9 Hz, 1H, Ar), 7.87 (d, J=8.2 Hz, 1H, Ar), 8.63 (d, J=6.1 Hz, 2H, Pyr).

EM-9254
$^1$H NMR (400 MHz, acetone-$d_6$) δ: 1.59 (s, 3H, Me), 1.61 (s, 3H, Me), 2.27 (p, J=6.9 Hz, 2H, CH$_2$), 2.29 (s, 3H, Me of aromatic group), 3.65 (t, J=7.2 Hz, 2H, CH$_2$N), 4.24 (t, J=6.1 Hz, 2H, CH$_2$O), 6.91 (dd, J=2.4 and 13.3 Hz, 1H, Ar), 6.95 (dd, J=2.5 and 8.5 Hz, 1H, Ar), 7.51 (d, J=8.3 Hz, 1H, Ar), 7.58 (d, J=8.4 Hz, 2H, Pyr), 7.60 (t, J=9.2 Hz, 1H, Ar), 7.86 (dd, J=0.4 and 8.3 Hz, 1H, Ar), 8.18 (d, J=7.4 Hz, 2H, Pyr).

EM-9290
$^1$H NMR (400 MHz, acetone-$d_6$) δ: 1.60 (s, 3H, Me), 1.62 (s, 3H, Me), 2.27 (p, J=7.2 Hz, 2H, CH$_2$), 2.29 (s, 3H, Me of aromatic group), 3.66 (t, J=7.2 Hz, 2H, CH$_2$N), 4.25 (t, J=6.1 Hz, 2H, CH$_2$O), 7.08 (dd, J=2.5 and 8.6 Hz, 1H, Ar), 7.16 (d, J=2.5 Hz, 1H, Ar), 7.41 (d, J=8.6 Hz, 1H, Ar), 7.43 (d, J=6.1 Hz, 2H, Pyr), 7.52 (d, J=8.3 Hz, 1H, Ar), 7.87 (dd, J=0.4 and 8.3 Hz, 1H, Ar), 8.64 (d, J=6.0 Hz, 2H, Pyr).

EM-9291
$^1$H NMR (400 MHz, acetone-$d_6$) δ: 1.60 (s, 3H, Me), 1.62 (s, 3H, Me), 2.27 (p, J=7.0 Hz, 2H, CH$_2$), 2.29 (s, 3H, Me of aromatic group), 3.66 (t, J=7.2 Hz, 2H, CH$_2$N), 4.24 (t, J=6.1 Hz, 2H, CH$_2$O), 7.07 (dd, J=2.6 and 8.6 Hz, 1H, Ar), 7.16 (d, J=2.5 Hz, 1H, Ar), 7.45 (d, J=8.6 Hz, 1H, Ar), 7.47 (d, J=7.2 Hz, 2H, Pyr), 7.51 (d, J=8.3 Hz, 1H, Ar), 7.87 (dd, J=0.4 and 8.3 Hz, 1H, Ar), 8.20 (d, J=7.3 Hz, 2H, Pyr).

EM-9297
$^1$H NMR (400 MHz, acetone-$d_6$) δ: 1.60 (s, 3H, Me), 1.62 (s, 3H, Me), 2.29 (s, 3H, Me of aromatic group), 2.30 (p, J=6.8 Hz, 2H, CH$_2$), 3.69 (dt, J=1.5 and 7.7 Hz, 2H, CH$_2$N), 4.31 (t, J=6.1 Hz, 2H, CH$_2$O), 7.29 (t, J=8.6 Hz, 1H, Ar), 7.50 (d, J=8.3 Hz, 1H, Ar), 7.60-7.67 (m, 4H, Ar and Pyr), 7.86 (d, J=8.2 Hz, 1H, Ar), 8.61 (d, J=6.2 Hz, 2H, Pyr).

EM-9300
$^1$H NMR (400 MHz, acetone-$d_6$) δ: 1.59 (s, 3H, Me), 1.61 (s, 3H, Me), 2.27 (p, J=6.7 Hz, 2H, CH$_2$), 2.29 (s, 3H, Me of aromatic group), 3.65 (t, J=7.2 Hz, 2H, CH$_2$N), 4.22 (t, J=6.1 Hz, 2H, CH$_2$O), 7.11 (d, J=8.8 Hz, 2H, Ar), 7.51 (d, J=8.3 Hz, 1H, Ar), 7.62 (d, J=6.2 Hz, 2H, Pyr), 7.76 (d, J=8.8 Hz, 2H, Ar), 7.86 (d, J=8.3 Hz, 1H, Ar), 8.59 (d, J=6.1 Hz, 2H, Pyr).

EM-9301
$^1$H NMR (400 MHz, acetone-$d_6$) δ: 1.60 (s, 3H, Me), 1.62 (s, 3H, Me), 2.28 (s, 3H, Me of aromatic group), 2.31 (p, J=6.8 Hz, 2H, CH$_2$), 3.69 (dt, J=1.3 and 7.6 Hz, 2H, CH$_2$N), 4.30 (t, J=6.1 Hz, 2H, CH$_2$O), 7.27 (t, J=8.7 Hz, 1H, Ar), 7.50 (d, J=8.3 Hz, 1H, Ar), 7.57 (ddd, J=1.1, 2.2 and 8.6 Hz, 1H, Ar), 7.63 (dd, J=2.3 and 12.7 Hz, 1H, Ar), 7.71 (d, J=7.4 Hz, 2H, Pyr), 7.86 (dd, J=0.4 and 8.3 Hz, 1H, Ar), 8.17 (d, J=7.4 Hz, 2H, Pyr).

EM-9305
$^1$H NMR (400 MHz, acetone-$d_6$) δ: 1.59 (s, 3H, Me), 1.61 (s, 3H, Me), 2.26 (p, J=6.8 Hz, 2H, CH$_2$), 2.29 (s, 3H, Me of aromatic group), 3.65 (t, J=7.2 Hz, 2H, CH$_2$N), 4.21 (t, J=6.2 Hz, 2H, CH$_2$O), 7.09 (d, J=8.9 Hz, 2H, Ar), 7.51 (d, J=8.3 Hz, 1H, Ar), 7.68 (d, J=7.4 Hz, 2H, Pyr), 7.73 (d, J=8.9 Hz, 2H, Ar), 7.86 (d, J=8.2 Hz, 1H, Ar), 8.16 (d, J=7.4 Hz, 2H, Pyr).

EM-9309
$^1$H NMR (400 MHz, acetone-$d_6$) δ: 1.58 (s, 3H, Me), 1.61 (s, 3H, Me), 2.30 (s and p, 5H, Me of aromatic group and CH$_2$), 3.65 (t, J=7.3 Hz, 2H, CH$_2$N), 4.38 (t, J=5.8 Hz, 2H, CH$_2$O), 7.41 (d, J=8.7 Hz, 1H, Ar), 7.53 (d, J=8.3 Hz, 1H, Ar), 7.70 (d, J=6.2 Hz, 2H, Pyr), 7.87 (d, J=8.4 Hz, 1H, Ar), 8.04 (s, 1H, Ar), 8.07 (dd, J=2.3 and 8.5 Hz, 1H, Ar), 8.64 (d, J=6.1 Hz, 2H, Pyr).

EM-9310
$^1$H NMR (400 MHz, acetone-$d_6$) δ: 1.60 (s, 3H, Me), 1.62 (s, 3H, Me), 2.27 (p, J=6.8 Hz, 2H, CH$_2$), 2.29 (s, 3H, Me of aromatic group), 3.66 (t, J=7.2 Hz, 2H, CH$_2$N), 4.23 (t, J=6.1 Hz, 2H, CH$_2$O), 7.11 (d, J=8.8 Hz, 2H, Ar), 7.42 (d, J=4.9 Hz, 1H, Pyr), 7.52 (d, J=8.5 Hz, 1H, Ar), 7.52 (d, J=8.8 Hz, 2H, Ar), 7.87 (d, J=8.4 Hz, 1H, Ar), 8.53 (d, J=4.9 Hz, 1H, Pyr), 8.65 (s, 1H, Pyr).

EM-9311
$^1$H NMR (400 MHz, acetone-$d_6$) δ: 1.60 (s, 3H, Me), 1.62 (s, 3H, Me), 2.27 (p, J=6.8 Hz, 2H, CH$_2$), 2.29 (s, 3H, Me of aromatic group), 3.66 (t, J=7.2 Hz, 2H, CH$_2$N), 4.23 (t, J=6.1 Hz, 2H, CH$_2$O), 7.12 (d, J=8.9 Hz, 2H, Ar), 7.51 (d, J=8.3 Hz, 1H, Ar), 7.55 (dd, J=5.0 and 7.0 Hz, 1H, Pyr), 7.67 (dd, J=1.4 and 8.8 Hz, 2H, Ar), 7.86 (d, J=8.3 Hz, 1H, Ar), 8.45 (d, J=4.9 Hz, 1H, Pyr), 8.53 (d, J=2.8 Hz, 1H, Pyr).

EM-9313
¹H NMR (400 MHz, acetone-d₆) δ: 1.60 (s, 3H, Me), 1.62 (s, 3H, Me), 2.27 (p, J=6.7 Hz, 2H, CH₂), 2.29 (s, 3H, Me of aromatic group), 3.66 (t, J=7.2 Hz, 2H, CH₂N), 4.22 (t, J=6.1 Hz, 2H, CH₂O), 7.09 (d, J=8.8 Hz, 2H, Ar), 7.43 (d, J=6.8 Hz, 1H, Pyr), 7.50 (d, J=8.8 Hz, 2H, Ar), 7.51 (d, J=8.3 Hz, 1H, Ar), 7.86 (d, J=8.3 Hz, 1H, Ar), 8.15 (dd, J=1.8 and 6.8 Hz, 1H, Pyr), 8.35 (d, J=1.7 Hz, 1H, Pyr).

EM-9318
¹H NMR (400 MHz, acetone-d₆) δ: 1.60 (s, 3H, Me), 1.61 (s, 3H, Me), 2.27 (p, J=6.8 Hz, 2H, CH₂), 2.29 (s, 3H, Me of aromatic group), 3.65 (t, J=7.2 Hz, 2H, CH₂N), 4.22 (t, J=6.1 Hz, 2H, CH₂O), 7.11 (d, J=8.9 Hz, 2H, Ar), 7.51 (d, J=8.3 Hz, 1H, Ar), 7.57 (dd, J=6.9 and 9.7 Hz, 1H, Pyr), 7.62 (dd, J=1.5 and 8.8 Hz, 2H, Ar), 7.86 (d, J=8.4 Hz, 1H, Ar), 8.08 (dd, J=1.0 and 6.8 Hz, 1H, Pyr), 8.29 (dd, J=1.7 and 6.6 Hz, 1H, Pyr).

EM-9319
¹H NMR (400 MHz, acetone-d₆) δ: 1.58 (s, 3H, Me), 1.60 (s, 3H, Me), 2.30 (s and p, 5H, Me of aromatic group and CH₂), 3.65 (t, J=7.3 Hz, 2H, CH₂N), 4.38 (t, J=5.9 Hz, 2H, CH₂O), 7.39 (d, J=8.6 Hz, 1H, Ar), 7.52 (d, J=8.3 Hz, 1H, Ar), 7.76 (d, J=7.3 Hz, 2H, Pyr), 7.87 (d, J=8.3 Hz, 1H, Ar), 8.02 (s, 1H, Ar), 8.04 (dd, J=2.2 and 8.7 Hz, 1H, Ar), 8.18 (d, J=7.3 Hz, 2H, Pyr).

EM-9333
¹H NMR (400 MHz, acetone-d₆) δ: 1.60 (s, 3H, Me), 1.63 (s, 3H, Me), 2.29 (s, 3H, Me of aromatic group), 2.31 (p, J=6.0 Hz, 2H, CH₂), 3.68 (t, J=7.2 Hz, 2H, CH₂N), 4.31 (t, J=6.1 Hz, 2H, CH₂O), 7.32-7.40 (m, 5H, Ar and Pyr), 7.52 (d, J=8.3 Hz, 1H, Ar), 7.87 (d, J=8.3 Hz, 1H, Ar), 8.63 (d, J=5.9 Hz, 2H, Pyr).

EM-9334
¹H NMR (400 MHz, acetone-d₆) δ: 1.60 (s, 3H, Me), 1.63 (s, 3H, Me), 2.29 (s, 3H, Me of aromatic group), 2.31 (p, J=6.0 Hz, 2H, CH₂), 3.68 (t, J=7.2 Hz, 2H, CH₂N), 4.31 (t, J=6.1 Hz, 2H, CH₂O), 7.34 (m, 3H, Ar and Pyr), 7.38 (d, J=2.5 Hz, 1H, Ar), 7.45 (d, J=8.5 Hz, 1H, Ar), 7.52 (d, J=8.3 Hz, 1H, Ar), 7.87 (d, J=8.4 Hz, 1H, Ar), 8.20 (d, J=7.2 Hz, 2H, Pyr).

EM-9337
¹H NMR (400 MHz, acetone-d₆) δ: 1.64 (s, 3H, Me), 1.66 (s, 3H, Me), 2.29 (s, 3H, Me of aromatic group), 3.87 (m, 2H, CH₂N), 4.37 (m, 2H, CH₂O), 7.14 (d, J=8.8 Hz, 2H, Ar), 7.53 (d, J=8.3 Hz, 1H, Ar), 7.63 (d, J=5.5 Hz, 2H, Pyr), 7.78 (d, J=8.8 Hz, 2H, Ar), 7.88 (d, J=8.3 Hz, 1H, Ar), 8.60 (bs, 2H, Pyr).

EM-9339
¹H NMR (400 MHz, acetone-d₆) δ: 1.64 (s, 3H, Me), 1.66 (s, 3H, Me), 2.28 (s, 3H, Me of aromatic group), 3.86 (m, 2H, CH₂N), 4.36 (m, 2H, CH₂O), 7.12 (d, J=8.9 Hz, 2H, Ar), 7.53 (d, J=8.3 Hz, 1H, Ar), 7.68 (d, J=7.3 Hz, 2H, Pyr), 7.74 (d, J=8.9 Hz, 2H, Ar), 7.88 (dd, J=0.4 and 8.3 Hz, 1H, Ar), 8.16 (d, J=7.3 Hz, 2H, Pyr).

The following compounds from Table 5 are obtained from the procedures described in Examples 1-10. The ¹H NMR description for each compound is presented:

EM-8728
¹H NMR (400 MHz, acetone-d₆) δ: 1.68 (s, 3H, Me), 1.69 (s, 3H, Me), 2.27 (s, 3H, Me of aromatic group), 2.47 (p, J=7.2 Hz, 2H, CH₂), 4.07 (m, 2H, CH₂N), 4.31 (t, J=6.1 Hz, 2H, CH₂O), 7.34 (d, J=2.7 Hz, 1H, Quinoline), 7.43 (t, J=2.1 Hz, 1H, Quinoline), 7.45 (t, J=3.0 Hz, 1H, Quinoline), 7.55 (d, J=8.3 Hz, 1H, Ar), 7.89 (d, J=8.3 Hz, 1H, Quinoline), 7.96 (d, J=9.2 Hz, 1H, Quinoline), 8.19 (d, J=8.3 Hz, 1H, Quinoline), 8.75 (dd, J=1.5 and 4.1 Hz, 1H, Quinoline).

EM-8729
¹H NMR (400 MHz, acetone-d₆) δ: 1.73 (s, 3H, Me), 1.77 (s, 3H, Me), 2.20 (s, 3H, Me of aromatic group), 2.52 (m, 2H, CH₂), 4.10 (m, 1H, CH₂N), 4.24 (m, 1H, CH₂N), 4.42 (m, 2H, CH₂O), 7.21 (m, 2H, Quinoline), 7.52 (m, 3H, Quinoline and Ar), 7.78 (d, J=8.2 Hz, 1H, Ar), 8.30 (dd, J=1.7 and 8.3 Hz, 1H, Quinoline), 8.86 (dd, J=1.7 and 4.1 Hz, 1H, Quinoline).

EM-8730
¹H NMR (400 MHz, acetone-d₆) δ: 1.69 (s, 3H, Me), 1.69 (s, 3H, Me), 2.27 (s, 3H, Me of aromatic group), 2.49 (p, J=7.3 Hz, 2H, CH₂), 4.09 (m, 2H, CH₂N), 4.34 (t, J=6.3 Hz, 2H, CH₂O), 7.28 (dd, J=2.5 and 8.9 Hz, 1H, Quinoline), 7.35 (dd, J=4.3 and 8.2 Hz, 1H, Quinoline), 7.42 (d, J=2.3 Hz, 1H, Quinoline), 7.56 (d, J=8.3 Hz, 1H, Ar), 7.87 (d, J=9.0 Hz, 1H, Quinoline), 7.89 (d, J=8.3 Hz, 1H, Ar), 8.23 (dd, J=1.0 and 8.1 Hz, 1H, Quinoline), 8.82 (dd, J=1.6 and 4.2 Hz, 1H, Quinoline).

EM-8786
¹H NMR (400 MHz, acetone-d₆) δ: 1.60 (s, 3H, Me), 1.63 (s, 3H, Me), 2.29 (s, 3H, Me of aromatic group), 2.33 (p, J=6.9 Hz, 2H, CH₂), 3.70 (t, J=7.2 Hz, 2H, CH₂N), 4.32 (t, J=6.1 Hz, 2H, CH₂O), 7.27 (dd, J=2.6 and 9.0 Hz, 1H, Quinoline), 7.35 (dd, J=4.3 and 8.2 Hz, 1H, Quinoline), 7.41 (d, J=2.4 Hz, 1H, Quinoline), 7.52 (d, J=8.2 Hz, 1H, Ar), 7.85 (d, J=8.3 Hz, 1H, Ar), 7.86 (d, J=9.0 Hz, 1H, Quinoline), 8.23 (d, J=7.9 Hz, 1H, Quinoline), 8.81 (dd, J=1.7 and 4.2 Hz, 1H, Quinoline).

EM-8869
¹H NMR (400 MHz, methanol-d₄) δ: 1.64 (s, 6H, Me), 2.24 (s, 3H, Me of aromatic group), 2.46 (p, J=6.4 Hz, 2H, CH₂), 4.03 (m, 2H, CH₂N), 4.31 (t, J=6.0 Hz, 2H, CH₂O), 7.32 (d, J=2.0 Hz, 1H, Isoquinoline), 7.36 (dd, J=2.4 and 8.9 Hz, 1H, Isoquinoline), 7.43 (d, J=8.2 Hz, 1H, Ar), 7.73 (d, J=5.6 Hz, 1H, Isoquinoline), 7.78 (d, J=8.3 Hz, 1H, Ar), 8.02 (d, J=9.0 Hz, 1H, Isoquinoline), 8.33 (bs, 1H, Isoquinoline), 9.08 (bs, 1H, Isoquinoline).

EM-8989
¹H NMR (400 MHz, acetone-d₆) δ: 1.68 (s, 6H, Me), 2.48 (m, 2H, CH₂), 4.08 (m, 2H, CH₂N), 4.35 (t, J=6.1 Hz, 2H, CH₂O), 7.46 (dd, J=2.5 and 8.9 Hz, 1H, Isoquinoline), 7.51 (d, J=2.4 Hz, 1H, Isoquinoline), 7.70 (d, J=5.6 Hz, 1H, Isoquinoline), 7.90 (d, J=8.9 Hz, 1H, Isoquinoline), 8.03 (dd, J=1.8 and 8.3 Hz, 1H, Ar), 8.17 (d, J=1.8 Hz, 1H, Ar), 8.25 (d, J=8.3 Hz, 1H, Ar), 8.38 (d, J=5.6 Hz, 1H, Isoquinoline), 9.17 (s, 1H, Isoquinoline).

EM-8990
¹H NMR (400 MHz, acetone-d₆) δ: 1.68 (s, 6H, Me), 2.47 (m, 2H, CH₂), 4.08 (m, 2H, CH₂N), 4.31 (t, J=6.1 Hz, 2H, CH₂O), 7.35 (d, J=2.8 Hz, 1H, Quinoline), 7.44 (m, 2H, Quinoline), 7.96 (d, J=9.2 Hz, 1H, Quinoline), 8.03 (dd, J=1.7 and 8.3 Hz, 1H, Ar), 8.17 (d, J=1.7 Hz, 1H, Ar), 8.20 (dd, J=1.0 and 8.4 Hz, 1H, Quinoline), 8.25 (d, J=8.3 Hz, 1H, Ar), 8.74 (dd, J=1.7 and 4.2 Hz, 1H, Quinoline).

EM-8991
¹H NMR (400 MHz, acetone-d₆) δ: 1.69 (s, 6H, Me), 2.48 (m, 2H, CH₂), 4.09 (m, 2H, CH₂N), 4.34 (t, J=6.2 Hz, 2H, CH₂O), 7.28 (dd, J=2.5 and 8.9 Hz, 1H, Quinoline), 7.35 (dd, J=4.3 and 8.2 Hz, 1H, Quinoline), 7.42 (d, J=2.4 Hz, 1H, Quinoline), 7.87 (d, J=9.0 Hz, 1H, Quinoline), 8.03 (dd, J=1.7 and 8.3 Hz, 1H, Ar), 8.17 (d, J=1.7 Hz, 1H, Ar), 8.23 (dd, J=1.3 and 8.1 Hz, 1H, Quinoline), 8.25 (d, J=8.3 Hz, 1H, Ar), 8.82 (dd, J=1.7 and 4.3 Hz, 1H, Quinoline).

EM-9010
¹H NMR (400 MHz, acetone-d₆) δ: 1.68 (s, 6H, Me), 2.49 (m, 2H, CH₂), 4.09 (m, 2H, CH₂N), 4.37 (t, J=6.1 Hz, 2H, CH₂O), 7.51 (d, J=2.8 Hz, 1H, Quinazoline), 7.70 (dd, J=2.8 and 9.2 Hz, 1H, Quinazoline), 7.96 (d, J=9.2 Hz, 1H, Quinazoline), 8.03 (dd, J=1.8 and 8.3 Hz, 1H, Ar), 8.16 (d, J=1.8 Hz, 1H, Ar), 8.26 (d, J=8.3 Hz, 1H, Ar), 9.14 (s, 1H, Quinazoline), 9.40 (s, 1H, Quinazoline).

EM-9021

$^1$H NMR (400 MHz, acetone-$d_6$) δ: 1.68 (s, 6H, Me), 2.47 (m, 2H, CH$_2$), 4.08 (m, 2H, CH$_2$N), 4.35 (t, J=6.2 Hz, 2H, CH$_2$O), 7.33 (m, 2H, Isoquinoline), 7.65 (d, J=5.8 Hz, 1H, Isoquinoline), 8.02 (d, J=8.1 Hz, 1H, Ar), 8.03 (d, J=9.7 Hz, 1H, Isoquinoline), 8.17 (d, J=1.8 Hz, 1H, Ar), 8.25 (d, J=8.3 Hz, 1H, Ar), 8.41 (d, J=5.7 Hz, 1H, Isoquinoline), 9.14 (s, 1H, Isoquinoline).

EM-9028

$^1$H NMR (400 MHz, acetone-$d_6$) δ: 1.68 (s, 6H, Me), 2.46 (m, 2H, CH$_2$), 4.07 (m, 2H, CH$_2$N), 4.33 (t, J=6.1 Hz, 2H, CH$_2$O), 7.38 (dd, J=6.0 and 8.3 Hz, 1H, Quinoline), 7.44 (m, 2H, Quinoline), 7.73 (d, J=8.5 Hz, 1H, Quinoline), 8.03 (dd, J=1.7 and 8.3 Hz, 1H, Ar), 8.17 (d, J=1.7 Hz, 1H, Ar), 8.25 (d, J=8.2 Hz, 1H, Ar), 8.35 (dd, J=0.7 and 6.0 Hz, 1H, Quinoline), 8.54 (d, J=9.1 Hz, 1H, Quinoline).

EM-9090

$^1$H NMR (400 MHz, acetone-$d_6$) δ: 1.60 (s, 6H, Me), 2.32 (p, J=7.1 Hz, 2H, CH$_2$), 2.62 (s, 3H, Me of quinoline), 3.70 (t, J=7.2 Hz, 2H, CH$_2$N), 4.27 (t, J=6.1 Hz, 2H, CH$_2$O), 7.27 (d, J=2.8 Hz, 1H, Quinoline), 7.32 (d, J=8.4 Hz, 1H, Quinoline), 7.37 (dd, J=2.8 and 9.1 Hz, 1H, Quinoline), 7.84 (d, J=9.1 Hz, 1H, Quinoline), 8.06 (d, J=8.4 Hz, 1H, Quinoline), 8.14 (dd, J=1.8 and 6.7 Hz, 1H, Ar), 8.19 (d, J=8.5 Hz, 1H, Ar), 8.27 (d, J=1.8 Hz, 1H, Ar).

EM-9093

$^1$H NMR (400 MHz, acetone-$d_6$) δ: 1.60 (s, 6H, Me), 2.33 (p, J=7.1 Hz, 2H, CH$_2$), 2.55 (s, 3H, Me of quinoline), 3.70 (t, J=7.2 Hz, 2H, CH$_2$N), 4.31 (t, J=6.1 Hz, 2H, CH$_2$O), 7.39 (dd, J=2.6 and 9.4 Hz, 1H, Quinoline), 7.43 (d, J=2.7 Hz, 1H, Quinoline), 7.44 (d, J=8.6 Hz, 1H, Quinoline), 7.64 (d, J=8.5 Hz, 1H, Quinoline), 8.15 (dd, J=1.7 and 8.5 Hz, 1H, Ar), 8.20 (d, J=8.4 Hz, 1H, Ar), 8.26 (d, J=2.0 Hz, 1H, Ar), 8.56 (d, J=9.4 Hz, 1H, Quinoline).

EM-9302

$^1$H NMR (400 MHz, acetone-$d_6$) δ: 1.61 (s, 3H, Me), 1.63 (s, 3H, Me), 2.29 (s, 3H, Me of aromatic group), 2.34 (p, J=6.5 Hz, 2H, CH$_2$), 3.70 (dt, J=1.8 and 7.1 Hz, 2H, CH$_2$N), 4.35 (t, J=6.2 Hz, 2H, CH$_2$O), 7.32 (dd, J=6.1 and 8.4 Hz, 1H, Quinoline), 7.38 (dd, J=1.6 and 9.0 Hz, 1H, Quinoline), 7.53 (d, J=8.3 Hz, 1H, Ar), 7.82 (d, J=8.3 Hz, 1H, Ar), 7.85 (d, J=8.3 Hz, 1H, Quinoline), 7.98 (d, J=9.0 Hz, 1H, Quinoline), 8.01 (d, J=2.5 Hz, 1H, Quinoline), 8.48 (dd, J=0.7 and 6.1 Hz, 1H, Quinoline).

Pharmaceutical Composition Examples

Set forth below, by way of example and not of limitation, are several pharmaceutical compositions utilizing a preferred active antiandrogen EM-9150 for systemic use. Other antiandrogens or SARMs of the invention or combination thereof, may be used in place of (or in addition to) EM-9150. The concentration of active ingredient may be varied over a wide range as discussed herein. The amounts and types of other ingredients that may be included are well known in the art.

Example A

Composition Suitable for Injection

| Ingredient | Weight % (by weight of total composition) |
|---|---|
| EM-9150 | 5.0 |
| Ethanol | 6.4 |
| NaCl | 0.8 |
| Water | 86.9 |
| Benzyl alcohol | 0.9 |

Example B

Tablet

| Ingredient | Weight % (by weight of total composition) |
|---|---|
| EM-9150 | 20.0 |
| Gelatin | 5.0 |
| Lactose | 47.5 |
| Starch | 27.5 |

Example C

Gelatin Capsule

| Ingredient | Weight % (by weight of total composition) |
|---|---|
| EM-9150 | 20.0 |
| Lactose hydrous | 62.0 |
| Starch | 4.8 |
| Cellulose microcrystalline | 12.8 |
| Magnesium stearate | 0.4 |

Other antiandrogens (i.e. EM-9198, EM-9204 or EM-9205) or SARMs (i.e. EM-9251, EM-9253, EM-9290 or EM-9309) may be substituted for EM-9150 in the above formulations. For combination therapies, 5alpha-reductase inhibitors, type 5 17beta-hydroxysteroid dehydrogenase inhibitors, type 15 17beta-hydroxysteroid dehydrogenase inhibitors and 17alpha-hydroxylase/17,20-lyase inhibitors could be added at weight % (with pro rata reduction of other components). More than one antiandrogen or SARM or more than one inhibitor may be included in the pharmaceutical compositions.

Example D

Composition Suitable for Injection

| Ingredient | Weight % (by weight of total composition) |
|---|---|
| EM-9150 | 5.0 |
| Finasteride | 0.4 |
| Ethanol | 6.0 |
| NaCl | 0.8 |

Example E

Tablet

| Ingredient | Weight % (by weight of total composition) |
|---|---|
| EM-9150 | 20.0 |
| Finasteride | 1.0 |
| Gelatin | 5.0 |
| Lactose | 46.5 |
| Starch | 27.5 |

Example F

Gelatin Capsule

| Ingredient | Weight % (by weight of total composition) |
|---|---|
| EM-9150 | 20.0 |
| Finasteride | 1.0 |
| Lactose hydrous | 61.0 |
| Starch | 4.8 |
| Cellulose microcrystalline | 12.8 |
| Magnesium stearate | 0.4 |

Example G

Composition Suitable for Injection

| Ingredient | Weight % (by weight of total composition) |
|---|---|
| EM-9150 | 5.0 |
| EM-1404 | 5.0 |
| Ethanol | 6.0 |
| NaCl | 0.8 |
| Water | 82.3 |
| Benzyl alcohol | 0.9 |

Example H

Tablet

| Ingredient | Weight % (by weight of total composition) |
|---|---|
| EM-9150 | 20.0 |
| EM-1404 | 20.0 |
| Gelatin | 5.0 |
| Lactose | 27.5 |
| Starch | 27.5 |

Example I

Gelatin Capsule

| Ingredient | Weight % (by weight of total composition) |
|---|---|
| EM-9150 | 20.0 |
| EM-1404 | 20.0 |
| Lactose hydrous | 42.0 |
| Starch | 4.8 |
| Cellulose microcrystalline | 12.8 |
| Magnesium stearate | 0.4 |

Example J

Composition Suitable for Injection

| Ingredient | Weight % (by weight of total composition) |
|---|---|
| EM-9150 | 5.0 |
| EM-1791 | 5.0 |
| Ethanol | 6.0 |
| NaCl | 0.8 |
| Water | 82.3 |
| Benzyl alcohol | 0.9 |

Example K

Tablet

| Ingredient | Weight % (by weight of total composition) |
|---|---|
| EM-9150 | 20.0 |
| EM-1791 | 20.0 |
| Starch | 27.5 |
| Gelatin | 5.0 |
| Lactose | 27.5 |

Example L

Gelatin Capsule

| Ingredient | Weight % (by weight of total composition) |
|---|---|
| EM-9150 | 20.0 |
| EM-1791 | 20.0 |
| Lactose hydrous | 42.0 |
| Cellulose microcrystalline | 12.8 |

-continued

| Ingredient | Weight % (by weight of total composition) |
|---|---|
| Water | 86.9 |
| Benzyl alcohol | 0.9 |

-continued

| Ingredient | Weight % (by weight of total composition) |
|---|---|
| Lactose | 27.5 |
| Starch | 27.5 |

Example M

Composition Suitable for Injection

| Ingredient | Weight % (by weight of total composition) |
| --- | --- |
| EM-9150 | 5.0 |
| Abiraterone Acetate | 5.0 |
| Ethanol | 6.0 |
| NaCl | 0.8 |
| Water | 82.3 |
| Benzyl alcohol | 0.9 |

Example N

Tablet

| Ingredient | Weight % (by weight of total composition) |
| --- | --- |
| EM-9150 | 20.0 |
| Abiraterone Acetate | 20.0 |
| Starch | 27.5 |
| Gelatin | 5.0 |
| Lactose | 27.5 |

Example O

Gelatin Capsule

| Ingredient | Weight % (by weight of total composition) |
| --- | --- |
| EM-9150 | 20.0 |
| Abiraterone Acetate | 20.0 |
| Lactose hydrous | 42.0 |
| Cellulose microcrystalline | 12.8 |
| Magnesium stearate | 0.4 |
| Starch | 4.8 |

Kit Examples

Set forth below, by way of example and not of limitation, are several kits utilizing preferred active antiandrogen EM-9150 and preferred LHRH agonist Leuprolide acetate (Lupron depot). Other compounds of the invention or combination thereof, may be used in place of (or in addition to) EM-9150 and Leuprolide acetate. LHRH antagonist could be used instead of LHRH agonist. The concentration of active ingredient may be varied over a wide range as discussed herein. The amounts and types of other ingredients that may be included are well known in the art.

Example A

Antiandrogen for Oral Administration (Tablet)

| Ingredient | Weight % (by weight of total composition) |
| --- | --- |
| EM-9150 | 20.0 |
| Gelatin | 5.0 |
| Lactose | 47.5 |
| Starch | 27.5 |

LHRH Agonist for Intramuscular Depot Injection

| Ingredient | Weight % (by weight of total composition) |
| --- | --- |
| Leuprolide acetate (Lupron depot ® - 3 months) | 0.7 |
| Polylactic acid | 6.1 |
| D-mannitol | 5.8 |
| Carboxymethylcellulose sodium | 0.5 |
| Polysorbate 80 | 0.1 |
| Glacial acetic acid (USP) | to control pH |
| Water for injection (USP) | 86.8 |

Example B

Antiandrogen for Oral Administration (Gelatin Capsule)

| Ingredient | Weight % (by weight of total composition) |
| --- | --- |
| EM-9150 | 20.0 |
| Lactose hydrous | 62.0 |
| Starch | 4.8 |
| Cellulose microcrystalline | 12.8 |
| Magnesium stearate | 0.4 |

LHRH Agonist for Intramuscular Depot Injection

| Ingredient | Weight % (by weight of total composition) |
| --- | --- |
| Leuprolide acetate (Lupron depot ® - 3 months) | 0.7 |
| Polylactic acid | 6.1 |
| D-mannitol | 5.8 |
| Carboxymethylcellulose sodium | 0.5 |
| Polysorbate 80 | 0.1 |
| Glacial acetic acid (USP) | to control pH |
| Water for injection (USP) | 86.8 |

Other antiandrogens (i.e. EM-9198, EM-9204 or EM-9205) or SARMs (i.e. EM-9251, EM-9253, EM-9290 or EM-9309) may be substituted for EM-9150 in the above formulations. In further combination therapies, 5alpha-reductase inhibitors, type 5 17beta-hydroxysteroid dehydrogenase inhibitors, type 15 17beta-hydroxysteroid dehydrogenase inhibitors or 17alpha-hydroxylase/17,20-lyase inhibitors could be added as an additional container to the first container containing the antiandrogen or SARM to give a kit, and optionally a third container containing the LHRH agonist or LHRH antagonist. The inhibitor could be included in the same formulation than the antiandrogen or SARM in the first container and the LHRH agonist or LHRH antagonist in the second container to give a kit. More than one antiandrogen or SARM or more than one LHRH agonist or LHRH antagonist or more than one inhibitor may be included in the kits.

The invention has been described in terms of preferred embodiments and examples, but is not limited thereby. Those of skill in the art will readily recognize the broader applicability and scope of the invention which is limited only by the patent claims that issue from this application or any patent application claiming priority (directly or indirectly) hereto.

REFERENCES

Ando, T., Yamawaki, J., Saito, Y., Takai, Y., Yamataka, H.; (1980). Neighboring group participation in solvolysis. X. Dissection of $Ar_1$-5 and $Ar_2$-6 pathways in trifluoroacetolysis of 4-arylbutyl 6-methyl-2-naphthalenesulfonates. Bull. Chem. Soc. Jpn., 53(8): 2348-2356.

Aucoin, M. W., Wassersug, R. J.; (2006). The sexuality and social performance of androgen-deprived (castrated) men throughout history: Implications for modern day cancer patients. Soc. Sci. Med., 63: 3162-3173.

Balog, A., Salvati, M. E., Shan, W., Mathur, A., Leith, L. W., Wei, D. D., Attar, R. M., Geng, J., Rizzo, C. A., Wang, C., Krystek, S. R., Tokarski, J. S., Hunt, J. T., Gottardis, M., Weinmann, R.; (2004). The synthesis and evaluation of [2.2.1]-bicycloazahydantoins as androgen receptor antagonists. Bioorg. Med. Chem. Lett., 14: 6107-6111.

Bhasin, S., Pencina, M., Kaur Jasuja, G., Travison, T. G., Coviello, A., Orwoll, E., Wang, P. Y., Nielson, C., Wu, F., Tajar, A., Labrie, F., Vesper, H., Zhang, A., Ulloor, J., Singh, R., D'Agostino, R., Vasan, R. S.; (2011). Reference ranges for testosterone in men generated using liquid chromatography tandem mass spectrometry in a community-based sample of healthy nonobese young men in the Framingham Heart Study and applied to three geographically distinct cohorts. J. Clin. Endocrinol. Metab., 96(8): 2430-2439.

Cantin, L., Faucher, F., Couture, J.-F., Pereira de Jésus-Tran, K., Legrand, P., Ciobanu, L. C., Fréchette, Y., Labrecque, R., Singh, S. M., Labrie, F., Breton, R.; (2007). Structural characterization of the human androgen receptor ligand-binding domain complexed with EM5744, a rationally designed steroidal ligand bearing a bulky chain directed toward helix 12. J. Biol. Chem., 282(42): 30910-30919.

Chengalvala, M., Oh, T., Roy, A. K.; (2003). Selective androgen receptor modulators. Expert Opin. Ther. Patents, 13(1): 59-66.

Cozzoli, A., Capogrosso, R. F., Sblendorio, V. T., Dinardo, M. M., Jagerschmidt, C., Namour, F., Camerino, G. M., De Luca, A.; (2013). GLPG0492, a novel selective androgen receptor modulator, improve muscle performance in the exercised-mdx mouse model of muscular dystrophy. Pharmacol. Res., 72: 9-24.

Duke III, C. B., Jones, A., Bohl, C. E., Dalton, J. T., Miller, D. D.; (2011). Unexpected binding orientation of bulky-B-ring anti-androgens and implications for future drug targets. J. Med. Chem., 54: 3973-3976.

Gauthier, S., Martel, C., Labrie, F.; (2012). Steroid derivatives as pure antagonists of the androgen receptor. J. Steroid Biochem. Mol. Biol., 132: 93-104.

Gryder, B. E., Akbashev, M. J., Rood, M. K., Raftery, E. D., Meyers, W. M., Dillard, P., Khan, S., Oyelere, A. K.; (2013). Selectively targeting prostate cancer with antiandrogen equipped histone deacetylase inhibitors. ACS Chem. Biol., 8: 2550-2560.

Guo, C., Linton, A., Kephart, S., Ornelas, M., Pairish, M., Gonzalez, J., Greasley, S., Nagata, A., Burke, B. J., Edwards, M., Hosea, N., Kang, P., Hu, W., Engebretsen, J., Briere, D., Shi, M., Gukasyan, H., Richardson, P., Dack, K., Underwood, T., Johnson, P., Morell, A., Felstead, R., Kuruma, H., Matsimoto, H., Zoubeidi, A., Gleave, M., Los, G., Fanjul, A. N.; (2011). Discovery of aryloxy tetramethylcyclobutanes as novel androgen receptor antagonists. J. Med. Chem., 54: 7693-7704.

Guo, C., Pairish, M., Linton, A., Kephart, S., Ornelas, M., Nagata, A., Burke, B., Dong, L., Engebretsen, J., Fanjul, A. N.; (2012). Design of oxobenzimidazoles and oxindoles as novel androgen receptor antagonists. Bioorg. Med. Chem. Lett., 22: 2572-2578.

Jones, J. O.; (2009). Improving selective androgen receptor modulator discovery and preclinical evaluation. Expert Opin. Drug Discov., 4(9): 981-993.

Kinoyama, I., Taniguchi, N., Yoden, Koutoku, H., Furutani, T., Kudoh, M., Okada, M.; (2004). Synthesis and pharmacological evaluation of novel arylpiperazine derivatives as nonsteroidal androgen receptor antagonists. Chem. Pharm. Bull., 52(11): 1330-1333.

Kinoyama, I., Taniguchi, N., Kawaminami, E., Nozawa, E., Koutoku, H., Furutani, T., Kudoh, M., Okada, M.; (2005). N-Arylpiperazine-1-carboxamide derivatives: a novel series of orally active nonsteroidal androgen receptor antagonists. Chem. Pharm. Bull., 53(4): 402-409.

Kinoyama, I., Taniguchi, N., Toyoshima, A., Nozawa, E., Kamikubo, T., Imamura, M., Matsuhisa, A., Samizu, K., Kawanimani, E., Niimi, T., Hamada, N., Koutoku, H., Furutani, T., Kudoh, M., Okada, M., Ohta, M., Tsukamoto, S.-I.; (2006). (+)-(2R,5S)-4-[4-cyano-3-(trifluoromethyl)phenyl]-2,5-dimethyl-N-[6-(trifluoromethyl) pyridin-3-yl]piperazine-1-carboxamide (YM580) as an orally potent and peripherally selective nonsteroidal androgen receptor antagonist. J. Med. Chem., 49(2): 716-726.

Labrie, F., Veilleux, R., Fournier, A.; (1988a). Maintenance of androgen responsiveness by glucocorticoids in Shionogi mammary carcinoma cells in culture. J. Natl. Cancer Inst., 80(12): 966-970.

Labrie, F., Veilleux, R., Fournier, A.; (1988b). Glucocorticoids stimulate the growth of mouse mammary carcinoma Shionogi cells in culture. Mol. Cell. Endocrinol., 58: 207-211.

Labrie, F., Veilleux, R., Fournier, A.; (1988c). Low androgen levels induce the development of androgen-hypersensitive cell clones in Shionogi mouse mammary carcinoma cells in culture. J. Natl. Cancer Inst., 80(14): 1138-1147.

Labrie, F.; (2004). Adrenal androgens and intracrinology. Semin. Reprod. Med., 22(4): 299-309.

Labrie, F., Archer, D., Bouchard, C., Fortier, M., Cusan, L., Gomez, J.-L., Girard, G., Baron, M., Ayotte, N., Moreau, M., Dubé, R., Côté, I., Labrie, C., Lavoie, L., Berger, L., Gilbert, L., Martel, C., Balser, J.; (2009). Effect of intravaginal dehydroepiandrosterone (Prasterone) on libido and sexual dysfunction in postmenopausal women. Menopause, 16(5): 923-931.

Labrie, F., Archer, D., Bouchard, C., Fortier, M., Cusan, L., Gomez, J.-L., Girard, G., Baron, M., Ayotte, N., Moreau, M., Dubé, R., Côté, I., Labrie, C., Lavoie, L., Gilbert, L., Martel, C., Balser, J.; (2014). Lack of influence of dyspareunia on the beneficial effect of intravaginal prasterone (dehydroepiandrosterone, DHEA) on sexual dysfunction in postmenopausal women. J. Sex. Med., 11: 1766-1785.

Li, J. J., Sutton, J. C., Nirschl, A., Zou, Y., Wang, H., Sun, C., Pi, Z., Johnson, R., Krystek, S. R., Seethala, R., Golla, R., Sleph, P. G., Beehler, B. C., Grover, G. J., Fura, A., Vyas, V. P., Li, C. Y., Gougoutas, J. Z., Galella, M. A., Zahier, R., Ostrowski, J., Hamann, L. G.; (2007), Discovery of potent and muscle selective androgen receptor modulators through scaffold modifications. J. Med. Chem., 50(13): 3015-3025.

Liu, P. Y., Death, A. K., Handelsman, D. J.; (2003). Androgens and cardiovascular disease. Endocr. Rev., 24: 313-340.

Liu, B., Su, L., Geng, J., Liu, J., Zhao, G.; (2010). Developments in nonsteroidal antiandrogens targeting the androgen receptor. ChemMedChem, 5: 1651-1661.

McGinley, P. L., Koh, J. T.; (2007). Circumventing antiandrogen resistance by molecular design. J. Am. Chem. Soc., 129(13): 3822-3823.

Mohler, M. L., Bohl, C. E., Jones, A, Coss, C. C., Narayanan, R., He, Y., Hwang, D. J., Dalton, J. T., Miller, D. D.; (2009). Nonsteroidal selective androgen receptor modulators (SARMs): dissociating the anabolic and androgenic activities of the androgen receptor for therapeutic benefit. J. Med. Chem., 52(12): 3597-3617.

Mohler, M. L., Coss, C. C., Duke III, C. B., Patil, S. A., Miller, D. D.; Dalton, J. T.; (2012). Androgen receptor antagonists: a patent review (2008-2011). Expert Opin. Ther. Patents, 22(5): 541-565.

Nagata, N., Kawai, K., Nakanishi, I.; (2012). Subtle structural changes in tetrahydroquinolines, a new class of nonsteroidal selective androgen receptor modulators, induce different functions. J. Chem. Inf. Model., 52: 2257-2264.

Negro-Vilar, A.; (1999). Selective androgen receptor modulators (SARMs): a novel approach to androgen therapy for the new millennium. J. Clin. Endocrinol. Metab., 84: 3459-3462.

Nique, F., Hebbe, S., Peixoto, C., Annoot, D., Lefrancois, J.-M., Duval, E., Michoux, L., Triballeau, N., Lemoullec, J.-M., Mollat, P., Thauvin, M., Prangé, T., Minet, D., Clément-Lacroix, P., Robin-Jagerschmidt, C., Fleury, D., Guédin, D., Deprez, P.; (2012a). Discovery of diarylhydantoins as new selective androgen receptor modulators. J. Med. Chem., 55, 8225-8235.

Nique, F., Hebbe, S., Triballeau, N., Peixoto, C., Lefrançois, J.-M., Jary, H., Alvey, L., Manioc M., Housseman, C., Klaassen, H., Van Beeck, K., Guédin, D., Namour, F., Minet, D., Van der Aar, E., Feyen, J., Fletcher, S., Blanqué, R., Robin-Jagerschmidt, C., Deprez, P.; (2012b). Identification of a 4-(hydroxymethyl)diarylhydantoin as a selective androgen receptor modulator. J. Med. Chem., 55, 8236-8247.

Pelletier, G., Ouellet, J., Martel, C., Labrie, F.; (2012). Effects of ovariectomy and dehydroepiandrosterone (DHEA) on vaginal wall thickness and innervation. J. Sex. Med., 9: 2525-2533.

Pelletier, G., Ouellet, J., Martel, C., Labrie, F.; (2013). Androgenic action of dehydroepiandrosterone (DHEA) on nerve density in the ovariectomized rat vagina. J. Sex. Med., 10: 1908-1914.

Poortmans, A., Wyndaele, J. J.; (1998). M. levator ani in the rat: does it really lift the anus? Anat. Rec., May, 251(1): 20-7.

Poutiainen, P. K., Oravilahti, T., Peräkylä, M., Palvimo, J. J., Ihalainen, J. A., Laatikainen, R., Pulkkinen, J. T.; (2012). Design, synthesis, and biological evaluation of nonsteroidal cycloalkane[d]isoxazole-containing androgen receptor modulators. J. Med. Chem., 55: 6316-6327.

Qi, H., Labrie, Y., Grenier, J., Fournier, A., Fillion, C., Labrie, C.; (2001). Androgens induce expression of SPAK, a STE20/SPS1-related kinase, in LNCaP human prostate cancer cells. Mol. Cell. Endocrinol., 182: 181-192.

Salvati, M., Attar, R. M., Balog, A., Dell-John, J., Jure-Kunkel, M., Krystek, S., Obermeier, M., Spires, T. J. R., Vite, G., Gottardis, M.; (2008). BMS-641988: a highly potent and rationally designed inhibitor of the androgen receptor (AR), with efficacy in castration resistant human prostate cancer xenograft models. Eur. J. Cancer Suppl., 6(12): 50.

Simard, J., Dauvois, S., Haagensen, D. E., Lévesque, C., Mérand, Y., Labrie, F.; (1990). Regulation of progesterone-binding breast cyst protein GCDFP-24 secretion by estrogens and androgens in human breast cancer cells: a new marker of steroid action in breast cancer. Endocrinology, 126(6): 3223-3231.

Singh, S. M., Gauthier, S., Labrie, F.; (2000). Androgen receptor antagonists (antiandrogens): structure-activity relationships. Curr. Med. Chem., 7(2): 211-247.

Tucker, H., Crook, J. W., Chesterson, G. J.; (1988). Non-steroidal antiandrogens. Synthesis and structure-activity relationships of 3-substituted derivatives of 2-hydroxy-propionanilides. J. Med. Chem., 31(5): 954-959.

Varchi, G., Guerrini, A., Tesei, A., Brigliadori, G., Bertucci, C., Di Donato, M., Castoria, G.; (2012). Nonsteroidal androgen receptor ligands: versatile syntheses and biological data. ACS Med. Chem. Lett., 3(6): 454-458.

Xiao, H.-Y., Balog, A., Attar, R. M., Faifax, D., Fleming, L. B., Holst, C. L., Martin, G. S., Rossiter, L. M., Chen, J., Cvjic, M.-E., Dell-John, J., Geng, J., Gottardis, M. M., Han, W.-C., Nation, A., Obermeier, M., Rizzo, C. A., Schweizer, L., Spires Jr., T., Shan, W., Gavai, A., Salvati, M. E., Vite, G.; (2010). Design and synthesis of 4-[3,5-dioxo-11-oxa-4,9-diazatricyclo[5.3.1.0$^{2,6}$]undec-4-yl]-2-trifluoromethyl-benzonitriles as androgen receptor antagonists. Bioorg. Med. Chem. Lett., 20: 4491-4495.

Yang, S. H., Song, C.-H., Van, H. T. M., Park, E., Khadka, D. B., Gong, E.-Y., Lee, K., Cho, W.-J.; (2013). SAR based design of nicotinamides as a novel class of androgen receptor antagonists for prostate cancer. J. Med. Chem., 56, 3414-3418.

Zhang, X., Lanter, J. C., Sui, Z.; (2009). Recent advances in the development of selective androgen receptor modulators. Expert Opin. Ther. Patents, 19(9): 1239-1258.

Zhang, X., Allan, G. F., Tannenbaum, P., Sbriscia, T., Linton, O., Lai, M.-T., Haynes-Johnson, D., Bhattacharjee, S., Lundeen, S. G., Sui, Z.; (2013). Pharmacological characterization of an imidazolopyrazole as novel selective androgen receptor modulator. J. Steroid Biochem. Mol. Biol., 134: 51-58.

Zhang, X., Sui, Z.; (2013). Deciphering the selective androgen receptor modulators paradigm. Expert Opin. Drug Discov., 8(2): 191-218.

Zhou, J., Geng, G., Shi, Q., Sauriol, F., Wu, J. H.; (2009). Design and synthesis of androgen receptor antagonists with bulky side chains for overcoming antiandrogen resistance. J. Med. Chem., 52(17): 5546-5550.

What is claimed is:

1. A compound of the formula

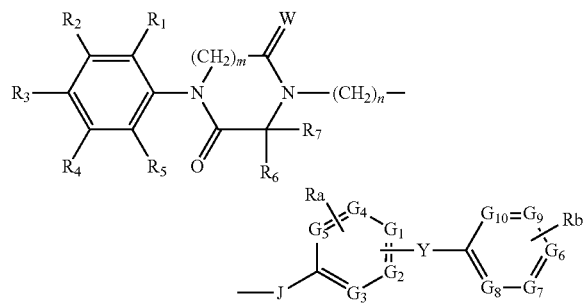

wherein n is an integer from 0 to 6;
wherein m is an integer from 0 to 1;
wherein J and Y are independently a direct bond or selected from the group consisting of —O— and —CH$_2$—
wherein Ra and Rb are independently absent or selected from the group consisting of hydrogen, halogen, —OCH$_3$, C$_1$-C$_3$ alkyl, C$_2$-C$_3$ alkenyl, nitrile, trifluoromethyl, amide, amine, and alkylsulfone;
wherein R$_1$ is selected from the group consisting of hydrogen, halogen and C$_1$-C$_3$ alkyl;
wherein R$_2$ is selected from the group consisting of hydrogen, halogen, —OCH$_3$, —SCH$_3$, alkylsulfoxide, alkylsulfone, nitrile, —NO$_2$, C$_1$-C$_3$ alkyl, and trifluoromethyl;
wherein R$_3$ is selected from the group consisting of halogen, nitrile, —COCH$_3$, —SO$_2$CH$_3$, and —NO$_2$;
wherein R$_4$ and R$_5$ are independently selected from the group consisting of hydrogen, C$_1$-C$_6$ alkyl, halogen, —OCH$_3$, —SCH$_3$, alkylsulfoxide, alkylsulfone, nitrile, —NO$_2$, and trifluoromethyl;
wherein R$_6$ and R$_7$ are independently selected from the group consisting of hydrogen and C$_1$-C$_6$ alkyl or R$_6$ and R$_7$ together form a cycle where R$_6$ and R$_7$ together are (CH$_2$)$_p$ and p is an integer from 2 to 6;
wherein W is selected from the group consisting of oxygen and sulfur;
wherein G$_1$, G$_2$, G$_3$, G$_4$, and G$_5$ are independently selected from the group consisting of carbon, methine, nitrogen and nitrogen-oxide with a maximum of one nitrogen or nitrogen-oxide in the ring;
wherein G$_6$, G$_7$, G$_8$, G$_9$, and G$_{10}$ are independently selected from the group consisting of carbon, methine, nitrogen and nitrogen-oxide with a minimum of one nitrogen or nitrogen-oxide in the ring and a maximum of two nitrogens or nitrogen-oxides in the ring; and
wherein Y is linked to G$_1$, G$_2$ or G$_4$; or a pharmaceutically acceptable salt thereof.

2. A compound according to claim 1 having the following formula:

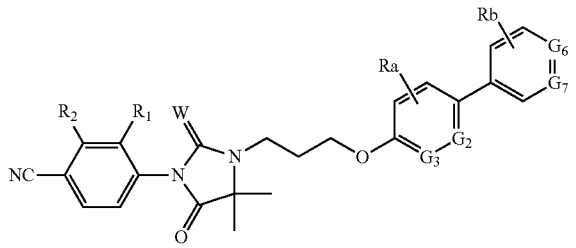

wherein Ra and Rb are independently absent or selected from the group consisting of hydrogen, halogen, —OCH$_3$, C$_1$-C$_3$ alkyl, C$_2$-C$_3$ alkenyl, nitrile, trifluoromethyl, amide, amine, and alkylsulfone;
wherein R$_1$ is selected from the group consisting of hydrogen, fluoro, and methyl;
wherein R$_2$ is selected from the group consisting of hydrogen, halogen, —OCH$_3$, —SCH$_3$, alkylsulfoxide, alkylsulfone, nitrile, —NO$_2$, C$_1$-C$_3$ alkyl, and trifluoromethyl;
wherein W is selected from the group consisting of oxygen and sulfur;
wherein G$_2$ and G$_3$ are independently selected from the group consisting of carbon, methine, nitrogen and nitrogen-oxide with a maximum of one nitrogen or nitrogen-oxide in the ring; and
wherein G$_6$ and G$_7$ are independently selected from the group consisting of carbon, methine, nitrogen and nitrogen-oxide with a minimum of one nitrogen or nitrogen-oxide in the ring; or a pharmaceutically acceptable salt thereof.

3. A compound according to claim 2 wherein said compound is selected from the group consisting of:

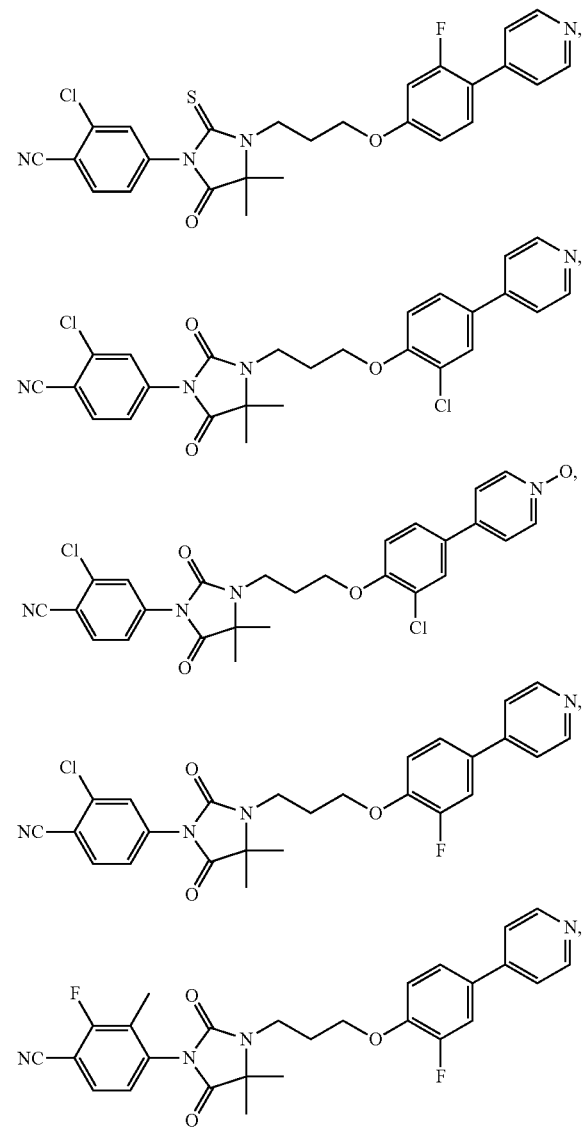

-continued

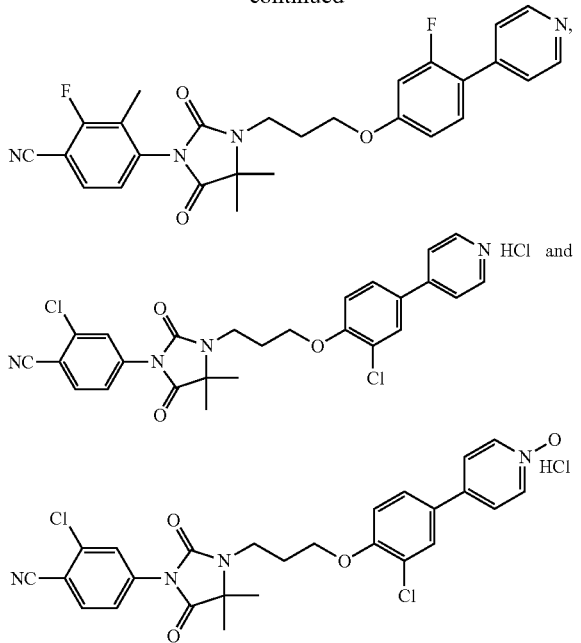

or a pharmaceutically acceptable salt thereof.

4. A compound according to claim 2 wherein said compound is selected from the group consisting of:

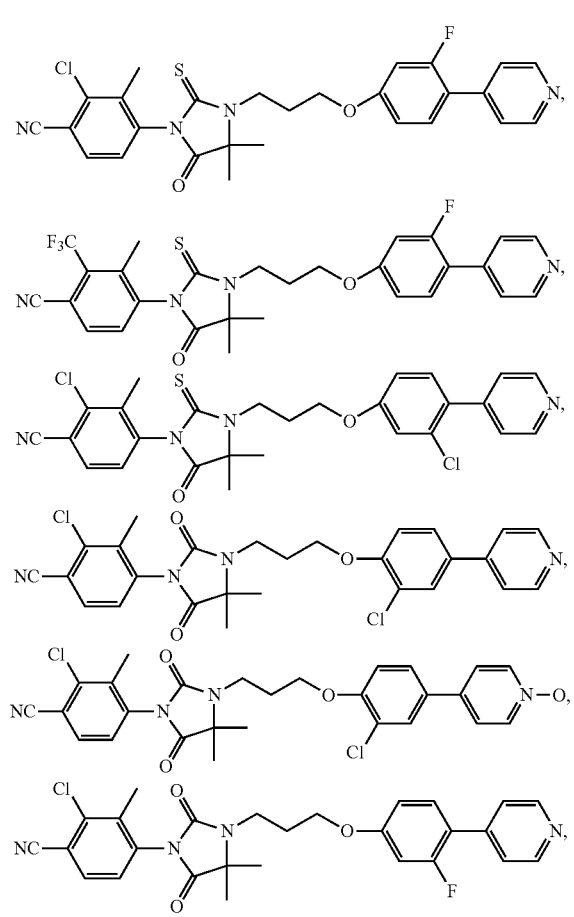

-continued

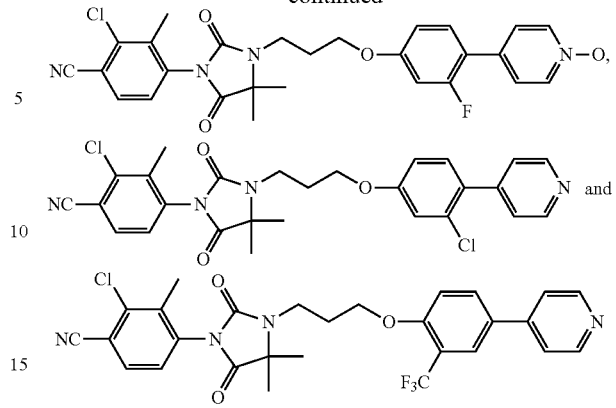

or a pharmaceutically acceptable salt thereof.

5. A compound according to claim 1 wherein m is 0; wherein n is 3; wherein J is an oxygen; wherein $G_1$, $G_8$ and $G_{10}$ are carbon or methine; wherein Y is a direct bond; wherein J and Y are in para position from each other; and wherein $G_6$ or $G_7$ or $G_9$ is a nitrogen or nitrogen-oxide.

6. A compound according to claim 1 wherein said compound is selected from the group consisting of

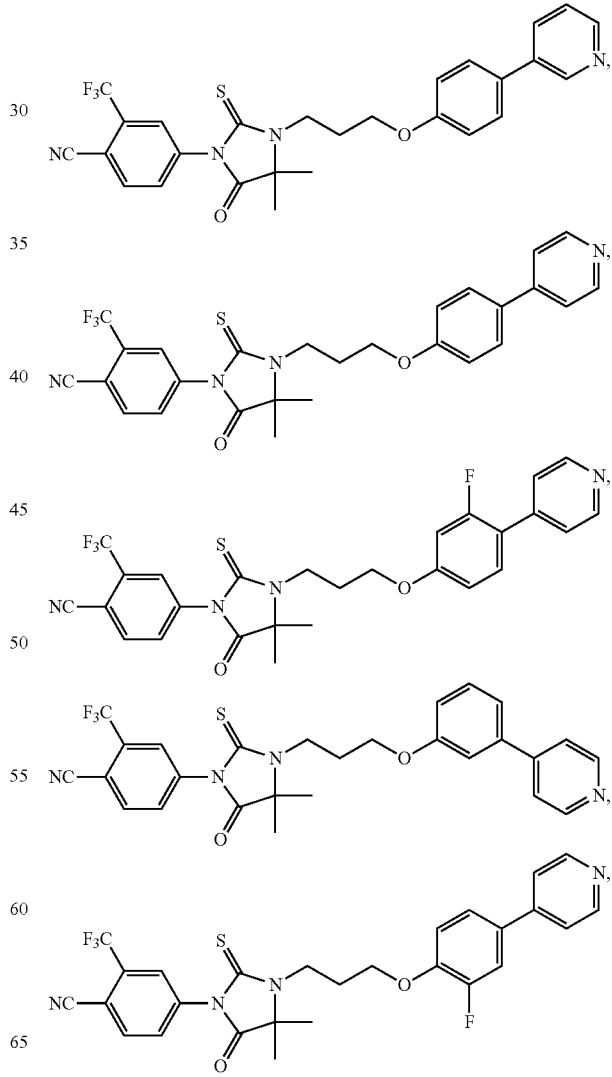

155
-continued
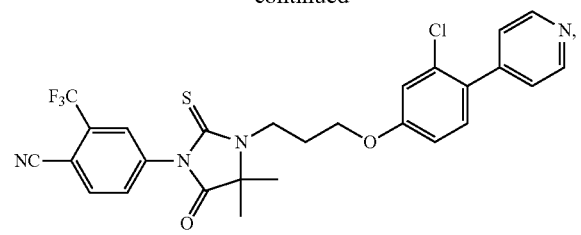
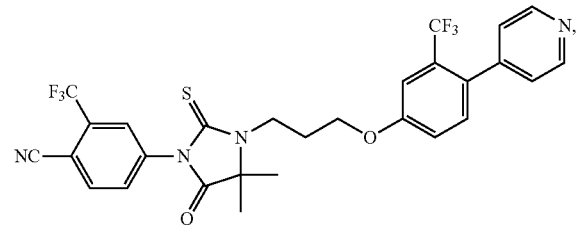
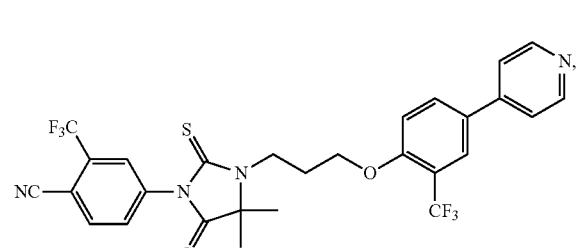
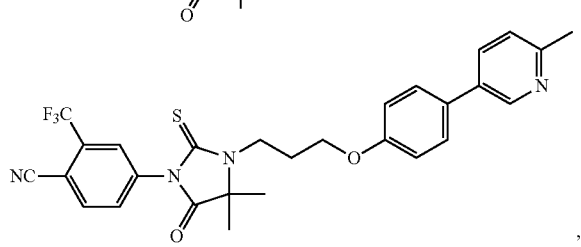
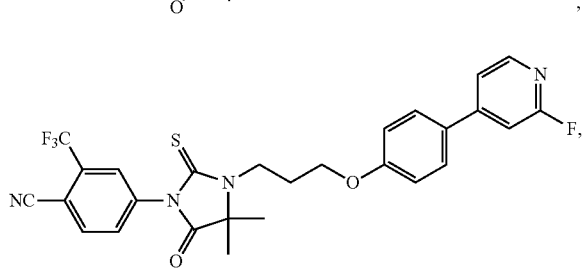
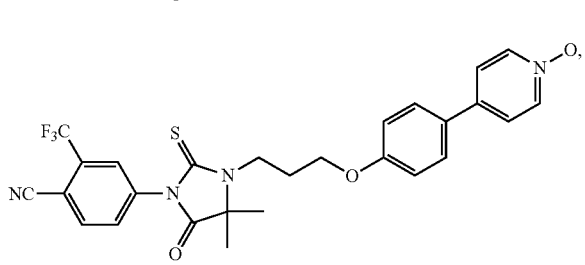
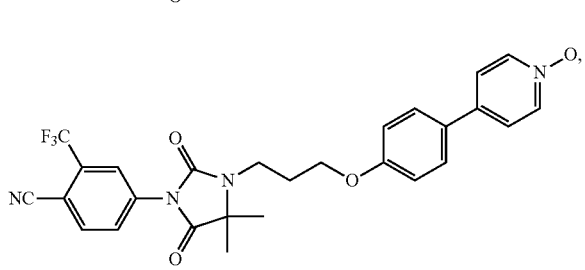
156
-continued
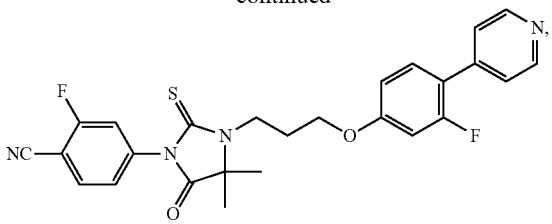
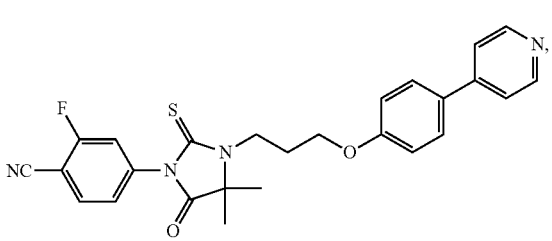
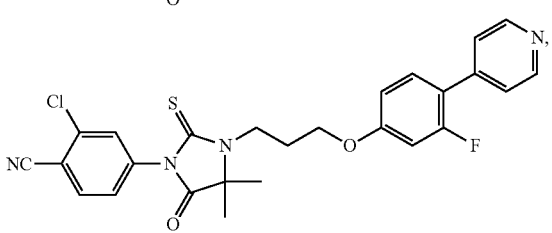
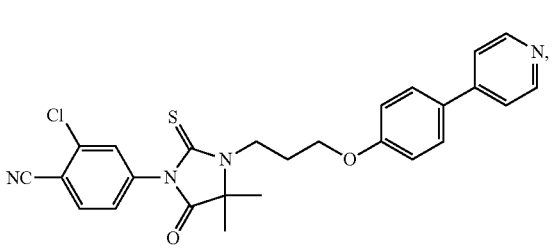
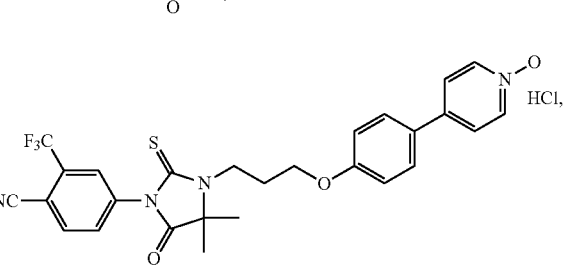
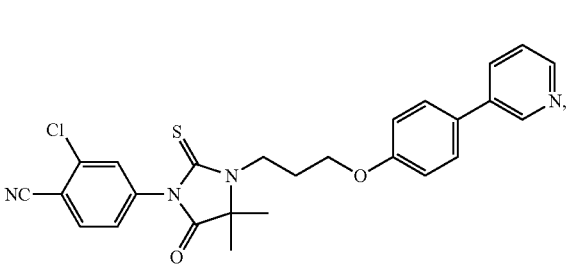
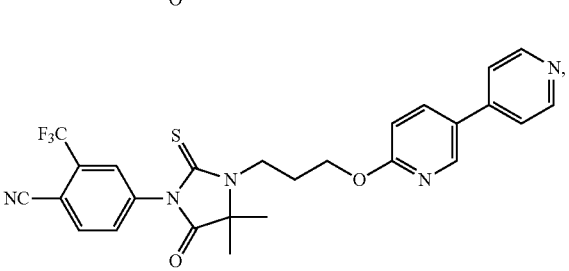

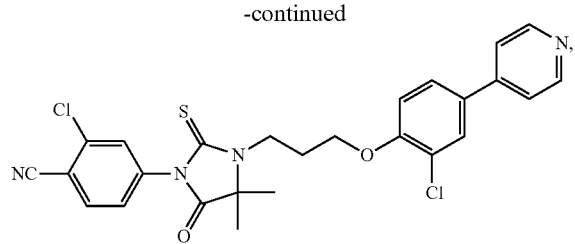
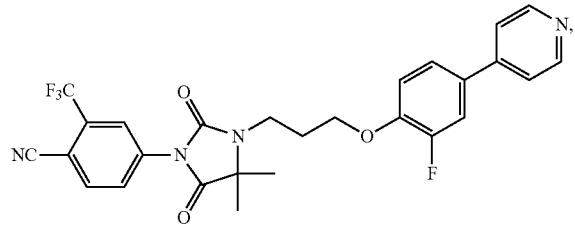 [SMILES: CC1(C)C(=O)N(c2ccc(C#N)c(Cl)c2)C(=O)N1CCCOc1ccc(-c2ccncc2)cc1Cl]
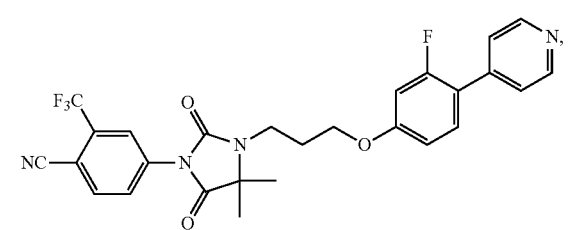
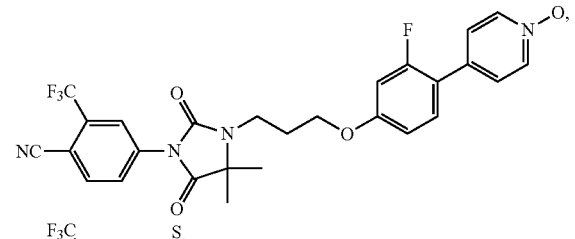
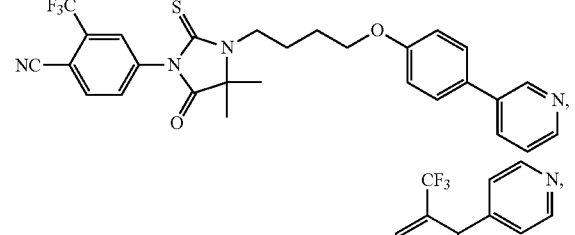
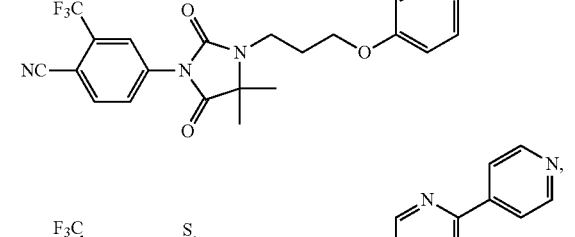
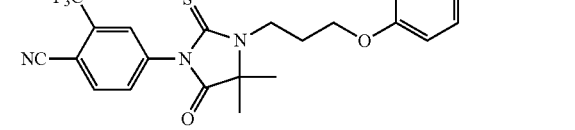
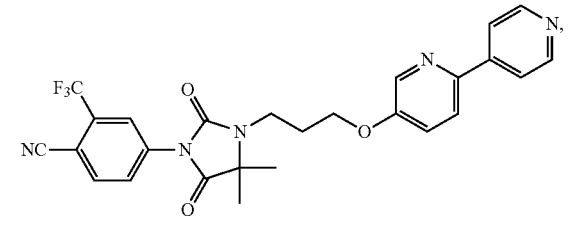
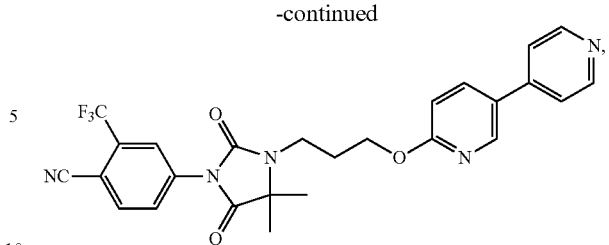
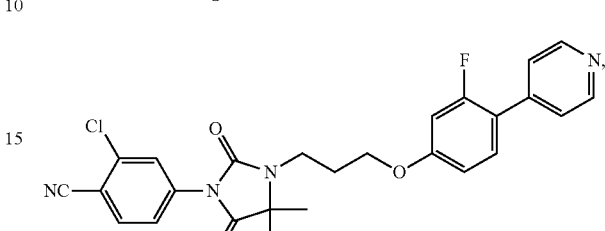
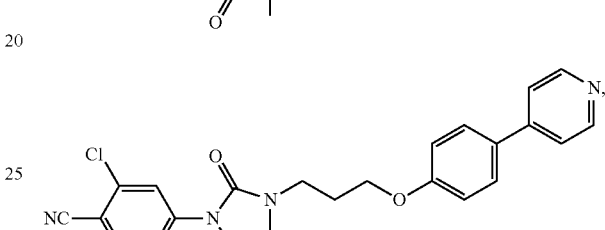
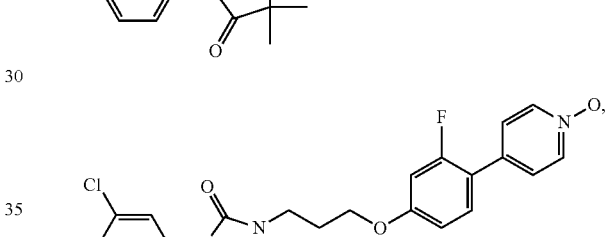
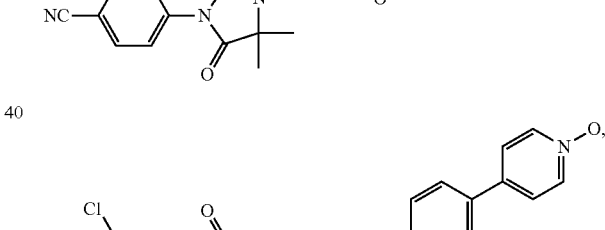
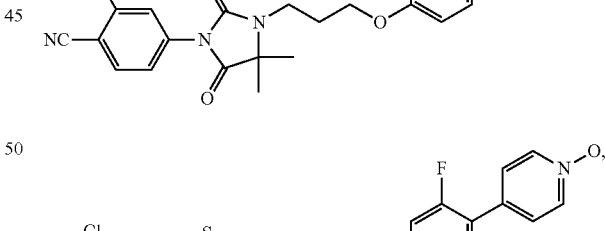
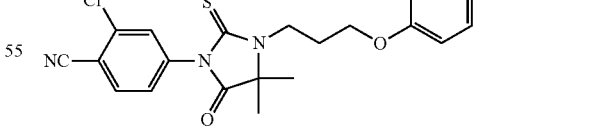
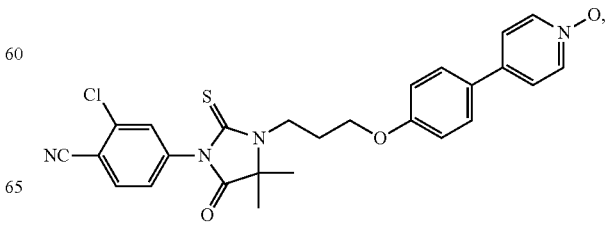

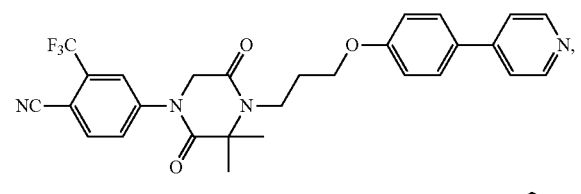
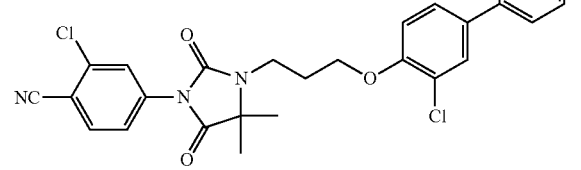
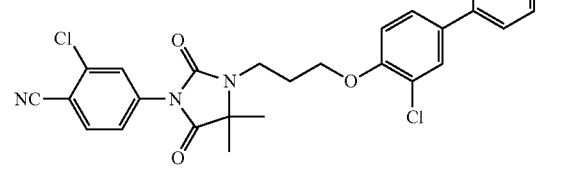
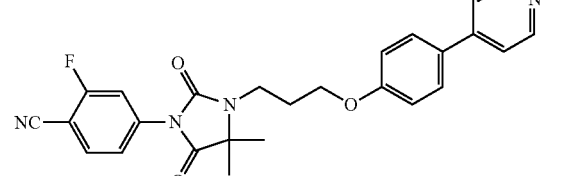
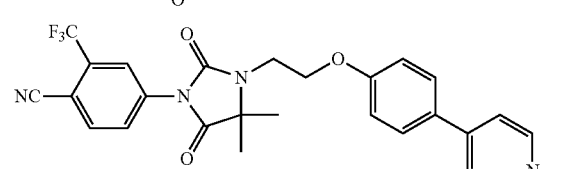
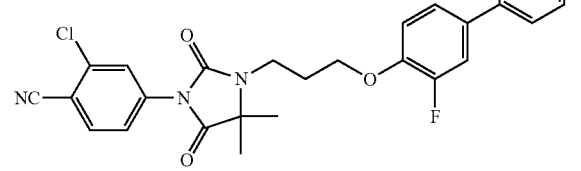
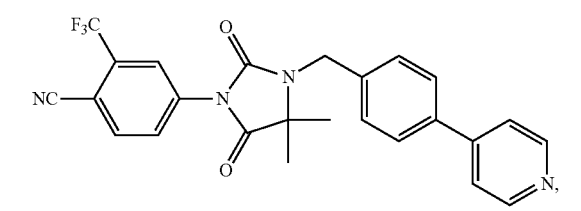
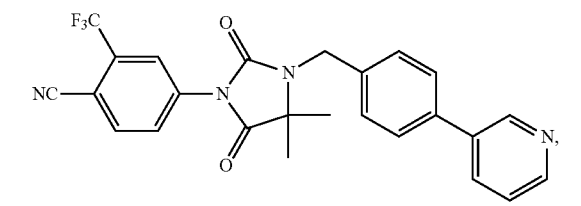 [SMILES: CC1(C)C(=O)N(c2ccc(C#N)c(C(F)(F)F)c2)C(=O)N1Cc1ccc(-c2cccnc2)cc1]
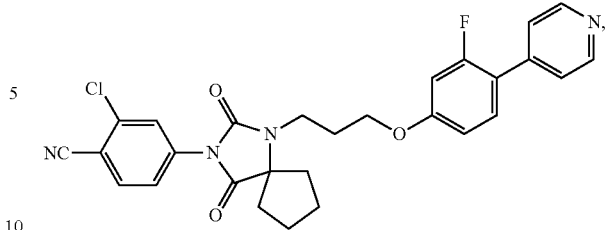
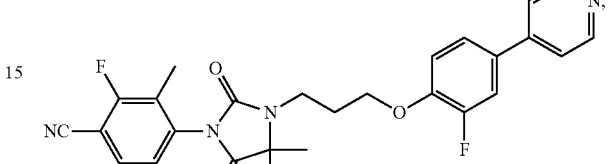
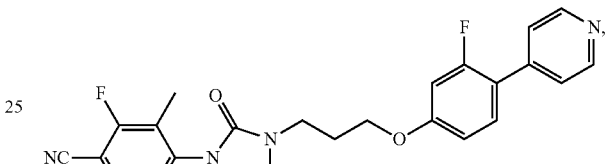
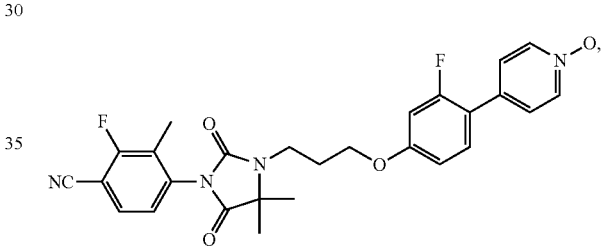
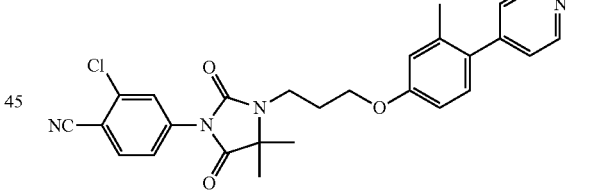
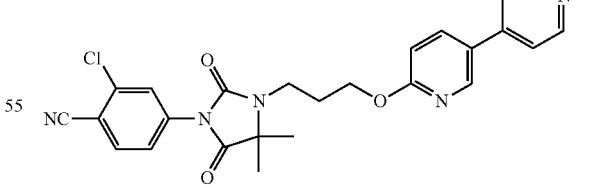
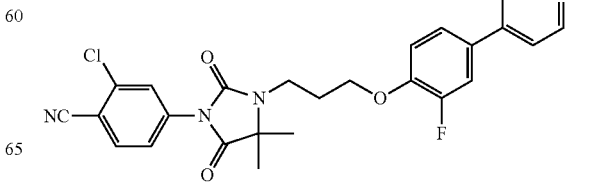

161
-continued
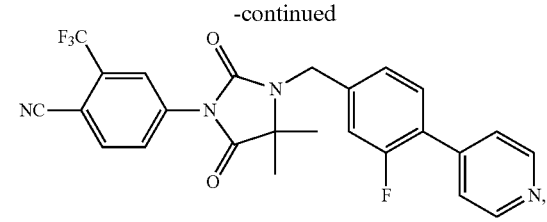
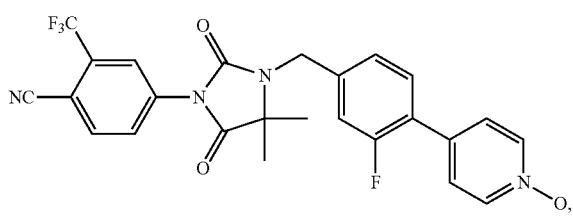
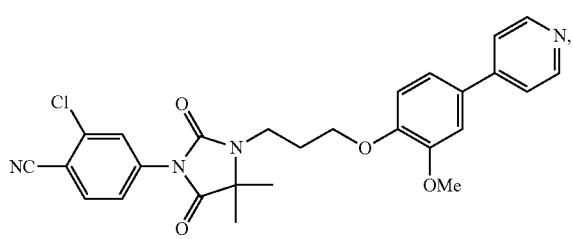
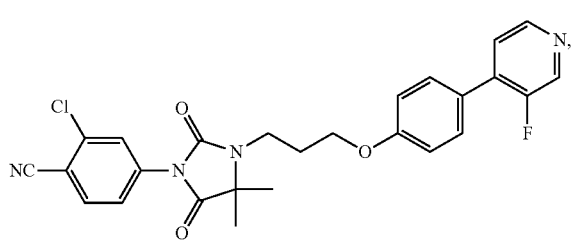
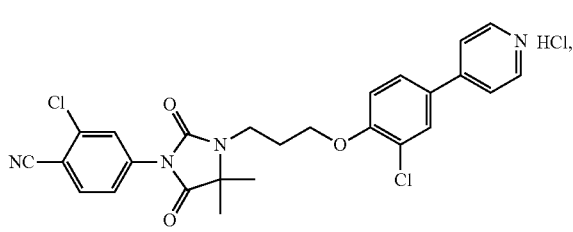
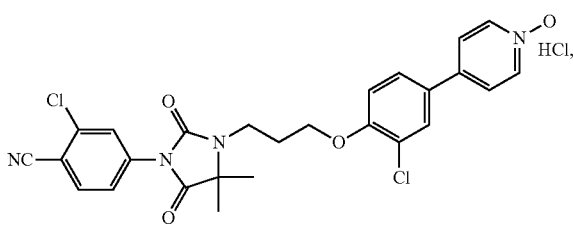
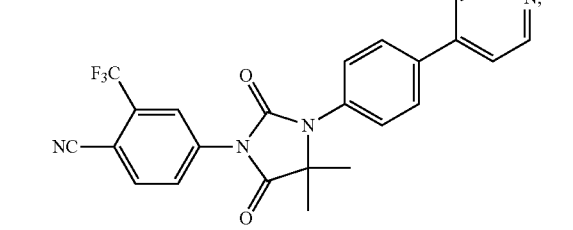
162
-continued
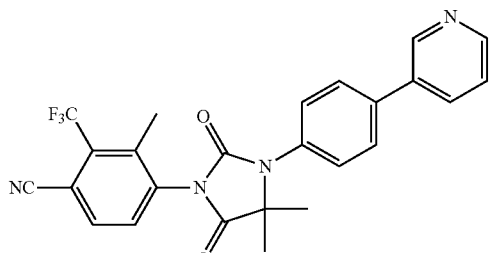
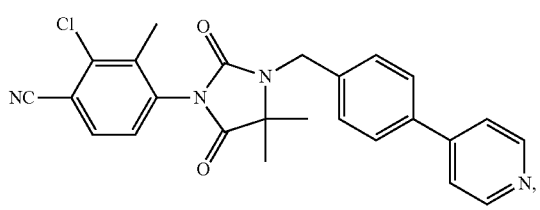
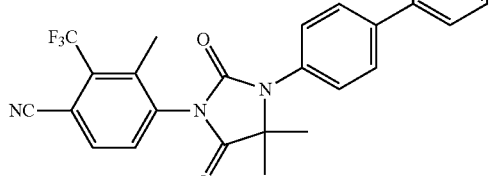
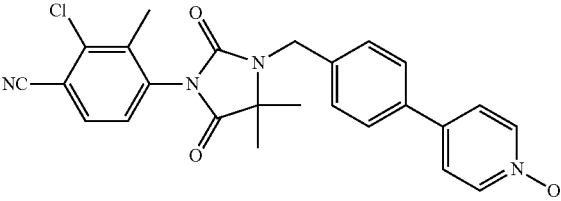
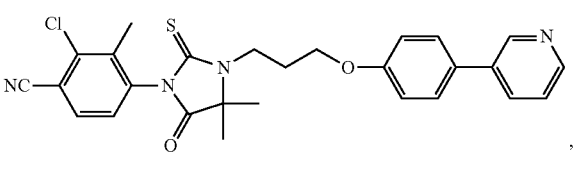
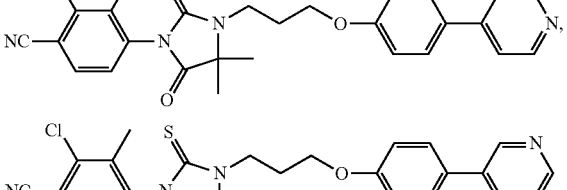
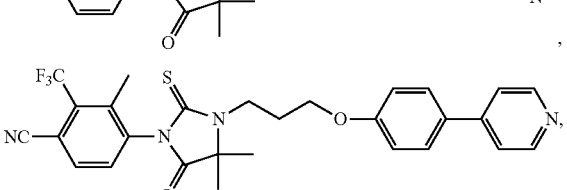
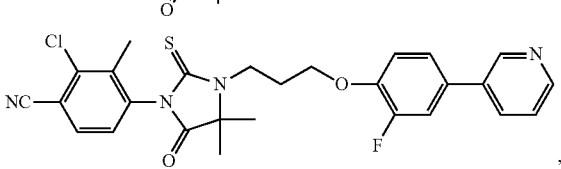

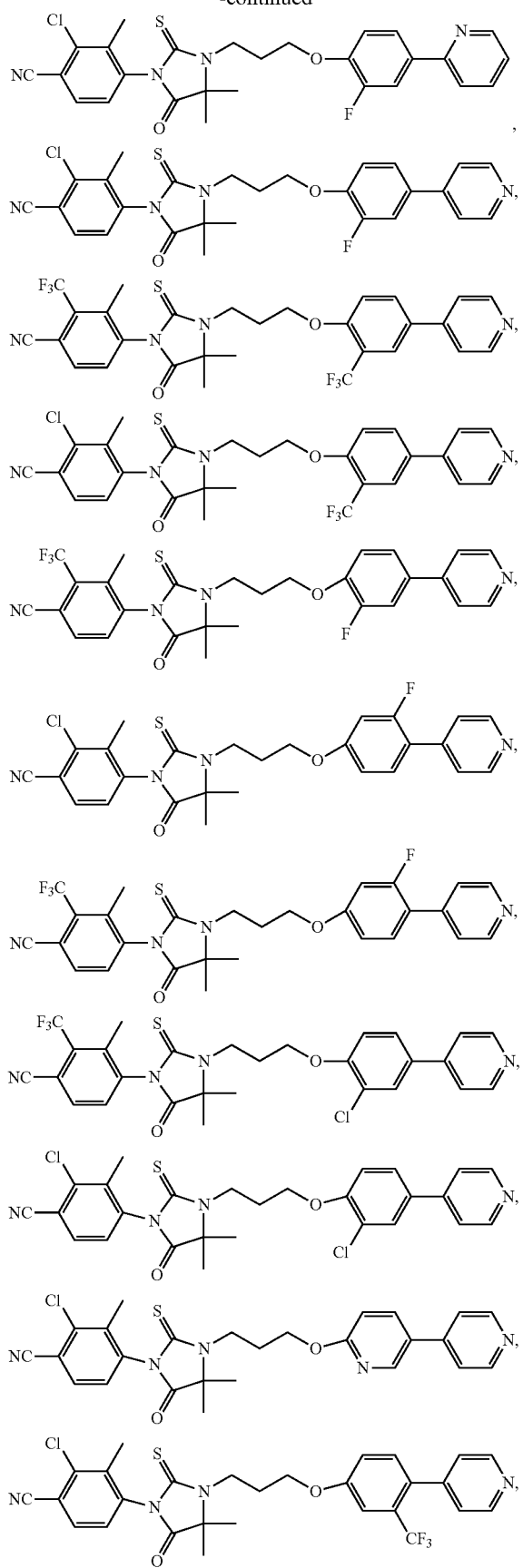
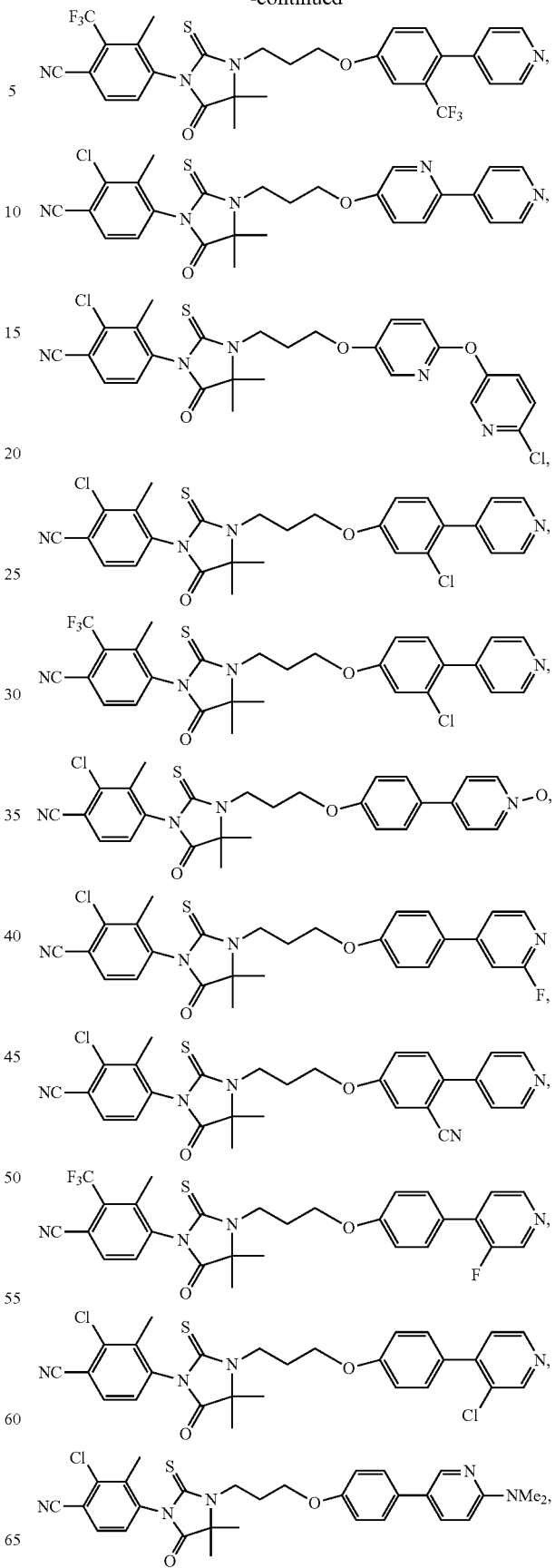

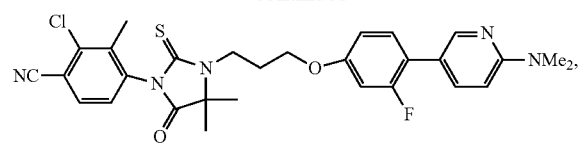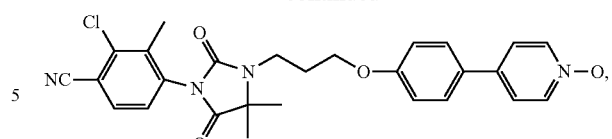

-continued

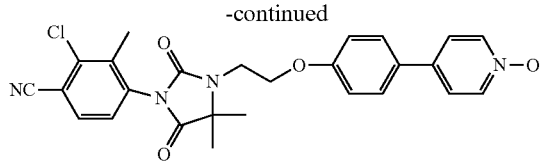

or a pharmaceutically acceptable salt thereof.

7. A compound having the following structure:

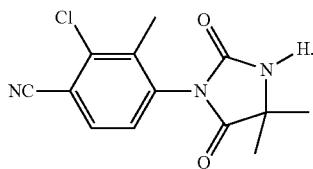

8. A pharmaceutical composition comprising at least one compound as defined in claim 1 and a pharmaceutically acceptable diluent or carrier.

9. The pharmaceutical composition of claim 8 wherein said diluent or carrier is suitable for oral administration.

10. A method of treating or reducing the risk of developing prostate cancer, comprising administering to a patient in need of such treatment or reduction of risk a therapeutically effective amount of at least one compound as defined in claim 1.

11. The method of claim 10, further comprising administering to said patient a therapeutically effective amount of at least one inhibitor of androgen-synthesizing enzymes selected from the group consisting of an inhibitor of type 15 17β-hydroxysteroid dehydrogenase, an inhibitor of type 5 17β-hydroxysteroid dehydrogenase, an inhibitor of 5α-reductase, and an inhibitor of 17α-hydroxylase/17,20-lyase.

12. The method of claim 11, wherein an inhibitor of 5α-reductase and an inhibitor of type 15 17β-hydroxysteroid dehydrogenase are administered.

13. The method of claim 10, further comprising orchiectomy or administering an LHRH agonist or antagonist.

14. The method of claim 11, further comprising orchectomy or administering an LHRH agonist or antagonist.

15. The method of claim 12, further comprising orchiectomy or administering an LHRH agonist or antagonist.

16. A method of treating or reducing the risk of developing benign prostatic hyperplasia, comprising administering to a patient in need of such treatment or reduction of risk a therapeutically effective amount of at least one compound as defined in of claim 1.

17. The method of claim 16, further comprising administering to said patient a therapeutically effective amount of at least one inhibitor selected from the group consisting of an antiestrogen, an inhibitor of aromatase, an inhibitor of type 15 17β-hydroxysteroid dehydrogenase, an inhibitor of type 5 17β-hydroxysteroid dehydrogenase, an inhibitor of 5α-reductase, an inhibitor of 17α-hydroxylase/17,20-lyase, and an inhibitor of androgen-synthesizing enzymes.

18. The method of claim 17, wherein an inhibitor of 5α-reductase and an inhibitor of type 15 17β-hydroxysteroid dehydrogenase are administered.

19. A method of treating or reducing the risk of developing prostate cancer or benign prostatic hyperplasia, comprising administering to a patient in need of such treatment or reduction of risk a therapeutically effective amount of at least one compound as defined in claim 1.

20. A method according to claim 10, wherein said compound is formulated for administration to a patient in a pharmaceutically acceptable diluent or carrier.

21. A kit comprising a first container containing a therapeutically effective amount of at least one compound as defined in claim 1 and further comprising a second container containing a therapeutically effective amount of at least one LHRH agonist or LHRH antagonist.

22. A method according to claim 16 wherein said compound is formulated for administration to a patient in a pharmaceutically acceptable diluent or carrier.

23. A method according to claim 19 wherein said compound is formulated for administration to a patient in a pharmaceutically acceptable diluent or carrier.

24. A method according to claim 19 wherein said compound is formulated for administration to a patient in a pharmaceutically acceptable diluent or carrier.

* * * * *

UNITED STATES PATENT AND TRADEMARK OFFICE
CERTIFICATE OF CORRECTION

PATENT NO. : 9,682,960 B2
APPLICATION NO. : 14/567970
DATED : June 20, 2017
INVENTOR(S) : Fernand Labrie et al.

Page 1 of 1

It is certified that error appears in the above-identified patent and that said Letters Patent is hereby corrected as shown below:

On the Title Page

Below Abstract, delete "24 Claims, 8 Drawing Sheets" and insert --23 Claims, 8 Drawing Sheets--.

In the Specification

Column 22:
Correct the second formula

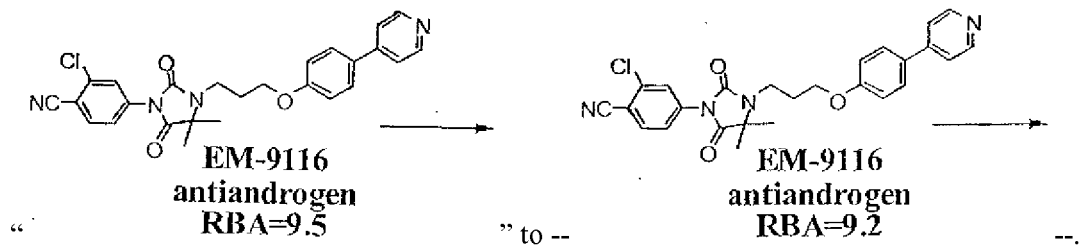

In the Claims

Column 168, Lines 39-41:
Delete Claim 24 in its entirety.

Signed and Sealed this
Eighth Day of May, 2018

Andrei Iancu
*Director of the United States Patent and Trademark Office*